US010370453B2

(12) United States Patent
Sexton et al.

(10) Patent No.: US 10,370,453 B2
(45) Date of Patent: *Aug. 6, 2019

(54) PLASMA KALLIKREIN BINDING PROTEINS

(71) Applicant: Dyax Corp., Burlington, MA (US)

(72) Inventors: Daniel J. Sexton, Melrose, MA (US);
Malini Viswanathan, Burlington, MA (US)

(73) Assignee: Dyax Corp., Lexington, MA (US)

( * ) Notice: Subject to any disclaimer, the term of this patent is extended or adjusted under 35 U.S.C. 154(b) by 563 days.

This patent is subject to a terminal disclaimer.

(21) Appl. No.: 14/969,498

(22) Filed: Dec. 15, 2015

(65) Prior Publication Data

US 2016/0102150 A1    Apr. 14, 2016

Related U.S. Application Data

(62) Division of application No. 14/310,814, filed on Jun. 20, 2014, now Pat. No. 9,266,964, which is a division of application No. 13/345,170, filed on Jan. 6, 2012, now Pat. No. 8,816,055.

(60) Provisional application No. 61/430,442, filed on Jan. 6, 2011.

(51) Int. Cl.
*C07K 16/40* (2006.01)
*G01N 33/573* (2006.01)
*A61K 39/00* (2006.01)

(52) U.S. Cl.
CPC ............ *C07K 16/40* (2013.01); *G01N 33/573* (2013.01); *A61K 2039/505* (2013.01); *C07K 2317/34* (2013.01); *C07K 2317/55* (2013.01); *C07K 2317/56* (2013.01); *C07K 2317/565* (2013.01); *C07K 2317/76* (2013.01); *C07K 2317/92* (2013.01); *C07K 2317/94* (2013.01); *G01N 2333/96455* (2013.01); *G01N 2500/04* (2013.01)

(58) Field of Classification Search
None
See application file for complete search history.

(56) References Cited

U.S. PATENT DOCUMENTS

| | | |
|---|---|---|
| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,946,778 A | 8/1990 | Ladner et al. |
| 4,966,852 A | 10/1990 | Wun et al. |
| 5,106,833 A | 4/1992 | Broze, Jr. et al. |
| 5,118,668 A | 6/1992 | Auerswald et al. |
| 5,166,133 A | 11/1992 | Houston et al. |
| 5,179,017 A | 1/1993 | Axel et al. |
| 5,212,091 A | 5/1993 | Diaz-Collier et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |
| 5,563,123 A | 10/1996 | Innis et al. |
| 5,576,294 A | 11/1996 | Norris et al. |
| 5,583,107 A | 12/1996 | Wolf et al. |
| 5,585,089 A | 12/1996 | Queen et al. |

(Continued)

FOREIGN PATENT DOCUMENTS

| | | |
|---|---|---|
| AT | 275583 T | 9/2004 |
| CA | 2180950 A1 | 8/1995 |

(Continued)

OTHER PUBLICATIONS

Nature [online]. Nature International Weekly Journal of Science. [retrieved on Dec. 10, 2018]. Retrieved from the Internet: < URL: http://www.nature.com/news/2010/100330/full/news.2010.158.html >. Animal studies paint misleading picture. pp. 1-3.*

[No Author Listed] Dyax's DX-2930 granted Orphan Drug designation in hereditary angioedema. Dec. 6, 2013.

Abdel-Salam et al., "Expression of mouse anticreatine kinase (MAK33) monoclonal antibody in the yeast Hansenula polymorpha", Appl. Microbiol. Biotechnol, vol. 56, p. 157-164 (2001).

Abuchowski et al., "Alteration of immunological properties of bovine serum albumin by covalent attachment of polyethylene glycol," J. Bio. Chem., 1977, vol. 252, pp. 3578-3581.

Abuchowski et al., "Cancer therapy with chemically modified enzymers, I., Antitumor properties of polyethylene glycol-asparaginase conjugates," Cancer Biochem. Biophys., 1984, vol. 7, pp. 175-186.

(Continued)

*Primary Examiner* — Sharon X Wen
(74) *Attorney, Agent, or Firm* — Wolf, Greenfield & Sacks, P.C.

(57) ABSTRACT

Plasma kallikrein binding proteins and methods of using such proteins are described.

9 Claims, 22 Drawing Sheets

Specification includes a Sequence Listing.

(56) References Cited

U.S. PATENT DOCUMENTS

| | | |
|---|---|---|
| 5,589,359 A | 12/1996 | Innis et al. |
| 5,618,696 A | 4/1997 | Norris et al. |
| 5,629,176 A | 5/1997 | Bj.o slashed.rn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ladner et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 8,816,055 B2 | 8/2014 | Sexton et al. |
| 8,822,653 B2 | 9/2014 | Sexton et al. |
| 9,266,964 B2 | 2/2016 | Sexton et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0038893 A1 | 2/2004 | Ladner et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |
| 2004/0180827 A1 | 9/2004 | Chen et al. |
| 2004/0209243 A1 | 10/2004 | Nixon et al. |
| 2005/0004021 A1 | 1/2005 | Sprecher et al. |
| 2005/0075665 A1 | 4/2005 | Brenzel et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |
| 2006/0069020 A1 | 3/2006 | Blair et al. |
| 2006/0194727 A1 | 8/2006 | Ladner et al. |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |
| 2007/0049522 A1 | 3/2007 | Ladner et al. |
| 2007/0065407 A1 | 3/2007 | Patten et al. |
| 2007/0079096 A1 | 4/2007 | Chen |
| 2007/0100133 A1 | 5/2007 | Beals et al. |
| 2007/0117752 A1 | 5/2007 | Larsen et al. |
| 2007/0213275 A1 | 9/2007 | Clark et al. |
| 2007/0249807 A1 | 10/2007 | Ladner et al. |

(56) References Cited

U.S. PATENT DOCUMENTS

| | | |
|---|---|---|
| 2007/0253949 A1 | 11/2007 | Golz et al. |
| 2008/0038276 A1 | 2/2008 | Sinha et al. |
| 2008/0038748 A1 | 2/2008 | Kojima et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | McPherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0285507 A1 | 11/2010 | Cho et al. |
| 2010/0286061 A1 | 11/2010 | Devy et al. |
| 2011/0008762 A1 | 1/2011 | Cicardi et al. |
| 2011/0086801 A1 | 4/2011 | Ladner et al. |
| 2011/0136746 A1 | 6/2011 | Markland et al. |
| 2011/0200611 A1 | 8/2011 | Sexton |
| 2012/0201756 A1 | 8/2012 | Sexton |
| 2012/0264798 A1 | 10/2012 | Sinha et al. |
| 2012/0328517 A1 | 12/2012 | Markland et al. |
| 2013/0012438 A1 | 1/2013 | Blair et al. |
| 2014/0302048 A1 | 10/2014 | Sexton et al. |
| 2014/0335023 A1 | 11/2014 | Sexton et al. |
| 2015/0274841 A1 | 10/2015 | Conley et al. |
| 2015/0362492 A1 | 12/2015 | Joseph et al. |
| 2016/0017055 A1 | 1/2016 | Nixon et al. |
| 2016/0102150 A1 | 4/2016 | Sexton et al. |
| 2017/0002094 A1 | 1/2017 | Sexton et al. |
| 2018/0002447 A1 | 1/2018 | Sexton et al. |
| 2018/0002448 A1 | 1/2018 | Sexton et al. |
| 2018/0002449 A1 | 1/2018 | Sexton et al. |
| 2018/0037664 A1 | 2/2018 | Sexton et al. |
| 2018/0037665 A1 | 2/2018 | Sexton et al. |
| 2018/0037666 A1 | 2/2018 | Sexton et al. |

FOREIGN PATENT DOCUMENTS

| | | |
|---|---|---|
| DE | 69533472 T2 | 1/2006 |
| EP | 0 132 732 A2 | 2/1985 |
| EP | 0 210 029 | 1/1987 |
| EP | 0 255 011 A2 | 2/1988 |
| EP | 0 274 826 | 7/1988 |
| EP | 0 285 123 A2 | 10/1988 |
| EP | 0 301 122 | 2/1989 |
| EP | 0 307 592 A2 | 3/1989 |
| EP | 0 318 451 | 5/1989 |
| EP | 0 401 508 A2 | 12/1990 |
| EP | 0 486 001 A1 | 5/1992 |
| EP | 0 621 870 A1 | 11/1994 |
| EP | 0 621 871 A1 | 11/1994 |
| EP | 0 739 355 A1 | 10/1996 |
| EP | 1 288 305 A2 | 3/2003 |
| EP | 1 484 339 A2 | 12/2004 |
| JP | 7504891 | 6/1995 |
| JP | 9-059838 | 3/1997 |
| JP | H9-509838 | 10/1997 |
| JP | 9511131 | 11/1997 |
| JP | 10-503375 | 3/1998 |
| JP | 2002-524076 A | 8/2002 |
| JP | 2008-514624 | 5/2008 |
| WO | WO 1989/010374 A1 | 11/1989 |
| WO | WO 1990/002809 | 3/1990 |
| WO | WO 1992/006111 A1 | 4/1992 |
| WO | WO 1993/009233 A2 | 5/1993 |
| WO | WO 1993/014120 A1 | 7/1993 |
| WO | WO 1993/014121 A1 | 7/1993 |
| WO | WO 1993/014122 A1 | 7/1993 |
| WO | WO 1995/018830 A2 | 7/1995 |
| WO | WO 1995/021601 A2 | 8/1995 |
| WO | WO 1995/023860 | 9/1995 |
| WO | WO 1996/004378 | 2/1996 |
| WO | WO 1996/020278 | 7/1996 |
| WO | WO 1996/035788 A2 | 11/1996 |
| WO | WO 1997/033996 | 9/1997 |
| WO | WO 1998/052976 A1 | 11/1998 |
| WO | WO 1999/063090 A2 | 12/1999 |
| WO | WO 2000/014235 A1 | 3/2000 |
| WO | WO 2000/034317 A2 | 6/2000 |
| WO | WO 2001/009968 | 2/2001 |
| WO | WO 2001/014424 A2 | 3/2001 |
| WO | WO 2001/068707 | 9/2001 |
| WO | WO 2001/079480 A1 | 10/2001 |
| WO | WO 2002/006334 | 1/2002 |
| WO | WO 2002/006539 | 1/2002 |
| WO | WO 2002/092147 | 11/2002 |
| WO | WO 2002/094200 | 11/2002 |
| WO | WO 2003/006860 | 1/2003 |
| WO | WO 2003/066824 A2 | 8/2003 |
| WO | WO 2003/103475 A2 | 12/2003 |
| WO | WO 2004/019968 A1 | 3/2004 |
| WO | WO 2004/062646 A1 | 7/2004 |
| WO | WO 2004/062689 A1 | 7/2004 |
| WO | WO 2005/021556 | 3/2005 |
| WO | WO 2005/021557 A2 | 3/2005 |
| WO | WO 2005/075665 | 8/2005 |
| WO | WO 2006/017538 | 2/2006 |
| WO | WO 2006/036860 | 4/2006 |
| WO | WO 2006/066878 A1 | 6/2006 |
| WO | WO 2006/089005 A2 | 8/2006 |
| WO | WO 2007/079096 A2 | 7/2007 |
| WO | WO 2007/104541 A2 | 9/2007 |
| WO | WO 2007/106746 | 9/2007 |
| WO | WO 2008/000833 | 1/2008 |
| WO | WO 2009/026334 A2 | 2/2009 |
| WO | WO 2009/026539 A1 | 2/2009 |
| WO | WO 2009/102927 A1 | 8/2009 |
| WO | WO 2010/003475 | 1/2010 |
| WO | WO 2010/006746 | 1/2010 |
| WO | WO 2010/080833 | 7/2010 |
| WO | WO 2011/085103 | 7/2011 |
| WO | WO 2012/094587 | 7/2012 |
| WO | WO 2014/113701 A1 | 7/2014 |
| WO | WO 2014/113712 A1 | 7/2014 |
| WO | WO 2014/152232 A2 | 9/2014 |
| WO | WO 2015/112578 A1 | 7/2015 |
| WO | WO 2016/160926 A1 | 10/2016 |

OTHER PUBLICATIONS

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs) and NSAIDs alone", Osteoarthritis and Cartilage, Bailliere Tindall, London, GB, vol. 3, No. 4, pp. 213-225, (Dec. 1, 1995).

(56) References Cited

OTHER PUBLICATIONS

Adelman et al., Proteolysis of Platelet Glycoprotein lb by Plasmin Is Facilitated by Plasmin Lysine-Binding Regions, Blood, vol. 68 (6): 1280-1284, (Dec. 1986).
Albrecht et al., Kunitz-Type Proteinase Inhibitors Derived by Limited Proteolysis of the Inter-Alpha-Trypsin Inhibitors From several Mammalian Sera, Hoppe-Seyler's Z. Physiol. Chem., vol. 364: 1703-1708, (Dec. 1983).
Albrecht et al.., Elastase Inhibition by the Inter-Alpha-Trypsin Inhibitor and Derived Inhibitors of Man and Cattle, Hoppe-Seyler's Z. Physiol. Chem., vol. 364: 1697-1702, (Dec. 1983).
Altschul et al. "Gapped BLAST and PSI-BLAST: a new generation of protein database search programs." (1997) Nucleic Acids Res. 25:3389-3402.
Anba et al., Improving the Stability of a Foreign Protein in the Periplasmic Space of *Escherichia coli*, Biochimie, vol. 70(6): 727-733, (1988).
Angliker et al., The Synthesis of Lysylflouromethanes and their Properties as Inhibitors of Trypsin, Plasmin and Cathepsin B, Biochemistry, 241:871-875, (1987).
Asano et al., "Effects of a nonpeptide bradykinin B2 receptor antagonist, FR167344, on different in vivo animal models of inflammation", Br J Pharmacol, vol. 122, p. 1436-1440 (1997).
Asano M. et al., Br J Pharmacol, vol. 122, p. 1436-1440 (1997).
Atherton et al., Peptide Synthesis. Part 2. Procedures for Solid Phase Synthesis using N?-Fluorenylmethycarbonylamino-acids on Polyamide Supports. Synthesis of Substance P and of Acyl Carrier Protein 65-74 Decapeptide, J. Chem. Soc. Perkins Trans,1:538-546, (1981).
Attwood, The Babel of Bioinformatics; Science, vol. 290, pp. 471-473 (2000).
Auerswald et al., Expression, Isolation and Characterization of Recombinant [Arg15, Glu52] Aprotinin, Bio. Chem. Hoppe-Seyler, 369:(Suppl)27-35 (1988).
Baba et al., States of Tyrosyl Residues and Circular Dichroism of Kunitz Trypsin Inhibitor, J. Biochem 65 (1):113-121 (1969).
Bagdasarian et al., Immunochemical studies of plasma kallikrein. J Clin Invest. Dec. 1974;54(6):1444-54.
Balduyck et al., Human Urinary Proteinase Inhibitor: Inhibitory Properties and Interaction with Bovine Trypsin, Bio. Chem. Hoppe-Seyler, vol. 366: 9-14, (1985).
Baneyx et al., "In Vivo Degradation of Secreted Fusion Proteins by the *Escherichia coli* Outer Membrane Protease OmpT", J. Bacteriol., 172:491-494, (1990).
Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).
Basu et al., "Structure-function engineering of interferon-b-1b for improving stability, solubility, potency, immunogenicity, and pharmacokinetic properties by site-selective mono-PEGylation," Bioconjugate Chemistry, 2006, vol. 17, pp. 618-630.
Baumann, "A multi-level study of recombinant Pichia pastoris in different oxygen conditions", BMC Syst Biol. 4:141 (Oct. 22, 2010).
Bayes et al., "Gateways to Clinical Trials" Methods Find Exp. Clin. Pharmacol., vol. 28(3): pp. 185-206 (2006).
Beckmann et al., "Preparation of chemically 'mutated' aprotinin homologues by semisynthesis-P1 substitutions change inhibitory specificity," Eur. J. Biochem., vol. 176, pp. 675-682 (1988).
Beech et al., "Further characterisation of a thromboembolic model of stroke in the rat" Brain Res, vol. 895, p. 18-24 (2001).
Berge et al., "Pharmaceutical salts", J. Pharm. Sci. 66:1-19 (1977).
Bergthorsdottir et al., "Signals that initiate somatic hypermutation of B cell in vitro", J. Immunol., p. 166:2228 (2001).
Berndt et al.,"Designed Replacement of an Internal Hydration Water Molecule in BPTI: Structural and Functional Implications of a Glycine-to-Serine Mutation," Biochemistry, 32:4564-4570 (1993).
Bhoola et al., "Bioregulation of Kinins: Kallikreins, Kininogens and Kininases," Pharmacological Reviews, 44 :1-80 (1992).
Bird et al. "Single chain antigen binding proteins", Science 242:423-426 (1988).
Blaber et al., "Targeting kallikrein 6-proteolysis attenuates CNS inflammatory disease," The FASEB Journal, express article published online Mar. 19, 2004.
Bodanszky et al., The Practice of Peptide Synthesis (Springer-Verlag, New York, 1984).
Bork, "Powers and pitfalls in sequence analysis: the 70% hurdle," Genome Research, vol. 10, pp. 398-400 (2000).
Borregaard et al., "Granules of the human neutrophilic polymorphonuclear leukocyte," Blood, 1997, vol. 89, No. 10, pp. 3503-3521.
Bowdish et al., "Yeast expression of a catalytic antibody with chorismate mutase activity.", J Biol Chem.; 266 (18):11901-8 (Jun. 25, 1991).
Bowie et al. "Deciphering the message in protein sequences: tolerance to amino acid substitutions." Science 247:1306-1310 (1990).
Branden et al., "Prediction, Engineering, and Design of Protein," Introduction to Protein Structure, 1991, pp. 247, Garland Publishing Inc., New York.
Breedveld, Therapeutic monoclonal antibodies. Lancet. Feb. 26, 2000;355(9205):735-40. Review.
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Browne et al., "Expression of Recombinant Human Plasminogen and Aglycoplasminogen in HeLa Cells," Genebank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin-Kallikrein Activity in Neonatal Respiratory Distress Syndrome," Pediatric Research, 41:120-127, (1997).
Buchan et al., "A new model of temporary focal neocortical ischemia in the rat", Stroke 23(2): 273-9 (1992).
Budavari, ed., Merck index, 11th ed., ISBN 911910-28-X, entries 923, 1745, 2740, 7425, (1989).
Buras et al., "Animal models of sepsis: setting the stage", Nat Rev Drug Discov. 4(10):854-65 (2005).
Burrage et al., "Matrix metalloproteinases: role in arthritis," Fronteirs in Bioscience, 2006, vol. 11, pp. 529-543.
Burton et al. "Human Antibody Effector Function", Adv. Immunol. 51:1-84 (1992).
Cantor et al., "Elastin and Elastases in Lung Disease", Elastin and Elastases, Chapter 16, vol. II, pp. 159-168 (1989).
Carey et al., Advanced Organic Chemistry, 3rd Edition, Part B: Reactions and Synthesis, Plenum Press, New York: 678-686 (1990).
Carmichael, "Rodent models of focal stroke: size, mechanism, and purpose", NeuroRx 2:396-409 (2005).
Carpenter et al., "Rational design of stable lyophilized protein formulations: theory and practice," Parmaceutical Biotechnology, vol. 13, pp. 109-133 (2002).
Casati et al., "Cardiopulmonary support and physiology—tranexamic acid compared with high-dose aprotinin in primary elective heart operations: effects on perioperative bleeding and allogeneic transfusions," The Journal of Thoracic and Cardiovascular Surgery, vol. 120, pp. 520-527 (2000).
Casset et al., A peptide mimetic of an anti-CD4 monoclonal antibody by rational design. Biochem Biophys Res Commun. Jul. 18, 2003;307(1):198-205.
Cassim et al., "Kallikrein cascade and cytokines in inflamed joints," Pharmacology and Therapeutics, 2002, vol. 94, pp. 1-34.
Cernak, "Animal models of head trauma", NeuroRx. 2(3): 410-422 (2005).
Chen et al., "A model of focal ischemic stroke in the rat: reproducible extensive cortical infarction", Stroke 17 (4): 738-43 (1986).

(56) References Cited

OTHER PUBLICATIONS

Chen et al., "Establishment of an animal model of oral mucositis induced by conditioning regimen of haematopoietic stem cell transplantation" Zhonghua Kou Qiang Yi Xue Za Zhi. 42(11):672-6 (2007). (Abstract only).
Chen et al., "Refined 2-5 a X-ray Crystal Structure of the Complex Formed by Porcine Kallikrein A and the Bovine Pancreatic Trypsin Inhibitor—Crystallization, Patterson Search, Structure Determination, Refinement, Structure and Comparison with itsComponents and with the Bovine Trypsin-Pancreatic Trypsin Inhibitor Complex" J. Mol. Biol., 164:283-311 (1983).
Chen et al., Selection and analysis of an optimized anti-VEGF antibody: crystal structure of an affinity-matured Fab in complex with antigen. J Mol Biol. Nov. 5, 1999;293(4):865-81.
Chen et al., Solution Structure of a Kunitz-type Chymotrypsin Inhibitor Isolated from the Elapid Snake Bungarus Fasciatus, J. Biological Chemistry 276:45079-45087 (2001).
Chouthia et al. "Canonical structures for the hypervariable regions of immunoglobulins." (1987) J. Mol. Biol. 196:901-917 (1987).
Chouthia et al. "Structural Repertoire of the Human VH Segments", J. Mol. Biol. 227:799-817 (1992).
Chung et al., "Human plasma prekallikrein, a zumogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Colman et al., "Contact System: A Vascular Biology Modulator With Anticoagulant, Profibrinolytic, Antiadhesive, and Proinflammatory Attributes" Blood, 90, 3819-3843 (1997).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman et al., Hemostasis and Thrombosis Basic Principles and Clinical Practice, Chapter 1, 2nd Edition, 3-17 (1987).
Colman R. W., "Plasma and tissue kallikrein in Arthritis and Inflammatory Bowel Disease", Immunopharmacology, Jan. 1, 1999, pp. 103-108, vol. 43, No. 2/03, Elsevier Science Publishers, BV.
Colman RW et al., "Activation of the kallikrein-kinin system in arthritis and enterocolitis in genetically susceptible rats: modulation by a selective plasma kallikrein inhibitor", Proceedings of the Association of American Physicians, Jan. 1, 1997,pp. 10-22, vol. 109, No. 1, Cambridge, MA US.
Cook et al., The human immunoglobulin VH repertoire. Immunol Today. May 1995;16(5):237-42.
Corpet, et al. "Recent improvements of the ProDom database of protein domain families" Nucl. Acids Res. 27:263-267 (1999).
Cumming et al., "Hemodynamic, Renal, and Hormonal Aprotinin in an Ovine Model of Septic Shock," Critical Care Medicine, 20:1134-1139 (1992).
Cunningham et al., "Structural and functional characterization of tissue factor pathway inhibitor following degradation by matrix metalloproteinase-8," Biochem. J., 2002, vol. 367, pp. 451-458.
Current Protocols in Molecular Biology, John Wiley & Sons, N.Y. (1989) 6.3.1-6.3.6.
Currie et al., "Design and Synthesis of a Bicyclic Non-Peptide ?-Bend Mimetic of Enkephalin," Tetrahedron, 49:3489-3500 (1993).
De Agostini et al., Human plasma kallikrein and C1 inhibitor form a complex possessing an epitope that is not detectable on the parent molecules: demonstration using a monoclonal antibody. Proc Natl Acad Sci U S A. Aug. 1985;82(15):5190-3.
De Campos et al., "Antioedematogenic and antinociceptive actions of NPC 18521, a novel bradykinin B2 receptor antagonist", Eur J Pharmacol316, 277-286 (1996).
De Haard et al. "A large non-immunized human Fab fragment phage library that permits rapid isolation and kinetic analysis of high affinity antibodies". J. Biol. Chem 274:18218-30, (1999).
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.

De Wildt et al. "Antibody arrays for high-throughput screening of antibody-antigen interactions", Nat. Biotechnol. 18:989-994 (2000).
De Wildt et al., "Characterization of human variable domain antibody fragments against the U1 RNA-associated A protein, selected from a synthetic and patient-derived combinatorial V gene library" Eur J Immunol. 26(3):629-39 (1996). cited byapplicant.
Debiopharm borchure, "Engineering protein inhibitor of human neutrophil elastase EPIO-hNE4 (DX-890)," Dated Oct. 2004, printed from www.debio.com/e/pdf/fiche.sub.--epi.sub.--hne4.sub.--e.pdf.
Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
Dela Cadena, et al., "Inhibition of Plasma Kallikrein Prevents Peptidoglycan-Induced Arthritis in the Lewis Rat," FASEB Journal, 9:446-452 (1995).
Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297. cited byapplicant.
Delaria et al., "Characterization of placental bikunin, a novel human serine protease inhibitor," J. Biological Chemistry, May 2, 1997, vol. 272, No. 18, pp. 12209-12214.
Delgado et al., "The uses and properties of PEG-linked proteins," Critical Review in Therapeutic Drug Carrier Systems, 1992, vol. 9, No. 3,4, pp. 249-304.
Deng et. al., "Production of recombinant humanized anti-HBsAg Fab antibody by fermentation" Sheng Wu Gong Cheng Xue Bao, 20(5):800-4 (Sep. 2004) (Abstact Only).
Dennis et al., "Kunitz Domain Inhibitors of Tissue Factor-Factor VIIa (I. Potent Inhibitors Selected from Libraries by Phage Display)," Journal of Biological Chemistry 269:22129-22136 (1994).
Dennis et al., "Kunitz Domain Inhibitors of Tissue Factor-Factor Vila (II. Potent and Specific Inhibitors by Competitive Phage Selection)," Journal of Biological Chemistry, 269:22137-22144 (1994).
Dennis et al., "Potent and Selective Kunitz Domain Inhibitors of Plasma Kallikrein Designed by Phage Display," J. Biol. Chem., 270:25411-25417 (1995).
Devani et al., "Kallikrein-kinin system in inflammatory bowel disease: intestinal involvement and correlation with the degree of tissue inflammation," Digestive and Liver Disease, 2005, vol. 37, pp. 665-673.
Dhalluin et al., "Structural, kinetic, and thermodynamic analysis of the binding of the 40kDa PEG-interferon-a-2a and its individual positional isomers to the extracellular domain of the receptor IFNAR2," Bioconjugate Chemistry, 2005, vol. 16, pp. 518-527.
Diaz et al., "The Design of Water Soluble ?-Sheet Structure Based on a Nucleation Strategy," Tetrahedron, 49:3533-3545 (1993).
Dimaio et al., "A New Class of Potent Thrombin Inhibitors That Incorporates a Scissile Pseudopeptide Bond," FEBS Lett, 282(1):47-52 (1991).
Dittmar et al., "External carotid artery territory ischemia impairs outcome in the endovascular filament model of middle cerebral artery occlusion in rats" Stroke 34: 2252-7 (2003).
Dittmar et al., "Fischer-344 rats are unsuitable for the MCAO filament model due to their cerebrovascular anatomy" J Neurosci Methods 156: 50 (2006).
Doerks et al., "Protein annotation: detective work for function prediction," Trends in Genetics, vol. 14, No. 6, pp. 248-250 (1998).
Donnelly et al., "Therapy for chronic obstructive pulmonary disease in the 21st century," Drugs, 2003, vol. 63, pp. 1973-1998.
Dragosits et. al., "The effect of temperature on the proteome of recombinant Pichia pastoris", J Proteome Res. Mar. 2009;8(3):1380-92.
Dragosits et. al., "The response to unfolded protein is involved in osmotolerance of Pichia pastoris" BMC Genomics. Mar. 26, 2010;11:207.
Druar et. al., Analysis of the expressed heavy chain variable-region genes of Macaca fascicularis and isolation of monoclonal antibodies specific for the Ebola virus' soluble glycoprotein Immunogenetics, 57(10):730-8 (2005).
Dufton, "Protein inhibitors and dendrotoxins," Eur. J. Biochem., vol. 153, pp. 647-654. (1985).

(56) References Cited

OTHER PUBLICATIONS

Edqvist, et al., "Production of functional IgM Fab fragments by *Saccharomyces cerevisiae*", J Biotechnol 20 (3):291-300 (1991).
Eigenbrot et al., "Structural Effects Induced by Removal of a Disulfide-Bridge: The X-ray Structure of the C30A/C51A Mutant of Basic Pancreatic Trypsin Inhibitor at 1.6 A," Protein Engineering, 3:591-598 (1990).
Ellis et al., "The Urokinase Receptor: Involvement in Cell Surface Proteolysis and Cancer Invasion," Ann. NY. Acad. Sci., 667:13-31 (1992).
Enzon Pharmaceuticals, Macromolecular Engineering Technologies, 2004, pp. 1-14.
Falquet et al., "The PROSITE database, its status in 2002." (2002) Nucleic Acids Res. 30:235-238.
Feener EP. Plasma kallikrein and diabetic macular edema. Curr Diab Rep. Aug. 2010;10(4):270-5. doi: 10.1007/s11892-010-0127-1.
Fidler et al., "The Implications of Angiogenesis for the Biology and Chemistry of Cancer Metastasis," Cell, 79:185-188 (1994).
Fields et al., "Solid Phase Peptide Synthesis Utilizing 9-fluorenylmethocarbonyl Amino Acids," Int. J. Peptide Protein Research, 35:161-214 (1990).
Fife et al., "Cartilage matrix glycoprotein is present in serum in experimental canine osteoarthritis" J Clin Invest. 84(5):1432-1439 (1989).
Fink et al., Cellular expression of plasma prekallikrein in human tissues. Biol Chem. Sep. 2007;388(9):957-63.
Fraedrich et al., "Reduction of Blood Transfusion requirement in Open Heart Surgery by Administration of High Doses of Aprotinin-Preliminary Results," Thorac Cardiovasc Surgeon, 37:89-91 (1989).
Frank, 8. Hereditary angioedema. J Allergy Clin Immunol. Feb. 2008;121(2 Suppl):S398-401; quiz S419. doi: 10.1016/j.jaci.2007. 07.057.
Fredrich et al., "A new animal model of venous thrombosis in rats with low flow conditions in the venous blood stream" Blood Coagul Fibrinolysis. 5(2):243-8 (1994).
Freidinger et al., "Protected Lactam-Bridged Dipeptides for Use as Conformational Constraints in Peptides," Journal of Organic Chemistry, 47:104-109 (1982).
Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
Galeffi et al., "Functional expression of a single-chain antibody to ErbB-2 in plants and cell-free systems" J Transl Med. Sep. 29, 2006;4:39.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gardell et al., "The Search for the Ideal Thrombolytic Agent: Maximize the Benefit and Minimize the Risk," Toxicologic Pathology, 21(2):190-198 (1993).
Gasser et al., "Engineering of Pichia pastoris for improved production of antibody fragments" Biotechnol Bioeng. Jun. 5, 2006;94(2):353-61.
GenBank Submission; NIH/NCBI, Accession No. NM_008455.2 (GI: 236465804): "Plasma kallikrein precursor", GenBank Record created on Dec. 29, 2010.
GenBank Submission; NIH/NCBI, Accession No. NM_012725.2 (GI:162138904): "Plasma kallikrein precursor", GenBank Record created on Dec. 26, 2010.
GenBank Submission; NIH/NCBI, Accession No. NP_000217.2 (GI:55956899): "keratin, type I cytoskeletal 9 ", GenBank Record created on Dec. 27, 2010.
GenBank Submission; NIH/NCBI, Accession No. NP_000418.2 (GI:109255251): "loricrin", GenBank Record created on Nov. 3, 2010.
GenBank Submission; NIH/NCBI, Accession No. NP_000883.2 (GI: 78191798): "Plasma kallikrein preproprotein", GenBank Record created on Nov. 21, 2010.
GenBank Submission; NIH/NCBI, Accession No. NP_000892 (GI: 158508572): "mineralocorticoid receptor isoform 1", GenBank Record created on Dec. 27, 2010.
GenBank Submission; NIH/NCBI, Accession No. NP_005850.1 (GI:5032007): "transcriptional activator protein Pur-alpha", GenBank Record created on Dec. 28, 2010.
GenBank Submission; NIH/NCBI, Accession No. NP_006228.3 (GI:110347449): "POU domain, class 4, transcription factor 1", GenBank Record created on Dec. 27, 2010.
GenBank Submission; NIH/NCBI, Accession No. NP_009060.2 (GI:22547197): "zinc finger protein ZIC 2", GenBank Record created on Dec. 24, 2010.
GenBank Submission; NIH/NCBI, Accession No. NP_031393.2 (GI:21396480): "RNA-binding protein Raly isoform 2", GenBank Record created on Dec. 25, 2010.
GenBank Submission; NIH/NCBI, Accession No. NP_032481.2 (GI: 236465805): "Plasma kallikrein precursor", GenBank Record created on Dec. 29, 2010.
GenBank Submission; NIH/NCBI, Accession No. NP_036857.2 (GI:162138905): "Plasma kallikrein precursor", GenBank Record created on Dec. 26, 2010.
GenBank Submission; NIH/NCBI, Accession No. NP_056932.2 (GI:153791670): "Plasma kallikrein preproprotein", GenBank Record created on Dec. 27, 2010.
GenBank Submission; NIH/NCBI, Accession No. NP_061856.1 (GI:9506713): "H/ACA ribonucleoprotein complex subunit 1", GenBank Record created on Dec. 24, 2010.
GenBank Submission; NIH/NCBI, Accession No. NP_065104.1 (GI:9966841): "cell death regulator Aven", GenBank Record created on Dec. 26, 2010.
GenBank Submission; NIH/NCBI, Accession No. NP_115818.2 (GI:53829370): "neuralized-like protein 4 isoform 1", GenBank Record created on Dec. 27, 2010.
GenBank Submission; NIH/NCBI, Accession No. NP_476429.2 (GI:109148552): "keratin, type II cytoskeletal 3 ", GenBank Record created on Dec. 24, 2010.
GenBank Submission; NIH/NCBI, Accession No. NP_631961.1 (GI:21327701): "TATA-binding protein-associated factor 2N isoform 1", GenBank Record created on Dec. 25, 2010.
GenBank Submission; NIH/NCBI, Accession No. NP_787059.2 (GI:40068462): "At-rich interactive domain-containing protein 1B isoform 3", GenBank Record created on Mar. 4, 2010.
GenBank Submission; NIH/NCBI, Accession No. XP_376532.2 (GI:51465288): "Predicted: KIAA0408", GenBank Record created on Aug. 19, 2004.
Gerriets et al., "Complications and pitfalls in rat stroke models for middle cerebral artery occlusion: a comparison between the suture and the macrosphere model using magnetic resonance angiography", Stroke 35: 2372-2377 (2004).
Gerriets et al., "The macrosphere model: evaluation of a new stroke model for permanent middle cerebral artery occlusion in rats" J Neurosci Methods 122: 201-11 (2003).
Girard et al., "Functional Significance of the Kunitz-type Inhibitory Domains of Liporotein-Associated Coagulation Inhibitor," Nature, 338:518-520 (1989).
Girard et al., "Structure of the Human Lipoprotein-associated Coagulation Inhibitor Gene," The Journal of Biological Chemistry, 266:5036-5041 (1991).
Goldenberg et al., "Circular and circularly permuted forms of bovine pancreatic trypsin inhibitor," J. Mol. Biol., vol. 165, pp. 407-413 (1983).
Gomez-Jorge et al., "The Double-Tuck Model: A New Animal Model of Arterial Thrombosis" J. Vasco Inter. Rad. 9 (4): 633-638 (1998).
Gonzalez-Quevedo et al., the Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al. "Whole genome protein domain analysis using a new method for domain clustering" (1999) Computers and Chemistry 23:333-340.

(56) References Cited

OTHER PUBLICATIONS

Graham et al., "Animal models of ischemic stroke: balancing experimental aims and animal care", Comp Med 54: 486-496 (2004).
Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Greilich et al., "Antigibrinolytic therapy during cardiopulmonary bypass reduces proinglammatory cytokine levels: a randomized, double-blind, placebo-controlled study of x-aminocaproic acid and aprotinin," J. Thorac. Cardiovasc. Surg., 2003, vol. 126, pp. 1498-1503.
Gribskov et al. "Profile analysis." (1990) Meth. Enzymol. 183:146-159.
Gribskov et al. "Profile analysis: detection of distantly related proteins." (1987) Proc. Natl. Acad. Sci. USA 84:4355-4358.
Grimaldi et al., "Trasylol in the treatment of acute arthritis due to microcrystals," Reumatismo, vol. 23, No. 5, pp. 217-221, (1971) (Abstract only).
Gulberg et al., "Biosynthesis, processing and sorting of neutrophil proteins: insight into neutrophil granule development," Eur. Journal of Haematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of bovine pancreatic trypsin inhibitor (BPTI)," The Journal of Biological Chemistry, 2002, vol. 277, No. 52, pp. 51043-51048.
Han et al., Increased Vascular Permeability in C1 Inhibitor-Deficient Mice Mediated by the Bradykinin Type 2 Receptor, J. Clinical Investigation 109(8):1057-1063 (2002).
Han, Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Hanes et al., "Selecting and evolving functional proteins in vitro by ribosome display" Methods Enzymol. 328:404-30 (2000).
Harvey et al., "Engineering of recombinant antibody fragments to methamphetamine by anchored periplasmic expression" J Immunol Methods. (Nov. 22, 2005).
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet et al., "Generation of high-affinity human antibodies by combining donor-derived and synthetic complementarity-determining-region diversity" Nat Biotechnol. 23(3)344-8 (2005).
Hoogenboom et al., "Antibody phage display technology and its applications" Immunotechnology 4:1-20 (1998).
Hoogenboom et al., "Natural and designer binding sites made by phage display technology" Immunol Today 2:371-8 (2000).
Hoover et al., "Amino Acids of the Recombinant Kringle 1 Domain of Human Plasminogen that Stabilize Its Interaction w-Amino Acids," Biochemistry, 32:10936-10943 (1993).
Hortin et al., "Allosteric Changes in Thrombin's Activity Produced by peptides Corresponding to Segments of Natural Inhibitors and Substrates," The Journal of Biological Chemistry, 266:6866-6871 (1991).
Horwitz et al., "Secretion of functional antibody and Fab fragment from yeast cells.", Proc Natl Acad Sci U S A. 85 (22):8678-82 (Nov. 1988).
Hostomsky et al., "Solid Phase Assembly of Cow Colostrum Trypsin Inhibitor Gene," Nucleic Acids Research, 15:4849-4856 (1987).

Huang et al., "Kinetics of factor Xa inhibition by tissue factor pathway inhibitor," The Journal of Biological Chemistry, 1993, vol. 268, No. 36, pp. 26950-26955.
Huang et al., "Novel peptide inhibitors of angiotensin-converting enzyme 2," The Journal of Biological Chemistry, 2003, vol. 278, No. 18, pp. 15532-15540.
Huge et al., "A model to investigate postoperative ileus with strain gauge transducers in awake rats" J Surg Res. 74 (2):112-8 (1998). (Abstact Only).
Huston et al., "Protein engineering of antibody binding sites: Recovery of specific activity in anti-digoxin single-chain Fv analogue produced in *Escherichia coli*", Proc. Natl. Acad. Sci. USA 85:5879-5883 (1988).
Hynes et al., "X-Ray Crystal Structure of the Protease Inhibitor Domain of Alzheimer's Amyloid, ?-Protein Precursor," Biochemistry, 29:10018-10022 (1990).
Jefferis et al., "IgG-Fc-mediated effector functions: Molecular definition of interaction site for effector ligands and the role of gylcosylation", Immunol. Rev. 163:59-76, (1998).
Jones et al., "Severe prekallikrein deficiency associated with homozygosity for an Arg94Stop nonsense mutation" Br J Haematol, 2004. 127(2): p. 220-223.
Jonkam et al., "Effects of the bradykinin B2 receptor antagonist icatibant on microvascular permeability after thermal injury in sheep" Shock, 28:704-709 (2007).
Jorg et al., Kinetic analysis of plasminogen activation by purified plasma kallikrein. Thromb Res. Aug. 1, 1985;39(3):323-31.
Jostock et. al., "Rapid generation of functional human IgG antibodies derived from Fab-on-phage display libraries" J. Immunol. Methods, 289(1-2):65-80 (2004).
Kabet et al. Sequences of Proteins of Immunological Interest, Fifth Edition, U.S. Dept. of Health and Human Services, NIH Publication No. 91-3242 (1991).
Kanppik et al., "Fully synthetic human combinatorial antibody libraries (HuCAL) based on modular consensus frameworks and CDRs randomized with trinucleotides", J. Mol. Biol. 296:57-86 (2000).
Kantor et al., "The experimental animal models for assessing treatment of restenosis" Cardiovasc Radiat Med. 1 (1):48-54 (1999).
Kaplan et al., "A Prealbumin Activator of Preallirrein. 3. Appearance of Chemotactic Activity for Human Neutrophils by the conversion of Human Prekallikrein", J. Exp. Med. vol. 135(1), p. 81-97; p. 92 Fig 10, p. 93 (1972).
Katre et al., "Chemical modification of recombinant interleukin 2 by polyethylene glycol increases its potency in the murine Meth A sarcoma model," PNAS USA, 1987, vol. 84, pp. 1487-1491.
Katre et al., "Immunogenicity of recombinant IL-2 modified by covalent attachment of polyethylene glycol," J. Immunol., 1990, vol. 144, pp. 209-213.
Katz et al., "Animal models of vasculitides" Clin Rev Allergy Immunol. 35(1-2): 11-8 (2008).
Kaufman et al., "Amplification and expression of sequences cotransfected with a modular dihydrofolate reductase complementary dna gene", Mol. Biol. 159:601 621 (1982).
Kelly et al., "Diabetes insipidus in uricase-deficient mice: a model for evaluating therapy with poly(ethylene glycol)-modified," J. Am. Soc. Nephrol., 2001, vol. 12, pp. 1001-1009.
Kemp et al., "Synthesis of Peptide-Functionalized Daicylaminoepinodolidiones," Tetrahedron Letters, 29:5077-5080 (1988).
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kettleborough et al., Humanization of a mouse monoclonal antibody by CDR-grafting: the importance of framework residues on loop conformation. Protein Eng. Oct. 1991;4(7):773-83.
Kido et al., "Kunitz-type Protease Found in Rat Mast Cells," J. Biol. Chem. 263(34):18104-18107 (1988).
Kido et al., "Protease Specificity of Kunitz Inhibitor Domain of Alzheimer's Disease Amyloid Protein Precursor," Biochemical and Biophysical Research Communications, 167:716-721 (1990).

(56) References Cited

OTHER PUBLICATIONS

Kirchhofer et al., "Hepsin activates pro-hepatocyte growth factor and is inhibited by hepatocyte growth factor activator-1B (HAI-1B) and HAI-2," FEBS Letters, 2005, vol. 579, pp. 1945-1950.
Kirchhoff et al., "A Major Human Epididymis-Specific cDNA Encodes a Protein with Sequence Homology to Extracellular Proteinase Inhibitors," Biology of Reproduction, 45:350-357 (1991).
Kline et al. "Hirulog Peptides with Scissile Bond Replacements Resistant to Thrombin Cleavage," Biochem. Biophys. Res. Comm., 177:1049-1055 (1991).
Ko et al., "Biotransformation of uridine monophosphate (UMP) and glucose to uridine diphosphate-glucose (UDPG) by Candida saitoana KCTC7249 cells." Appl Biochem Biotechnol.; 60(1):41-8 (Jul. 1996).
Kobayashi et al., "Amended structure of side chains in a cell wall mannan from Candida albicans serotype A strain grown in yeast extract—Sabouraud liquid medium under acidic conditions: detection of the branched side chains corresponding toantigenic factor 4.", FEMS Microbiol Lett.;152(2):235-42 (Jul. 15, 1997).
Koizumi et al., Experimental studies of ischemic brain edema. 1. A new experimental model of cerebral embolism in rats in which recirculation can be introduced in the ischemic area. Jpn J Stroke 1986;8:1-8.
Kozyr et al., "Production of DNA-hydrolyzing antibody BV04-01 Fab fragment in methylotrophic yeast Pichia pastoris" Mol Biol (Mosk). Nov.-Dec. 2004;38(6):1067-75.
Krough et al. "Hidden Markov models in computational biology. Applications to protein modeling." (1994) J. Mol. Biol. 235:1501-1531.
Kuno et al., "Possible involvement of neutrophil elastase in impaired mucosal repair in patients with ulcerative colitis," Journal of Gastroenterology, 2002, vol. 37, Supple XIV, pp. 22-32.
Kurjan et al., "Structure of a Yeast Pheromone Gene (MF?): A putative ?-Factor Precursor Contains Four Tandem Copies of Mature ?-Factor," Cell, 30: 933-943 (1982).
Lamminmaki et al., Crystal structure of a recombinant anti-estradiol Fab fragment in complex with 17beta -estradiol. J Biol Chem. Sep. 28, 2001;276(39):36687-94. Epub Jul. 12, 2001.
Laskowski et al., "Inhibitors with Class-Specific Reactive Sites," Ann. Rev. Biochem., 49:593-626 (1980).
Leatherbarrow et al., "Design of a Small Peptide-Based Proteinase Inhibitor by Modeling the Active-Site Region of Barley Chymotrypsin Inhibitor 2," Biochemistry, 30:10717-10721 (1991).
Lederman et al., A Single Amino Acid Substitution in a Common African Allele of the CD4 Molecule Ablates Binding of the Monoclonal Antibody, OKT4. Molecular Immunology. 1991;28(11):1171-1181.
Leeb-Lundberg et al. "International union of pharmacology. XLV. Classification of the kinin receptor family: from molecular mechanisms to pathophysiological consequences", (2005) Pharmacol Rev 57, 27-77.
Leonetti et al., "Increasing immunogenicity of antigens fused to Ig-binding proteins by cell surface targeting," The Journal of Immunology, 1998, vol. 160, pp. 3820-3827.
Levy et al., The therapeutic potential of a kallikrein inhibitor for treating hereditary angioedema. Expert Opin Investig Drugs. Sep. 2006;15(9):1077-90.
Ley et al., "Obtaining a Family of High-Affinity, High Specificity Protein Inhibitors of Plasmin and Plasma Kallikrein," Molecular Diversity, 2:119-124, (1996).
Li et al., β-Endorphin omission analogs: Dissociation of immunoreactivity from other biological activities. Proc. Natl. Acad. Sci. USA. Jun. 1980;77(6):3211-3214.
Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).
Liu et al., Plasma kallikrein-kinin system and diabetic retinopathy. Biol Chem. Mar. 2013;394(3):319-28. doi: 10.1515/hsz-2012-0316. Author manuscript.
Lohmann et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993). cited byapplicant.
Longa et al., "Reversible middle cerebral artery occlusion without craniectomy in rats" Stroke 20 (1): 84-91 (1989).
Lucas et al., "The Binding of Human Plasminogen to Fibrin and Fibrinogen," J. Biol. Chem., 258:4249-4256 (1983).
Lumry et al., Interim Results of EDEMA2, A Multicenter, Open-Label, Repeat-Dosing Study of Intravenous and Subcutaneous Administration of Ecallantide (DX-88) in Hereditory Angioedema. J. Allergy and Clinical Immunology 117(2)(Suppl. 1):S179 Abstract699 (2006).
MacCallum et al., Antibody-antigen interactions: contact analysis and binding site topography. J Mol Biol. Oct. 11, 1996;262(5):732-45.
MacGilchrist, "Effect of the Serine Protease Inhibitor, Aprotinin, on Systemic Haemodynamics and Renal Function in Patients with Hepatic Cirrhosis and Ascites," Clin. Sci., 87:329-335 (1994).
Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.
Mann et al., Hemostasis and Thrombosis, Chapter 10, 2nd Edition, Basic Principles and Clinical Practice: 148-161 (1987).
Mannucci, "Hemostatic Drugs" New England Journal of Medicine, Drug Therapy, 339(4):245-253 (1998).
March, Advanced Organic Chemistry, 3rd Edition, Reactions, Mechanisms, and Structure, John Wiley and Sons, New York: 396-398; 1057-1060; 1099-1100 (1985).
Markland et al., "Iterative Optimization of High-Affinity Protease Inhibitors Using Phage Display. 1. Plasmin," Biochemistry, 35:8045-8057 (1996).
Markland et al., "Iterative Optimization of High-Affinity Protease Inhibitors Using Phage Display. 2. Plasma Kallikrein and Thrombin," Biochemistry 35(24):8058-67 (1996).
Markland et al., "Selection for Protease Inhibitors Using Bacteriophage Display," Methods Enzymol., 267:28-51 (1996).
Markland, Cell. Biochem. Supp., 1994, O, vol. 18D, pp. 157, Abstract S 331.
Martin et al., "Animal models of neuropathic pain" Methods Mol Med. 84:233-42 (2003).
Mathews et al., Biochemistry, The Benjamin Cummins Publishing Co., Inc. Redwood City CA: 208-212 (1990).
Mattheakis et al. "An in vitro polysome display system for identifying ligands from very large peptide libraries" Proc. Natl. Acad. Sci. USA 91:9022 (1994).
Maxfield et al., "Conformation of poly(ethylene oxide) in the solid state, melt and solution measured by Raman scattering," Polymer, 1975, vol. 16, pp. 505-509.
Mayzel-Oreg, "Microsphere-induced embolic stroke: an MRI study" Magn Reson Med 51:1232-8 (2004).
McCarty, "Crystal-induced inflammation of the joints," Annual Reviews of Medicine, vol. 21, pp. 357-366 (1970).
McConnell et al., "New Leupeptin Analogues: Synthesis and Inhibition Data," J. Med. Chem., 33:86-93 (1990).
Merriam-Webster reference for the term "prevent." web date: 2010. 2 pages.
Merrifield, "Solid Phase Peptide Synthesis. I. The Synthesis of a Tetrapeptide," Am. Chem. Soc. 85:2149-2154 (1963).
Migliore et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).
Mine et al., "Structural mechanism for heparin-binding of the third Kunitz domain of human tissue factor pathway inhibitor," Biochemistry, 2002, vol. 41, pp. 78-85.
Miyajima et al., Secretion of Mature Mouse Interleukin-2 by *Saccharomyces cerevisiae*: Use of a General Secretion vector Containing Promoter and Leader Sequences of the Mating Pheromone ?-factor, Gene, 37:155-161 (1985).

(56) References Cited

OTHER PUBLICATIONS

Molineux, "Pegylation: engineering improved pharmaceuticals for enhanced therapy," Cancer Treatment Reviews, 2002, vol. 28, pp. 13-16.
Monteseirin et al., "Plasma Kallikrein Amidolytic Activity in Bronchial Asthma," Allergol. Immunopathol., (Madr)., 20:211-214 (1992).
Moreland, "Intra-articular hyaluronan (hyaluronic acid) and hylans for the treatment of osteoarthritis: mechanisms of action," Arthritis Res. Ther, 2003, vol. 5, pp. 54-67.
Morishita et al., "Novel factor Xa and plasma kallikrein inhibitory-activities of the second Kunitz-type inhibitory domain of urinary trypsin inhibitor" Thromb Res, 73(3-4): p. 193-204 (1994).
Morrison "Transfectomas provide novel chimeric antibodies." (1985) Science 229:1202-1207.
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Nadkarni et al., "Optimization of a mouse recombinant antibody fragment for efficient production from *Escherichia coli*" 2007 Protein Expr Purif 52(1):219-29.
Naess et al., "Effects of a Combined Drug Regimen on Tumour Necrosis Factor and Plasma Kallikrein Activity in Experimental Endotoxaemia," Eur. J. Surg., 160:77-86 (1994).
Nagai et al., "Synthesis of a Bicyclic Dipeptide with the Shape of ?-Turn Central Part," Tetrahedron Letters, 26 (5):647-650 (1985).
Nagai et al., Bicyclic Turned Dipeptide (BTD) as a ?-Turn Mimetic; its Design, Synthesis, and Incorporation into Bioactive Peptides, Tetrahedron, 49:3577-3592 (1993).
Needleman et al. "A general method applicable to the search for similarities in the amino acid sequences of two proteins" (1970) J. Mol. Biol. 48:444-453.
Nektartm—Transforming Therapeutics, Nektar Advanced PEGylation: Polyethylene Glycol and Derivatives for Advanced PEGylation, pp. 1-24, catalogue 2004.
Nektartm—Transforming Therapeutics, Nektar Molecule Engineering: Polyethylene Glycol and Derivatives for Advanced PEGylation, pp. 1-20, catalogue-2003.
Neuhaus et al., "Effect of Aprotinin on Intraoperative Bleeding and Fibrinolysis in Liver Transplantation," Lancet, 2: 924-925 (1989).
Ngo et al., "Computational Complexity, Protein Structure Prediction, and the Levinthal Paradox", The Protein Folding Problem and Tertiary Structure Prediction, Chapter 14, pp. 433-440 and 492-495 only (1994).
Ngo et al., "The protein folding problem and tertiary structure prediction, Chapter 14: Computational complexity protein structure prediction, and the Levinthal paradox," pp. 433-440 and 492-495 only (1994).
Ning et al., "Production of recombinant humanized anti-HBsAg Fab fragment from Pichia pastoris by fermentation.", J Biochem Mol Biol. ;38(3):294-9. (May 31, 2005).
Nof Corporation, "PEG Derivatives, Phospholipid and Drug Delivery Materials for Pharmaceutical Products and Formulations," pp. 1-59, catalogue Ver. 8—Apr. 2006.
Nof Corporation, "PEG Derivatives, Phospholipid and Drug Delivery Materials for Pharmaceuticals," pp. 1-46, catalogue—2003, 1st.
Nof Corporation, "PEG Derivatives, Phospholipid and Drug Delivery Materials for Pharmaceuticals," pp. 1-50, catalogue—2003 2nd.
Novotney et al., "Purification and Characterization of the Lipoprotein-associated Coagulation Inhibitor from Human Plasma," J. Biol. Chem. 264:18832-18837 (1989).
Nwariaku et al., "Effect of a bradykinin antagonist on the local inflammatory response following thermal injury" Burns, 22:324-327 (1996). (Abstract only).
Oi et al. "Chimeric Antibodies" (1986) BioTechniques 4:214.
Okamoto et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).

O'Reilly et al., "Angiostatin: A Novel Angiogenesis Inhibitor That Mediates the Suppression of Metases by a Lewis Lung Carcinoma," Cell, 79 317-328 (1994).
Padlan et al., Structure of an antibody-antigen complex: crystal structure of the HyHEL-10 Fab-lysozyme complex. Proc Natl Acad Sci U S A. Aug. 1989;86(15):5938-42.
Pan et al., "Reperfusion inury following cerebral ischemia: pathophysiology, MR imaging, and potential therapies," Neuroradiology, 2007, vol. 49, pp. 93-102.
Park et al., "Three Dimensional Structure of the Kringle Sequence: Structure of Prothrombin Fragment 1," Biochemistry, 25:3977-3982 (1986).
Paul, Fv Structure and Diversity in Three Dimensions. Fundamental Immunology, 3rd Edition. 1993: 292-5.
Peng, "Experimental use of murine lupus models" Methods Mol Med. 102:227-72 (2004).
Petersen et al., "Inhibitory propterties of separate recombinant Kunitz-type-protease-inhibitor domains from tissue-factor-pathway inhibitor," Eur. J. Biochem., 1996, vol. 235, pp. 310-316.
Phillips, "The challenge of gene therapy and DNA dellicery," J. Pharm. Pharmacology, vol. 53, pp. 1169-1174 (2001).
Phipps et al., Plasma kallikrein mediates angiotensin II type 1 receptor-stimulated retinal vascular permeability. Hypertension. Feb. 2009;53(2):175-81. doi: 10.1161/HYPERTENSTIONAHA.108.117663. Epub Jan. 5, 2009. With 5 page Online Supplement.
Pintigny et al., "Aprotinin can inhibit the proteolytic activity of thrombin: a fluorescence and an enzymatic study," Eur. J. Biochem., 1992, vol. 207, pp. 89-95.
Piro et al., "Role for the Kunitz-3 domain of tissue factor pathway inhibitor-a in cell surface binding," Circulation, 2004, vol. 110, pp. 3567-3572.
Pirollo et al., "Targeted delivery of small interfering RNA: approaching effective cancer therapies," Cancer Res., 2008, vol. 68, No. 5, pp. 1247-1250.
Pitt et al., "Rabbit monoarticular arthritis as a model for intra-articular drug injections. The local action of administered cortisol and a-1 proteinase inhibitor," Agents and Actions, vol. 15, No. 5-6, abstract online, retrieved from internet<URL:http://www.springerlink.com/content/j82860503948741/p> (Dec. 1984).
Polypure, Products; PEG amines; PEG acids and amino acids, PEG thils and disulfides; Biotins, Apr. 2005.
Polypure, Products; PEG amines; PEG acids and amino acids; PEG thiols and disulfides; Biotins, Apr. 2004.
Powers et al., "Expression of Single-Chain Fv-Fc Fusions in Pichia pastoris", J. Immunol. Methods. 251:123-35 (2001).
Poznansky et al., "Growth hormone-albumin-conjugates reduced renal toxicity and altered plasma clearance," 1988, vol. 239, pp. 18-22.
Putterman, "Aprotinin Therapy in Septic Shock," ACTA Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Nov. 17, 2005.
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Raspi, Kallikrein and kallikrein-like proteinases: purification and determination by chromatographic and electrophoretic methods. J Chromatogr B Biomed Appl. Sep. 20, 1996;684(1-2):265-87.
Reginato et al., "Genetics and experimental models of crystal-induced arthritis. Lessons learned from mice and men: is it crystal clear?" Curr Opin Rheumatol. 19(2):134-45 (2007).
Reichert, "Technology evaluation: lumiliximab, Biogen Idec" Curr Opin Mol Ther., 6(6):675-83 (2004). (Abstract only).
Ren et al., "Inflammatory Models of Pain and Hyperalgesia" Ilar J. 40(3): 111-118 (1999).

(56) References Cited

OTHER PUBLICATIONS

Robbins et al., Hemostasis and Thrombosis, Chapter 21, 2nd Edition, Basic Principles and Clinical Practice: 340-357 (1987).
Roberts et al., "Chemistry for peptide and protein PEGylation", Advanced Drug Delivery Reviews, 54, pp. 459-476, 2002.
Roberts et al., "Directed evolution of a protein: seleciton of potent neurtophil elastase inhibitor displayed on M13 fusion phage," PNAS USA, vol. 89, pp. 2429-2433 (1992).
Roberts et al., "Protease inhibitor display M13 phage: selection of high-affinity neurtophil elastase inhibitors," Gene, vol. 121, pp. 9-15 (1992).
Rossi et al., The Synthetic Peptide DX88 Binds to Endothelial Cells In Vitro and Retains the Inhibitory Activity on Kallikrein, International Immunopharmacology 2(9):1313, Abstract 142 (2002).
Rudikoff et al., Single amino acid substitution altering antigen-binding specificity. Proc Natl Acad Sci U S A. Mar. 1982;79(6):1979-83.
Sainz et al., "Fifty years of research on the plasma kallikrein-kinin system: from protein structure and function to cell biology and in-vivo pathophysiology" Thromb Haemost 98, 77-83, 2007.
Sartor et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, The Attractions of Proteins for Small Molecules and Ions, Ann. NY Acad. Sci, 51:660-672 (1949).
Schaffirzel et al., "Ribosome display: an in vitro method for selection and evolution of antibodies from libraries" J Immunol Methods. 231(1-2):119-35 (1999).
Schechter et al., On the Active Site of Proteases, III Mapping the Active Site of Papain; Specific Peptide Inhibitors of Papain, Biochemical and Biophysical Research Communications 32(5):898-902 (1968).
Schechter et al., On the Size of the Active Site on Proteases, I Papain, Biochemical and Biophysical Research Communications 27(2):157-162 (1967).
Schmaier et al., Hemostasis and Thrombosis, Chapter 2, 2nd Edition, Basic Principals and Clinical Practice: 18-38 (1987).
Schmaier, "Assembly, activation, and physiologic influence of the plasma kallikrein/kinin system" (2008) Int Immunopharmaco18, 161-165.
Schmid-Elsaesser et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70(1989).
Schmidt et al., "A male accessory gland peptide with protease inhibitory activity in Drosophila funebris," Swiss-Prot, Accession #P11424 (1992).
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.
Schofield et al., "Monoclonal antibodies that neutralize HEV recognize an antigenic site at the carboxyterminus of an ORF2 protein vaccine" Vaccine (2003) 22(2):257-67.
Schoonbroodt et al., Human antibodies selected by phage display as potent and selective protease inhibitors. Human Antibodies. 2007;16(1-2):18-22.
Schoonooghe et al., "Efficient production of human bivalent and trivalent anti-MUC1 Fab-scFv antibodies in Pichia pastoris", BMC Biotechnol. Aug. 11, 2009;9:70.
Schopf, "IDEC-114 (IDEC)" Curr Opin Investig Drugs, 2(5):635-8 (2001). (Abstact only).

Schultz et al. "SMART, a simple modular architecture research tool: identification of signaling domains" (1998) Proc. Natl. Acad. Sci. USA 95:5857.
Schultz et al., "SMART: a web-based tool for the study of genetically mobile domains" (2000) Nucl. Acids Res 28:231.
Schwartz et al., "Stability studies on derivatives of the bovine trypsin inhibitor," Biochemistry, vol. 26, pp. 3544-3551 (1987).
Sekiguchi et al., "Experimental spinal stenosis: relationship between degree of cauda equina compression, neuropathology, and pain" Spine 29, 1105-1111 (2004)).
Sexton et al., Discovery and characterization of fully human monoclonal antibody inhibitor of plasma kallikrein for the treatment of plasma kallikrein-mediated edema. J Allergy Clin Immunol. Feb. 2013;131(2):AB32. Suppl S. Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Sharma et al., "The kinin antagonist hoe 140 reduces acute paw oedema in rats caused by carrageenan, bradykinin and kaolin" Inflammopharmacology 6,9-17 (1998).
Shearwater Corporation, Polyethylene Glycol and Derivatives for Biomedical Applications, pp. 1-17, catalogue—2001.
Shearwater Polymers, Inc., Polyethylene Glycol and Derivatives, pp. 1-50, catalogue—Jul. 1997.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard et al., Acid-Labile Resin Linkage Agents for Use in Solid Phase Peptide Synthesis, Int. J. Peptide Protein Res., 20:451-454 (1982).
Sheridan et al., A Multicenter Trial of the Use of the Proteolytic Enzyme Inhibitor Aprotinin in Colorectal Surgery, Dis. Colon Rectum, 32:505-508 (1989).
Shibuya et al., "Primary Structure of Guinea Pig Plasma Prekallikrein", Immunopharmacology, vol. 45 (1-3), p. 127-134, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Silverberg et al. "The Contact System and Its Disorders," in Blood: Principles and Practice of Hematology, Handin R. et al., eds. J B. Lippincott Co., Philadelphia, (1995).
Singer et al., "A porcine burn model" Methods Mol Med. 78: 107-19 (2003).
Skolnick et al., "From genes to protein structure and function: novel applications of computational apporaches in the genomic era," Trends in Biotech., 2000, vol. 18, No. 1, pp. 34-39.
Slootstra et al., "Structural aspects of antibody-antigen interaction revealed through small random peptide libraries", Molecular Diversity, 1, 87-96 (1996).
Smith et al. "Prolonged in vivo residence times of antibody fragments associated with albumin" Bioconjug Chem 12(5):750-756 (2001).
Smith, "Filamentous fusion phage: novel expression vectors that display cloned antigens on the virion surface" Science 228:1315-1317 (1985).
Sonhammer et al., "Pfam: a comprehensive database of protein domain families based on seed alignments" (1997) Proteins 28(3):405-420.
Sonis et al., "An animal model for mucositis induced by cancer chemotherapy" (1990) Oral Surg Oral Med Oral Pathol. 69:437-43.
Sonis et al., "Validation of a new scoring system for the assessment of clinical trial research of oral mucositis induced by radiation or chemotherapy. Mucositis Study Group." (1999) Cancer 85:2103-13.
Sprecher et al., "Molecular Cloning, Expression, and Partial Characterization of a Second Human Tissue-Factor-Pathway Inhibitor," Proc. Natl. Acad. Sci. USA, 91:3353-3357 (1994).

(56) References Cited

OTHER PUBLICATIONS

Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the contact system and circulating neutrophil elastase in ulcerative colitis patients" 10th World Congress of Gastroenterology, p. 1166, 1994.
Stadnicki et al., "Activation of the Kallikrein-Kinin System in Indomethacin-Induced Entercolitis in Genetically Suseprible Rats," J. Invest. Med., 44:299A (1996).
Stadnicki et al., "Selective Plasma Kallikrein Inhibitor Attenuates Acute Intestinal Inflammation in Lewis Rat," Dig. Dis. Sci., 41:912-920 (1996).
Stevenson et al., "A mouse model of burn wounding and sepsis" Methods Mol Med. 78:95-105 (2003).
Stewart et al., Solid-Phase Peptide Synthesis (W.H. Freeman Co., San Francisco 1989.
Stultz et al., "Structural analysis based on state-space modeling." Protein Sci. 2:305-314 (1993).
Sunkureddi et al., "Clinical signs of gout," Hospital Physician, 2006, pp. 39-41.
Taby et al., "Inhibition of activated protein C by aprotinin and the uses of the insolubilized inhibitor for its purification," Thrombosis Research, 1990, vol. 59, pp. 27-35.
Taggart et al., "Inactiviation of human-b-defensins 2 and 3 by elastolytic cathepsins1," The Journal of Immunology, 2003, vol. 170, pp. 931-937.
Takahashi et al., "Production of humanized Fab fragment against human high affinity IgE receptor in Pichia pastoris" Biosci Biotechnol Biochem 64(10):2138-44 (2000).
Tamura et al., "Focal cerebral ischaemia in the rat: 1. Description of technique and early neuropathological consequences following middle cerebral artery occlusion" J Cereb Blood Flow Metab 1: 53-60 (1981).
Tanaka et al. "A novel rat model of abdominal aortic aneurysm using a combination of intraluminal elastase infusion and extraluminal calcium chloride exposure" J Vasc Surg. 50(6):1423-32 (2009).
Tang et al., Expression, crystallization, and three-dimensional structure of the catalytic domain of human plasma kallikrein. J Biol Chem. Dec. 9, 2005;280(49):41077-89. Epub Sep. 30, 2005.
The Merck Index: 145, 263, 427, 428, 1183, and 1184 (1989).
Tian et al., "Synthesis of Optically Pure C?-methyl-arginine," Int. J. Peptide Res., 40:119-126 (1992).
Timmerman et al., "Functional reconstruction and synthetic mimicry of a conformational epitope using CLIPS™ technology" J. Mol. Recognit. 20:283-99 (2007).
Tomlinson et al. "Structural repertoire of the human Vk domain" EMBO J. 14(18):4628-3 (1995).
Tomlinson et al. "The repertoire of human germline VH sequences reveals about 50 groups of VH segments with different hypervariable loops"J. Mol. Biol. 227:776-798 (1992).
Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, vol. 913, pp. 97-101 (1987).
Uebel, Die Behandlung von Kniegelenksarthrosen mit Trasylol [The treatment of arthroses of the knee joint with Trasylol]. Langenbacks Arch. Chir., vol. 325, pp. 356-358 (1969).
Urlaub et al., "Isolation of Chinese hamster cell mutants deficient in dihydrofolate reductase activity", Proc. Natl. Acad. Sci. USA 77:4216-4220 (1980).
Vajdos et al., Comprehensive functional maps of the antigen-binding site of an anti-ErbB2 antibody obtained with shotgun scanning mutagenesis. J Mol Biol. Jul. 5, 2002;320(2):415-28.

Van Der Logt et al., "Intron-Exon Organization of the Human Gene Coding for the Lipoprotein-associated Coagulation Inhibitor: The Factor Xa Dependent of Inhibitor of the Extrinsic Pathway of Coagulation," Biochemistry, 30:1571-1577 (1991). cited byapplicant.
Van Dijl et al., "Signal Peptidase 1 of Bacillus subtillis: Patterns of Conserved Amino Acids in Prokaryotic and Eukaryotic Type 1 Signal Peptidases," The EMBO Journal, 11:2819-2828 (1992).
Varadi et al., "Location of Plasminogen-Binding Sites in Human Fibrin(ogen)," Biochemistry, 22:2440-2446 (1983).
Varadi et al., Segment of Fibrinogen Is in a Region Essential for Plasminogen Binding by Fibrin Fragment E, Biochemistry, 23:2108-2112 (1984).
Vedvick et al., "High-Level Secretion of Biologically Active Aprotinin from the Yeast Pichia pastoris," J. Ind. Microbiol., 7:197-201 (1991).
Veloso et al., A monoclonal anti-human plasma prekallikrein antibody that inhibits activation of prekallikrein by factor XIIa on a surface. Blood. Oct. 1987;70(4):1053-62.
Veronese, "Peptide and protein PEGylation: a review of problems and solutions," Biomaterials, Mar. 1, 2001, vol. 22, No. 5, pp. 405-417.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Vidal et al., "Making sense of antisense," European Journal of Cancer, 2005, vol. 41, pp. 2812-2818.
Viswanathan et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade et al., "Solid-Phase Synthesis of ?-Human Atrial Natriuretic Factor: Comparison of the Boc-Polystyrene and Fmoc-Polyamide Methods," Biopolymers, 25: S21-S37 (1986).
Wagner et al., High Level Expression, Purification, and Characterization of the Kunitz-Type Protease Domain of Protease Nexin-2/ Amyloid ?-Protein Precursor, Biochemical and Biophysical Research Communications, 186: 1138-1145 (1992). cited byapplicant.
Wang et al., "Monitoring of heparin-induced anticoagulation with kaolin-activated clotting time in cadiac surgical patients treated with aprotinin," Anesthesiology, vol. 77, pp. 1080-1084 (1992).
Ward et al. "Binding activities of a repertoire of single immunoglobulin variable domains secreted from *Escherichia coli*" (1989) Nature 341:544-546.
Wark et al., Latest technologies for the enhancement of antibody affinity. Adv Drug Deliv Rev. Aug. 7, 2006;58(5-6):657-70. Epub May 22, 2006.
Wark, "DX-890 (Dyax)", iDrugs, 5, pp. 586-589, Jun. 2002.
Watson et al., "Induction of reproducible brain infarction by photochemically initiated thrombosis" Ann Neurol17: 497-504 (1985).
Weaver, Animal studies paint misleading picture. Nature International Weekly Journal of Science. Published online Mar. 30, 2010. Retrieved on Aug. 1, 2017 from http://www.nature.com/news.2010.158.html.
Wei et al., "Production and characterization of ectoine by *Marinococcus* sp. *ECT1* isolated from a high-salinity environment." J Biosci Bioeng. Mar. 2011;111(3):336-42. Epub Dec. 15, 2010.
Wellington et al., "Tranexamic Acid: A review of its use in the management of menorrhagia", Drugs, vol. 63, No. 13, pp. 1417-1433, 2003.
Wells, "Addivity of Mutational Effects in Proteins", Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Williams et al. "Collagen-induced arthritis as a model for rheumatoid arthritis" Methods Mol Med. 98:207-16 (2004).

(56) References Cited

OTHER PUBLICATIONS

Wilson et al., "An animal model of chronic inflammatory pain: pharmacological and temporal differentiation from acute models" Eur J Pain. 10(6):537-49 (2006).
Wilson et al., "The Calculation and Synthesis of a Template Molecule," Tetrahedron, 49:3655-3663 (1993).
Wood, "Hemostatic Drugs" New England Journal of Medicine, Drug Therapy, 339(4):245-253 (1998).
Worthy et al., "Current status review kallikreins and kinins: mediators in inflammatory joint disease," Int. J. Exp, 1990.
Worthy et al., "Kallikreins and Kinins: Mediators in Inflammatory Joint Disease?", International Review of Experimental Pathology, pp. 587-601, vol. 71, No. 4, Blackwell Scientific, Oxford GB (Aug. 1, 1990).
Wu et al., Humanization of a murine monoclonal antibody by simultaneous optimization of framework and CDR residues. J Mol Biol. Nov. 19, 1999;294(1):151-62.
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem. 263:6001-6004 (1988).
Yetkin et al., "The healing effect of TGF-[alpha] on gastric ulcer induced by acetylsalicylic acid in rats", International Journal of Pharmaceutics, vol. 277, No. 1-2, Jun. 1, 2004, pp. 163-172.
Zuraw et al., "Clinical practice. Hereditary angioedema" N Engl J Med 359, 1027-1036, (2008).
Published U.S. Appl. No. 14/773,766, filed Sep. 9, 2015, U.S. Publication No. 2016-0017055.
Granted U.S. Appl. No. 13/345,170, filed Jan. 6, 2012, U.S. Pat. No. 8,816,055.
Granted U.S. Appl. No. 14/310,814, filed Jun. 20, 2014, U.S. Pat. No. 9,266,964.
Granted U.S. Appl. No. 12/985,914, filed Jan. 6, 2011, U.S. Pat. No. 8,822,653.
Published U.S. Appl. No. 14/339,053, filed Jul. 23, 2014, U.S. Publication No. 2014-0335023.
Published U.S. Appl. No. 15/706,622, filed Sep. 15, 2017, U.S. Publication No. 2018-0037665.
Published U.S. Appl. No. 15/706,631, filed Sep. 15, 2017, U.S. Publication No. 2018-0037666.
Published U.S. Appl. No. 15/706,613, filed Sep. 15, 2017, U.S. Publication No. 2018-0037664.
Published U.S. Appl. No. 15/706,603, filed Sep. 15, 2017, U.S. Publication No. 2018-0002447.
Published U.S. Appl. No. 15/706,621, filed Sep. 15, 2017, U.S. Publication No. 2018-0002448.
Published U.S. Appl. No. 15/706,623, filed Sep. 15, 2017, U.S. Publication No. 2018-0002449.
Published U.S. Appl. No. 15/113,297, filed Jul. 21, 2016, U.S. Publication No. 2017-0002094.
Published U.S. Appl. No. 14/669,607, filed Mar. 26, 2015, U.S. Publication No. 2015-0274841.
Extended European Search Report Serial No. EP 14769643.9 dated Oct. 27, 2016.
Invitation to Pay Additional Fees Serial No. PCT/US2014/027100 dated Jun. 18, 2014.
International Search Report and Written Opinion Serial No. PCT/US2014/027100 dated Sep. 10, 2014.
International Preliminary Report on Patentability Serial No. PCT/US2014/027100 dated Sep. 24, 2015.
Supplementary European Search Report Serial No. EP12732149 dated Mar. 25, 2014.
International Search Report and Written Opinion Serial No. PCT/US2012/020470 dated Apr. 30, 2012.
International Preliminary Report on Patentability Serial No. PCT/US2012/020470 dated Jul. 18, 2013.
Extended European Search Report Serial No. EP11732145.5 dated May 15, 2013.
International Search Report and Written Opinion Serial No. PCT/US2011/020377 dated Jun. 28, 2011.
International Preliminary Report on Patentability Serial No. PCT/US2011/020377 dated Jul. 19, 2012.
Supplementary European Search Report Serial No. EP 15740774.3 dated Jul. 24, 2017.
International Search Report and Written Opinion Serial No. PCT/US2015/012212 dated Apr. 9, 2015.
International Preliminary Report on Patentability Serial No. PCT/US2015/012212 dated Aug. 4, 2016.
Supplementary European Search Report Serial No. EP 15769534.7 dated Aug. 11, 2017.
International Search Report and Written Opinion Serial No. PCT/US2015/022715 dated Jul. 2, 2015.
International Preliminary Report on Patentability Serial No. PCT/US2015/022715 dated Oct. 6, 2016.
Pending U.S. Appl. No. 15/562,671, filed Sep. 28, 2017.
Pending U.S. Appl. No. 16/061,103, filed Jun. 11, 2018.
Partial Supplementary European Search Report Serial No. EP 16774069.5 dated Jul. 19, 2018.
International Search Report and Written Opinion Serial No. PCT/US2016/024921 dated Jun. 30, 2016.
International Preliminary Report on Patentabiltiy Serial No. PCT/US2016/024921 dated Oct. 12, 2017.
International Search Report and Written Opinion Serial No. PCT/US2016/065980 dated Mar. 1, 2017.
International Preliminary Report on Patentability Serial No. PCT/US2016/065980 dated Jun. 21, 2018.
[No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Ferrara et al., Recombinant renewable polyclonal antibodies. MAbs. 2015;7(1):32-41. doi: 10.4161/19420862.2015.989047.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

* cited by examiner

```
X63-G06        CAAGACATCCAGATGACCCAGTCTCCAGGCACCCTGTCTTTGTCTCCAGGGGAAAGAGCC
X81-B01        -----GAGATCGTGCTGACCCAGTCCCCTGCCACCCTGTCTCTGTCTCCGGGCGAGAGAGCC
               *    ********* ** ************ ** ********  **  ********

X63-G06        ACCCTCTCCTGCAGGACCAGTCAATTGTTAACAGCAACTACTTAGCCTGGTACCAACAG
X81-B01        ACCCTGTCCTGCCGGGACCTCCCAGTTCGTGAACTCCAACTACCTGGCTTGGTATCAGCAG
               ***** ****** * **** * ****** *  *** * ****** ** *** ** ****

X63-G06        ACACCTGGCCAGGCTCCCAGGCTCCTCATCTATGTCGATCAGCCACTGGCATC
X81-B01        AAGCCAGGCCAGGCCCCCAGGCTAGACTGCTGATCTACGGCGCCTCTTCCAGAGCCACCGGCATC
                * ** ******* * *******   **   ** **   **    *  ****** *******

X63-G06        CCAGACAGGTTCAGTGGCACTGGGTATGGGACAGAGTTCACTCTCACCATCAGCAGACTG
X81-B01        CCTGACCGGTTCTCCGGCTCTGGCTCCGGCACCGACTTCACCCTGACCATCTCCCGGCTG
               ** *** ***** * *** ***  *  *  ** ** ******  * ***** *  * ***

X63-G06        GAGCCTGAAGATTATGGAACTTACTACTGTCAGCAGAGTTCCAGAACCCGTGGACGTTC
X81-B01        GAACCTGAGGACTTCGCCGTGTACTACTGCCAGCAGTACTACTCCACCCCGGACCCCTTGGACTTT
               ** ***** **  *  *  ** ******* ******   * *   **  ** **  * *

X63-G06        GGCCAAGGGACCAGAGTGGAAATCAAA
X81-B01        GGCCAGGGCACCAAGGTGGAGATCAAG
               ***** ** **** * ****  *****
```

FIGURE 4

```
X63-G06   QDIQMTQSPGTLSLSPGERATLSCRTSQFVNSNYLAWYQQTPGQAPRLLIYGASSRATGI
X81-B01   -EIVLTQSPGTLSLSPGERATLSCRTSQFVNSNYLAWYQQKPGQAPRLLIYGASSRATGI
           * ************************************ *******************

X63-G06   PDRFSGTGYGTDFTLTISRLEPEDYGTYCQQSSRTPWTFGQGTRVEIK
X81-B01   PDRFSGSGSGTDFTLTISRLEPEDFAVYYCQQSSRTPWTFGQGTKVEIK
          ****** * ************** * * ************** ****
```

FIGURE 5

```
X81-B01    GAGGTGCAATTGCTGTGGAATCCGGCGAGGTCTGGTGTGCAGCCTGGCGGCTC
X63-G06    GAAGTTCAATTGTTAGAGTCTGGTGGCGGTCTTCAGCCTGGTGGTC
           ***** ******** **** ***** **** ********  *****

X81-B01    CCTGAGACTGTCTTGCGCCCGCCTCCGGCTTCACCTTCTCCCACTACCTGA
X63-G06    TTTACGTCTTTCTTGCGCTGCCTCCGGATTCACTTTCTCTCATTACTTA
            * ** ** ****** ***********  **** ** *** ** ** **

X81-B01    TGACCTGGGTGCGGCCAGGCTCCCTGGCAAGGGCCTCGAATGGGTGTCCTAC
X63-G06    TGACTGGGGTTCGCCAAGCTCCTGGTAAAGGTTGCAGTGGGTTTCTTAT
           *** * **** **** ***** *** * *** *  ** ***** ** **

X81-B01    ATCTCCCCCTCTGGGGCCACACCATCTACGCCGACTCCGTGAAGGGCCG
X63-G06    ATCTCCTTCTGGTGGCCATACTATTATGCTGACTCCGTTAAAGGTCG
           ****** * ***  ***** ** ** * ** ****** ** *** **

X81-B01    GTTCACCATCTCCCGGGACAACTCCAAGAACACCCTGTATCTGCAGATGA
X63-G06    CTTCACTATCTCTAGAGACAACTCTAAGAATACTCTACTTGCAGATGA
            ***** ***** * ********* ***** ** ** ** ********

X81-B01    ACTCCCTGAGGGCCGAGGACACGGCCGTGTACTACTGCGCCAGGGTGGCC
X63-G06    ACAGCTTAAGGGCTGAGGACACGGCCGTGTATTACTGTGCGAGAGTGGCC
           **  * * ***** ***************** ***** **  * *****

X81-B01    AGAGGAATCGCCGCCAGGTCCCCGGACCTCCTACTTGACTACTGGGGCCA
X63-G06    CGGGGGATAGCAGCTCGATCGGAACCGCCTACTTTGACTACTGGGGCCA
            * **  ** **  *  * ** * **** ******* ***********

X81-B01    GGGCACCCTGGTGACCGTGCCCTCC
X63-G06    GGGAACCCTGGTCACCGTCTCCAAGC
           *** ******** ***** **  * 
```

FIGURE 6

```
X81-B01   EVQLLESGGGLVQPGGSLRLSCAASGFTFSHYLMTWVRQAPGKGLEWVSY
X63-G06   EVQLLESGGGLVQPGGSLRLSCAASGFTFSHYLMTWVRQAPGKGLEWVSY
          **************************************************

X81-B01   ISPSGGHTIYADSVKGRFTISRDNSKNTLYLQMNSLRAEDTAVYYCARVA
X63-G06   ISPSGGHTIYADSVKGRFTISRDNSKNTLYLQMNSLRAEDTAVYYCARVA
          **************************************************

X81-B01   RGIAARSRTSYFDYWGQGTLVTVSS
X63-G06   RGIAARSRTSYFDYWGQGTLVTVSS
          *************************
```

NOTE: The underlined positions are the amino acids that form the catalytic triad (His434, Asp483, and Ser578, numbering based on the human sequence).

PLASMA KALLIKREIN BINDING PROTEINS

This application is a divisional application of U.S. Ser. No. 14/310,814, filed on Jun. 20, 2014, which is a divisional application of U.S. Ser. No. 13/345,170, filed on Jan. 6, 2012, which claims priority to U.S. Application Ser. No. 61/430,442, filed on Jan. 6, 2011. The content of each of the prior applications is incorporated by reference herein in their entirety.

BACKGROUND

Plasma kallikrein is a serine protease. Prekallikrein is the precursor of plasma kallikrein.

SUMMARY

Plasma kallikrein is a serine protease component of the contact system and a potential drug target for different inflammatory, cardiovascular, infectious (sepsis) and oncology diseases (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (FIG. 1) (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

Plasma kallikrein binding proteins (e.g., antibodies, e.g., inhibitory antibodies) are useful therapeutic agents for a variety of diseases and conditions, e.g., diseases and conditions that involve plasma kallikrein activity, due to their high potency, specificity, and prolonged serum residency. High potency can translate to efficacy and a low drug dosage, and high specificity can reduce side effects due to the inhibition of related off target serine proteases. In general, small molecule serine proteases are not as specific as antibody inhibitors. Prolonged serum residency can permit infrequent dosing.

In some aspects, the disclosure features an isolated protein (e.g., antibody, e.g., human antibody) that binds to the active form of plasma kallikrein (e.g., human plasma kallikrein and/or mouse plasma kallikrein), and, e.g., does not bind preplasma kallikrein (e.g., human preplasma kallikrein and/or mouse preplasma kallikrein).

In some embodiments, the plasma kallikrein binding protein binds the same epitope or competes for binding with a kallikrein binding protein described herein. In some embodiments, the plasma kallikrein binding protein binds the same epitope or competes for binding with a protein (e.g., epi-Kal2) and/or a small molecule (e.g., AEBSF) described herein and does not bind pre-plasma kallikrein.

In some embodiments, the protein described herein is selected from the group consisting of M162-A04, M199-A08, M160-G12, M142-H08, X63-G06, X101-A01 (also referred to herein as DX-2922), X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In some embodiments, the plasma kallikrein binding protein competes with or binds the same epitope as X81-B01 and, e.g., does not bind pre-plasma kallikrein.

In some embodiments, the plasma kallikrein binding protein competes with or binds the same epitope as X67-D03 and, e.g., does not bind pre-plasma kallikrein.

In some embodiments, the plasma kallikrein binding protein competes with or binds to the same site as X101-A01 and, e.g., does not bind pre-plasma kallikrein.

In some embodiments, the plasma kallikrein binding protein competes with or binds to the same site as M162-A04 and, e.g., does not bind pre-plasma kallikrein.

In some embodiments, the plasma kallikrein binding protein competes with or binds to the same site as X115-F02 and, e.g., does not bind pre-plasma kallikrein.

In some embodiments, the plasma kallikrein binding protein competes with or binds to the same site as X124-G01 and, e.g., does not bind pre-plasma kallikrein.

In some embodiments, the plasma kallikrein binding protein competes with or binds to the same site as X63-G06 and, e.g., does not bind pre-plasma kallikrein.

In some embodiments, the plasma kallikrein binding protein does not bind prekallikrein (e.g., human prekallikrein and/or mouse prekallikrein), but binds to the active form of plasma kallikrein (e.g., human plasma kallikrein and/or mouse plasma kallikrein).

In certain embodiments, the protein binds at or near the active site of the catalytic domain of plasma kallikrein, or a fragment thereof, or binds an epitope that overlaps with the active site of plasma kallikrein and, e.g., does not bind pre-plasma kallikrein.

In some embodiments, the protein binds to one or more amino acids that form the catalytic triad of plasma kallikrein: His434, Asp483, and/or Ser578 (numbering based on the human sequence) and, e.g., does not bind pre-plasma kallikrein.

In some embodiments, the protein binds to one or more amino acids of: Ser479, Tyr563, and/or Asp585 (numbering based on the human sequence) and, e.g., does not bind pre-plasma kallikrein.

In some embodiments, the plasma kallikrein binding protein binds one or more amino acids of: Arg551, Gln553, Tyr555, Thr558, and/or Arg560 (numbering based on the human kallikrein sequence). In other embodiments, the plasma kallikrein binding protein binds two, three, four or five (i.e., all) amino acids of: Arg551, Gln553, Tyr555, Thr558, and/or Arg560 (numbering based on the human sequence) and, e.g., does not bind pre-plasma kallikrein.

In some embodiments, the plasma kallikrein binding protein binds one or more amino acids of: S478, N481, S525, and K526 (numbering based on the human kallikrein sequence). In other embodiments, the plasma kallikrein binding protein binds two, three or four (i.e., all) amino acids of: S478, N481, S525, and K526 (numbering based on the human kallikrein sequence).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the plasma kallikrein binding protein has an apparent inhibition constant ($K_{i,app}$) of less than 1000, 500, 100, 10, 1, 0.5 or 0.2 nM.

In one embodiment, the HC and LC variable domain sequences are components of the same polypeptide chain.

In another embodiment, the HC and LC variable domain sequences are components of different polypeptide chains. For example, the plasma kallikrein binding protein is an IgG, e.g., IgG1, IgG2, IgG3, or IgG4. The plasma kallikrein binding protein can be a soluble Fab (sFab).

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein binding protein is physically associated with a moiety that improves serum residence time, e.g., a moiety described herein. In one embodiment, the plasma kallikrein binding protein is modified to include, e.g., PEGylation, fusion to serum albumin (e.g., human serum albumin), conjugation to human serum albumin, HESylation (HESylation utiliseshydroxyethyl starch ("HES") derivatives linked to drug substances in order to modify the drug characteristics or fusion to a unstructured recombinant polymer (URPs).

In other embodiments, the plasma kallikrein binding protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC:: HSA+VH::CH1, HSA::LC+VH::CH1, or other appropriate construction.

In one embodiment, the plasma kallikrein binding protein is a human or humanized antibody or is non-immunogenic in a human. For example, the protein includes one or more human antibody framework regions, e.g., all human framework regions.

In one embodiment, the plasma kallikrein binding protein includes a human Fc domain, or an Fc domain that is at least 95, 96, 97, 98, or 99% identical to a human Fc domain.

In one embodiment, the plasma kallikrein binding protein is a primate or primatized antibody or is non-immunogenic in a human. For example, the protein includes one or more primate antibody framework regions, e.g., all primate framework regions.

In one embodiment, the plasma kallikrein binding protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In one embodiment, the plasma kallikrein binding protein includes human framework regions, or framework regions that are at least 95, 96, 97, 98, or 99% identical to human framework regions.

In certain embodiments, the plasma kallikrein binding protein includes no sequences from mice or rabbits (e.g., is not a murine or rabbit antibody).

In certain embodiments, the plasma kallikrein binding protein is capable of binding to a cell or tissue, e.g., that expresses plasma kallikrein.

In one embodiment, the plasma kallikrein binding protein is physically associated with a nanoparticle, and can be used to guide a nanoparticle to a cell or tissue expressing plasma kallikrein.

In some aspects, the disclosure features an isolated protein (e.g., antibody, e.g., human antibody) that binds the same epitope or competes for binding with a kallikrein binding protein described herein.

In some embodiments, the protein binds the same epitope or competes for binding with a protein (e.g., epi-Kal2) and/or a small molecule (e.g., AEBSF) described herein.

In some embodiments, the isolated protein comprises a heavy chain immunoglobulin variable domain sequence and a light chain immunoglobulin variable domain sequence, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the heavy chain immunoglobulin variable domain sequence comprises one, two, or three (e.g., three) CDR regions from the heavy chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

the light chain immunoglobulin variable domain sequence comprises one, two, or three (e.g., three) CDR regions from the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein inhibits plasma kallikrein (e.g., human plasma kallikrein and/or mouse plasma kallikrein).

In some embodiments, the one, two, or three (e.g., three) CDR regions from the heavy chain variable domain are from X81-B01 and/or the one, two, or three (e.g., three) CDR regions from the light chain variable domain are from X81-B01.

In some embodiments, the one, two, or three (e.g., three) CDR regions from the heavy chain variable domain are from X67-D03 and/or the one, two, or three (e.g., three) CDR regions from the light chain variable domain are from X67-D03.

In some embodiments, the one, two, or three (e.g., three) CDR regions from the heavy chain variable domain are from X63-G06 and/or the one, two, or three (e.g., three) CDR regions from the light chain variable domain are from X63-G06.

In some embodiments, the one, two, or three (e.g., three) CDR regions from the heavy chain variable domain are from M162-A04 and/or the one, two, or three (e.g., three) CDR regions from the light chain variable domain are from MJ162-A04.

In some embodiments, the one, two, or three (e.g., three) CDR regions from the heavy chain variable domain are from X115-F02 and/or the one, two, or three (e.g., three) CDR regions from the light chain variable domain are from X115-F02.

In some embodiments, the one, two, or three (e.g., three) CDR regions from the heavy chain variable domain are from X124-G01 and/or the one, two, or three (e.g., three) CDR regions from the light chain variable domain are from X124-G01.

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the heavy chain immunoglobulin variable domain sequence comprises the heavy chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain immunoglobulin variable domain sequence comprises the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the heavy chain immunoglobulin variable domain sequence comprises the heavy chain variable domain of X81-B01, and/or the light chain immunoglobulin variable domain sequence comprises the light chain variable domain of X81-B01.

In some embodiments, the heavy chain immunoglobulin variable domain sequence comprises the heavy chain variable domain of X67-D03, and/or the light chain immunoglobulin variable domain sequence comprises the light chain variable domain of X67-D03.

In some embodiments, the protein comprises the heavy chain of a protein described herein, and/or the light chain of a protein described herein.

In some embodiments, the protein comprises the heavy chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

and/or the light chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein comprises the heavy chain of X81-B01, and/or the light chain of X81-B01.

In some embodiments, the protein comprises the heavy chain of X67-D03, and/or the light chain of X67-D03.

In some embodiments, the protein comprises the heavy chain of M162-A04, and/or the light chain of M162-A04.

In some embodiments, the protein comprises the heavy chain of X115-F02, and/or the light chain of X115-F02.

In some embodiments, the protein comprises the heavy chain of X124-G01, and/or the light chain of X124-G01.

In some embodiments, the plasma kallikrein binding protein does not bind prekallikrein (e.g., human prekallikrein and/or mouse prekallikrein), but binds to the active form of plasma kallikrein (e.g., human plasma kallikrein and/or mouse plasma kallikrein).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the protein includes one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

In some embodiments, the protein has an apparent inhibition constant ($K_{i,app}$) of less than 1000, 500, 100, 10, 1, 0.5 or 0.2 nM.

In some embodiments, the antibody does not bind prekallikrein (e.g., human prekallikrein and/or mouse prekallikrein), but binds to the active form of plasma kallikrein (e.g., human plasma kallikrein and/or mouse plasma kallikrein).

In a preferred embodiment, the protein is an antibody (e.g., a human antibody) having the light and heavy chains of antibodies selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the heavy chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the light chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having light and heavy antibody variable regions of an antibody selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a heavy chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a light chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

and one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In a preferred embodiment, the protein is an antibody (e.g., a human antibody) having the light and heavy chains of X81-B01.

In a preferred embodiment, the protein is an antibody (e.g., a human antibody) having the heavy chain of X81-B01.

In a preferred embodiment, the protein is an antibody (e.g., a human antibody) having the light chain of X81-B01.

In a preferred embodiment, the protein is an antibody (e.g., a human antibody) having light and heavy antibody variable regions of an antibody selected from X81-B01.

In a preferred embodiment, the protein is an antibody (e.g., a human antibody) having a heavy chain antibody variable region of X81-B01.

In a preferred embodiment, the protein is an antibody (e.g., a human antibody) having a light chain antibody variable region of X81-B01.

In a preferred embodiment, the protein is an antibody (e.g., a human antibody) having one or more (e.g., 1, 2, or 3) heavy chain CDRs from the corresponding CDRs of the heavy chain of X81-B01.

In a preferred embodiment, the protein is an antibody (e.g., a human antibody) having one or more (e.g., 1, 2, or 3) light chain CDRs from the corresponding CDRs of the light chain of X81-B01.

In a preferred embodiment, the protein is an antibody (e.g., a human antibody) having one or more (e.g., 1, 2, or 3) heavy chain CDRs from the heavy chain of X81-B01 and one or more (e.g., 1, 2, or 3) light chain CDRs from the corresponding CDRs of the light chain of X81-B01.

In a preferred embodiment, the protein is an antibody (e.g., a human antibody) having the light and heavy chains of X67-D03.

In a preferred embodiment, the protein is an antibody (e.g., a human antibody) having the heavy chain of X67-D03.

In a preferred embodiment, the protein is an antibody (e.g., a human antibody) having the light chain of X67-D03.

In a preferred embodiment, the protein is an antibody (e.g., a human antibody) having light and heavy antibody variable regions of an antibody selected from X67-D03.

In a preferred embodiment, the protein is an antibody (e.g., a human antibody) having a heavy chain antibody variable region of X67-D03.

In a preferred embodiment, the protein is an antibody (e.g., a human antibody) having a light chain antibody variable region of X67-D03.

In a preferred embodiment, the protein is an antibody (e.g., a human antibody) having one or more (e.g., 1, 2, or 3) heavy chain CDRs from the corresponding CDRs of the heavy chain of X67-D03.

In a preferred embodiment, the protein is an antibody (e.g., a human antibody) having one or more (e.g., 1, 2, or 3) light chain CDRs from the corresponding CDRs of the light chain of X67-D03.

In a preferred embodiment, the protein is an antibody (e.g., a human antibody) having one or more (e.g., 1, 2, or 3) heavy chain CDRs from the heavy chain of X67-D03 and one or more (e.g., 1, 2, or 3) light chain CDRs from the corresponding CDRs of the light chain of X67-D03.

In a preferred embodiment, the protein is an antibody (e.g., a human antibody) having the light and heavy chains of X124-G01 or X115-F02.

In a preferred embodiment, the protein is an antibody (e.g., a human antibody) having the heavy chain of X124-G01 or X115-F02.

In a preferred embodiment, the protein is an antibody (e.g., a human antibody) having the light chain of X124-G01 or X115-F02.

In a preferred embodiment, the protein is an antibody (e.g., a human antibody) having light and heavy antibody variable regions of an antibody selected from X124-G01 or X115-F02.

In a preferred embodiment, the protein is an antibody (e.g., a human antibody) having a heavy chain antibody variable region of X124-G01 or X115-F02.

In a preferred embodiment, the protein is an antibody (e.g., a human antibody) having a light chain antibody variable region of X124-G01 or X115-F02.

In a preferred embodiment, the protein is an antibody (e.g., a human antibody) having one or more (e.g., 1, 2, or 3) heavy chain CDRs from the corresponding CDRs of the heavy chain of X124-G01 or X115-F02.

In a preferred embodiment, the protein is an antibody (e.g., a human antibody) having one or more (e.g., 1, 2, or 3) light chain CDRs from the corresponding CDRs of the light chain of X124-G01 or X115-F02.

In a preferred embodiment, the protein is an antibody (e.g., a human antibody) having one or more (e.g., 1, 2, or 3) heavy chain CDRs from the heavy chain of X124-G01 or X115-F02 and one or more (e.g., 1, 2, or 3) light chain CDRs from the corresponding CDRs of the light chain of X124-G01 or X115-F02.

In one embodiment, the HC and LC variable domain sequences are components of the same polypeptide chain.

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein binding protein is physically associated with a moiety that improves serum residence time, e.g., a moiety described herein. In one embodiment, the plasma kallikrein binding protein is modified to include, e.g., PEGylation, fusion to serum albumin (e.g., human serum albumin), conjugation to human serum albumin, HESylation (HESylation utiliseshydroxyethyl starch ("HES") derivatives linked to drug substances in order to modify the drug characteristics or fusion to a unstructured recombinant polymer (URPs).

In another embodiment, the HC and LC variable domain sequences are components of different polypeptide chains.

For example, the protein is an IgG, e.g., IgG1, IgG2, IgG3, or IgG4. The protein can be a soluble Fab (sFab).

In other embodiments, the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions.

In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions.

In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In one embodiment, the protein includes human framework regions, or framework regions that are at least 95, 96, 97, 98, or 99% identical to human framework regions.

In certain embodiments, the protein includes no sequences from mice or rabbits (e.g., is not a murine or rabbit antibody).

In certain embodiments, the protein is capable of binding to a cell or tissue, e.g., that expresses plasma kallikrein.

In one embodiment, protein is physically associated with a nanoparticle, and can be used to guide a nanoparticle to a cell or tissue expressing plasma kallikrein.

In some aspects, the disclosure features a pharmaceutical composition comprising a kallikrein binding protein described herein, e.g., including a pharmaceutically acceptable carrier. In some embodiments, the composition can be at least 10, 20, 30, 50, 75, 85, 90, 95, 98, 99, or 99.9% free of other protein species. In one embodiment, the pharmaceutical composition can be at least 10, 20, 30, 50, 75, 85, 90, 95, 98, 99, or 99.9% free of fragments of the binding protein that do not binding plasma kallikrein (e.g., human plasma kallikrein) or bind plasma kallikrein (e.g., human plasma kallikrein with a Ki, app of 5000 nM or greater.

In some aspects, the disclosure features a method of treating or preventing a plasma kallikrein associated disorder in a subject, the method comprising:

administering an isolated protein (e.g., antibody, e.g., human antibody) that binds plasma kallikrein (e.g., human plasma kallikrein and/or mouse plasma kallikrein) and, e.g., does not bind prekallikrein (e.g., human prekallikrein and/or mouse prekallikrein) to the subject, In some embodiments, the protein binds the same epitope or competes for binding with a protein (e.g., epi-Kal2) and/or a small molecule (e.g., AEBSF) described herein.

In some embodiments, the protein binds the same epitope or competes for binding with a kallikrein binding protein described herein.

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting on ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, and burn injury. In some embodiments, the plasma kallikrein binding protein reduces abberent clotting associated with the contact activation system (i.e., intrinsic activation system) by at least 10% as measured by e.g., an APTT clotting assay. In other embodiments, the plasma kallikrein binding protein reduces abberent clotting associated with the contact activation system by at least 20%, at least 30%, at least 40%, at least 50%, at least 60%, at least 70%, at least 80%, at least 90%, at least 95%, at least 99%, or even 100% (i.e., no detectable abberent clotting).

In some embodiments, the plasma kallikrein binding protein is administered in combination with another treatment for the disorder.

In some embodiments, the protein described herein is selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In some embodiments, the plasma kallikrein binding protein competes with or binds the same epitope as X81-B01.

In some embodiments, the plasma kallikrein binding protein competes with or binds the same epitope as X67-D03.

In some embodiments, the plasma kallikrein binding protein competes with or binds to the same epitope as M162-A04 or X115-F02.

In some embodiments, the plasma kallikrein binding protein does not bind prekallikrein (e.g., human prekallikrein and/or mouse prekallikrein), but binds to the active form of plasma kallikrein (e.g., human plasma kallikrein and/or mouse plasma kallikrein).

In certain embodiments, the protein binds at or near the active site of the catalytic domain of plasma kallikrein, or a fragment thereof, or binds an epitope that overlaps with the active site of plasma kallikrein.

In some embodiments, the protein binds to one or more amino acids that form the catalytic triad of plasma kallikrein: His434, Asp483, and/or Ser578 (numbering based on the human sequence).

In some embodiments, the protein binds to one or more amino acids of Ser479, Tyr563, and/or Asp585 (numbering based on the human sequence).

In other embodiments, the protein binds to one or more amino acids of Arg551, Gln553, Tyr555, Thr558, and/or Arg560 (numbering based on the human sequence). In some embodiments, the plasma kallikrein binding protein binds one or more amino acids of: S478, N481, S525, and K526 (numbering based on the human kallikrein sequence).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the plasma kallikrein binding protein has an apparent inhibition constant ($K_{i,app}$) of less than 1000, 500, 100, 10, 5, 1, 0.5, or 0.2 nM.

In one embodiment, the HC and LC variable domain sequences are components of the same polypeptide chain.

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein bindihng protein is physically associated with a moiety that improves serum residence time, e.g., a moiety described herein.

In another embodiment, the HC and LC variable domain sequences are components of different polypeptide chains. For example, the plasma kallikrein binding protein is an IgG, e.g., IgG1, IgG2, IgG3, or IgG4. The plasma kallikrein binding protein can be a soluble Fab (sFab).

In other implementations the plasma kallikrein binding protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the plasma kallikrein binding protein is a human or humanized antibody or is non-immunogenic in a human. For example, the protein includes one or more human antibody framework regions, e.g., all human framework regions.

In one embodiment, the plasma kallikrein binding protein includes a human Fc domain, or an Fc domain that is at least 95, 96, 97, 98, or 99% identical to a human Fc domain.

In one embodiment, the plasma kallikrein binding protein is a primate or primatized antibody or is non-immunogenic in a human. For example, the protein includes one or more primate antibody framework regions, e.g., all primate framework regions.

In one embodiment, the plasma kallikrein binding protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (Daubentonia *madagascariensis*), and tarsiers.

In one embodiment, the plasma kallikrein binding protein includes human framework regions, or framework regions that are at least 95, 96, 97, 98, or 99% identical to human framework regions.

In certain embodiments, the plasma kallikrein binding protein includes no sequences from mice or rabbits (e.g., is not a murine or rabbit antibody).

In certain embodiments, the plasma kallikrein binding protein is capable of binding to a cell or tissue, e.g., that expresses plasma kallikrein.

In one embodiment, the plasma kallikrein binding protein is physically associated with a nanoparticle, and can be used to guide a nanoparticle to a cell or tissue expressing plasma kallikrein.

A method of treating or preventing a plasma kallikrein associated disorder in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein (e.g., human plasma kallikrein and/or mouse plasma kallikrein).

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting of ventrical assistance devices or stents, head trauma or peri-tumor brain edema, sepsis, acute middle cerebral artery (MCA) ischemic event (stroke), restenosis (e.g., after angioplasty), systemic lupus erythematosis nephritis, and burn injury. In some embodiments, the plasma kallikrein binding protein reduces abberent clotting associated with the contact activation system (i.e., intrinsic activation system) by at least 10% as measured by e.g., an APTT clotting assay (e.g., by at least 20%, at least 30%, at least 40%, at least 50%, at least 60%, at least 70%, at least 80%, at least 90%, at least 95%, at least 99%, or even 100% (i.e., no detectable abberent clotting)).

In some embodiments, the protein is administered in combination with another treatment for the disorder.

In some embodiments, the protein is administered in combination with a second agent selected from the group consisting of ecallantide, a C1 esterase inhibitor, aprotinin, a bradykinin B2 receptor inhibitor (e.g., icatibant).

In some embodiments, the heavy chain immunoglobulin variable domain sequence comprises one, two or three (e.g., three) CDR regions from the heavy chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain immunoglobulin variable domain sequence comprises one, two, or three (e.g., three) CDR regions from the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein inhibits plasma kallikrein.

In some embodiments, the one, two, or three (e.g., three) CDR regions from the heavy chain variable domain are from X81-B01 and/or the one, two, or three (e.g., three) CDR regions from the light chain variable domain are from X81-B01.

In some embodiments, the one, two, or three (e.g., three) CDR regions from the heavy chain variable domain are from X67-D03 and/or the one, two, or three (e.g., three) CDR regions from the light chain variable domain are from X67-D03.

In some embodiments, the one, two, or three (e.g., three) CDR regions from the heavy chain variable domain are from M162-A04 and/or the one, two, or three (e.g., three) CDR regions from the light chain variable domain are from M162-A04.

In some embodiments, the one, two, or three (e.g., three) CDR regions from the heavy chain variable domain are from X115-F02 and/or the one, two, or three (e.g., three) CDR regions from the light chain variable domain are from X115-F02.

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the heavy chain immunoglobulin variable domain sequence comprises the heavy chain variable domain of M162-A04, M199-A08, M160-G12, M142-H08 X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain immunoglobulin variable domain sequence comprises the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In some embodiments, the heavy chain immunoglobulin variable domain sequence comprises the heavy chain variable domain of X81-B01, and/or the light chain immunoglobulin variable domain sequence comprises the light chain variable domain of X81-B01.

In some embodiments, the heavy chain immunoglobulin variable domain sequence comprises the heavy chain variable domain of X67-D03, and/or the light chain immunoglobulin variable domain sequence comprises the light chain variable domain of X67-D03.

In some embodiments, the protein comprises the heavy chain of a protein described herein, and/or the light chain of a protein described herein.

In some embodiments, the protein comprises the heavy chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein comprises the heavy chain of X81-B01, and/or the light chain of X81-B01.

In some embodiments, the protein comprises the heavy chain of X67-D03, and/or the light chain of X67-D03.

In some embodiments, the protein comprises the heavy chain of M162-A04, and/or the light chain of M162-A04.

In some embodiments, the protein comprises the heavy chain of X115-F02 or X124-G01, and/or the light chain of X115-F02 or X124-G01.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the protein includes one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; and (g) a primate CDR or primate framework region.

In some embodiments, the protein has an apparent inhibition constant ($K_{i,app}$) of less than 1000, 500, 100, 10, 5, 1, 0.5 or 0.2 nM.

In some embodiments, the antibody does not bind prekallikrein (e.g., human prekallikrein), but binds to the active form of plasma kallikrein (e.g., human plasma kallikrein).

In a preferred embodiment, the protein is an antibody (e.g., a human antibody) having the light and heavy chains of antibodies selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the heavy chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the light chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having light and heavy antibody variable regions of an antibody selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a heavy chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a light chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 and one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In a preferred embodiment, the protein is an antibody (e.g., a human antibody) having the light and heavy chains of X81-B01.

In a preferred embodiment, the protein is an antibody (e.g., a human antibody) having the heavy chain of X81-B01.

In a preferred embodiment, the protein is an antibody (e.g., a human antibody) having the light chain of X81-B01.

In a preferred embodiment, the protein is an antibody (e.g., a human antibody) having light and heavy antibody variable regions of an antibody selected from X81-B01.

In a preferred embodiment, the protein is an antibody (e.g., a human antibody) having a heavy chain antibody variable region of X81-B01.

In a preferred embodiment, the protein is an antibody (e.g., a human antibody) having a light chain antibody variable region of X81-B01.

In a preferred embodiment, the protein is an antibody (e.g., a human antibody) having one or more (e.g., 1, 2, or 3) heavy chain CDRs from the corresponding CDRs of the heavy chain of X81-B01.

In a preferred embodiment, the protein is an antibody (e.g., a human antibody) having one or more (e.g., 1, 2, or 3) light chain CDRs from the corresponding CDRs of the light chain of X81-B01.

In a preferred embodiment, the protein is an antibody (e.g., a human antibody) having one or more (e.g., 1, 2, or 3) heavy chain CDRs from the heavy chain of X81-B01 and one or more (e.g., 1, 2, or 3) light chain CDRs from the corresponding CDRs of the light chain of X81-B01.

In a preferred embodiment, the protein is an antibody (e.g., a human antibody) having the light and heavy chains of X67-D03.

In a preferred embodiment, the protein is an antibody (e.g., a human antibody) having the heavy chain of X67-D03.

In a preferred embodiment, the protein is an antibody (e.g., a human antibody) having the light chain of X67-D03.

In a preferred embodiment, the protein is an antibody (e.g., a human antibody) having light and heavy antibody variable regions of an antibody selected from X67-D03.

In a preferred embodiment, the protein is an antibody (e.g., a human antibody) having a heavy chain antibody variable region of X67-D03.

In a preferred embodiment, the protein is an antibody (e.g., a human antibody) having a light chain antibody variable region of X67-D03.

In a preferred embodiment, the protein is an antibody (e.g., a human antibody) having one or more (e.g., 1, 2, or 3) heavy chain CDRs from the corresponding CDRs of the heavy chain of X67-D03.

In a preferred embodiment, the protein is an antibody (e.g., a human antibody) having one or more (e.g., 1, 2, or 3) light chain CDRs from the corresponding CDRs of the light chain of X67-D03.

In a preferred embodiment, the protein is an antibody (e.g., a human antibody) having one or more (e.g., 1, 2, or 3) heavy chain CDRs from the heavy chain of X67-D03 and one or more (e.g., 1, 2, or 3) light chain CDRs from the corresponding CDRs of the light chain of X67-D03.

In a preferred embodiment, the protein is an antibody (e.g., a human antibody) having the light and heavy chains of X115-F02 or X124-G01.

In a preferred embodiment, the protein is an antibody (e.g., a human antibody) having the heavy chain of X115-F02 or X124-G01.

In a preferred embodiment, the protein is an antibody (e.g., a human antibody) having the light chain of X115-F02 or X124-G01.

In a preferred embodiment, the protein is an antibody (e.g., a human antibody) having light and heavy antibody variable regions of an antibody selected from X115-F02 or X124-G01.

In a preferred embodiment, the protein is an antibody (e.g., a human antibody) having a heavy chain antibody variable region of X115-F02 or X124-G01.

In a preferred embodiment, the protein is an antibody (e.g., a human antibody) having a light chain antibody variable region of X115-F02 or X124-G01.

In a preferred embodiment, the protein is an antibody (e.g., a human antibody) having one or more (e.g., 1, 2, or 3) heavy chain CDRs from the corresponding CDRs of the heavy chain of X115-F02 or X124-G01.

In a preferred embodiment, the protein is an antibody (e.g., a human antibody) having one or more (e.g., 1, 2, or 3) light chain CDRs from the corresponding CDRs of the light chain of X115-F02 or X124-G01.

In a preferred embodiment, the protein is an antibody (e.g., a human antibody) having one or more (e.g., 1, 2, or 3) heavy chain CDRs from the heavy chain of X115-F02 or X124-G01 and one or more (e.g., 1, 2, or 3) light chain CDRs from the corresponding CDRs of the light chain of X115-F02 or X124-G01.

In one embodiment, the HC and LC variable domain sequences are components of the same polypeptide chain.

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein bindihng protein is physically associated with a moiety that improves serum residence time, e.g., a moiety described herein.

In another embodiment, the HC and LC variable domain sequences are components of different polypeptide chains. For example, the protein is an IgG, e.g., IgG1, IgG2, IgG3, or IgG4. The protein can be a soluble Fab (sFab).

In other implementations the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions.

In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions.

In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In one embodiment, the protein includes human framework regions, or framework regions that are at least 95, 96, 97, 98, or 99% identical to human framework regions.

In certain embodiments, the protein includes no sequences from mice or rabbits (e.g., is not a murine or rabbit antibody).

In certain embodiments, the protein is capable of binding to a cell or tissue, e.g., that expresses plasma kallikrein.

In one embodiment, protein is physically associated with a nanoparticle, and can be used to guide a nanoparticle to a cell or tissue expressing plasma kallikrein.

In some aspects, the disclosure features a method of promoting wound healing in a subject, the method comprising:

administering an isolated protein (e.g., antibody, e.g., human antibody) that binds plasma kallikrein (e.g., human plasma kallikrein and/or mouse plasma kallikrein) and, e.g., does not bind prekallikrein (e.g., human prekallikrein and/or mouse prekallikrein) to the subject.

In some embodiments, the protein binds the same epitope or competes for binding with a kallikrein binding protein described herein. In some embodiments, the protein binds the same epitope or competes for binding with a protein (e.g., epi-Kal2) and/or a small molecule (e.g., AEBSF) described herein.

In some embodiments, the plasma kallikrein binding protein is administered in combination with another treatment for wound healing.

In some embodiments, the protein described herein is selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In some embodiments, the plasma kallikrein binding protein competes with or binds the same epitope as X81-B01.

In some embodiments, the plasma kallikrein binding protein competes with or binds the same epitope as X67-D03.

In some embodiments, the plasma kallikrein binding protein competes with or binds the same epitope as M162-A04.

In some embodiments, the plasma kallikrein binding protein competes with or binds the same epitope as X115-F02 or X124-G01.

In some embodiments, the plasma kallikrein binding protein does not bind prekallikrein (e.g., human prekallikrein), but binds to the active form of plasma kallikrein (e.g., human plasma kallikrein).

In certain embodiments, the protein binds at or near the active site of the catalytic domain of plasma kallikrein, or a fragment thereof, or binds an epitope that overlaps with the active site of plasma kallikrein.

In some embodiments, the protein binds to one or more amino acids that form the catalytic triad of plasma kallikrein: His434, Asp483, and/or Ser578 (numbering based on the human sequence). In other embodiments, the protein binds to one or more amino acids that form a region for substrate recognition: Arg551, Gln553, Tyr555, Thr558, and/or Arg560 (numbering based on the human sequence). In some embodiments, the plasma kallikrein binding protein binds one or more amino acids of: S478, N481, S525, and K526 (numbering based on the human kallikrein sequence).

In some embodiments, the protein binds to one or more amino acids of Ser479, Tyr563, and/or Asp585 (numbering based on the human sequence).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the plasma kallikrein binding protein has an apparent inhibition constant ($K_{i,app}$) of less than 1000, 500, 100, 10, 5, 1, 0.5 or 0.2 nM.

In one embodiment, the HC and LC variable domain sequences are components of the same polypeptide chain.

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein bindihng protein is physically associated with a moiety that improves serum residence time, e.g., a moiety described herein.

In another embodiment, the HC and LC variable domain sequences are components of different polypeptide chains. For example, the plasma kallikrein binding protein is an IgG, e.g., IgG1, IgG2, IgG3, or IgG4. The plasma kallikrein binding protein can be a soluble Fab (sFab).

In other implementations the plasma kallikrein binding protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the plasma kallikrein binding protein is a human or humanized antibody or is non-immunogenic in a human. For example, the protein includes one or more human antibody framework regions, e.g., all human framework regions.

In one embodiment, the plasma kallikrein binding protein includes a human Fc domain, or an Fc domain that is at least 95, 96, 97, 98, or 99% identical to a human Fc domain.

In one embodiment, the plasma kallikrein binding protein is a primate or primatized antibody or is non-immunogenic in a human. For example, the protein includes one or more primate antibody framework regions, e.g., all primate framework regions.

In one embodiment, the plasma kallikrein binding protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In one embodiment, the plasma kallikrein binding protein includes human framework regions, or framework regions that are at least 95, 96, 97, 98, or 99% identical to human framework regions.

In certain embodiments, the plasma kallikrein binding protein includes no sequences from mice or rabbits (e.g., is not a murine or rabbit antibody).

In certain embodiments, the protein is capable of binding to a cell or tissue, e.g., that expresses plasma kallikrein.

In one embodiment, the plasma kallikrein binding protein is physically associated with a nanoparticle, and can be used to guide a nanoparticle to a cell or tissue expressing plasma kallikrein.

In some aspects, the disclosure features a method promoting wound healing in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the protein is administered in combination with another treatment for wound healing.

In some embodiments, the heavy chain immunoglobulin variable domain sequence comprises one, two, or three (e.g., three) CDR regions from the heavy chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain immunoglobulin variable domain sequence comprises one, two, or three (e.g., three) CDR regions from the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein inhibits plasma kallikrein.

In some embodiments, the one, two, or three (e.g., three) CDR regions from the heavy chain variable domain are from X81-B01 and/or the one, two, or three (e.g., three) CDR regions from the light chain variable domain are from X81-B01.

In some embodiments, the one, two, or three (e.g., three) CDR regions from the heavy chain variable domain are from X67-D03 and/or the one, two, or three (e.g., three) CDR regions from the light chain variable domain are from X67-D03.

In some embodiments, the one, two, or three (e.g., three) CDR regions from the heavy chain variable domain are from M162-A04 and/or the one, two, or three (e.g., three) CDR regions from the light chain variable domain are from M162-A04.

In some embodiments, the one, two, or three (e.g., three) CDR regions from the heavy chain variable domain are from M199-A08 and/or the one, two, or three (e.g., three) CDR regions from the light chain variable domain are from M199-A08.

In some embodiments, the one, two, or three (e.g., three) CDR regions from the heavy chain variable domain are from X115-F02 or X124-G01 and/or the one, two, or three (e.g., three) CDR regions from the light chain variable domain are from X115-F02 or X124-G01.

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the heavy chain immunoglobulin variable domain sequence comprises the heavy chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain immunoglobulin variable domain sequence comprises the light chain variable domain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the heavy chain immunoglobulin variable domain sequence comprises the heavy chain variable domain of X81-B01, and/or the light chain immunoglobulin variable domain sequence comprises the light chain variable domain of X81-B01.

In some embodiments, the heavy chain immunoglobulin variable domain sequence comprises the heavy chain variable domain of X67-D03, and/or the light chain immunoglobulin variable domain sequence comprises the light chain variable domain of X67-D03.

In some embodiments, the protein comprises the heavy chain of a protein described herein, and/or the light chain of a protein described herein.

In some embodiments, the protein comprises the heavy chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04, and/or the light chain of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In some embodiments, the protein comprises the heavy chain of X81-B01, and/or the light chain of X81-B01.

In some embodiments, the protein comprises the heavy chain of X67-D03, and/or the light chain of X67-D03.

In some embodiments, the protein comprises the heavy chain of M162-A04, and/or the light chain of M162-A04.

In some embodiments, the protein comprises the heavy chain of X115-F02 or X124-G01, and/or the light chain of X115-F02 or X124-G01.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the protein includes one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; and (g) a primate CDR or primate framework region.

In some embodiments, the protein has an apparent inhibition constant ($K_{i,app}$) of less than 1000, 500, 100, 5, 1, 0.5 or 0.2 nM.

In some embodiments, the antibody does not bind prekallikrein (e.g., human prekallikrein and/or murine prekallikrein), but binds to the active form of plasma kallikrein (e.g., human plasma kallikrein and/or murine plasma kallikrein).

In a preferred embodiment, the protein is an antibody (e.g., a human antibody) having the light and heavy chains of antibodies selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X-124-G01, X115-G04, M29-D09, M145-D11, M06-D09 and M35-G04.

In a preferred embodiment, the protein is an antibody (e.g., a human antibody) having the heavy chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the light chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having light and heavy antibody variable regions of an antibody selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a heavy chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a light chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 and one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04 (respectively).

In a preferred embodiment, the protein is an antibody (e.g., a human antibody) having the light and heavy chains of X81-B01.

In a preferred embodiment, the protein is an antibody (e.g., a human antibody) having the heavy chain of X81-B01.

In a preferred embodiment, the protein is an antibody (e.g., a human antibody) having the light chain of X81-B01.

In a preferred embodiment, the protein is an antibody (e.g., a human antibody) having light and heavy antibody variable regions of an antibody selected from X81-B01.

In a preferred embodiment, the protein is an antibody (e.g., a human antibody) having a heavy chain antibody variable region of X81-B01.

In a preferred embodiment, the protein is an antibody (e.g., a human antibody) having a light chain antibody variable region of X81-B01.

In a preferred embodiment, the protein is an antibody (e.g., a human antibody) having one or more (e.g., 1, 2, or 3) heavy chain CDRs from the corresponding CDRs of the heavy chain of X81-B01.

In a preferred embodiment, the protein is an antibody (e.g., a human antibody) having one or more (e.g., 1, 2, or 3) light chain CDRs from the corresponding CDRs of the light chain of X81-B01.

In a preferred embodiment, the protein is an antibody (e.g., a human antibody) having one or more (e.g., 1, 2, or 3) heavy chain CDRs from the heavy chain of X81-B01 and one or more (e.g., 1, 2, or 3) light chain CDRs from the corresponding CDRs of the light chain of X81-B01.

In a preferred embodiment, the protein is an antibody (e.g., a human antibody) having the light and heavy chains of X67-D03.

In a preferred embodiment, the protein is an antibody (e.g., a human antibody) having the heavy chain of X67-D03.

In a preferred embodiment, the protein is an antibody (e.g., a human antibody) having the light chain of X67-D03.

In a preferred embodiment, the protein is an antibody (e.g., a human antibody) having light and heavy antibody variable regions of an antibody selected from X67-D03.

In a preferred embodiment, the protein is an antibody (e.g., a human antibody) having a heavy chain antibody variable region of X67-D03.

In a preferred embodiment, the protein is an antibody (e.g., a human antibody) having a light chain antibody variable region of X67-D03.

In a preferred embodiment, the protein is an antibody (e.g., a human antibody) having one or more (e.g., 1, 2, or 3) heavy chain CDRs from the corresponding CDRs of the heavy chain of X67-D03.

In a preferred embodiment, the protein is an antibody (e.g., a human antibody) having one or more (e.g., 1, 2, or 3) light chain CDRs from the corresponding CDRs of the light chain of X67-D03.

In a preferred embodiment, the protein is an antibody (e.g., a human antibody) having one or more (e.g., 1, 2, or 3) heavy chain CDRs from the heavy chain of X67-D03 and one or more (e.g., 1, 2, or 3) light chain CDRs from the corresponding CDRs of the light chain of X67-D03.

In a preferred embodiment, the protein is an antibody (e.g., a human antibody) having the light and heavy chains of X115-F02 or X124-G01.

In a preferred embodiment, the protein is an antibody (e.g., a human antibody) having the heavy chain of X115-F02 or X124-G01.

In a preferred embodiment, the protein is an antibody (e.g., a human antibody) having the light chain of X115-F02 or X124-G01.

In a preferred embodiment, the protein is an antibody (e.g., a human antibody) having light and heavy antibody variable regions of an antibody selected from X115-F02 or X124-G01.

In a preferred embodiment, the protein is an antibody (e.g., a human antibody) having a heavy chain antibody variable region of X115-F02 or X124-G01.

In a preferred embodiment, the protein is an antibody (e.g., a human antibody) having a light chain antibody variable region of X115-F02 or X124-G01.

In a preferred embodiment, the protein is an antibody (e.g., a human antibody) having one or more (e.g., 1, 2, or 3) heavy chain CDRs from the corresponding CDRs of the heavy chain of X115-F02 or X124-G01.

In a preferred embodiment, the protein is an antibody (e.g., a human antibody) having one or more (e.g., 1, 2, or 3) light chain CDRs from the corresponding CDRs of the light chain of X115-F02 or X124-G01.

In a preferred embodiment, the protein is an antibody (e.g., a human antibody) having one or more (e.g., 1, 2, or 3) heavy chain CDRs from the heavy chain of X115-F02 or X124-G01and one or more (e.g., 1, 2, or 3) light chain CDRs from the corresponding CDRs of the light chain of X115-F02 or X124-G01.

In one embodiment, the HC and LC variable domain sequences are components of the same polypeptide chain.

In some embodiments, the plasma kallikrein binding protein has a serum residence time of 1 week, 2 weeks, 3 weeks, 4 weeks, 5 weeks or more, in vivo, e.g., in humans. In one embodiment, the plasma kallikrein binding protein is an IgG, e.g., an IgG1, IgG2, IgG3 or IgG4, that has a serum residence time of 1 week, 2 weeks, 3 weeks, 4 weeks, 5 weeks or more in vivo, e.g., in humans.

In some embodiments, the plasma kallikrein bindihng protein is physically associated with a moiety that improves serum residence time, e.g., a moiety described herein.

In another embodiment, the HC and LC variable domain sequences are components of different polypeptide chains. For example, the protein is an IgG, e.g., IgG1, IgG2, IgG3, or IgG4. The protein can be a soluble Fab (sFab).

In other implementations the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions.

In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions.

In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In one embodiment, the protein includes human framework regions, or framework regions that are at least 95, 96, 97, 98, or 99% identical to human framework regions.

In certain embodiments, the protein includes no sequences from mice or rabbits (e.g., is not a murine or rabbit antibody).

In certain embodiments, the protein is capable of binding to a cell or tissue, e.g., that expresses plasma kallikrein.

In one embodiment, protein is physically associated with a nanoparticle, and can be used to guide a nanoparticle to a cell or tissue expressing plasma kallikrein.

In some aspects, the disclosure features a method of treating or preventing rheumatoid arthritis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for rheumatoid arthritis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing gout in a subject, the method comprising:
  administering an isolated protein (e.g., antibody, e.g., human antibody) comprising a heavy chain immunoglobulin variable domain sequence and a light chain immunoglobulin variable domain sequence to the subject, wherein:
    the heavy chain immunoglobulin variable domain sequence comprises one, two, or three (e.g., three) CDR regions from the heavy chain variable domain of a protein described herein, and/or
    the light chain immunoglobulin variable domain sequence comprises one, two, or three (e.g., three) CDR regions from the light chain variable domain of a protein described herein,
      wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for gout.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing intestinal bowel disease in a subject, the method comprising:
  administering an isolated protein (e.g., antibody, e.g., human antibody) comprising a heavy chain immunoglobulin variable domain sequence and a light chain immunoglobulin variable domain sequence to the subject, wherein:
    the heavy chain immunoglobulin variable domain sequence comprises one, two, or three (e.g., three) CDR regions from the heavy chain variable domain of a protein described herein, and/or
    the light chain immunoglobulin variable domain sequence comprises one, two, or three (e.g., three) CDR regions from the light chain variable domain of a protein described herein,
      wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for intestinal bowel disease.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing oral mucositis in a subject, the method comprising:
  administering an isolated protein (e.g., antibody, e.g., human antibody) comprising a heavy chain immunoglobulin variable domain sequence and a light chain immunoglobulin variable domain sequence to the subject, wherein:
    the heavy chain immunoglobulin variable domain sequence comprises one, two, or three (e.g., three) CDR regions from the heavy chain variable domain of a protein described herein, and/or
    the light chain immunoglobulin variable domain sequence comprises one, two, or three (e.g., three) CDR regions from the light chain variable domain of a protein described herein,
      wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for oral mucositis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing neuropathic pain in a subject, the method comprising:
  administering an isolated protein (e.g., antibody, e.g., human antibody) comprising a heavy chain immunoglobulin variable domain sequence and a light chain immunoglobulin variable domain sequence to the subject, wherein:
    the heavy chain immunoglobulin variable domain sequence comprises one, two, or three (e.g., three) CDR regions from the heavy chain variable domain of a protein described herein, and/or
    the light chain immunoglobulin variable domain sequence comprises one, two, or three (e.g., three) CDR regions from the light chain variable domain of a protein described herein,
      wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for neuropathic pain.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing inflammatory pain in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for inflammatory pain.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing spinal stenosis-degenerative spine disease in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for spinal stenosis-degenerative spine disease.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing arterial or venous thrombosis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for arterial or venous thrombosis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing post operative ileus in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for post operative ileus.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing aortic aneurysm in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for aortic aneurysm.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing osteoarthritis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for osteoarthritis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing vasculitis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for vasculitis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing head trauma or peri-tumor brain edema in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for head trauma or peri-tumor brain edema.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing sepsis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for sepsis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing acute middle cerebral artery (MCA) ischemic event (stroke) in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for acute middle cerebral artery (MCA) ischemic event (stroke).

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing restenosis (e.g., after angioplasty) in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for restenosis (e.g., after angioplasty).

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing systemic lupus erythematosis nephritis in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for systemic lupus erythematosis nephritis.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of treating or preventing burn injury in a subject, the method comprising:

administering an isolated protein (e.g., antibody, e.g., human antibody) comprising a heavy chain immunoglobulin variable domain sequence and a light chain immunoglobulin variable domain sequence to the subject, wherein:

the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the protein is administered in combination with another treatment for burn injury.

In some embodiments, the protein inhibits plasma kallikrein (e.g., human plasma kallikrein and/or murine plasma kallikrein).

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the protein comprises the heavy chain of a protein described herein, and/or the light chain of a protein described herein.

In some aspects, the disclosure features a method of detecting plasma kallikrein in a sample, the method comprising: contacting the sample with a plasma kallikrein binding protein (e.g., a plasma kallikrein binding protein described herein); and detecting an interaction between the protein and the plasma kallikrein, if present.

In some embodiments, the protein includes a detectable label.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein). In some embodiments, the plasma kallikrein binding protein binds prekallikrein (e.g., human prekallikrein and/or murine prekallikrein) and the active form of plasma kallikrein (e.g., human plasma kallikrein and/or murine plasma kallikrein).

In some aspects, the disclosure features a method of detecting plasma kallikrein in a subject, the method comprising: administering a plasma kallikrein binding protein (e.g., a plasma kallikrein binding protein described herein) to a subject; and detecting an interaction between the protein and the plasma kallikrein in the subject, if present. For example, the detecting comprises imaging the subject.

In some embodiments, the protein further includes a detectable label.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein). In some embodiments, the plasma kallikrein binding protein binds prekallikrein (e.g., human prekallikrein and/or murine prekallikrein) and the active form of plasma kallikrein (e.g., human plasma kallikrein and/or murine plasma kallikrein).

In some aspects, the disclosure features a method of modulating plasma kallikrein activity, e.g., in a method of treating or preventing a plasma kallikrein associated disorder. The method includes: contacting plasma kallikrein with a plasma kallikrein binding protein (e.g., a plasma kallikrein binding protein described herein) (e.g., in a human subject), thereby modulating plasma kallikrein activity.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis/vasculitis, and burn injury.

In some embodiments, the plasma kallikrein binding protein reduces abberent clotting associated with the contact activation system (i.e., intrinsic activation system) by at least 10% as measured by e.g., an APTT clotting assay. In other embodiments, the plasma kallikrein binding protein reduces abberent clotting associated with the contact activation system by at least 20%, at least 30%, at least 40%, at least 50%, at least 60%, at least 70%, at least 80%, at least 90%, at least 95%, at least 99%, or even 100% (i.e., no detectable abberent clotting).

In some aspects, the disclosure features a method of treating a plasma kallikrein associated disorder, the method comprising administering, to a subject, a plasma kallikrein binding protein (e.g., a plasma kallikrein binding protein described herein) in an amount sufficient to treat a plasma kallikrein associated disorder in the subject. The method can further include providing to the subject a second therapy that is therapy for the plasma kallikrein associated disorder, e.g., as described herein.

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis/vasculitis, and burn injury.

In some aspects, the disclosure features a method of imaging a subject. The method includes administering a plasma kallikrein binding protein (e.g., a plasma kallikrein binding protein described herein) to the subject, and e.g., detecting an interaction between the protein and the plasma kallikrein in the subject, if present.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein). In some embodiments, the plasma kallikrein binding protein binds prekallikrein (e.g., human prekallikrein and/or murine prekallikrein) and the active form of plasma kallikrein (e.g., human plasma kallikrein and/or murine plasma kallikrein).

In some embodiments, the protein does not inhibit plasma kallikrein activity.

In some embodiments, the protein inhibits plasma kallikrein activity (e.g., human plasma kallikrein and/or murine plasma kallikrein).

In some embodiments, the plasma kallikrein binding protein may include a detectable label (e.g., a radionuclide or an MRI-detectable label).

In some embodiments, the subject has or is suspected of having a plasma kallikrein associated disorder. The method is useful, e.g., for diagnosis of a plasma kallikrein associated disorder.

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, and burn injury.

In some embodiments, the plasma kallikrein binding protein reduces abberent clotting associated with the contact activation system (i.e., intrinsic activation system) by at least 10% as measured by e.g., an APTT clotting assay (e.g., by at least 20%, at least 30%, at least 40%, at least 50%, at least 60%, at least 70%, at least 80%, at least 90%, at least 95%, at least 99%, or even 100% (i.e., no detectable abberent clotting)).

In some aspects, the disclosure features a method of imaging plasma kallikrein, e.g., in a subject or sample (e.g., biopsy sample). The method includes administering a plasma kallikrein binding protein (e.g., a plasma kallikrein binding protein described herein), e.g., to the subject or the sample, and detecting an interaction between the protein and the plasma kallikrein, if present.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein). In some embodiments, the plasma kallikrein binding protein binds prekallikrein (e.g., human prekallikrein and/or murine prekallikrein) and the active form of plasma kallikrein (e.g., human plasma kallikrein and/or murine plasma kallikrein).

In some embodiments, the protein does not inhibit plasma kallikrein activity. In some embodiments, the protein inhibits plasma kallikrein activity (e.g., human plasma kallikrein and/or murine plasma kallikrein).

In some embodiments, the plasma kallikrein binding protein may include a detectable label (e.g., a radionuclide or an MRI-detectable label).

In some embodiments, the subject has or is suspected of having a plasma kallikrein associated disorder. The method is useful, e.g., for diagnosis of a plasma kallikrein associated disorder.

In some embodiments, the plasma kallikrein associated disorder is selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, and burn injury.

In some embodiments, the plasma kallikrein binding protein reduces abberent clotting associated with the contact activation system (i.e., intrinsic activation system) by at least 10% as measured by e.g., an APTT clotting assay (e.g., by at least 20%, at least 30%, at least 40%, at least 50%, at least 60%, at least 70%, at least 80%, at least 90%, at least 95%, at least 99%, or even 100% (i.e., no detectable abberent clotting)).

In one aspect, the disclosure features the use of a plasma kallikrein binding protein described herein for the treatment of a disorder described herein, e.g., rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, or burn injury; or to promote wound healing.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein). In some embodiments, the plasma kallikrein binding protein binds prekallikrein (e.g., human prekallikrein and/or murine prekallikrein) and the active form of plasma kallikrein (e.g., human plasma kallikrein and/or murine plasma kallikrein).

In one aspect, the disclosure features the use of a plasma kallikrein binding protein described herein for the manufacture of a medicament for the treatment of a disorder described herein, e.g., rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, or burn injury; or for the manufacture of a medicament for wound healing.

In some embodiments, the plasma kallikrein binding protein reduces abberent clotting associated with the contact activation system (i.e., intrinsic activation system) by at least 10% as measured by e.g., an APTT clotting assay (e.g., by at least 20%, at least 30%, at least 40%, at least 50%, at least 60%, at least 70%, at least 80%, at least 90%, at least 95%, at least 99%, or even 100% (i.e., no detectable abberent clotting)).

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine plasma kallikrein).

The details of one or more embodiments of the invention are set forth in the accompanying drawings and the description below. Other features, objects, and advantages of the invention will be apparent from the description and drawings, and from the claims.

The contents of all cited references including literature references, issued patents, published or non-published patent applications cited throughout this application as well as those listed below are hereby expressly incorporated by reference in their entireties. In case of conflict, the present application, including any definitions herein, will control.

BRIEF DESCRIPTION OF DRAWINGS

FIG. 4 depicts the alignment of the light chain DNA sequence of nongermlined (X63-G06) and germlined, codon optimized (X81-B01) versions of the same antibody discovered using ROLIC affinity maturation. Positions indicated with an asterisk (*) are conserved, whereas blank spaces correspond to bases changed in X81-B01 due to either codon optimization or germlining.

FIG. 5 depicts the alignment of the light chain amino acid sequence of nongermlined (X63-G06) and germlined, codon optimized (X81-B01) versions of the same antibody discovered using ROLIC affinity maturation. Positions indicated with an asterisk (*) are conserved, whereas blank spaces correspond to amino acids changed in X81-B01 due to germlining. A total of 11 amino acids differ between the nongermlined (X63-G06) and germlined, codon optimized antibody (X81-B01).

FIG. 6 depicts the alignment of the heavy chain DNA sequence of nongermlined (X63-G06) and germlined, codon optimized (X81-B01) versions of the same antibody discovered using ROLIC affinity maturation. Positions indicated with an asterisk (*) are conserved, whereas blank spaces correspond to DNA bases changed in X81-B01 due to codon optimization.

FIG. 7 depicts the alignment of the heavy chain amino acid sequence of nongermlined (X63-G06) and germlined, codon optimized (X81-B01) versions of the same antibody discovered using ROLIC affinity maturation. Positions indicated with an asterisk (*) are conserved. The two antibodies have the same amino acid sequence in the heavy chain.

FIGS. 10A-10C depict ClustalW alignment of pKal sequences from different species. Positions indicated by a "*" are conserved positions between, whereas positions indicated ":" indicate conservative substitutions between species. Positions indicated by a "." have nonconservative substitutions in some species. Stretches of amino acids indicated by the symbol "@" were shown to be highly solvent exposed by solvent accessible surface area calculation. Stretches of amino acids indicated by a "+" were identified as potential epitopes of antibodies listed in Table 12. Amino acids highlighted in grey were found by solvent accessible surface area calculation to be buried when complexed with a Kunitz domain active site inhibitor. The underlined positions are the amino acids that form the catalytic triad (His434, Asp483, and Ser578, numbering based on the human sequence).

DETAILED DESCRIPTION

Definitions

Figure 1:
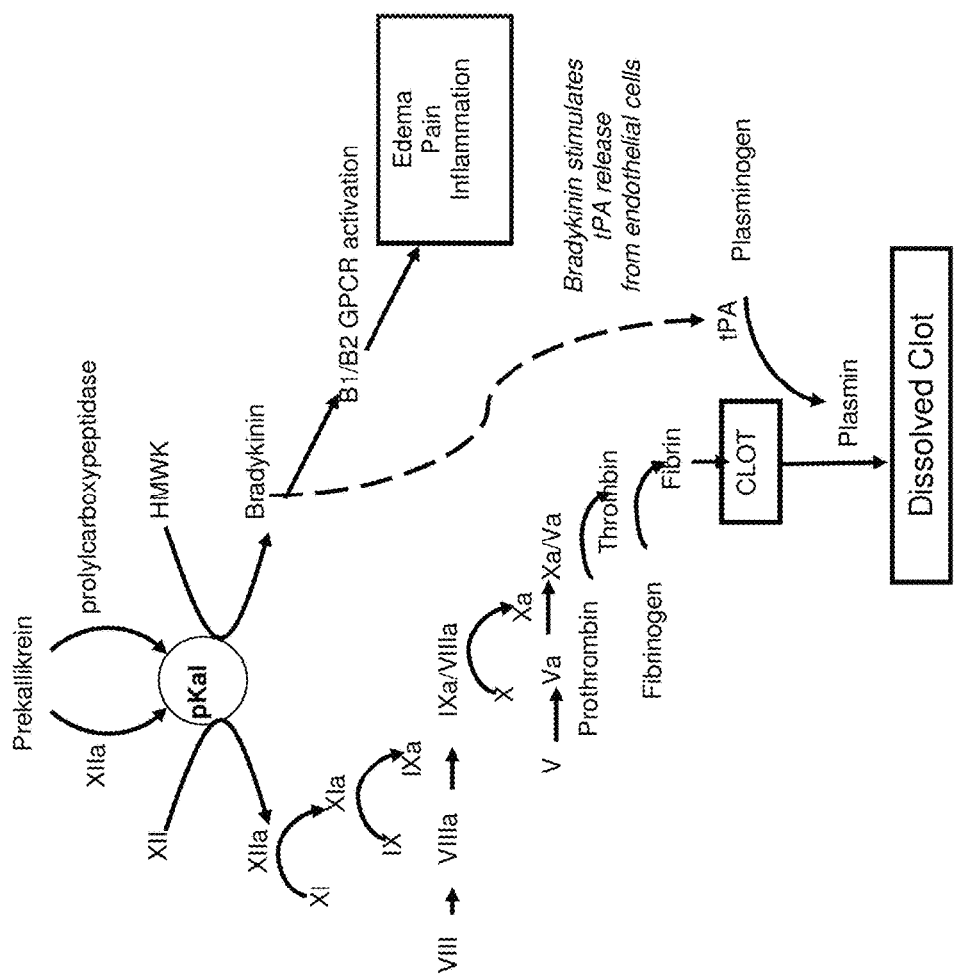
FIG. 1 is a schematic representation of the role of plasma kallikrein (pKal) in intrinsic coagulation pathway and inflammation.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

The term "agonist," as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound which increases at least one bioactivity of a protein. An agonist can also be a compound which increases the interaction of a polypeptide with another molecule, e.g., a target peptide or nucleic acid.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound which reduces the amount of expressed protein present.

The term "antibody" refers to a protein that includes at least one immunoglobulin variable domain (variable region) or immunoglobulin variable domain (variable region) sequence. For example, an antibody can include a heavy (H) chain variable region (abbreviated herein as VH or HV), and a light (L) chain variable region (abbreviated herein as VL or LV). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDRs"), interspersed with regions that are more conserved, termed "framework regions" ("FRs"). The extent of the framework region and CDRs have been defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with plasma kallikrein.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, and/or CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody and that retain functionality include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refers to a preparation of antibodies or fragments thereof of single molecular composition, irrespective of how the antibody was generated.

Antibodies are "germlined" by reverting one or more non-germline amino acids in framework regions to corresponding germline amino acids of the antibody, so long as binding properties are substantially retained.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

Where v=measured velocity; $v_o$=velocity in the absence of inhibitor; $K_{i,app}$=apparent inhibition constant; I=total inhibitor concentration; and E=total enzyme concentration.

As used herein, "binding affinity" refers to the apparent association constant or $K_A$. The $K_A$ is the reciprocal of the dissociation constant ($K_D$). A binding protein may, for example, have a binding affinity of at least $10^5$, $10^6$, $10^7$, $10^8$, $10^9$, $10^{10}$ and $10^{11}$ $M^{-1}$ for a particular target molecule, e.g., plasma kallikrein. Higher affinity binding of a binding protein to a first target relative to a second target can be indicated by a higher $K_A$ (or a smaller numerical value $K_D$) for binding the first target than the $K_A$ (or numerical value $K_D$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/K_A) + [\text{Free}]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein that can interact with a target molecule. This term is used interchangeably with "ligand." A "plasma kallikrein binding protein" refers to a protein that can interact with (e.g., bind) plasma kallikrein, and includes, in particular, proteins that preferentially or specifically interact with and/or inhibit plasma kallikrein. A protein inhibits plasma kallikrein if it causes a decrease in the activity of plasma kallikrein as compared to the activity of plasma kallikrein in the absence of the protein and under the same conditions. In some embodiments, the plasma kallikrein binding protein is an antibody.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues of a binding protein to include one or more mutations (e.g., substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity, can be predicted, e.g., by evaluating whether the mutation is conservative or by the method of Bowie, et al. (1990) Science 247:1306-1310.

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding protein (e.g., antibody) "binds to the same epitope" as a second binding protein (e.g., antibody) if the first binding protein binds to the same site on a target compound that the second binding protein binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding protein binds.

A first binding protein (e.g., antibody) "competes for binding" with a second binding protein (e.g., antibody) if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first binding protein binds to an epitope that is the same as, or overlaps with, the epitope bound by the second binding protein), or indirect (e.g., the binding of the first binding protein to its epitope causes a steric change in the target compound that decreases the ability of the second binding protein to bind to its epitope).

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human Descriptions of "humanized" immunoglobulins include, for example, U.S. Pat. Nos. 6,407,213 and 5,693,762.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interest is at least 5, 10, 25, 50, 75, 80, 90, 92, 95, 98, or 99% pure on a weight-weight basis.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

A "patient," "subject" or "host" (these terms are used interchangeably) to be treated by the subject method may mean either a human or non-human animal.

The terms "prekallikrein" and "preplasma kallikrein" are used interchangeably herein and refer to the zymogen form of active plasma kallikrein, which is also known as prekallikrein.

The term "preventing" or to "prevent" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In some embodiments, a plasma kallikrein binding protein can have about 85%, 90%, 91%, 92%, 93%, 94%, 95%, 96%, 97%, 98%, 99% or higher sequence identity to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a binding protein described herein. In some embodiments, a plasma kallikrein binding protein can have about 85%, 90%, 91%, 92%, 93%, 94%, 95%, 96%, 97%, 98%, 99% or higher sequence identity in the constant region (e.g., CH1, CH2, CH3, and/or CL1) to a binding protein described herein.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value <0.05 or 0.02). The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., rheumatoid arthritis or oral mucositis. Alternatively, this property of a composition can be evaluated by examining the ability of the compound to modulate a parameter in vitro.

"Treating" a disease (or condition) in a subject or "treating" a subject having a disease refers to subjecting the subject to a pharmaceutical treatment, e.g., the administration of a drug, such that at least one symptom of the disease is cured, alleviated or decreased.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

As used herein the term "DX-2922" as used inchangeably with the term "X101-A01". Other variants of this antibody are described below.

| Antibody Identification | Description |
| --- | --- |
| X63-G06 | Non-germlined Fab discovered using ROLIC, same HC but different LC as M160-G12 |
| X81-B01 | Germlined IgG produced in HEK 293T cells |
| X101-A01 | Germlined IgG produced in CHO cells, same HC and LC sequence as X81-B01 |
| DX-2922 | Alternate nomenclature for X101-A01 |

As used herein the term "DX-2930" as used inchangeably with the term "X124-G01". Other variants of this antibody are described below.

| Antibody Identification | Description |
| --- | --- |
| M162-A04 | Non-germlined Fab discovered using phage display |
| M199-A08 | Heavy chain CDR3 varied Fab derived by affinity maturation of M162-A04 |
| X115-F02 | Germlined Fab produced in 293T cells, same variable heavy chain as X124-G01 |
| X124-G01 or DX-2930 | Germlined IgG produced in CHO cells, same variable heavy chain as X115-F02, same variable LC as X115-F02 except C-terminal Lys is removed |

As used herein the term "unstructured recombinant polymer" (URP) refers to an amino acid sequence that lacks a secondary structure and shares commonality with denatured peptide sequences, e.g., exhibiting a typical behavior like denatured peptide sequences, under physiological conditions. URP sequences lack a defined tertiary structure and they have limited or no secondary structure as detected by, e.g., Chou-Fasman algorithm.

Plasma Kallikrein Binding Proteins

Plasma kallikrein binding proteins can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment. The binding protein can include two heavy chain immunoglobulins and two light chain immunoglobulins, or can be a single chain antibody. Plasma kallikrein binding proteins can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding protein is a monoclonal antibody.

In one aspect, the disclosure features a protein (e.g., an isolated protein) that binds to plasma kallikrein (e.g., human plasma kallikrein and/or murine kallikrein) and includes at least one immunoglobulin variable region. For example, the protein includes a heavy chain (HC) immunoglobulin variable domain sequence and/or a light chain (LC) immunoglobulin variable domain sequence. In one embodiment, the protein binds to and inhibits plasma kallikrein, e.g., human plasma kallikrein and/or murine kallikrein.

The protein can include one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

The plasma kallikrein binding protein may be an isolated protein (e.g., at least 70, 80, 90, 95, or 99% free of other proteins). In some embodiments, the plasma kallikrein binding protein, or composition thereof, is isolated from antibody cleavage fragments (e.g., cleaved DX-2922) that are inactive or partially active (e.g., bind plasma kallikrein with a Ki, app of 5000 nM or greater) compared to the plasma kallikrein binding protein. For example, the plasma kallikrein binding protein is at least 70% free of such antibody cleavage fragments; in other embodiments the binding protein is at least 80%, at least 90%, at least 95%, at least 99% or even 100% free from antibody cleavage fragments that are inactive or partially active.

The plasma kallikrein binding protein may additionally inhibit plasma kallikrein, e.g., human plasma kallikrein.

In some embodiments, the plasma kallikrein binding protein does not bind prekallikrein (e.g., human prekallikrein and/or murine prekallikrein), but binds to the active form of plasma kallikrein (e.g., human plasma kallikrein and/or murine kallikrein).

In certain embodiments, the protein binds at or near the active site of the catalytic domain of plasma kallikrein, or a fragment thereof, or binds an epitope that overlaps with the active site of plasma kallikrein.

In some aspects, the protein binds the same epitope or competes for binding with a protein described herein.

In some embodiments, the protein competes with or binds the same epitope as M162-A04, M160-G12, M142-H08, X63-G06, X101-A01, X81-B01, X67-D03, X67-G04, X115-B07, X115-D05, X115-E09, X115-H06, X115-A03, X115-D01, X115-F02, X115-G04, M29-D09, M145-D11, M06-D09 and M35-G04.

In some embodiments, the protein binds to (e.g., positions on plasma kallikrein corresponding to) CLIPS peptide C1, C2, C3, C4, C5, C6, or C7, or more than one of these peptides, e.g., the protein binds to C5 and C6. CLIPS peptides C1-C7 are peptides in plasma kallikrein identified by CLIPS epitope mapping (see FIGS. 9 and 10A-10C). C1 corresponds to positions 55-67 of the catalytic domain, C2 to positions 81-94, C3 to positions 101-108, C4 to positions 137-151, C5 to positions 162-178, C6 to positions 186-197, and C7 to positions 214-217 of plasma kallikrein.

Figure 9:
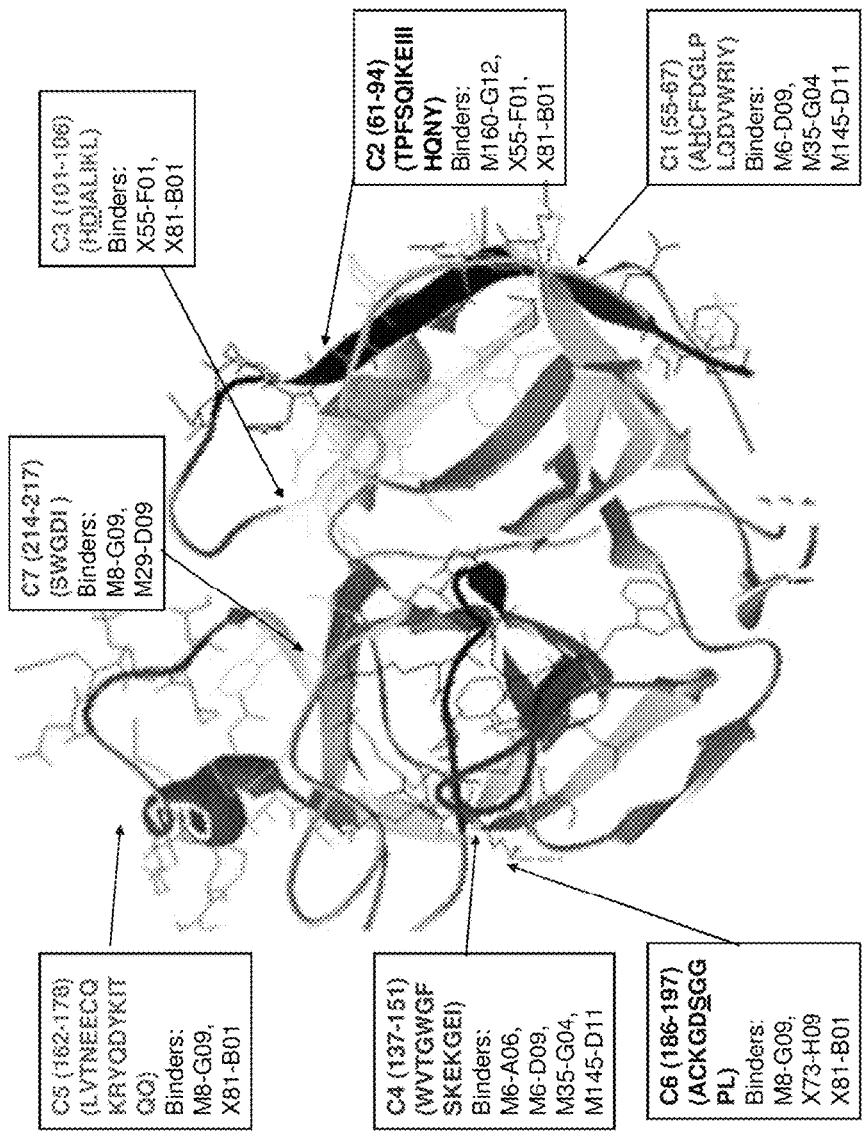
FIG. 9 depicts the results of CLIPS epitope mapping for antibodies listed in Table 12.

In some embodiments, the protein binds to an epitope shown in FIG. 9.

In some embodiments, the protein binds to one or more amino acids that form the catalytic triad of plasma kallikrein: His434, Asp483, and/or Ser578 (numbering based on the human sequence).

In some embodiments, the protein binds one or more amino acids of: Arg551, Gln553, Tyr555, Thr558, and/or Arg560 (numbering based on the human sequence). In some embodiments, the plasma kallikrein binding protein binds one or more amino acids of: S478, N481, S525, and K526 (numbering based on the human kallikrein sequence).

In some embodiments, the protein binds to one or more amino acids of Ser479, Tyr563, and/or Asp585 (numbering based on the human sequence).

The active site cleft of plasma kallikrein contains three amino acids that form the catalytic triad (His434, Asp483, and Ser578) and result in enzymatic hydrolysis of bound substrate (catalytic triad residues are underlined in FIG. 10). The peptides selected for the CLIPS epitope mapping analysis were determined to be surface accessible and either form or surround the vicinity of the active site. Peptide C1 contains the active site histidine 434. Peptide C3 contains the active site aspartate 483. Peptide C6 contains the active site serine 578. It is possible for an antibody to bind multiple surface exposed amino acids that are discontinuous in amino acid sequence. For example, by CLIPs analysis, X81-B01 appears to bind the C2, C3, C5 and the C6 peptides.

In some embodiments, the protein binds to an epitope that includes one or more amino acids from CLIPS peptide C1, peptide C2, peptide C3, peptide C4, peptide C5, peptide C6, or peptide C7.

In some embodiments, the protein binds to an epitope that includes amino acids from at least 2 different CLIPS peptides, e.g., from at least two of peptide C1, peptide C2, peptide C3, peptide C4, peptide C5, peptide C6, or peptide C7.

The protein can bind to plasma kallikrein, e.g., human plasma kallikrein, with a binding affinity of at least $10^5$, $10^6$, $10^7$, $10^8$, $10^9$, $10^{10}$ and $10^{11}$ M. In one embodiment, the protein binds to human plasma kallikrein with a $K_{off}$ slower than $1\times10^{-3}$, $5\times10^{-4}$ s$^{-1}$, or $1\times10^{-4}$ s$^{-1}$. In one embodiment, the protein binds to human plasma kallikrein with a $K_{on}$ faster than $1\times10^2$, $1\times10^3$, or $5\times10^3$ M$^{-1}$ s$^{-1}$. In one embodiment, the protein binds to plasma kallikrein, but does not bind to tissue kallikrein and/or plasma prekallikrein (e.g., the protein binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the protein inhibits human plasma kallikrein activity, e.g., with a Ki of less than $10^{-5}$, $10^{-6}$, $10^{-7}$, $10^{-8}$, $10^{-9}$, and $10^{-10}$ M. The protein can have, for example, an IC$_{50}$ of less than 100 nM, 10 nM, 1, 0.5, or 0.2 nM. For example, the protein may modulate plasma kallikrein activity, as well as the production of Factor XIIa (e.g., from Factor XII) and/or bradykinin (e.g., from high-molecular-weight kininogen (HMWK)). The protein may inhibit plasma kallikrein activity, and/or the production of Factor XIIa (e.g., from Factor XII) and/or bradykinin (e.g., from high-molecular-weight kininogen (HMWK)). The affinity of the protein for human plasma kallikrein can be characterized by a $K_D$ of less than 100 nm, less than 10 nM, less than 5 nM, less than 1 nM, less than 0.5 nM. In one embodiment, the protein inhibits plasma kallikrein, but does not inhibit tissue kallikrein (e.g., the protein inhibits tissue kallikrein less effectively (e.g., 5-, 10-, 50-, 100-, or 1000-fold less or not at all, e.g., as compared to a negative control) than it inhibits plasma kallikrein.

In some embodiments, the protein has an apparent inhibition constant ($K_{i,app}$) of less than 1000, 500, 100, 5, 1, 0.5 or 0.2 nM.

Plasma kallikrein binding proteins may be antibodies. Plasma kallikrein binding antibodies may have their HC and LC variable domain sequences included in a single polypeptide (e.g., scFv), or on different polypeptides (e.g., IgG or Fab).

In a preferred embodiment, the protein is an antibody (e.g., a human antibody) having the light and heavy chains of antibodies selected from the group consisting of M162-A04, M199-A08, M160-G12, M142-H08 X63-G06, X101-A01, X81-B01, X67-D03, X67-G04, DX-2922, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the heavy chain of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having the light chain of an antibody selected from the group consisting of: M162-A04, M199-A08, M160-G12, M142-H08 X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having light and heavy antibody variable regions of an antibody selected from the group consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a heavy chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having a light chain antibody variable region of an antibody selected from the group consisting of: M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In a preferred embodiment, the protein is an antibody (e.g., a human antibody) having one or more (e.g., 1, 2, or 3) heavy chain CDRs and one or more (e.g., 1, 2, or 3) light chain CDRs selected from the corresponding CDRs of the group of light chains consisting of M162-A04, M199-A08, M160-G12, M142-H08, X63-G06, X101-A01, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab. In other implementations the protein includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC:: HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions, or framework regions at least 85, 88, 89, 90, 91, 92, 93, 94, 95, 96, 97, 98, 99% identical to human framework regions. In one embodiment, the protein includes a human Fc domain, or an Fc domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (Gorilla gorilla), gibons, monkeys, lemurs, aye-ayes (Daubentonia *madagascariensis*), and tarsiers.

In some embodiments, the affinity of the primate antibody for human plasma kallikrein is characterized by a $K_D$ of less than 1000, 500, 100, 10, 5, 1, 0.5 nM, e.g., less than 10 nM, less than 1 nM, or less than 0.5 nM.

In certain embodiments, the protein includes no sequences from mice or rabbits (e.g., is not a murine or rabbit body).

In some aspects, the disclosure provides the use of proteins (e.g., binding proteins, e.g., antibodies) (e.g., the proteins described herein) that bind to plasma kallikrein (e.g., human plasma kallikrein) and include at least one immunoglobin variable region in methods for treating (or preventing) a plasma kallikrein associated disorder or condition. For example, the plasma kallikrein binding protein includes a heavy chain (HC) immunoglobulin variable domain sequence and a light chain (LC) immunoglobulin variable domain sequence. A number of exemplary plasma kallikrein binding proteins are described herein.

The plasma kallikrein binding protein may be an isolated protein (e.g., at least 70, 80, 90, 95, or 99% free of other proteins).

The plasma kallikrein binding protein may additionally inhibit plasma kallikrein, e.g., human plasma kallikrein and/or murine plasma kallikrein. In some embodiments, it may be preferred to have an plasma kallikrein binding protein bind to both human and murine plasma kallikrein, as these antibodies can be tested for efficacy in a mouse model.

Plasma Kallikrein

Exemplary plasma kallikrein sequences against which plasma kallikrein binding proteins may be developed can include human, mouse, or rat plasma kallikrein amino acid sequences, a sequence that is 80%, 85%, 90%, 95%, 96%, 97%, 98%, or 99% identical to one of these sequences, or a fragment thereof, e.g., of a sequence provided below.

The sequence of human plasma kallikrein that was used in selections and subsequent screening is shown below (accession number NP_000883.2). The human plasma kallikrein (86 kDa) that was used was purified from human plasma and activated with factor XIIa by a commercial vendor. Factor XIIa activates prekallikrein by cleaving the polypeptide sequence at a single site (between Arg371-Ile372, cleavage site marked by "/" in the sequence below) to generate active plasma kallikrein, which then consists of two disulfide linked polypeptides; a heavy chain of approximately 52 kDa and a catalytic domain of approximately 34 kDa [Colman and Schmaier, (1997) "Contact System: A Vascular Biology Modulator With Anticoagulant, Profibrinolytic, Antiadhesive, and Proinflammatory Attributes" Blood, 90, 3819-3843]

GCLTQLYENAFFRGGDVASMYTPNAQYCQMRCTFHPRCLLFSFLPASSI

NDMEKRFGCFLKDSVTGTLPKVHRTGAVSGHSLKQCGHQISACHRDIYK

GVDMRGVNFNVSKVSSVEECQKRCTSNIRCQFFSYATQTFHKAEYRNNC

LLKYSPGGTPTAIKVLSNVESGFSLKPCALSEIGCHMNIFQHLAFSDVD

```
VARVLTPDAFVCRTICTYHPNCLFFTFYTNVWKIESQRNVCLLKTSESG

TPSSSTPQENTISGYSLLTCKRTLPEPCHSKIYPGVDFGGEELNVTFVK

GVNVCQETCTKMIRCQFFTYSLLPEDCKEEKCKCFLRLSMDGSPTRIAY

GTQGSSGYSLRLCNTGDNSVCTTKTSTR/IVGGTNSSWGEWPWQVSLQV

KLTAQRHLCGGSLIGHQWVLTAAHCFDGLPLQDVWRIYSGILNLSDITK

DTPFSQIKEIIIHQNYKVSEGNHDIALIKLQAPLNYTEFQKPICLPSKG

DTSTIYTNCWVTGWGFSKEKGEIQNILQKVNIPLVTNEECQKRYQDYKI

TQRMVCAGYKEGGKDACKGDSGGPLVCKHNGMWRLVGITSWGEGCARRE

QPGVYTKVAEYMDWILEKTQSSDGKAQMQSPA
```

The human, mouse, and rat prekallikrein amino acid sequences, and the mRNA sequences encoding the same, are illustrated below. The sequences of prekallikrein are the same as plasma kallikrein, except that active plasma kallikrein (pkal) has the single polypeptide chain cleaved at a single position (indicated by the "/") to generate two chains. The sequences provided below are full sequences that include signal sequences. On secretion from the expressing cell, it is expected that the signal sequences are removed.

```
Human plasma kallikrein (ACCESSION: NP_000883.2)
>gi|78191798|ref|NP_000883.2| plasma kallikrein B1
precursor [Homo sapiens]
MILFKQATYFISLFATVSCGCLTQLYENAFFRGGDVASMYTPNAQYCQM

RCTFHPRCLLFSFLPASSINDMEKREGCFLKDSVTGTLPKVHRTGAVSG

HSLKQCGHQISACHRDIYKGVDMRGVNENVSKVSSVEECQKRCTSNIRC

QFFSYATQTFHKAEYRNNCLLKYSPGGTPTAIKVLSNVESGESLKPCAL

SEIGCHMNIFQHLAFSDVDVARVLTPDAFVCRTICTYHPNCLFFTFYTN

VWKIESQRNVCLLKTSESGTPSSSTPQENTISGYSLLTCKRTLPEPCHS

KIYPGVDEGGEELNVTFVKGVNVCQETCTKMIRCQFFTYSLLPEDCKEE

KCKCFLRLSMDGSPTRIAYGTQGSSGYSLRLCNTGDNSVCTTKTSTRIV

GGTNSSWGEWPWQVSLQVKLTAQRHLCGGSLIGHQWVLTAAHCFDGLPL

QDVWRIYSGILNLSDITKDTPFSQIKEIIIHQNYKVSEGNHDIALIKLQ

APLNYTEFQKPICLPSKGDTSTIYTNCWVTGWGESKEKGEIQNILQKVN

IPLVTNEECQKRYQDYKITQRMVCAGYKEGGKDACKGDSGGPLVCKHNG

MWRLVGITSWGEGCARREQPGVYTKVAEYMDWILEKTQSSDGKAQMQSP

A

Human plasma kallikrein mRNA (ACCESSION:
NM_000892)
>gi|78191797|ref|NM_000892.3| Homo sapiens
kallikrein B, plasma (Fletcher factor) 1 (KLKB1),
mRNA
AGAACAGCTTGAAGACCGTTCATTTTTAAGTGACAAGAGACTCACCTCC

AAGAAGCAATTGTGTTTTCAGAATGATTTTATTCAAGCAAGCAACTTAT

TTCATTTCCTTGTTTGCTACAGTTTCCTGTGGATGTCTGACTCAACTCT

ATGAAAACGCCTTCTTCAGAGGTGGGGATGTAGCTTCCATGTACACCCC

AAATGCCCAATACTGCCAGATGAGGTGCACATTCCACCCAAGGTGTTTG

CTATTCAGTTTTCTTCCAGCAAGTTCAATCAATGACATGGAGAAAAGGT

TTGGTTGCTTCTTGAAAGATAGTGTTACAGGAACCCTGCCAAAAGTACA

TCGAACAGGTGCAGTTTCTGGACATTCCTTGAAGCAATGTGGTCATCAA

ATAAGTGCTTGCCATCGAGACATTTATAAAGGAGTTGATATGAGAGGAG

TCAATTTTAATGTGTCTAAGGTTAGCAGTGTTGAAGAATGCCAAAAAAG

GTGCACCAGTAACATTCGCTGCCAGTTTTTTTCATATGCCACGCAAACA

TTTCACAAGGCAGAGTACCGGAACAATTGCCTATTAAAGTACAGTCCCG

GAGGAACACCTACCGCTATAAAGGTGCTGAGTAACGTGGAATCTGGATT

CTCACTGAAGCCCTGTGCCCTTTCAGAAATTGGTTGCCACATGAACATC

TTCCAGCATCTTGCGTTCTCAGATGTGGATGTTGCCAGGGTTCTCACTC

CAGATGCTTTTGTGTGTCGGACCATCTGCACCTATCACCCCAACTGCCT

CTTCTTTACATTCTATACAAATGTATGGAAAATCGAGTCACAAAGAAAT

GTTTGTCTTCTTAAAAACATCTGAAAGTGGCACACCAAGTTCCTCTACTC

CTCAAGAAAACACCATATCTGGATATAGCCTTTTAACCTGCAAAAGAAC

TTTACCTGAACCCTGCCATTCTAAAATTTACCCGGGAGTTGACTTTGGA

GGAGAAGAATTGAATGTGACTTTTGTTAAAGGAGTGAATGTTTGCCAAG

AGACTTGCACAAAGATGATTCGCTGTCAGTTTTTCACTTATTCTTTACT

CCCAGAAGACTGTAAGGAAGAGAAGTGTAAGTGTTTCTTAAGATTATCT

ATGGATGGTTCTCCAACTAGGATTGCGTATGGGACACAAGGGAGCTCTG

GTTACTCTTTGAGATTGTGTAACACTGGGGACAACTCTGTCTGCACAAC

AAAAACAAGCACACGCATTGTTGGAGGAACAAACTCTTCTTGGGGAGAG

TGGCCCTGGCAGGTGAGCCTGCAGGTGAAGCTGACAGCTCAGAGGCACC

TGTGTGGAGGGTCACTCATAGGACACCAGTGGGTCCTCACTGCTGCCCA

CTGCTTTGATGGGCTTCCCCTGCAGGATGTTTGGCGCATCTATAGTGGC

ATTTTAAATCTGTCAGACATTACAAAAGATACACCTTTCTCACAAATAA

AAGAGATTATTATTCACCAAAACTATAAAGTCTCAGAAGGGAATCATGA

TATCGCCTTGATAAAACTCCAGGCTCCTTTGAATTACACTGAATTCCAA

AAACCAATATGCCTACCTTCCAAAGGTGACACAAGCACAATTTATACCA

ACTGTTGGGTAACCGGATGGGGCTTCTCGAAGGAGAAAGGTGAAATCCA

AAATATTCTACAAAAGGTAAATATTCCTTTGGTAACAAATGAAGAATGC

CAGAAAAGATATCAAGATTATAAAATAACCCAACGGATGGTCTGTGCTG

GCTATAAAGAAGGGGAAAAGATGCTTGTAAGGGAGATTCAGGTGGTCC

CTTAGTTTGCAAACACAATGGAATGTGGCGTTTGGTGGGCATCACCAGC

TGGGGTGAAGGCTGTGCCCGCAGGGAGCAACCTGGTGTCTACACCAAAG

TCGCTGAGTACATGGACTGGATTTTAGAGAAAACACAGAGCAGTGATGG

AAAAGCTCAGATGCAGTCACCAGCATGAGAAGCAGTCCAGAGTCTAGGC

AATTTTTACAACCTGAGTTCAAGTCAAATTCTGAGCCTGGGGGGTCCTC

ATCTGCAAAGCATGGAGAGTGGCATCTTCTTTGCATCCTAAGGACGAAA

AACACAGTGCACTCAGAGCTGCTGAGGACAATGTCTGGCTGAAGCCCGC

TTTCAGCACGCCGTAACCAGGGGCTGACAATGCGAGGTCGCAACTGAGA

TCTCCATGACTGTGTGTTGTGAAATAAAATGGTGAAAGATCAAAAAA
```

Mouse plasma kallikrein (ACCESSION: NP_032481.1)
>gi|16680584|ref|NP_032481.1| kallikrein B, plasma
1 [Mus musculus]
MILFNRVGYFVSLFATVSCGCMTQLYKNTFFRGGDLAAIYTPDAQYCQK
MCTFHPRCLLFSFLAVTPPKETNKRFGCFMKESITGTLPRIHRTGAISG
HSLKQCGHQISACHRDIYKGLDMRGSNFNISKTDNIEECQKLCTNNFHC
QFFTYATSAFYRPEYRKKCLLKHSASGTPTSIKSADNLVSGFSLKSCAL
SEIGCPMDIFQHSAFADLNVSQVITPDAFVCRTICTFHPNCLFFTFYTN
EWETESQRNVCFLKTSKSGRPSPPIPQENAISGYSLLTCRKTRPEPCHS
KIYSGVDFEGEELNVTFVQGADVCQETCTKTIRCQFFIYSLLPQDCKEE
GCKCSLRLSTDGSPTRITYGMQGSSGYSLRLCKLVDSPDCTTKINARIV
GGTNASLGEWPWQVSLQVKLVSQTHLCGGSIIGRQWVLTAAHCFDGIPY
PDVWRIYGGILSLSEITKETPSSRIKELIIHQEYKVSEGNYDIALIKLQ
TPLNYTEFQKPICLPSKADTNTIYTNCWVTGWGYTKEQGETQNILQKAT
IPLVPNEECQKKYRDYVINKQMICAGYKEGGTDACKGDSGGPLVCKHSG
RWQLVGITSWGEGCGRKDQPGVYTKVSEYMDWILEKTQSSDVRALETSS
A Mouse plasma kallikrein mRNA (ACCESSION:
NM_008455.2)
>gi|236465804|ref|NM_008455.2| Mus musculus
kallikrein B, plasma 1 (Klkb1), mRNA
AGACCGCCTCGGTGCCATATTCAGAGGGCTTGAAGACCATCTTCATGT
GAAGACTCCCTCTCCTCCAGAACCACAACGTGACCATCCTTCCAGGATG
ATTTTATTCAACCGAGTGGGTTATTTTGTTTCCTTGTTTGCTACCGTCT
CCTGTGGGTGTATGACTCAACTGTATAAAAATACCTTCTTCAGAGGTGG
GGATCTAGCTGCCATCTACACCCCAGATGCCCAGTACTGTCAGAAGATG
TGCACTTTTCACCCCAGGTGCCTGCTGTTCAGCTTTCTCGCCGTGACTC
CACCCAAAGAGACAAATAAACGGTTTGGTTGCTTCATGAAAGAGAGCAT
TACAGGGACTTTGCCAAGAATACACCGGACAGGGGCCATTTCTGGTCAT
TCTTTAAAGCAGTGTGGCCATCAAATAAGTGCTTGCCACCGAGACATAT
ACAAAGGACTTGATATGAGAGGGTCCAACTTTAATATCTCTAAGACCGA
CAATATTGAAGAATGCCAGAAACTGTGCACAAATAATTTTCACTGCCAA
TTTTTCACATATGCTACAAGTGCATTTTACAGACCAGAGTACCGGAAGA
AGTGCCTGCTGAAGCACAGTGCAAGCGGAACACCCACCAGCATAAAGTC
AGCGGACAACCTGGTGTCTGGATTCTCACTGAAGTCCTGTGCGCTTTCG
GAGATAGGTTGCCCCATGGATATTTTCCAGCACTCTGCCTTTGCAGACC
TGAATGTAAGCCAGGTCATCACCCCCGATGCCTTTGTGTGTCGCACCAT
CTGCACCTTCCATCCCAACTGCCTTTTCTTCACGTTCTACACGAATGAA
TGGGAGACAGAATCACAGAGAAATGTTTGTTTTCTTAAGACGTCTAAAA
GTGGAAGACCAAGTCCCCCTATTCCTCAAGAAACGCTATATCTGGATA
TAGTCTCCTCACCTGCAGAAAAACTCGCCCTGAACCCTGCCATTCCAAA
ATTTACTCTGGAGTTGACTTTGAAGGGGAAGAACTGAATGTGACCTTCG
TGCAAGGAGCAGATGTCTGCCAAGAGACTTGTACAAAGACAATCCGCTG
CCAGTTTTTTATTTACTCCTTACTCCCCCAAGACTGCAAGGAGGAGGGG TGTAAATGTTCCTTAAGGTTATCCACAGATGGCTCCCCAACTAGGATCA
CCTATGGCATGCAGGGGAGCTCCGGTTATTCTCTGAGATTGTGTAAACT
TGTGGACAGCCCTGACTGTACAACAAAAATAAATGCACGTATTGTGGGA
GGAACAAACGCTTCTTTAGGGGAGTGGCCATGGCAGGTCAGCCTGCAAG
TGAAGCTGGTATCTCAGACCCATTTGTGTGGAGGGTCCATCATTGGTCG
CCAATGGGTACTGACAGCTGCCCATTGCTTTGATGGAATTCCCTATCCA
GATGTGTGGCGTATATATGGCGGAATTCTTAGTCTGTCCGAGATTACGA
AAGAAACGCCTTCCTCGAGAATAAAGGAGCTTATTATTCATCAGGAATA
CAAAGTCTCAGAAGGCAATTATGATATTGCCTTAATAAAGCTTCAGACG
CCCCTGAATTATACTGAATTCCAAAAACCAATATGCCTGCCTTCCAAAG
CTGACACAAATACAATTTATACCAACTGTTGGGTGACTGGATGGGGCTA
CACGAAGGAACAAGGTGAAACGCAAAATATTCTACAAAAGGCTACTATT
CCTTTGGTACCAAATGAAGAATGCCAGAAAAAATACAGAGATTATGTTA
TAAACAAGCAGATGATCTGTGCTGGCTACAAAGAAGGCGGAACAGACGC
TTGTAAGGGAGATTCCGGTGGCCCCTAGTCTGTAAACACAGTGGACGG
TGGCAGTTGGTGGGTATCACCAGCTGGGGTGAAGGCTGCGCCCGCAAGG
ACCAACCAGGAGTCTACACCAAAGTTTCTGAGTACATGGACTGGATATT
GGAGAAGACACAGAGCAGTGATGTAAGAGCTCTGGAGACATCTTCAGCC
TGAGGAGGCTGGGTACCAAGGAGGAAGAACCCAGCTGGCTTTACCACCT
GCCCTCAAGGCAAACTAGAGCTCCAGGATTCTCGGCTGTAAAATGTTGA
TAATGGTGTCTACCTCACATCCGTATCATTGGATTGAAAATTCAAGTGT
AGATATAGTTGCTGAAGACAGCGTTTTGCTCAAGTGTGTTTCCTGCCTT
GAGTCACAGGAGCTCCAATGGGAGCATTACAAAGATCACCAAGCTTGTT
AGGAAAGAGAATGATCAAAGGGTTTTATTAGGTAATGAAATGTCTAGAT
GTGATGCAATTGAAAAAAAGACCCCAGATTCTAGCACAGTCCTTGGGAC
CATTCTCATGTAACTGTTGACTCTGGACCTCAGCAGATCTCAGAGTTAC
CTGTCCACTTCTGACATTTGTTTATTAGAGCCTGATGCTATTCTTTCAA
GTGGAGCAAAAAAAAAAAAAA Rat plasma kallikrein (ACCESSION: NP 036857.2)
>gi|162138905|ref|NP_036857.2| kallikrein B,
plasma 1 [Rattus norvegicus]
MILFKQVGYFVSLFATVSCGCLSQLYANTFFRGGDLAAIYTPDAQHCQK
MCTFHPRCLLFSFLAVSPTKETDKRFGCFMKESITGTLPRIHRTGAISG
HSLKQCGHQLSACHQDIYEGLDMRGSNFNISKTDSIEECQKLCTNNIHC
QFFTYATKAFHRPEYRKSCLLKRSSSGTPTSIKPVDNLVSGFSLKSCAL
SEIGCPMDIFQHFAFADLNVSHVVTPDAFVCRTVCTFHPNCLFFTFYTN
EWETESQRNVCFLKTSKSGRPSPPIIQENAVSGYSLFTCRKARPEPCHF
KIYSGVAFEGEELNATFVQGADACQETCTKTIRCQFFTYSLLPQDCKAE
GCKCSLRLSTDGSPTRITYEAQGSSGYSLRLCKVVESSDCTTKINARIV
GGTNSSLGEWPWQVSLQVKLVSQNHMCGGSIIGRQWILTAAHCFDGIPY
PDVWRIYGGILNLSEITNKTPFSSIKELIIHQKYKMSEGSYDIALIKLQ
TPLNYTEFQKPICLPSKADTNTIYTNCWVTGWGYTKERGETQNILQKAT

```
IPLVPNEECQKKYRDYVITKQMICAGYKEGGIDACKGDSGGPLVCKHSG

RWQLVGITSWGEGCARKEQPGVYTKVAEYIDWILEKIQSSKERALETSP

A

Rat plasma kallikrein mRNA (ACCESSION: NM_012725)
>gi|162138904|ref|NM_012725.2| Rattus norvegicus
kallikrein B, plasma 1 (Klkb1), mRNA
TGAAGACTAGCTTCATGTGAAGACTCCTTCTCCTCCAGCAGCACAAAGC

AACCATCCTTCCAGGATGATTTTATTCAAACAAGTGGGTTATTTTGTTT

CCTTGTTCGCTACAGTTTCCTGTGGGTGTCTGTCACAACTGTATGCAAA

TACCTTCTTCAGAGGTGGGGATCTGGCTGCCATCTACACCCCGGATGCC

CAGCACTGTCAGAAGATGTGCACGTTTCACCCCAGGTGCCTGCTCTTCA

GCTTCCTTGCCGTGAGTCCAACCAAGGAGACAGATAAAAGGTTTGGGTG

CTTCATGAAAGAGAGCATTACAGGGACTTTGCCAAGAATACACCGGACA

GGGGCCATTTCTGGTCATTCTTTAAAACAGTGTGGCCATCAATTAAGTG

CTTGCCACCAAGACATATACGAAGGACTGGATATGAGAGGGTCCAACTT

TAATATATCTAAGACCGACAGTATTGAAGAATGCCAGAAACTGTGCACA

AATAATATTCACTGCCAATTTTTCACATATGCTACAAAAGCATTTCACA

GACCAGAGTACAGGAAGAGTTGCCTGCTGAAGCGCAGTTCAAGTGGAAC

GCCCACCAGTATAAAGCCAGTGGACAACCTGGTGTCTGGATTCTCACTG

AAGTCCTGTGCTCTCTCAGAGATCGGTTGCCCCATGGATATTTTCCAGC

ACTTTGCCTTTGCAGACCTGAATGTAAGCCATGTCGTCACCCCCGATGC

CTTCGTGTGTCGCACCGTTTGCACCTTCCATCCCAACTGCCTCTTCTTC

ACATTCTACACGAATGAGTGGGAGACGGAATCACAGAGGAATGTTTGTT

TTCTTAAGACATCTAAAAGTGGAAGACCAAGTCCCCCTATTATTCAAGA

AAATGCTGTATCTGGATACAGTCTCTTCACCTGCAGAAAAGCTCGCCCT

GAACCCTGCCATTTCAAGATTTACTCTGGAGTTGCCTTCGAAGGGGAAG

AACTGAACGCGACCTTCGTGCAGGGAGCAGATGCGTGCCAAGAGACTTG

TACAAAGACCATCCGCTGTCAGTTTTTTACTTACTCATTGCTTCCCCAA

GACTGCAAGGCAGAGGGGTGTAAATGTTCCTTAAGGTTATCCACGGATG

GCTCTCCAACTAGGATCACCTATGAGGCACAGGGGAGCTCTGGTTATTC

TCTGAGACTGTGTAAAGTTGTGGAGAGCTCTGACTGTACGACAAAAATA

AATGCACGTATTGTGGGAGGAACAAACTCTTCTTTAGGAGAGTGGCCAT

GGCAGGTCAGCCTGCAAGTAAAGTTGGTTTCTCAGAATCATATGTGTGG

AGGGTCCATCATTGGACGCCAATGGATACTGACGGCTGCCCATTGCTTT

GATGGGATTCCCTATCCAGACGTGTGGCGTATATATGGCGGGATTCTTA

ATCTGTCAGAGATTACAAACAAAACGCCTTTCTCAAGTATAAAGGAGCT

TATTATTCATCAGAAATACAAAATGTCAGAAGGCAGTTACGATATTGCC

TTAATAAAGCTTCAGACACCGTTGAATTATACTGAATTCCAAAAACCAA

TATGCCTGCCTTCCAAAGCTGACACAAATACAATTTATACCAACTGCTG

GGTGACTGGATGGGCTACACAAAGGAACGAGGTGAGACCCAAAATATT

CTACAAAAGGCAACTATTCCCTTGGTACCAAATGAAGAATGCCAGAAAA

AATATAGAGATTATGTTATAACCAAGCAGATGATCTGTGCTGGCTACAA

AGAAGGTGGAATAGATGCTTGTAAGGGAGATTCCGGTGGCCCCTTAGTT

TGCAAACATAGTGGAAGGTGGCAGTTGGTGGGTATCACCAGCTGGGGCG

AAGGCTGTGCCCGCAAGGAGCAACCAGGAGTCTACACCAAAGTTGCTGA

GTACATTGACTGGATATTGGAGAAGATACAGAGCAGCAAGGAAAGAGCT

CTGGAGACATCTCCAGCATGAGGAGGCTGGGTACTGATGGGGAAGAGCC

CAGCTGGCACCAGCTTTACCACCTGCCCTCAAGTCCTACTAGAGCTCCA

GAGTTCTCTTCTGCAAAATGTCGATAGTGGTGTCTACCTCGCATCCTTA

CCATAGGATTAAAAGTCCAAATGTAGACACAGTTGCTAAAGACAGCGCC

ATGCTCAAGCGTGCTTCCTGCCTTGAGCAACAGGAACGCCAATGAGAAC

TATCCAAAGATTACCAAGCCTGTTTGGAAATAAAATGGTCAAAGGATTT

TTATTAGGTAGTGAAATTAGGTAGTTGTCCTTGGAACCATTCTCATGTA

ACTGTTGACTCTGGACCTCAGCAGATCACAGTTACCTTCTGTCCACTTC

TGACATTTGTGTACTGGAACCTGATGCTGTTCTTCCACTTGGAGCAAAG

AACTGAGAAACCTGGTTCTATCCATTGGGAAAAAGAGATCTTTGTAACA

TTTCCTTTACAATAAAAAGATGTTCTACTTGGACTTGAAAAAAAAAAAA

AAAAAAAAAAAAAA
```

Display Libraries

A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a sFab. In one exemplary implementation, a display library can be used to identify proteins that bind to plasma kallikrein. In a selection, the polypeptide component of each member of the library is probed with plasma kallikrein (or fragment thereof) and if the polypeptide component binds to the plasma kallikrein, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display: The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) J. Biol. Chem 274:18218-30; Hoogenboom et al. (1998) Immunotechnology 4:1-20; Hoogenboom et al. (2000) Immunol Today 2:371-8 and Hoet et al. (2005) Nat Biotechnol. 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), ribosome display (See, e.g., Mattheakis et al. (1994) Proc. Natl. Acad. Sci. USA 91:9022 and Hanes et al. (2000) Nat Biotechnol. 18:1287-92; Hanes et al. (2000) Methods Enzymol. 328: 404-30; and Schaffitzel et al. (1999) J Immunol Methods. 231(1-2):119-35), and E. coli periplasmic display (J Immunol Methods. 2005 Nov. 22; PMID: 16337958).

Scaffolds. Scaffolds useful for display include: antibodies (e.g., Fab fragments, single chain Fv molecules (scFv), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., U.S. 2004-0005709.

Display technology can also be used to obtain binding proteins (e.g., antibodies) that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more binding proteins for a target. These identified binding proteins are then varied using a mutagenesis method to form a second display library. Higher affinity binding proteins are then selected from the second library, e.g., by using higher stringency or more competitive binding and washing conditions.

In some implementations, the mutagenesis is targeted to regions at the binding interface. If, for example, the identified binding proteins are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Exemplary mutagenesis techniques include: error-prone PCR, recombination, DNA shuffling, site-directed mutagenesis and cassette mutagenesis.

In one example of iterative selection, the methods described herein are used to first identify a protein from a display library that binds plasma kallikrein, with at least a minimal binding specificity for a target or a minimal activity, e.g., an equilibrium dissociation constant for binding of less than 0.5 nM, 1 nM, 10 nM, or 100 nM. The nucleic acid sequences encoding the initial identified proteins are used as a template nucleic acid for the introduction of variations, e.g., to identify a second protein that has enhanced properties (e.g., binding affinity, kinetics, or stability) relative to the initial protein.

Off-Rate Selection. Since a slow dissociation rate can be predictive of high affinity, particularly with respect to interactions between polypeptides and their targets, the methods described herein can be used to isolate binding proteins with a desired (e.g., reduced) kinetic dissociation rate for a binding interaction to a target.

To select for slow dissociating binding proteins from a display library, the library is contacted to an immobilized target. The immobilized target is then washed with a first solution that removes non-specifically or weakly bound biomolecules. Then the bound binding proteins are eluted with a second solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target.

In one implementation, a so-called "negative selection" step is used to discriminate between the target and related non-target molecule and a related, but distinct non-target molecule. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target as well as for cross species reactivity to related targets or subunits of the target (e.g., plasma kallikrein) and also under different condition such as pH 6 or pH 7.5. The non-target and target binding data are compared (e.g., using a computer and software) to identify library members that specifically bind to the target.

Other Exemplary Expression Libraries

Other types of collections of proteins (e.g., expression libraries) can be used to identify proteins with a particular property (e.g., ability to bind plasma kallikrein), including, e.g., protein arrays of antibodies (see, e.g., De Wildt et al. (2000) Nat. Biotechnol. 18:989-994), lambda gt11 libraries, two-hybrid libraries and so forth.

Exemplary Libraries

It is possible to immunize a non-human primate and recover primate antibody genes that can be displayed on phage (see below). From such a library, one can select antibodies that bind the antigen used in immunization. See, for example, Vaccine. (2003) 22(2):257-67 or Immunogenetics. (2005) 57(10):730-8. Thus one could obtain primate antibodies that bind and inhibit plasma kallikrein by immunizing a chimpanzee or macaque and using a variety of means to select or screen for primate antibodies that bind and inhibit plasma kallikrein. One can also make chimeras of primatized Fabs with human constant regions, see Curr Opin Mol Ther. (2004) 6(6):675-83. "PRIMATIZED antibodies, genetically engineered from cynomolgus macaque monkey and human components, are structurally indistinguishable from human antibodies. They may, therefore, be less likely to cause adverse reactions in humans, making them potentially suited for long-term, chronic treatment" Curr Opin Investig Drugs. (2001) 2(5):635-8.

One exemplary type of library presents a diverse pool of polypeptides, each of which includes an immunoglobulin domain, e.g., an immunoglobulin variable domain. Of interest are display libraries where the members of the library include primate or "primatized" (e.g., such as human, non-human primate or "humanized") immunoglobin domains (e.g., immunoglobin variable domains) or chimeric primatized Fabs with human constant regions. Human or humanized immunoglobin domain libraries may be used to identify human or "humanized" antibodies that, for example, recognize human antigens. Because the constant and framework regions of the antibody are human, these antibodies may avoid themselves being recognized and targeted as antigens when administered to humans. The constant regions may also be optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules Immunoglobulin domains typically contain two β-sheets formed of about seven β-strands, and a conserved disulphide bond (see, e.g., A. F. Williams and A. N. Barclay, 1988, Ann. Rev. Immunol. 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, J. Biol. Chem. 274:18218-30; Hoogenboom et al., 1998, Immunotechnology 4:1-20; Hoogenboom et al., 2000, Immunol. Today 21:371-378, and Hoet et al. (2005) Nat Biotechnol. 23(3): 344-8. Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and/or FR4, referring to such regions of either and both of heavy and light chain variable domains. For example, the variation(s) may be introduced into all three CDRs of a given variable domain, or into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al., 2000, J. Mol. Biol. 296:57-86 describe a method for constructing CDR encoding oligonucleotides using trinucleotide synthesis and a template with engineered restriction sites for accepting the oligonucleotides.

In another process, an animal (e.g., a rodent) is immunized with plasma kallikrein. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a primate (e.g., a human), mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cells are cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin, or pokeweed mitogen.

In another embodiment, the cells are isolated from a subject that has a disease of condition described herein, e.g., a plasma kallikrein associated disease or condition.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al., 2001, J. Immunol. 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al., 1999, J. Biol. Chem. 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Secondary Screening Methods

After selecting candidate library members that bind to a target, each candidate library member can be further analyzed, e.g., to further characterize its binding properties for the target, e.g., plasma kallikrein. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties include the following.

ELISA. Binding proteins can be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Homogeneous Binding Assays. The ability of a binding protein described herein to bind a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Another example of a homogenous assay is ALPHASCREEN™ (Packard Bioscience, Meriden Conn.). ALPHASCREEN™ uses two labeled beads. One bead generates singlet oxygen when excited by a laser. The other bead generates a light signal when singlet oxygen diffuses from the first bead and collides with it. The signal is only generated when the two beads are in proximity One bead can be attached to the display library member, the other to the target. Signals are measured to determine the extent of binding.

Surface Plasmon Resonance (SPR). The interaction of binding protein and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, Anal. Chem. 63:2338-2345; Szabo et al., 1995, Curr. Opin. Struct. Biol. 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Cellular Assays. Binding proteins can be screened for ability to bind to cells which transiently or stably express and display the target of interest on the cell surface. For example, plasma kallikrein binding proteins can be fluorescently labeled and binding to plasma kallikrein in the presence of absence of antagonistic antibody can be detected by a change in fluorescence intensity using flow cytometry e.g., a FACS machine.

Other Exemplary Methods for Obtaining Plasma Kallikrein Binding Proteins

In addition to the use of display libraries, other methods can be used to obtain a plasma kallikrein binding protein (e.g., antibody). For example, plasma kallikrein protein or a fragment thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. Nos. 5,585,089, 5,693,761 and 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Reducing Immunogenicity of Plasma Kallikrein Binding Proteins

Immunoglobin plasma kallikrein binding proteins (e.g., IgG or Fab plasma kallikrein binding proteins) may be modified to reduce immunogenicity. Reduced immunogenicity is desirable in plasma kallikrein binding proteins intended for use as therapeutics, as it reduces the chance that the subject will develop an immune response against the therapeutic molecule. Techniques useful for reducing immunogenicity of plasma kallikrein binding proteins include deletion/modification of potential human T cell epitopes and "germlining" of sequences outside of the CDRs (e.g., framework and Fc).

A plasma kallikrein-binding antibody may be modified by specific deletion of human T cell epitopes or "deimmunization," e.g., by the methods disclosed in WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al., 1992, J. Mol. Biol. 227:776-798; Cook, G. P. et al., 1995, Immunol. Today Vol. 16 (5): 237-242; Chothia, D. et al., 1992, J. Mol. Bio. 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should betested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Plasma kallikrein binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to plasma kallikrein, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion of the sequence. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the INTERNATIONAL IMMUNOGENETICS INFORMATION SYSTEM® (IMGT), and the V BASE directory (compiled by Tomlinson, I. A. et al. MRC Centre for Protein Engineering, Cambridge, UK).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, EMBO J. 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, J. Mol. Biol. 227:799-817; Tomlinson et al., 1992, J. Mol. Biol. 227:776-798); and Tomlinson et al., 1995, EMBO J. 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Protein Production

Standard recombinant nucleic acid methods can be used to express a protein that binds to plasma kallikrein. Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells (see e.g., Nadkarni, A. et al., 2007 Protein Expr Purif 52(1):219-29). For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, J. Immunol. Methods. 251:123-35; Schoonooghe S. et al., 2009 BMC Biotechnol. 9:70; Abdel-Salam, H A. et al., 2001 Appl Microbiol Biotechnol 56(1-2):157-64; Takahashi K. et al., 2000 Biosci Biotechnol Biochem 64(10):2138-44; Edqvist, J. et al., 1991 J Biotechnol 20(3):291-300), *Han-*

*seula*, or *Saccharomyces*. One of skill in the art can optimize antibody production in yeast by optimizing, for example, oxygen conditions (see e.g., Baumann K., et al. 2010 BMC Syst. Biol. 4:141), osmolarity (see e.g., Dragosits, M. et al., 2010 BMC Genomics 11:207), temperature (see e.g., Dragosits, M. et al., 2009 J Proteome Res. 8(3):1380-92), fermentation conditions (see e.g., Ning, D. et al. 2005 J. Biochem. and Mol. Biol. 38(3): 294-299), strain of yeast (see e.g., Kozyr, A V et al. 2004 Mol Biol (Mock) 38(6): 1067-75; Horwitz, A H. et al., 1988 Proc Natl Acad Sci USA 85(22):8678-82; Bowdish, K. et al. 1991 J Biol Chem 266(18):11901-8), overexpression of proteins to enhance antibody production (see e.g., Gasser, B. et al., 2006 Biotechol. Bioeng. 94(2):353-61), level of acidity of the culture (see e.g., Kobayashi H., et al., 1997 FEMS Microbiol Lett 152(2):235-42), concentrations of substrates and/or ions (see e.g., Ko J H. et al., 2996 Appl Biochem Biotechnol 60(1): 41-8). In addition, yeast systems can be used to produce antibodies with an extended half-life (see e.g., Smith, B J. et al. 2001 Bioconjug Chem 12(5):750-756), In one preferred embodiment, antibodies are produced in mammalian cells. Preferred mammalian host cells for expressing the clone antibodies or antigen-binding fragments thereof include Chinese Hamster Ovary (CHO cells) (including dhfr- CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NSO myeloma cells and SP2 cells, COS cells, HEK293T cells (J. Immunol. Methods (2004) 289(1-2):65-80), and a cell from a transgenic animal, e.g., a transgenic mammal. For example, the cell is a mammary epithelial cell.

In some embodiments, plasma kallikrein binding proteins are produced in a plant or cell-free based system (see e.g., Galeffi, P., et al., 2006 J Transl Med 4:39).

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Characterization of Plasma Kallikrein Binding Proteins $IC_{50}$ (Inhibitory Concentration 50%) and $EC_{50}$ (Effective Concentration 50%). Within a series or group of binding proteins, those having lower $IC_{50}$ or $EC_{50}$ values are considered more potent inhibitors of plasma kallikrein than those binding proteins having higher $IC_{50}$ or $EC_{50}$ values. Exemplary binding proteins have an $IC_{50}$ value of less than 800 nM, 400 nM, 100 nM, 25 nM, 5 nM, or 1 nM, e.g., as measured in an in vitro assay for inhibition of plasma kallikrein activity when the plasma kallikrein is at 2 pM.

Plasma kallikrein binding proteins may also be characterized with reference to the activity of Factor XII and HMWK (high-molecular-weight kininogen) signaling events, e.g., the production of Factor XIIa and/or bradykinin.

The binding proteins can also be evaluated for selectivity toward plasma kallikrein. For example, a plasma kallikrein binding protein can be assayed for its potency toward plasma kallikrein and a panel of kallikreins and an $IC_{50}$ value or $EC_{50}$ value can be determined for each kallikrein. In one embodiment, a compound that demonstrates a low $IC_{50}$ value or $EC_{50}$ value for the plasma kallikrein, and a higher $IC_{50}$ value or $EC_{50}$ value, e.g., at least 2-, 5-, or 10-fold higher, for another kallikrein within the test panel is considered to be selective toward plasma kallikrein.

A pharmacokinetics study in rat, mice, or monkey can be performed with plasma kallikrein binding proteins for determining plasma kallikrein half-life in the serum. Likewise, the effect of the binding protein can be assessed in vivo, e.g., in an animal model for a disease (e.g., carrageenin-induced edema in rat hind paw (Winter et al. Proc Soc Exp Biol Med. 1962; 111:544-7)), for use as a therapeutic, for example, to treat a disease or condition described herein, e.g., a plasma kallikrein associated disorder.

Pharmaceutical Compositions

Proteins (e.g., binding proteins) that bind to plasma kallikrein (e.g., human plasma kallikrein and/or murine plasma kallikrein) and, e.g., include at least one immunoglobin variable region can be used in methods for treating (or preventing) a plasma kallikrein associated disease or condition. The binding proteins can be present in a composition, e.g., a pharmaceutically acceptable composition or pharmaceutical composition, which includes a plasma kallikrein-binding protein, e.g., an antibody molecule or other polypeptide or peptide identified as binding to plasma kallikrein, as described herein. The plasma kallikrein binding protein can be formulated together with a pharmaceutically acceptable carrier. Pharmaceutical compositions include therapeutic compositions and diagnostic compositions, e.g., compositions that include labeled plasma kallikrein binding proteins for in vivo imaging, and compositions that include labeled plasma kallikrein binding proteins for treating (or preventing) a plasma kallikrein associated disease.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated. Depending on the route of administration, the plasma kallikrein binding protein may be coated in a material to protect the compound from the action of acids and other natural conditions that may inactivate the compound.

A pharmaceutically acceptable salt is a salt that retains the desired biological activity of the compound and does not impart any undesired toxicological effects (see e.g., Berge, S. M., et al., 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the plasma kallikrein binding protein is administered by intravenous infusion or injection. In another preferred embodiment, the plasma kallikrein binding protein is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A plasma kallikrein binding protein can be administered by a variety of methods, although for many applications, the preferred route/mode of administration is intravenous injection or infusion. For example, for therapeutic applications, the plasma kallikrein binding protein can be administered by intravenous infusion at a rate of less than 30, 20, 10, 5, or 1 mg/min to reach a dose of about 1 to 100 m g/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, a plasma kallikrein binding protein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, J. Clin. Pharmacol. 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a binding protein (e.g., an antibody) disclosed herein is 0.1-20 mg/kg, more preferably 1-10 mg/kg. An anti-plasma kallikrein antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. For binding proteins smaller in molecular weight than an antibody, appropriate amounts can be proportionally less. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a "therapeutically effective amount" or a "prophylactically effective amount" of a plasma kallikrein binding protein disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effects of the composition are outweighed by the therapeutically beneficial effects.

A "therapeutically effective dosage" preferably modulates a measurable parameter, e.g., levels of circulating IgG antibodies by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions, e.g., a plasma kallikrein associated disease. Alternatively, this property of a composition can be evaluated by examining the ability of the compound to modulate a parameter in vitro.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Stabilization and Retention

In one embodiment, a plasma kallikrein binding protein is physically associated with a moiety that improves its stabilization and/or retention in circulation, e.g., in blood, serum, lymph, or other tissues, e.g., by at least 1.5, 2, 5, 10, or 50 fold. For example, a plasma kallikrein binding protein can be associated with a polymer, e.g., a substantially non-antigenic polymer, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, a plasma kallikrein binding protein can be conjugated to a water soluble polymer, e.g., hydrophilic polyvinyl polymers, e.g., polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

A plasma kallikrein binding protein can also be associated with a carrier protein, e.g., a serum albumin, such as a human serum albumin (see e.g., Smith, B J. et al., 2001 Bioconjug Chem 12(5): 750-756). For example, a translational fusion can be used to associate the carrier protein with the plasma kallikrein binding protein.

A plasma kallikrein binding protein can also be modified as a HESylation derivative. Processes for HESylation of a plasma kallikrein binding protein utilize hydroxyethyl starch to modify the protein. HESylation of a protein can extend the circulating half-life of the protein and also reduce renal clearance.

In some embodiments, the plasma kallikrein binding proteins as described herein are fused to an unstructured recombinant polymer (URP) (see e.g., U.S. Pat. No. 7,846,445, the contents of which are incorporated herein by reference in its entirety).

URPs are polypeptides composed of Gly, Ala, Ser, Thr, Glu, and Pro that have no secondary structure. In aqueous solvents, URPs are highly solvated and give the protein they are attached to an apparent molecular mass that is much larger than that of the polypeptide alone. A URP sequence can be fused to a plasma kallikrein binding protein to (i) increase circulating half-life, (ii) improve tissue selectivity, (iii) protect the binding protein from degradation, (iv) reduce immunogenicity, (v) interrupt T-cell epitopes, (vi) enhance solubility, (vii) improve pH profile and homogeneity of protein charge, (viii) improve purification properties due to a sharper pKa, (ix) improve formulation and delivery, and (x) improve protein production (see e.g., U.S. Pat. No. 7,846,445, which is incorporated herein by reference in its entirety).

In general, a URP sequence should be designed such that it lacks unintended activities such as interactions with serum proteins (e.g., antibodies). One of skill in the art can test a URP for unintended activities using e.g., an ELISA assay to detect the level of binding to an immobilized serum protein. In some embodiments, it may be desirable for a URP to interact with a serum protein (e.g., albumin) to increase the circulating half-life of the plasma kallikrein binding protein.

In general, it is desired that URP sequences behave like denatured peptide sequences under physiological conditions and as such, lack well defined secondary and tertiary structures under physiological conditions. Methods to ascertain the second and tertiary structures of a given polypeptide are known to those of skill in the art and include, but are not limited to, CD spectroscopy in the "far-UV" spectral region (190-250 nm), and computer programs or algorithms such as the Chou-Fasman algorithm (Chou, P. Y., et al. (1974) Biochemistry, 13: 222-45). URP sequences typically have a high degree of conformational flexibility under physiological conditions (e.g., pH 6.5-7.8 and 30-37° C.) and also have large hydrodynamic radii (Stokes' radius) compared to globular proteins of similar molecular weight.

In one embodiment, the URP sequences have low immunogenicity. Preferred URPs are designed to avoid formation of conformational epitopes. For example, of particular interest are URP sequences having a low tendency to adapt compactly folded conformations in aqueous solution. In particular, low immunogenicity can be achieved by choosing sequences that resist antigen processing in antigen presenting cells, choosing sequences that do not bind MHC well and/or by choosing sequences that are derived from host (e.g., human) sequences.

In some embodiments, the URP sequences have a high degree of protease resistance to extend serum half-life. URPs can also be characterized by the effect they have on a protein sequence e.g., the protein exhibits a longer serum half-life and/or higher solubility as compared to the corresponding protein that is deficient in the URP. Methods of ascertaining serum half-life are known in the art (see e.g., Alvarez, P., et al. (2004) J Biol Chem, 279: 3375-81). One can readily determine whether the resulting protein has a longer serum half-life as compared to the unmodified protein by practicing any methods available in the art or exemplified herein.

The URP can be of any length necessary to effect (a) extension of serum half-life of a protein comprising the URP; (b) an increase in solubility of the resulting protein; (c) an increased resistance to protease; and/or (d) a reduced immunogenicity of the resulting protein that comprises the URP. In some embodiments, the URP has about 30, 40, 50, 60, 70, 80, 90, 100, 150, 200, 300, 400 or more contiguous amino acids. When incorporated into a protein, the URP can be fragmented such that the resulting protein contains multiple URPs, or multiple fragments of URPs. Some or all of these individual URP sequences may be shorter than 40 amino acids, provided that the combined length of all URP sequences in the resulting protein is at least 40 amino acids. Preferably, the resulting protein has a combined length of URP sequences exceeding 40, 50, 60, 70, 80, 90, 100, 150, 200 or more amino acids.

In some embodiments, the isoelectric point (pI) of the URP is 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5 or even 13.0.

In general, URP sequences are rich in hydrophilic amino acids and contain a low percentage of hydrophobic or aromatic amino acids. Suitable hydrophilic residues include but are not limited to glycine, serine, aspartate, glutamate, lysine, arginine, and threonine. Hydrophobic residues that are less favored in construction of URPs include tryptophan, phenylalanine, tyrosine, leucine, isoleucine, valine, and methionine. URP sequences can be rich in glycine but URP sequences can also be rich in the amino acids glutamate, aspartate, serine, threonine, alanine or proline. Thus the predominant amino acid may be G, E, D, S, T, A or P. The inclusion of proline residues tends to reduce sensitivity to proteolytic degradation.

In some embodiments, the URP sequences include hydrophilic residues to increase their solubility in water and aqueous media under physiological conditions. The inclusion of hydrophilic residues reduces the formation of aggregates in aqueous formulations and the fusion of URP sequences to other proteins or peptides (e.g., a plasma kallikrein binding protein) can enhance their solubility and reduce aggregate formation and immunogenicity.

URP sequences can be further designed to avoid amino acids that confer undesirable properties to the protein, for example, cysteine (to avoid disulfide formation and oxidation), methionine (to avoid oxidation), asparagine and glutamine (to avoid desamidation).

In some embodiments, a URP is designed to be glycine-rich (e.g., 30%, 35%, 40%, 45%, 50%, 55%, 60%, 65%, 70%, 75%, 80%, 85%, 90%, 95%, or 100% of the total amino acids are glycine). Glycine-rich URPs are contemplated for use with the methods and compositions described herein since glycine-rich peptides have an increased conformational freedom (e.g., a characteristic of denatured peptides). The length of a glycine-rich sequence can vary between about 5 amino acids and 400 amino acids. For example, the length of a single, contiguous glycine-rich sequence can contain 5, 10, 15, 20, 25, 30, 35, 40, 45, 50, 55, 60, 70, 80, 90, 100, 120, 140, 160, 180, 200, 240, 280, 320 or 400 or more amino acids. A glycine-rich sequence may comprise glycine residues at both ends.

In some embodiments, a URP sequence is optimized to enhance the selectivity of the fusion protein for a particular tissue, cell-type or cell lineage. One can also utilize such URPs to direct the resulting protein to a specific subcellular location: extracellular matrix, nucleus, cytoplasm, cytoskeleton, plasma and/or intracellular membranous structures which include, but are not limited, to coated pits, Golgi apparatus, endoplasmic reticulum, endosome, lysosome, and mitochondria. A variety of these tissue-specific, cell-type specific, subcellular location specific sequences are known and available from numerous protein databases. Such selective URP sequences can be obtained by generating libraries of random or semi-random URP sequences, injecting them into animals or patients, and determining sequences with the desired tissue selectivity in tissue samples. Sequence determination can be performed by mass spectrometry. Using similar methods one can select URP sequences that facilitate oral, buccal, intestinal, nasal, thecal, peritoneal, pulmonary, rectal, or dermal uptake.

In one embodiment, a URP sequence is rich in positively charged amino acids such as arginine or lysine, which favors cellular uptake or transport through membranes. In some embodiments, URP sequences can be designed to contain one or more protease-sensitive sequences. Such URP sequences can be cleaved once the product of the invention has reached its target location. URP sequences can be designed to carry excess negative charges by introducing aspartic acid or glutamic acid residues. Of particular interest are URPs that contain greater than 5%, greater than 6%, 7%, 8%, 9%, 10%, 15%, 30% or more glutamic acid and less than 2% lysine or arginine. Such URPs carry an excess negative charge and as a result have a tendency to adopt open conformations due to electrostatic repulsion between individual negative charges of the peptide. Such an excess negative charge leads to an effective increase in their hydrodynamic radius and as a result it can lead to reduced kidney clearance of such molecules. Thus, one can modulate the effective net charge and hydrodynamic radius of a URP sequence by controlling the frequency and distribution of negatively charged amino acids in the URP sequences.

URPs can include a repetitive amino acid sequence of the format (Motif)x in which a sequence motif forms a direct repeat (ie ABCABCABCABC) or an inverted repeat (ABC-CBAABCCBA) and the number of these repeats can be 2, 3, 4, 5, 6, 7, 8, 9, 10, 12, 14, 16, 18, 20, 22, 24, 26, 28, 30, 35, 40, 50 or more. URPs (or the repeats inside URPs) often contain only 1, 2, 3, 4, 5 or 6 different types of amino acids. URPs typically consist of repeats of human amino acid sequences that are 4, 5, 6, 7, 8, 9, 10, 11, 12, 13, 14, 15, 16, 17, 18, 19, 20, 22, 24, 26, 28, 30, 32, 34, 36 or more amino acids long, but URPs may also consist of non-human amino acid sequences that are 20, 22, 24, 26, 28, 30, 32, 34 36, 38 40, 42, 44, 46, 48, 50 amino acids long.

In one embodiment, URPs are derived from human sequences. The human genome contains many subsequences that are rich in one particular amino acid. Of particular interest are such amino acid sequences that are rich in a hydrophilic amino acid like serine, threonine, glutamate, aspartate, or glycine. Of particular interest are such subsequences that contain few hydrophobic amino acids and are predicted to be unstructured and highly soluable in an aqeuous solution. Such human subsequences can be modified to further improve their utility. Exemplary human sequences for use in designing URPs are shown herein in Tables 24 and 25.

The use of sequences from human proteins is particularly desirable in design of URPs with reduced immunogenicity in a human subject. The URP sequence can be designed to eliminate T cell epitopes to reduce immunogenicity. For instance, one can synthesize a series of semi-random sequences with amino acid compositions that favor denatured, unstructured conformations and evaluate these sequences for the presence of human T cell epitopes and whether they are human sequences. Assays for human T cell epitopes have been described (Stickler, M., et al. (2003) J Immunol Methods, 281: 95-108). One can incorporate human sequences into the design of URP sequences by oligomerizing or concatenating human sequences that have suitable amino acid compositions. These can be direct repeats or inverted repeats or mixtures of different repeats. In one embodiment, the entire URP sequence is from a human sequence.

Non-limiting examples of URPs containing repeating amino acids are: poly-glycine, poly-glutamic acid, poly-aspartic acid, poly-serine, poly-threonine, (GX)n where G is glycine and X is serine, aspartic acid, glutamic acid, threonine, or proline and n is at least 20, (GGX)n where X is serine, aspartic acid, glutamic acid, threonine, or proline and n is at least 13, (GGGX)n where X is serine, aspartic acid, glutamic acid, threonine, or proline and n is at least 10, (GGGGX)n where X is serine, aspartic acid, glutamic acid, threonine, or proline and n is at least 8, (GzX)n where X is serine, aspartic acid, glutamic acid, threonine, or proline, n is at least 15, and z is between 1 and 20.

The number of such repeats can be any number between 10 and 100. Products of the invention may contain URP sequences that are semi-random sequences. Examples are semi-random sequences containing at least 30, 40, 50, 60 or 70% glycine in which the glycines are well dispersed and in which the total concentration of tryptophan, phenylalanine, tyrosine, valine, leucine, and isoleucine is less then 70, 60, 50, 40, 30, 20, or 10% when combined. A preferred semi-random URP sequence contains at least 40% glycine and the total concentration of tryptophan, phenylalanine, tyrosine, valine, leucine, and isoleucine is less then 10%. A more preferred random URP sequence contains at least 50% glycine and the total concentration of tryptophan, phenylalanine, tyrosine, valine, leucine, and isoleucine is less then 5%. URP sequences can be designed by combining the sequences of two or more shorter URP sequences or fragments of URP sequences. Such a combination allows one to better modulate the pharmaceutical properties of the product containing the URP sequences and it allows one to reduce the repetitiveness of the DNA sequences encoding the URP sequences, which can improve expression and reduce recombination of the URP encoding sequences.

A URP sequence can be placed at the N terminus of either the light chain (LC) or heavy chain (HC) of a plasma kallikrein binding protein and a single URP can be attached to either HC or LC at either end. For example, one could combine the VH::CDR3::JH via a linker to VL::JL to make a scFv which could then be fused to a URP.

In one embodiment, a plasma kallikrein binding protein comprises a Fab fragment that inhibits plasma kallikrein and does not bind plasma prekallikrein wherein the LC is fused to a URP of 100 or more (e.g., 120, 140, 160, 180, 200, 300, 400 or more) amino acids and the HC is fused to a URP of 200 or more amino acids (e.g., 220, 240, 260, 280, 300, 350, 400, 450, 500, 600 or more). In one embodiment, the URP is fused to the carboxy terminus of LC and the carboxy terminus of HC. In one embodiment, the URPs have essentially equal amounts of Gly, Ala, Ser, Thr, Glu, and Pro residues. In one embodiment, the URP sequence does not comprise a hexamer repeat. In one embodiment, the plasma kallikrein binding protein (e.g., Fab fragment) is selected from the group consisting of M162-A04, M142-H08, X63-G06, X81-B01, X67-D03, X67-G04, and M160-G12.

In one embodiment, the HC::URP2 and LC::URP1 are produced in a yeast strain such as *Pichia pastoris* (BMC Biotechnol. 2009 Aug. 11; 9:70. PMID 19671134; J Biochem Mol Biol. 2005 May 31; 38(3):294-9. PMID 15943904; Biotechnol Bioeng. 2006 Jun. 5; 94(2):353-61. PMID 16570317), *Saccharomyces cerevisiae* (BMC Syst Biol. 2010 Oct. 22; 4:141. PMID 20969759; BMC Genomics. 2010 Mar. 26; 11:207. PMID 20346137), or *Hansenula polymorpha* (Appl Microbiol Biotechnol. 2001 July; 56(1-2):157-64. PMID 11499924). One of skill in the art can utilize appropriate promoters and signal sequences for a particular strain of yeast desired for use in producing a fusion protein comprising a plasma kallikrein binding protein and a URP polypeptide.

In one embodiment, the HC::URP2 and LC::URP1 are produced in mammalian cells such as Chinese hamster ovary (CHO) cells. Signal sequences and promoters that are useful for protein production using CHO cells are known in the literature.

Kits

A plasma kallikrein binding protein described herein can be provided in a kit, e.g., as a component of a kit. For example, the kit includes (a) a plasma kallikrein binding protein, e.g., a composition (e.g., a pharmaceutical composition) that includes a plasma kallikrein binding protein, and, optionally (b) informational material. The informational material can be descriptive, instructional, marketing or other material that relates to a method described herein and/or the use of a plasma kallikrein binding protein, e.g., for a method described herein.

The informational material of the kit is not limited in its form. In one embodiment, the informational material can include information about production of the compound, molecular weight of the compound, concentration, date of expiration, batch or production site information, and so forth. In one embodiment, the informational material relates to using the binding protein to treat, prevent, or diagnosis of disorders and conditions, e.g., a plasma kallikrein associated disease or condition.

In one embodiment, the informational material can include instructions to administer a plasma kallikrein binding protein in a suitable manner to perform the methods described herein, e.g., in a suitable dose, dosage form, or mode of administration (e.g., a dose, dosage form, or mode of administration described herein). In another embodiment, the informational material can include instructions to administer a plasma kallikrein binding protein to a suitable subject, e.g., a human, e.g., a human having, or at risk for, a disorder or condition described herein, e.g., a plasma kallikrein associated disease or condition. For example, the material can include instructions to administer a plasma kallikrein binding protein to a patient with a disorder or condition described herein, e.g., a plasma kallikrein associated disease. The informational material of the kits is not limited in its form. In many cases, the informational material, e.g., instructions, is provided in print but may also be in other formats, such as computer readable material.

A plasma kallikrein binding protein can be provided in any form, e.g., liquid, dried or lyophilized form. It is preferred that a plasma kallikrein binding protein be substantially pure and/or sterile. When a plasma kallikrein binding protein is provided in a liquid solution, the liquid solution preferably is an aqueous solution, with a sterile aqueous solution being preferred. When a plasma kallikrein binding protein is provided as a dried form, reconstitution generally is by the addition of a suitable solvent. The solvent, e.g., sterile water or buffer, can optionally be provided in the kit.

The kit can include one or more containers for the composition containing a plasma kallikrein binding protein. In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a plasma kallikrein binding protein. For example, the kit includes a plurality of syringes, ampules, foil packets, or blister packs, each containing a single unit dose of a plasma kallikrein binding protein. The containers of the kits can be air tight, waterproof (e g, impermeable to changes in moisture or evaporation), and/or light-tight.

The kit optionally includes a device suitable for administration of the composition, e.g., a syringe, inhalant, dropper (e.g., eye dropper), swab (e.g., a cotton swab or wooden swab), or any such delivery device. In one embodiment, the device is an implantable device that dispenses metered doses of the binding protein. The disclosure also features a method of providing a kit, e.g., by combining components described herein.

Treatments

Proteins that bind to plasma kallikrein, e.g., as described herein, have therapeutic and prophylactic utilities, particularly in human subjects. These binding proteins are administered to a subject to treat, prevent, and/or diagnose a variety of disorders and conditions, including e.g., a plasma kallikrein associated disease, or even to cells in culture, e.g., in vitro or ex vivo. For example, these binding proteins can be used to modify the effects of plasma kallikrein released from cells in culture (Lilla et al., J Biol Chem. 284(20): 13792-13803 (2009)). Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

As used herein, an amount of a target-binding agent effective to prevent a disorder, or a prophylactically effective amount of the binding agent refers to an amount of a target binding agent, e.g., an plasma kallikrein binding protein, e.g., an anti-plasma kallikrein antibody described herein, which is effective, upon single- or multiple-dose administration to the subject, for preventing or delaying the occurrence of the onset or recurrence of a disorder, e.g., a disorder described herein, e.g., a plasma kallikrein associated disease.

Methods of administering plasma kallikrein binding proteins and other agents are also described in "Pharmaceutical Compositions." Suitable dosages of the molecules used can depend on the age and weight of the subject and the particular drug used. The binding proteins can be used as competitive agents to inhibit, reduce an undesirable interaction, e.g., between plasma kallikrein and its substrate (e.g., Factor XII or HMWK). The dose of the plasma kallikrein binding protein can be the amount sufficient to block 90%, 95%, 99%, or 99.9% of the activity of plasma kallikrein in the patient, especially at the site of disease. Depending on the disease, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In one embodiment, the plasma kallikrein binding proteins are used to inhibit an activity (e.g., inhibit at least one activity of plasma kallikrein, e.g., reduce Factor XIIa and/or bradykinin production) of plasma kallikrein, e.g., in vivo. The binding proteins can be used by themselves or conjugated to an agent, e.g., a cytotoxic drug, cytotoxin enzyme, or radioisotope. This method includes: administering the binding protein alone or attached to an agent (e.g., a cytotoxic drug), to a subject requiring such treatment. For example, plasma kallikrein binding proteins that do not substantially inhibit plasma kallikrein may be used to deliver nanoparticles containing agents, such as toxins, to plasma kallikrein associated cells or tissues, e.g., to treat a plasma kallikrein-associate disorder.

Because the plasma kallikrein binding proteins recognize plasma kallikrein expressing cells and can bind to cells that are associated with (e.g., in proximity of or intermingled with) a plasma kallikrein associated disorder or condition, plasma kallikrein binding proteins can be used to inhibit an activity (e.g., inhibit at least one activity of plasma kallikrein, e.g., reduce Factor XIIa and/or bradykinin production) any such cells and inhibit the plasma kallikrein associated disease. Reducing plasma kallikrein activity can indirectly inhibit cells which may be dependent on the plasma kallikrein activity for the development and/or progression of a plasma kallikrein-associated disorder.

The binding proteins may be used to deliver an agent (e.g., any of a variety of cytotoxic and therapeutic drugs) to cells and tissues where plasma kallikrein is present. Exemplary agents include a compound emitting radiation, molecules of plants, fungal, or bacterial origin, biological proteins, and mixtures thereof. The cytotoxic drugs can be intracellularly acting cytotoxic drugs, such as toxins short range radiation emitters, e.g., short range, high energy α-emitters.

To target plasma kallikrein expressing cells, a prodrug system can be used. For example, a first binding protein is conjugated with a prodrug which is activated only when in close proximity with a prodrug activator. The prodrug activator is conjugated with a second binding protein, preferably one which binds to a non competing site on the target molecule. Whether two binding proteins bind to competing or non competing binding sites can be determined by conventional competitive binding assays. Exemplary drug prodrug pairs are described in Blakely et al., (1996) Cancer Research, 56:3287 3292.

The plasma kallikrein binding proteins can be used directly in vivo to eliminate antigen-expressing cells via natural complement-dependent cytotoxicity (CDC) or antibody dependent cellular cytotoxicity (ADCC). The binding proteins described herein can include complement binding effector domain, such as the Fc portions from IgG1, -2, or -3 or corresponding portions of IgM which bind complement. In one embodiment, a population of target cells is ex vivo treated with a binding agent described herein and appropriate effector cells. The treatment can be supplemented by the addition of complement or serum containing complement. Further, phagocytosis of target cells coated with a binding protein described herein can be improved by binding of complement proteins. In another embodiment target, cells coated with the binding protein which includes a complement binding effector domain are lysed by complement.

Methods of administering plasma kallikrein binding proteins are described in "Pharmaceutical Compositions." Suitable dosages of the molecules used will depend on the age and weight of the subject and the particular drug used. The binding proteins can be used as competitive agents to inhibit or reduce an undesirable interaction, e.g., between a natural or pathological agent and the plasma kallikrein.

The plasma kallikrein binding protein can be used to deliver macro and micromolecules, e.g., a gene into the cell for gene therapy purposes into the endothelium or epithelium and target only those tissues expressing the plasma kallikrein. The binding proteins may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy $\alpha$ emitters, as described herein.

In the case of polypeptide toxins, recombinant nucleic acid techniques can be used to construct a nucleic acid that encodes the binding protein (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Alternatively, the plasma kallikrein binding protein can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{213}$Bi, and $^{211}$At, and b emitters, such as $^{186}$Re and $^{90}$Y. Moreover, $^{177}$Lu may also be used as both an imaging and cytotoxic agent. Radioimmunotherapy (RIT) using antibodies labeled with $^{131}$I, $^{90}$Y and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Exemplary Diseases and Conditions

A plasma kallikrein binding protein described herein is useful to treat (or prevent) a disease or condition in which plasma kallikrein activity is implicated, e.g., a disease or condition described herein, or to treat (or prevent) one or more symptoms associated therewith. In some embodiments, the plasma kallikrein binding protein (e.g., plasma kallikrein binding IgG or Fab) inhibits plasma kallikrein activity.

Examples of such diseases and conditions which can be treated (or prevented) by a plasma kallikrein binding protein described herein include: rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, and burn injury. A plasma kallikrein binding protein described herein can also be used to promote wound healing. A plasma kallikrein binding protein described herein can also be used as an oncology treatment by mechanisms that include, but are not limited to, blocking production of pro-angiogenic bradykinin A therapeutically effective amount of a plasma kallikrein binding protein can be administered to a subject having or suspected of having a disorder in which plasma kallikrein activity is implicated, thereby treating (e.g., ameliorating or improving a symptom or feature of a disorder, slowing, stabilizing and/or halting disease progression) the disorder.

The plasma kallikrein binding protein can be administered in a therapeutically effective amount. A therapeutically effective amount of a plasma kallikrein binding protein is the amount which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition are outweighed by the therapeutically beneficial effects. A therapeutically effective dosage preferably modulates a measurable parameter, favorably, relative to untreated subjects. The ability of a compound to affect (e.g., inhibit) a measurable parameter can be evaluated in an animal model system predictive of efficacy in a human disorder.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Rheumatoid Arthritis

Rheumatoid arthritis (RA) is an autoimmune, chronic inflammatory disease that causes joint swelling and pain and normally results in joint destruction. RA generally follows a relapsing/remitting course, with "flares" of disease activity interspersed with remissions of disease symptoms. RA is associated with a number of additional inflammatory disorders, including Sjogren's syndrome (dry eyes and mouth caused by inflammation of tear and saliva glands), pleuritis (inflammation of the pleura that causes pain upon deep breath and coughing), rheumatoid nodules (nodular sites of inflammation that develop within the lungs), pericarditis (inflammation of the pericardium that causes pain when lying down or leaning forward), Felty syndrome (splenomegaly and leucopenia observed in conjunction with RA, making the subject prone to infection), and vasculitis (an inflammation of the blood vessels which can block blood flow). Plasma kallikrein has been implicated in rheumatoid arthritis.

Symptoms of active RA include fatigue, lack of appetite, low grade fever, muscle and joint aches, and stiffness. Muscle and joint stiffness are usually most notable in the morning and after periods of inactivity. During flares, joints frequently become red, swollen, painful, and tender, generally as a consequence of synovitis.

Treatment for rheumatoid arthritis involves a combination of medications, rest, joint strengthening exercises, and joint protection. Two classes of medications are used in treating rheumatoid arthritis: anti-inflammatory "first-line drugs," and "Disease-Modifying Antirheumatic Drugs" (DMARDs). The first-line drugs include NSAIDS (e.g., aspirin, naproxen, ibuprofen, and etodolac) and cortisone (corticosteroids). DMARDs, such as gold (e.g., gold salts, gold thioglucose, gold thiomalate, oral gold), methotrexate, sulfasalazine, D-penicillamine, azathioprine, cyclophosphamide, chlorambucil, and cyclosporine, leflunomide, etanercept, infliximab, anakinra, and adalimumab, and hydroxychloroquine, promote disease remission and prevent progressive joint destruction, but they are not anti-inflammatory agents.

The disclosure provides methods of treating (e.g., ameliorating, stabilizing, or eliminating one or more symptoms or ameliorating or stabilizing the subject's score on a RA scale) rheumatoid arthritis by administering a plasma kallikrein binding protein (e.g., a therapeutically effective amount of a plasma kallikrein binding protein) to a subject having or suspected of having RA. Additionally provided are methods of treating RA by administering a plasma kallikrein binding protein (e.g., a therapeutically effective amount of a plasma kallikrein binding protein) in combination with a second therapy, e.g., with at least one anti-inflammatory "first line drug" (e.g., an NSAID and/or cortisone) and/or a DMARD. The disclosure also provides methods of preventing rheumatoid arthritis or a symptom thereof by administering a plasma kallikrein binding protein (e.g., a prophylactically effective amount of a plasma kallikrein binding protein) to a subject at risk of developing RA (e.g., a subject having a family member with RA or a genetic predisposition thereto).

Further provided are methods of treating (e.g., ameliorating, stabilizing, or eliminating one or more symptoms) rheumatoid arthritis associated disorders (Sjogren's syndrome, pleuritis, pulmonary rheumatoid nodules, pericarditis, Felty syndrome, and vasculitis) by administering a plasma kallikrein binding protein (e.g., a therapeutically effective amount of a plasma kallikrein binding protein) to a subject having or suspected of having RA.

Scales useful for assessing RA and symptoms of RA include, e.g., the Rheumatoid Arthritis Severity Scale (RASS; Bardwell et al., (2002) *Rheumatology* 41(1):38-45), SF-36 Arthritis Specific Health Index (ASHI; Ware et al., (1999) *Med. Care.* 37(5 Suppl):MS40-50), Arthritis Impact Measurement Scales or Arthritis Impact Measurement Scales 2 (AIMS or AIMS2; Meenan et al. (1992) *Arthritis Rheum.* 35(1):1-10); the Stanford Health Assessment Questionnaire (HAQ), HAQII, or modified HAQ (see, e.g., Pincus et al. (1983) *Arthritis Rheum.* 26(11):1346-53).

Guidance for the determination of the dosage that delivers a therapeutically effective amount of a plasma kallikrein binding protein may be obtained from animal models of rheumatoid arthritis, such as collagen-induced arthritis (CIA), which is induced, typically in rodents, by immunization with autologous or heterologous type II collagen in adjuvant (Williams et al. Methods Mol Med. 98:207-16 (2004)).

Gout

Gout is a condition that results from crystals of uric acid depositing in tissues of the body. Gout is characterized by an overload of uric acid in the body and recurring attacks of joint inflammation (arthritis). Chronic gout can lead to deposits of hard lumps of uric acid in and around the joints, decreased kidney function, and kidney stones. Gout is often related to an inherited abnormality in the body's ability to process uric acid. Uric acid is a breakdown product of purines, which are part of many foods. An abnormality in handling uric acid can cause attacks of painful arthritis (gout attack), kidney stones, and blockage of the kidney filtering tubules with uric acid crystals, leading to kidney failure. Some patients may only develop elevated blood uric acid levels (hyperuricemia) without having arthritis or kidney problems.

Symptoms of gout include, e.g., excruciating and unexpected pain, swelling, redness, warmth and stiffness in the affected foot or other parts of the body, and low-grade fever.

Treatments for gout include, e.g., nonsteroidal anti-inflammatory drugs (NSAIDs), colchicine and oral glucocorticoids, intra-articular glucocorticoids administered via a joint injection, xanthine oxidase inhibitors (e.g., allopurinol, febuxostat), uricosurics (e.g., probenecid, EDTA), urate oxidases (e.g., pegloticase), sodium bicarbonate, and low purine diet.

The disclosure provides methods of treating (e.g., ameliorating, stabilizing, or eliminating one or more symptoms or the worsening of) gout by administering a plasma kallikrein binding protein (e.g., a therapeutically effective amount of a plasma kallikrein binding protein) to a subject having or suspected of having gout. Additionally provided are methods of treating gout by administering a plasma kallikrein binding protein (e.g., a therapeutically effective amount of a kallikrein binding protein) in combination with a second therapy, e.g., an NSAID, a colchicine, an oral glucocorticoid, an intra-articular glucocorticoid administered via a joint injection, a xanthine oxidase inhibitor (e.g., allopurinol, febuxostat), a uricosuric (e.g., probenecid, EDTA), a urate oxidase (e.g., pegloticase), sodium bicarbonate, and/or low purine diet. The disclosure also provides methods of preventing gout or a symptom thereof by administering a plasma kallikrein binding protein (e.g., a prophylactically effective amount of a plasma kallikrein binding protein) to a subject at risk of developing gout (e.g., a subject having a family member with gout or a genetic predisposition thereto).

Guidance for the determination of the dosage that delivers a therapeutically effective amount of a plasma kallikrein binding protein may be obtained from animal models of gout, see, e.g., Reginato and Olsen, Curr Opin Rheumatol. 19(2):134-45 (2007) and references cited therein.

Intestinal Bowel Disease (IBD)

Inflammatory bowel disease (IBD) is a group of inflammatory conditions of the large intestine and, in some cases, the small intestine. The main forms of IBD are Crohn's disease and ulcerative colitis (UC). Accounting for far fewer cases are other forms of IBD: collagenous colitis, lymphocytic colitis, ischaemic colitis, diversion colitis, Behçet's syndrome, infective colitis, and indeterminate colitis. The main difference between Crohn's disease and UC is the location and nature of the inflammatory changes. Crohn's can affect any part of the gastrointestinal tract, from mouth to anus (skip lesions), although a majority of the cases start in the terminal ileum. Ulcerative colitis, in contrast, is restricted to the colon and the rectum. Microscopically, ulcerative colitis is restricted to the mucosa (epithelial lining of the gut), while Crohn's disease affects the whole bowel wall. Finally, Crohn's disease and ulcerative colitis present with extra-intestinal manifestations (such as liver problems, arthritis, skin manifestations and eye problems) in different proportions.

Symptoms of IBD include abdominal pain, vomiting, diarrhea, hematochezia, weight loss, weight gain and various associated complaints or diseases (arthritis, pyoderma gangrenosum, primary sclerosing cholangitis). Diagnosis is generally by colonoscopy with biopsy of pathological lesions. Rarely, a definitive diagnosis of neither Crohn's disease nor ulcerative colitis can be made because of idiosyncrases in the presentation. In this case, a diagnosis of indeterminate colitis may be made.

Treatment for IBD, depending on the level of severity, may require immunosuppression to control the symptoms Immunosuppresives such as azathioprine, methotrexate, or 6-mercaptopurine can be used. More commonly, treatment of IBD requires a form of mesalamine. Often, steroids are used to control disease flares and were once acceptable as a maintenance drug. Biologicals, such as infliximab, have been used to treat patients with Crohn's disease or Ulcerative Colitis. Severe cases may require surgery, such as bowel resection, strictureplasty or a temporary or permanent colostomy or ileostomy. Alternative medicine treatments for IBD exist in various forms however such methods concentrate on controlling underlying pathology in order to avoid prolonged steroidal exposure or surgical excision. Usually the treatment is started by administering drugs, such as prednisone, with high anti-inflammatory affects. Once the inflammation is successfully controlled, the patient is usually switched to a lighter drug, such as asacol-a mesalamine- to keep the disease in remission. If unsuccessful, a combination of the aforementioned immunosuppressant drugs with a mesalamine (which may also have an anti-inflammatory effect) may or may not be administered, depending on the patient.

The disclosure provides methods of treating (e.g., ameliorating, stabilizing, or eliminating one or more symptoms of) IBD by administering a plasma kallikrein binding protein (e.g., a therapeutically effective amount of a plasma kallikrein binding protein) to a subject having or suspected of having IBD. Additionally provided are methods of treating IBD by administering a plasma kallikrein binding protein (e.g., a therapeutically effective amount of a kallikrein binding protein) in combination with a second therapy, e.g., an immunosuppressive (e.g., azathioprine, methotrexate, 6-mercaptopurine), a mesalamine, a steroid, and/or infliximab. The disclosure also provides methods of preventing IBD or a symptom thereof by administering a plasma kallikrein binding protein (e.g., a prophylactically effective amount of a plasma kallikrein binding protein) to a subject at risk of developing IBD (e.g., a subject having a family member with IBD or a genetic predisposition thereto).

Guidance for the determination of the dosage that delivers a therapeutically effective amount of a plasma kallikrein binding protein may be obtained from animal models of IBD, see, e.g., those described in U.S. Pat. No. 6,114,382, WO 2004/071186, and references cited therein.

Oral Mucositis

Oral mucositis is the painful inflammation and ulceration of the mucous membranes in the mouth, usually as an adverse effect of chemotherapy and radiotherapy treatment for cancer.

Symptoms of oral mucositis include, e.g., ulcers, peripheral erythema, burning sensation accompanied by reddening, trouble speaking, eating, or even opening the mouth, and dyseusia (alteration in taste perception).

Treatment for oral mucositis includes oral hygiene (salt mouthwash, GELCLAIR®, CAPHOSOL®, MUGARD®), palifermin (a human keratinocyte growth factor), cytokines and other modifiers of inflammation (e.g., IL-1, IL-11, TGF-beta3), amino acid supplementation (e.g., glutamine), vitamins, colony-stimulating factors, cryotherapy, and laser therapy.

The disclosure provides methods of treating (e.g., ameliorating, reducing, or eliminating one or more symptoms, or stabilizing the subject's score on a mucositis scale) oral mucositis by administering a plasma kallikrein binding protein (e.g., a therapeutically effective amount of a plasma kallikrein binding protein) to a subject having or suspected of having oral mucositis. Additionally provided are methods of treating oral mucositis by administering a plasma kallikrein binding protein (e.g., a therapeutically effective amount of a plasma kallikrein binding protein) in combination with a second therapy, e.g., oral hygiene (salt mouthwash, GELCLAIR®, CAPHOSOL®, MUGARD®), palifermin (a human keratinocyte growth factor), a cytokine and/or a modifier of inflammation (e.g., IL-1, IL-11, TGF-beta3), an amino acid supplementation (e.g., glutamine), a vitamin, a colony-stimulating factor, cryotherapy, and/or laser therapy. The disclosure also provides methods of preventing oral mucositis or a symptom thereof by administering a plasma kallikrein binding protein (e.g., a prophylactically effective amount of a plasma kallikrein binding protein) to a subject at risk of developing oral mucositis (e.g., a subject that has undergone or is undergoing chemotherapy or radiotherapy).

Scales useful for assessing oral mucositis include the World Health Organization (WHO) Oral Toxicity score (Handbook for reporting results of cancer treatment.

Geneva, Switzerland: World Health Organization; 1979:15-22), National Cancer Institute Common Toxicity Criteria (NCI-CTC) for Oral Mucositis (National Cancer Institute Common Toxicity Criteria. Version 2.0, Jun. 1, 1999, Sonis et al., Cancer. 85:2103-2113 (1999)), and Oral Mucositis Assessment Scale (OMAS).

Guidance for the determination of the dosage that delivers a therapeutically effective amount of a plasma kallikrein binding protein may be obtained from animal models of oral mucositis, such as an animal model of oral mucositis induced by conditioning regimen of haematopoietic stem cell transplantation (Chen et al., Zhonghua Kou Qiang Yi Xue Za Zhi. 42(11):672-6 (2007)).

Neuropathic Pain

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

Symptoms of neuropathic pain include, e.g., shooting and burning pain and tingling and numbness.

Treatments for neuropathic pain include, e.g., medications (e.g., non-steroidal anti-inflammatory drugs (NSAIDs) (e.g., ALEVE®, MOTRIN®, or morphine), anticonvulsant, and antidepressant drugs), and invasive or implantable devices (e.g., electrical stimulation).

The disclosure provides methods of treating (e.g., ameliorating, reducing, or eliminating one or more symptoms of or stabilizing the subject's score on a pain scale) neuropathic pain by administering a plasma kallikrein binding protein (e.g., a therapeutically effective amount of a plasma kallikrein binding protein) to a subject having or suspected of having neuropathic pain. Additionally provided are methods of treating neuropathic pain by administering a plasma kallikrein binding protein (e.g., a therapeutically effective amount of a plasma kallikrein binding protein) in combination with a second therapy, e.g., a nonsurgical treatment ((e.g., a non-steroidal anti-inflammatory drug (NSAID) (e.g., ALEVE®, MOTRIN®, or morphine), an anticonvulsant, and/or an antidepressant drug), and/or an invasive or implantable device (e.g., electrical stimulation). The disclosure also provides methods of preventing neuropathic pain or a symptom thereof by administering a plasma kallikrein binding protein (e.g., a prophylactically effective amount of a plasma kallikrein binding protein) to a subject at risk of developing neuropathic pain (e.g., a subject that has experienced tissue injury).

Scales useful for the assessment of neuropathic pain include, e.g., Wong-Baker FACES Pain Rating Scale (Wong-Baker FACES Pain Rating Scale Foundation), Visual analog scale (VAS) (Huskinson, J. Rheumatol. 9 (5): 768-9 (1982)), McGill Pain Questionnaire (MPQ) (Melzack, Pain 1 (3): 277-99 (1975)), Descriptor differential scale (DDS) (Gracely and Kwilosz, Pain 35 (3): 279-88 (1988)), Faces Pain Scale—Revised (FPS-R) (Hicks et al., Pain 93 (2): 173-83 (2001)), Numerical 11 point box (BS-11) (Jensen et al., Clin J Pain 5 (2): 153-9 (1989)), Numeric Rating Scale (NRS-11) (Hartrick et al., Pain Pract 3 (4): 310-6 (2003)), Dolorimeter Pain Index (DPI) (Hardy et al., (1952). Pain Sensations and Reactions. Baltimore: The Williams & Wilkins Co.), and Brief Pain Inventory (BPI) (Cleeland and Ryan Ann. Acad. Med. Singap. 23 (2): 129-38 (1994)).

Guidance for the determination of the dosage that delivers a therapeutically effective amount of a plasma kallikrein binding protein may be obtained from animal models of neuropathic pain, see, e.g., those described in Martin et al., Methods Mol Med. 84:233-42 (2003) and references cited therein.

Inflammatory Pain

Inflammatory pain is caused by an insult such as penetration wounds, burns, extreme cold, fractures, arthritis, autoimmune conditions, excessive stretching, infections and vasoconstriction to the integrity of tissues at a cellular level. During inflammation a complex neuro-immune interaction results in primary hyperalgesia, in which a large range of inflammatory molecules including prostaglandins and bradykinin induce and maintain the altered nociceptor sensitivity.

Treatments for inflammatory pain include, e.g., non-steroidal anti-inflammatory drugs (NSAIDs) and corticosteroids.

The disclosure provides methods of treating (e.g., ameliorating, reducing, or eliminating one or more symptoms of) inflammatory pain by administering a plasma kallikrein binding protein (e.g., a therapeutically effective amount of a plasma kallikrein binding protein) to a subject having or suspected of having inflammatory pain. Additionally provided are methods of treating inflammatory pain by administering a plasma kallikrein binding protein (e.g., a therapeutically effective amount of a plasma kallikrein binding protein) in combination with a second therapy, e.g., a non-steroidal anti-inflammatory drug (NSAID) and/or a corticosteroid. The disclosure also provides methods of preventing inflammatory pain or a symptom thereof by administering a plasma kallikrein binding protein (e.g., a prophylactically effective amount of a plasma kallikrein binding protein) to a subject at risk of developing inflammatory pain (e.g., a subject that has experienced an insult, e.g., such as a penetration wound, a burn, extreme cold, a fracture, arthritis, an autoimmune condition, excessive stretching, or infection).

Scales useful for the assessment of inflammatory pain include, e.g., Wong-Baker FACES Pain Rating Scale (Wong-Baker FACES Pain Rating Scale Foundation), Visual analog scale (VAS) (Huskinson, J. Rheumatol. 9 (5): 768-9 (1982)), McGill Pain Questionnaire (MPQ) (Melzack, Pain 1 (3): 277-99 (1975)), Descriptor differential scale (DDS) (Gracely and Kwilosz, Pain 35 (3): 279-88 (1988)), Faces Pain Scale—Revised (FPS-R) (Hicks et al., Pain 93 (2): 173-83 (2001)), Numerical 11 point box (BS-11) (Jensen et al., Clin J Pain 5 (2): 153-9 (1989)), Numeric Rating Scale (NRS-11) (Hartrick et al., Pain Pract 3 (4): 310-6 (2003)), Dolorimeter Pain Index (DPI) (Hardy et al., (1952). Pain Sensations and Reactions. Baltimore: The Williams & Wilkins Co.), and Brief Pain Inventory (BPI) (Cleeland and Ryan Ann. Acad. Med. Singap. 23 (2): 129-38 (1994)).

Guidance for the determination of the dosage that delivers a therapeutically effective amount of a plasma kallikrein binding protein may be obtained from animal models of inflammatory pain such as an animal model of chronic inflammatory pain (Wilson et al., Eur J Pain. 10(6):537-49 (2006)) and an inflammatory model of pain and hyperalgesia (Ren and Dubner, ILAR J. 40(3):111-118 (1999)).

Spinal Stenosis

Spinal stenosis is a medical condition in which the spinal canal narrows and compresses the spinal cord and nerves. This is usually due to the common occurrence of spinal degeneration that occurs with aging. It can also sometimes be caused by spinal disc herniation, osteoporosis or a tumor. Spinal stenosis may affect the cervical, thoracic or lumbar spine. In some cases, it may be present in all three places in the same patient.

Symptoms of spinal stenosis include, e.g., pain or cramping in the legs, radiating back and hip pain, pain in the neck and shoulders, loss of balance, and loss of bowel or bladder function (cauda equina syndrome).

Treatments for spinal stenosis include, e.g., nonsurgical treatments (e.g., physical therapy, non-steroidal anti-inflammatory drugs (NSAIDs) (e.g., aspirin, ibuprofen and indomethacin), analgesics (e.g., acetaminophen), chondroitin sulfate, glucosamine, rest or restricted activity, back brace or corset, epidural steroid injections (e.g., corticosteroid)), and surgery (e.g., decompressive laminectomy, laminotomy and fusion).

The disclosure provides methods of treating (e.g., ameliorating, reducing, or eliminating one or more symptoms of) spinal stenosis by administering a plasma kallikrein binding protein (e.g., a therapeutically effective amount of a plasma kallikrein binding protein) to a subject having or suspected of having spinal stenosis. Additionally provided are methods of treating spinal stenosis by administering a plasma kallikrein binding protein (e.g., a therapeutically effective amount of a plasma kallikrein binding protein) in combination with a second therapy, e.g., a nonsurgical treatment (e.g., physical therapy and/or a nonsteroidal anti-inflammatory drug (NSAID) (e.g., aspirin, ibuprofen or indomethacin), an analgesic (e.g., acetaminophen), chondroitin sulfate, glucosamine, rest or restricted activity, a back brace or corset, an epidural steroid injection (e.g., corticosteroid), and/or surgery (e.g., decompressive laminectomy, laminotomy and/or fusion). The disclosure also provides methods of preventing spinal stenosis or a symptom thereof by administering a plasma kallikrein binding protein (e.g., a prophylactically effective amount of a plasma kallikrein binding protein) to a subject at risk of developing spinal stenosis (e.g., a subject that has spinal degeneration).

Guidance for the determination of the dosage that delivers a therapeutically effective amount of a plasma kallikrein binding protein may be obtained from animal models of spinal stenosis, such as a model of lumbar spinal stenosis (Sekiguchi et al., Spine 29, 1105-1111 (2004)).

Arterial and Venous Thrombosis

Arterial thrombosis is the formation of a thrombus within an artery. In most cases, arterial thrombosis follows rupture of atheroma, and is therefore referred to as atherothrombosis.

Arterial thrombosis is associated with a number of disorders, including stroke and myocardial infarction. In thrombotic stroke, a thrombus (blood clot) usually forms around atherosclerotic plaques. Since blockage of the artery is gradual, onset of symptomatic thrombotic strokes is slower. Thrombotic stroke can be divided into two categories—large vessel disease and small vessel disease. The former affects vessels such as the internal carotids, vertebral and the circle of Willis. The latter can affect smaller vessels such as the branches of the circle of Willis. Myocardial infarction (MI) is caused by an infarct (death of tissue due to ischemia), often due to the obstruction of the coronary artery by a thrombus. MI can quickly become fatal if emergency medical treatment is not received promptly.

Venous thrombosis is a blood clot that forms within a vein. If a piece of a blood clot formed in a vein breaks off, it can be transported to the right side of the heart, and from there into the lungs. A piece of thrombus that is transported in this way is an embolism and the process of forming a thrombus that becomes embolic is called a thromboembolism. An embolism that lodges in the lungs is a pulmonary embolism (PE). A pulmonary embolus is a very serious condition that can be fatal if not recognized and treated promptly.

Superficial venous thromboses can cause discomfort but generally do not cause serious consequences, unlike the deep venous thromboses (DVTs) that form in the deep veins of the legs or in the pelvic veins. Systemic embolisms of venous origin can occur in patients with an atrial or ventricular septal defect, through which an embolus may pass into the arterial system. Such an event is termed a paradoxical embolism.

Prevention of arterial and/or venous thrombosis includes medications (e.g., anticoagulants (e.g., heparin), aspirin, and vitamin E) and mechanical methods (e.g., mechanical leg pumps (pneumatic compression stockings)).

The disclosure provides methods of treating (e.g., ameliorating, reducing, or eliminating one or more symptoms of) arterial and/or venous thrombosis by administering a plasma kallikrein binding protein (e.g., a therapeutically effective amount of a plasma kallikrein binding protein) to a subject having or suspected of having arterial and/or venous thrombosis. Additionally provided are methods of treating arterial and/or venous thrombosis by administering a plasma kallikrein binding protein (e.g., a therapeutically effective amount of a plasma kallikrein binding protein) in combination with a second therapy, e.g., an anticoagulant (e.g., heparin), aspirin, and/or vitamin E and/or a mechanical method (e.g., a mechanical leg pump (pneumatic compression stockings). The disclosure also provides methods of preventing arterial and/or venous thrombosis or a symptom thereof by administering a plasma kallikrein binding protein (e.g., a prophylactically effective amount of a plasma kallikrein binding protein) to a subject at risk of developing arterial and/or venous thrombosis (e.g., a subject that has experienced a stroke or myocardial infarction).

Guidance for the determination of the dosage that delivers a therapeutically effective amount of a plasma kallikrein binding protein may be obtained from animal models of arterial or venous thrombosis, such as a double-tuck model of arterial thrombosis (Gomez-Jorge et al., J. Vasc. Inter. Rad. 9(4): 633-638 (1998), a model of venous thrombosis in rat with low flow conditions in the venous blood stream (Fredrich et al., Blood Coagul Fibrinolysis. 5(2):243-8 (1994)), and a canine model for venous thrombosis and spontaneous pulmonary embolism (Frisbiel, Spinal Cord 43, 635-639 (2005)).

Postoperative Ileus

Postoperative ileus is a temporary paralysis of a portion of the intestines typically after an abdominal surgery. Postoperative ileus commonly occurs for 24 to 72 hours after abdominal surgery.

Symptoms of postoperative ileus include, e.g., moderate and diffuse abdominal discomfort, constipation, abdominal distension, nausea or vomiting, lack of bowel movement and/or flatulence, and excessive belching.

Treatments for postoperative ileus include, e.g., nil per os (NPO or "Nothing by Mouth") until peristaltic sound is heard from auscultation of the area where this portion lies, nasogastric suction, parenteral feeds, and medications (e.g., lactulose and erythromycin).

The disclosure provides methods of treating (e.g., ameliorating, reducing, or eliminating one or more symptoms of) postoperative ileus by administering a plasma kallikrein binding protein (e.g., a therapeutically effective amount of a plasma kallikrein binding protein) to a subject having or suspected of having postoperative ileus. Additionally provided are methods of treating postoperative ileus by administering a plasma kallikrein binding protein (e.g., a therapeutically effective amount of a plasma kallikrein binding protein) in combination with a second therapy, e.g., nil per os, nasogastric suction, parenteral feeds, and/or a medication (e.g., lactulose and/or erythromycin). The disclosure also provides methods of preventing postoperative ileus or a symptom thereof by administering a plasma kallikrein binding protein (e.g., a prophylactically effective amount of a plasma kallikrein binding protein) to a subject at risk of developing postoperative ileus (e.g., a subject that has had abdominal surgery).

Guidance for the determination of the dosage that delivers a therapeutically effective amount of a plasma kallikrein binding protein may be obtained from animal models of postoperative ileus, such as a model to investigate postoperative ileus with strain gauge transducers in awake rats (Huge et al. J Surg Res. 74(2):112-8 (1998)).

Aortic Aneurysm

An aortic aneurysm is a general term for any swelling (dilatation or aneurysm) of the aorta, usually representing an underlying weakness in the wall of the aorta at that location. Types of aortic aneurysms include aortic root aneurysm, thoracic aortic aneurysm, abdominal aortic aneurysm, and thoracoabdominal aortic aneurysm.

Most intact aortic aneurysms do not produce symptoms. As they enlarge, symptoms of aortic aneurysm include, e.g., anxiety or feeling of stress, nausea or vomiting, clammy skin, rapid heart rate, abdominal pain, back pain may develop, leg pain or numbness, erythema nodosum (leg lesions typically found near the ankle region), and a hoarse voice as the left recurrent laryngeal nerve winding around the arch of the aorta is stretched. Once an aneurysm is ruptured, it can cause severe pain and massive internal hemorrhage, and is fatal in the absence of prompt treatment.

Treatments for aortic aneurysm include, e.g., medications, surgical treatment and endovascular treatment. Smaller aneurysms that are not at high risk for rupturing can be treated with drugs to treat high blood pressure, such as beta-blockers; or doxycycline for matrix metalloproteinase-9 inhibition. Surgical treatment typically involves opening up of the dilated portion of the aorta and insertion of a synthetic (Dacron or Gore-tex) patch tube. Endovascular treatment, as a minimally invasive alternative to open surgery repair, involves the placement of an endovascular stent via a percutaneous technique (usually through the femoral arteries) into the diseased portion of the aorta.

The disclosure provides methods of treating (e.g., stabilizing, reducing, or eliminating one or more symptoms of) aortic aneurysm by administering a plasma kallikrein binding protein (e.g., a therapeutically effective amount of a plasma kallikrein binding protein) to a subject having or suspected of having aortic aneurysm. Additionally provided are methods of treating aortic aneurysm by administering a plasma kallikrein binding protein (e.g., a therapeutically effective amount of a plasma kallikrein binding protein) in combination with a second therapy, e.g., a medication (e.g., a drug to treat high blood pressure (e.g., a beta-blocker) or doxycycline), surgery, and/or an endovascular treatment. The disclosure also provides methods of preventing aortic aneurysm or a symptom thereof by administering a plasma kallikrein binding protein (e.g., a prophylactically effective amount of a plasma kallikrein binding protein) to a subject at risk of developing aortic aneurysm (e.g., a subject that has high blood pressure).

Guidance for the determination of the dosage that delivers a therapeutically effective amount of a plasma kallikrein binding protein may be obtained from an animal model of aortic aneurysm, e.g., a rat model of abdominal aortic aneurysm using a combination of intraluminal elastase infusion and extraluminal calcium chloride exposure (Tanaka et al. J Vasc Surg. 50(6):1423-32 (2009)).

Osteoarthritis

Osteoarthritis, also known as degenerative arthritis, is characterized by the breakdown and eventual loss of the cartilage of one or more joints. Osteoarthritis occurs when the cartilage that cushions the ends of bones in the joints deteriorates over time. The smooth surface of the cartilage becomes rough, causing irritation. If the cartilage wears down completely, the ends of the bones will be damaged. Osteoarthritis commonly affects the hands, feet, spine, and large weight-bearing joints, such as the hips and knees.

Symptoms of osteoarthritis include, e.g., pain, tenderness, stiffness, loss of flexibility, grating sensation, and bone spurs.

Treatments for osteoarthritis include, e.g., conservative measures (e.g., rest, weight reduction, physical and occupational therapy) and medications (e.g., acetaminophen, pain-relieving creams applied to the skin over the joints (e.g., capsaicin, salycin, methyl salicylate, and menthol), non-steroidal anti-inflammatory drugs (NSAIDs) (e.g., aspirin, ibuprofen, nabumetone and naproxen), and Cox-2 inhibitors.

The disclosure provides methods of treating (e.g., stabilizing, reducing, or eliminating one or more symptoms or stabilizing the subject's score on an osteoarthritis scale) osteoarthritis by administering a plasma kallikrein binding protein (e.g., a therapeutically effective amount of a plasma kallikrein binding protein) to a subject having or suspected of having osteoarthritis. Additionally provided are methods of treating osteoarthritis by administering a plasma kallikrein binding protein (e.g., a therapeutically effective amount of a plasma kallikrein binding protein) in combination with a second therapy, e.g., a conservative measure (e.g., rest, weight reduction, physical and/or occupational therapy) and/or a medication (e.g., acetaminophen, a topical pain-relieving cream, an NSAID (e.g., aspirin, ibuprofen, nabumetone, or naproxen), and/or a Cox-2 inhibitor. The disclosure also provides methods of preventing osteoarthritis or a symptom thereof by administering a plasma kallikrein binding protein (e.g., a prophylactically effective amount of a plasma kallikrein binding protein) to a subject at risk of developing osteoarthritis (e.g., a subject that has had a joint injury).

Scales useful for the assessment of osteoarthritis include, e.g., the Knee Injury and Osteoarthritis Outcome Score (KOOS; Roos et al. (1998) J. Orthop. Sports Phys. Ther. 28(2):88-96), Western Ontario and McMaster Universities Osteoarthrtis Index (WOMAC; Roos et al. (2003) *Health Qual. Life Outcomes* 1(1):17), and the 36-item Short Form General Health Scale (SF-36 GHS), as well as other assessment tools known in the art.

Guidance for the determination of the dosage that delivers a therapeutically effective amount of a plasma kallikrein binding protein may be obtained from an animal model of osteoarthritis, e.g., injection of mono-iodoacetate (MIA) into the femorotibial joint of rodents which promotes loss of articular cartilage similar to that noted in human osteoarthritis (Guzman et al. Toxicol Pathol. 31(6):619-24 (2003)), and transection of the anterior cruciate ligament (ACL) in canines to induce osteoarthritis (Fife and Brandt J Clin Invest. 84(5): 1432-1439 (1989)).

Vasculitis

Vasculitis refers to a heterogeneous group of disorders that are characterized by inflammatory destruction of blood vessels. Both arteries and veins can be affected. Lymphangitis is sometimes considered a type of vasculitis. Vasculitis is primarily due to leukocyte migration and resultant damage. Vasculitis can be classified by the underlying cause, the location of the affected vessels, or the type or size of the blood vessels. Vasculitis is associated with a number of additional disorders and conditions, e.g., Kawasaki disease, Behçet's disease, Polyarteritis nodosa, Wegener's granulomatosis, Cryoglobulinemia, Takayasu's arteritis, Churg-Strauss syndrome, Giant cell arteritis (temporal arteritis), Henoch-Schönlein purpura, Rheumatic diseases (e.g., rheumatoid arthritis and systemic lupus erythematosus), cancer (e.g., lymphomas), infections (e.g., hepatitis C), exposure to chemicals and drugs (e.g., amphetamines, cocaine, and anthrax vaccines which contain the Anthrax Protective Antigen as the primary ingredient).

Symptoms of vasculitis include, e.g., fever, weight loss, palpable purpura, livedo reticularis, myalgia or myositis, arthralgia or arthritis, mononeuritis multiplex, headache, stroke, tinnitus, reduced visual acuity, acute visual loss, myocardial infarction, hypertension, gangrene, nose bleeds, bloody cough, lung infiltrates, abdominal pain, bloody stool, perforations, and glomerulonephritis.

Treatments for vasculitis include, e.g., cortisone-related medications (e.g., prednisone) and immune suppression drugs (e.g., cyclophosphamide).

The disclosure provides methods of treating (e.g., stabilizing, reducing, or eliminating one or more symptoms or stabilizing the subject's score on a vasculitis scale) vasculitis by administering a plasma kallikrein binding protein (e.g., a therapeutically effective amount of a plasma kallikrein binding protein) to a subject having or suspected of having vasculitis. Additionally provided are methods of treating vasculitis by administering a plasma kallikrein binding protein (e.g., a therapeutically effective amount of a plasma kallikrein binding protein) in combination with a second therapy (e.g., a cortisone-related medication (e.g., prednisone) and/or an immune suppression drug (e.g., cyclophosphamide)). The disclosure also provides methods of preventing vasculitis or a symptom thereof by administering a plasma kallikrein binding protein (e.g., a prophylactically effective amount of a plasma kallikrein binding protein) to a subject at risk of developing vasculitis (e.g., a subject that has had Kawasaki disease, Behçet's disease, Polyarteritis nodosa, Wegener's granulomatosis, Cryoglobulinemia, or Takayasu's arteritis, and so forth).

The disclosure also provides methods of treating (e.g., stabilizing, reducing, or eliminating one or more symptoms or stabilizing the subject's score on a vasculitis scale) vasculitis associated with systemic lupus erythematosis by administering a plasma kallikrein binding protein (e.g., a therapeutically effective amount of a plasma kallikrein binding protein) to a subject having or suspected of having vasculitis associated with systemic lupus erythematosis. Additionally provided are methods of treating vasculitis associated with systemic lupus erythematosis by administering a plasma kallikrein binding protein (e.g., a therapeutically effective amount of a plasma kallikrein binding protein) in combination with a second therapy, e.g., a cortisone-related medication (e.g., prednisone) and/or an immune suppression drug (e.g., cyclophosphamide).

Further provided are methods of treating (e.g., ameliorating, stabilizing, or eliminating one or more symptoms) a vasculitis associated disorder (Kawasaki disease, Behçet's disease, Polyarteritis nodosa, Wegener's granulomatosis, Cryoglobulinemia, Takayasu's arteritis, Churg-Strauss syndrome, Giant cell arteritis (temporal arteritis), Henoch-Schönlein purpura, Rheumatic diseases (e.g., rheumatoid arthritis and systemic lupus erythematosus), cancer (e.g., lymphomas), infections (e.g., hepatitis C), exposure to chemicals and drugs (e.g., amphetamines, cocaine, and anthrax vaccines which contain the Anthrax Protective Antigen as the primary ingredient)) by administering a plasma kallikrein binding protein (e.g., a therapeutically effective amount of a plasma kallikrein binding protein) to a subject having or suspected of having a vasculitis associated disorder. The disclosure also provides methods of preventing a vasculitis associated disorder or a symptom thereof by administering a plasma kallikrein binding protein (e.g., a prophylactically effective amount of a plasma kallikrein binding protein) to a subject at risk of developing a vasculitis associated disorder.

Scales useful for the assessment of osteoarthritis include, e.g., Birmingham Vasculitis Activity score (BVAS) version 3 (Mukhtyar et al. Ann Rheum Dis. 68(12):1827-32 (2009)), as well as other assessment tools known in the art.

Guidance for the determination of the dosage that delivers a therapeutically effective amount of a plasma kallikrein binding protein may be obtained from an animal model of vasculitis, see e.g., those described in Katz et al., Clin Rev Allergy Immunol. 35(1-2):11-8 (2008) and references cited therein.

Head Trauma

Head trauma refers to trauma to the head, which may or may not include injury to the brain. Types of head trauma include concussion, epidural hematoma, subdural hematoma, cerebral contusion, and diffuse axonal injury.

Symptoms of head trauma include, e.g., coma, confusion, drowsiness, personality change, seizures, nausea and vomiting, headache and a lucid interval, during which a patient appears conscious only to deteriorate later, leaking cerebrospinal fluid, visible deformity or depression in the head or face, an eye that cannot move or is deviated to one side can indicate that a broken facial bone is pinching a nerve that innervates eye muscles, wounds or bruises on the scalp or face, basilar skull fractures, a subcutaneous bleed over the mastoid, hemotympanum, cerebrospinal fluid rhinorrhea, and otorrhea.

Treatments for head trauma include, e.g., controlling elevated intracranial pressure (e.g., sedation, paralytics, cerebrospinal fluid diversion), decompressive craniectomy, barbiturate coma, hypertonic saline, and hypothermia.

The disclosure provides methods of treating (e.g., stabilizing, reducing, or eliminating one or more symptoms or stabilizing the subject's score on a head trauma scale) head trauma by administering a plasma kallikrein binding protein (e.g., a therapeutically effective amount of a plasma kallikrein binding protein) to a subject having or suspected of having head trauma. Additionally provided are methods of treating head trauma by administering a plasma kallikrein binding protein (e.g., a therapeutically effective amount of a plasma kallikrein binding protein) in combination with a second therapy, e.g., controlling elevated intracranial pressure (e.g., sedation, a paralytic, and/or cerebrospinal fluid diversion), decompressive craniectomy, barbiturate coma, hypertonic saline, and/or hypothermia. The disclosure also provides methods of preventing head trauma or a symptom thereof by administering a plasma kallikrein binding protein (e.g., a prophylactically effective amount of a plasma kallikrein binding protein) to a subject at risk of developing head trauma (e.g., a subject that will be participating in a dangerous activity or contact sport).

Scales useful for assessing head trauma and symptoms of head trauma include, e.g., the Glasgow Coma Scale (Teasdale and Jennett, Lancet 13; 2(7872):81-4 (1974)), as well as other assessment tools known in the art.

Guidance for the determination of the dosage that delivers a therapeutically effective amount of a plasma kallikrein binding protein may be obtained from animal models of head trauma, see, e.g., those described in Cernak, NeuroRx. 2(3): 410-422 (2005) and references cited therein.

Brain Edema

Brain edema (cerebral edema) is an excess accumulation of water in the intracellular and/or extracellular spaces of the brain. Types of brain edema include, e.g., vasogenic cerebral edema, cytotoxic cerebral edema, osmotic cerebral edema, and interstitial cerebral edema.

Vasogenic cerebral edema is due to a breakdown of tight endothelial junctions which make up the blood-brain barrier (BBB). This allows normally excluded intravascular proteins and fluid to penetrate into cerebral parenchymal extracellular space. Once plasma constituents cross the BBB, the edema spreads; this may be quite fast and widespread. As water enters white matter it moves extracellularly along fiber tracts and can also affect the gray matter. This type of edema is seen in response to trauma, tumors, focal inflammation, late stages of cerebral ischemia and hypertensive encephalopathy. Some of the mechanisms contributing to BBB dysfunction are: physical disruption by arterial hypertension or trauma, tumor-facilitated release of vasoactive and endothelial destructive compounds (e.g., arachidonic acid, excitatory neurotransmitters, eicosanoids, bradykinin, histamine and free radicals). Some of the special subcategories of vasogenic edema include: hydrostatic cerebral edema, cerebral edema from brain cancer, high altitude cerebral edema.

Cytotoxic cerebral edema is due to the derangement in cellular metabolism resulting in inadequate functioning of the sodium and potassium pump in the glial cell membrane. As a result there is cellular retention of sodium and water. Cytoxotic edema is seen with various intoxications (dinitrophenol, triethyltin, hexachlorophene, isoniazid), in Reye's syndrome, severe hypothermia, early ischemia, encephalopathy, early stroke or hypoxia, cardiac arrest, pseudotumor cerebri, and cerebral toxins.

Osmotic cerebral edema occurs when plasma is diluted by excessive water intake (or hyponatremia), syndrome of inappropriate antidiuretic hormone secretion (SIADH), hemodialysis, or rapid reduction of blood glucose in hyperosmolar hyperglycemic state (HHS), formerly hyperosmolar non-ketotic acidosis (HONK) and brain osmolality exceeds the serum osmolality creating an abnormal pressure.

Interstitial cerebral edema occurs in obstructive hydrocephalus. This form of edema is due to rupture of cerebralspinal fluid (CSF)-brain barrier resulting in trans-ependymal flow of CSF, which permits CSF to penetrate brain and spread in the extracellular space of white matter.

Symptoms of brain edema (e.g., peritumoral brain edema) include, e.g., headache, loss of coordination (ataxia), weakness, and decreasing levels of consciousness including disorientation, loss of memory, hallucinations, psychotic behavior, and coma.

Treatments for brain edema (e.g., peritumoral brain edema) include, e.g., medications (e.g. dexamethasone, mannitol, diuretics) and surgical decompression.

The disclosure provides methods of treating (e.g., stabilizing, reducing, or eliminating one or more symptoms of) brain edema (e.g., peritumoral brain edema) by administering a plasma kallikrein binding protein (e.g., a therapeutically effective amount of a plasma kallikrein binding protein) to a subject having or suspected of having brain edema (e.g., peritumoral brain edema). Additionally provided are methods of treating brain edema (e.g., peritumoral brain edema) by administering a plasma kallikrein binding protein (e.g., a therapeutically effective amount of a plasma kallikrein binding protein) in combination with a second therapy, e.g., a medication (e.g. dexamethasone, mannitol, and/or diuretics) and/or surgical decompression. The disclosure also provides methods of preventing brain edema or a symptom thereof by administering a plasma kallikrein binding protein (e.g., a prophylactically effective amount of a plasma kallikrein binding protein) to a subject at risk of developing brain edema (e.g., a subject that has been diagnosed with a brain tumor).

Guidance for the determination of the dosage that delivers a therapeutically effective amount of a plasma kallikrein binding protein may be obtained from animal models of brain edema, e.g., a rat model of cerebral embolism in which recirculation can be introduced in the ischemic area (Koizumi et al., Jpn J Stroke 8: 1-8 (1986)).

Sepsis

Sepsis is a serious medical condition that is characterized by a whole-body inflammatory state and the presence of a known or suspected infection. This immunological response may be caused by microbes in the blood, urine, lungs, skin, or other tissues and can lead to widespread activation of acute-phase proteins, affecting the complement system and the coagulation pathways, which then cause damage to the vasculature as well as to the organs. Different levels of sepsis include systemic inflammatory response syndrome (SIRS), sepsis (SIRS in response to a confirmed infectious process), severe sepsis (sepsis with organ dysfunction, hypoperfusion, or hypotension), and septic shock (sepsis with refractory arterial hypotension or hypoperfusion abnormalities in spite of adequate fluid resuscitation).

Symptoms of sepsis include, e.g., general symptoms related to the infection, acute inflammation present throughout the entire body, hypothermia or fever, tachycardia, tachypnea or hypocapnia due to hyperventilation, leukopenia, leukocytosis, bandemia, and organ (e.g., lung, brain, liver, kidney, and/or heart) dysfunction.

Treatments for sepsis include, e.g., antibiotics, vasopressor drugs, insulin, corticosteroids, drotrecogin alfa, surgical drainage of infected fluid collections, fluid replacement, and appropriate support for organ dysfunction (e.g., hemodialysis in kidney failure, mechanical ventilation in pulmonary dysfunction, transfusion of blood products, and drug and fluid therapy for circulatory failure). Early Goal Directed Therapy (EGDT), a systematic approach to resuscitation, can be used to treat severe sepsis and septic shock.

The disclosure provides methods of treating (e.g., stabilizing, reducing, or eliminating one or more symptoms or stabilizing the subject's score on a sepsis scale) sepsis by administering a plasma kallikrein binding protein (e.g., a therapeutically effective amount of a plasma kallikrein binding protein) to a subject having or suspected of having sepsis. Additionally provided are methods of treating sepsis by administering a plasma kallikrein binding protein (e.g., a therapeutically effective amount of a plasma kallikrein binding protein) in combination with a second therapy, e.g., an antibiotic, a vasopressor drug, insulin, a corticosteroid, drotrecogin alfa, surgical drainage of infected fluid collections, fluid replacement, an appropriate support for organ dysfunction (e.g., hemodialysis in kidney failure, mechanical ventilation in pulmonary dysfunction, transfusion of blood products, and/or drug and fluid therapy for circulatory failure), and/or an Early Goal Directed Therapy (EGDT). The disclosure also provides methods of preventing sepsis or a symptom thereof by administering a plasma kallikrein binding protein (e.g., a prophylactically effective amount of a plasma kallikrein binding protein) to a subject at risk of developing sepsis (e.g., a subject that has been diagnosed as having an infection).

Scales useful for assessing sepsis and symptoms of sepsis include, e.g., the Baltimore Sepsis Scale (Meek et al. *J Burn Care Rehabil.* 12(6):564-8 (1991)) as well as other assessment tools known in the art.

Guidance for the determination of the dosage that delivers a therapeutically effective amount of a plasma kallikrein binding protein may be obtained from animal models of sepsis, see, e.g., those described in U.S. Pat. No. 6,964,856, and Buras et al. Nat Rev Drug Discov. 4(10):854-65 (2005) and references cited therein.

Acute Middle Cerebral Artery (MCA) Ischemic Event (Stroke)

An acute middle cerebral artery (MCA) ischemic event (stroke) is the rapidly developing loss of brain function(s) due to disturbance in the blood supply to the brain due to ischemia (lack of glucose and oxygen supply) caused by thrombosis (e.g., venous thrombosis), embolism, or systemic hypoperfusion. As a result, the affected area of the brain is unable to function, leading to inability to move one or more limbs on one side of the body, inability to understand or formulate speech, or inability to see one side of the visual field. A stroke is a medical emergency and can cause permanent neurological damage, complications, and/or death.

Symptoms of acute middle cerebral artery (MCA) ischemic event (stroke) include, e.g., hemiplegia, decreased sensation and muscle weakness of the face, numbness, reduction in sensory or vibratory sensation, altered smell, taste, hearing or vision (total or partial), drooping of eyelid (ptosis) and weakness of ocular muscles, decreased reflexes, balance problems and nystagmus, altered breathing and heart rate, weakness in sternocleidomastoid muscle with inability to turn head to one side, weakness in tongue (inability to protrude and/or move from side to side), aphasia, apraxia, visual field defect, memory deficits, hemineglect, disorganized thinking, confusion, hypersexual gestures, anosognosia, trouble walking, altered movement coordination, and vertigo and/or disequilibrium.

Treatment for acute middle cerebral artery (MCA) ischemic event (stroke) includes, e.g., thrombolysis (e.g., tissue plasminogen activator (tPA)), thrombectomy, angioplasty and stenting, therapeutic hypothermia, and medications (e.g., aspirin, clopidogrel and dipyridamole).

The disclosure provides methods of treating (e.g., stabilizing, reducing, or eliminating one or more symptoms or stabilizing the subject's score on a stroke scale) acute middle cerebral artery (MCA) ischemic event (stroke) by administering a plasma kallikrein binding protein (e.g., a therapeutically effective amount of a plasma kallikrein binding protein) to a subject having or suspected of having acute middle cerebral artery (MCA) ischemic event (stroke). Additionally provided are methods of treating acute middle cerebral artery (MCA) ischemic event (stroke) by administering a plasma kallikrein binding protein (e.g., a therapeutically effective amount of a plasma kallikrein binding protein) in combination with a second therapy, e.g., thrombolysis (e.g., tissue plasminogen activator (tPA)), thrombectomy, angioplasty and stenting, therapeutic hypothermia, and/or a medication (e.g., aspirin, clopidogrel and dipyridamole). The disclosure also provides methods of preventing acute middle cerebral artery (MCA) ischemic event (stroke) or a symptom thereof by administering a plasma kallikrein binding protein (e.g., a prophylactically effective amount of a plasma kallikrein binding protein) to a subject at risk of developing acute middle cerebral artery (MCA) ischemic event (stroke) (e.g., a subject that has experienced systemic hypoperfusion).

Scales useful for assessing acute middle cerebral artery (MCA) ischemic event (stroke) and symptoms of acute middle cerebral artery (MCA) ischemic event (stroke) include, e.g., Oxford Community Stroke Project classification (OCSP, also known as the Bamford or Oxford classification) (Bamford et al., Lancet 337 (8756): 1521-6 (1991)), and TOAST (Trial of Org 10172 in Acute Stroke Treatment) (Adams et al., Stroke 24 (1): 35-41 (1993)).

Guidance for the determination of the dosage that delivers a therapeutically effective amount of a plasma kallikrein binding protein may be obtained from animal models of acute middle cerebral artery (MCA) ischemic event (stroke), see, e.g., those described in Beech et al., Brain Res 895: 18-24 (2001), Buchan et al., Stroke 23 (2): 273-9 (1992), Carmichael, NeuroRx 2: 396-409 (2005), Chen et al., Stroke 17 (4): 738-43 (1986), Dittmar et al., Stroke 34: 2252-7 (2003), Dittmar et al., J Neurosci Methods 156: 50 (2006), Gerriets et al., J Neurosci Methods 122: 201-11 (2003), Gerriets et al., Stroke 35: 2372-2377 (2004), Graham et al., Comp Med 54: 486-496 (2004), Koizumi et al., Jpn J Stroke 8: 1-8 (2004), Longa et al., Stroke 20 (1): 84-91 (1989), Mayzel-Oreg, Magn Reson Med 51: 1232-8 (2004), Schmid-Elsaesser et al., Stroke 29 (10): 2162-70 (1989), Tamura et al., J Cereb Blood Flow Metab 1: 53-60 (1981), Watson et al., Ann Neurol 17: 497-504 (1985), and Zhang et al., J Cereb Blood Flow Metab 17: 123-35 (1997).

Restenosis

Restenosis is the reoccurrence of stenosis, a narrowing of a blood vessel, leading to restricted blood flow. Restenosis usually pertains to an artery or other large blood vessel that has become narrowed, received treatment to clear the blockage such as angioplasty, and subsequently become renarrowed. It can be defined as a reduction in the circumference of the lumen of 50% or more, and had a high incidence rate (25-50%) in patients who had undergone balloon angioplasty, with the majority of patients needing further angioplasty within 6 months.

Treatments for restenosis include, e.g., additional angioplasty if restenosis occurs without a stent or at either end of a stent, repeated angioplasty and insertion of another stent inside the original if restenosis occurs within a stent, drug-eluted stents, brachytherapy, and intracoronary radiation.

The disclosure provides methods of treating (e.g., stabilizing, reducing, or eliminating one or more symptoms of) restenosis (e.g., after angioplasty) by administering a plasma kallikrein binding protein (e.g., a therapeutically effective amount of a plasma kallikrein binding protein) to a subject having or suspected of having restenosis (e.g., after angioplasty). Additionally provided are methods of treating restenosis (e.g., after angioplasty) by administering a plasma kallikrein binding protein (e.g., a therapeutically effective amount of a plasma kallikrein binding protein) in combination with a second therapy, e.g., angioplasty if restenosis occurs without a stent or at either end of a stent, repeated angioplasty and insertion of another stent inside the original if restenosis occurs within a stent, a drug-eluted stent, brachytherapy, and/or intracoronary radiation. The disclosure also provides methods of preventing restenosis or a symptom thereof by administering a plasma kallikrein binding protein (e.g., a prophylactically effective amount of a plasma kallikrein binding protein) to a subject at risk of developing restenosis (e.g., a subject that has had stenosis).

Guidance for the determination of the dosage that delivers a therapeutically effective amount of a plasma kallikrein binding protein may be obtained from animal models of restenosis, see, e.g., those described in U.S. Pat. Nos. 5,304,122 and 6,034,053, and Kantor et al., Cardiovasc Radiat Med. 1(1):48-54 (1999), and references cited therein.

Systemic Lupus Erythematosus Nephritis

Systemic lupus erythematosus nephritis is an inflammation of the kidney caused by systemic lupus erythematosus (SLE), a chronic autoimmune connective tissue disease. SLE can be associated with vasculitis which are disorders characterized by inflammatory destruction of blood vessels.

Symptoms of systemic lupus erythematosus nephritis include, e.g., general symptoms of kidney disease, weight gain, high blood pressure, darker foamy urine, and swelling around the eyes, legs, ankles or fingers.

Treatments for systemic lupus erythematosus nephritis include, e.g., steroid therapy (e.g., corticosteroids), chemotherapy (e.g., cyclophosphamide, azathioprine, mycophenolate mofetil, or cyclosporine), and immunosuppressant agents (e.g., mycophenolate mofetil and intravenous cyclophosphamide).

The disclosure provides methods of treating (e.g., stabilizing, reducing, or eliminating one or more symptoms or stabilizing the subject's score on a lupus scale) systemic lupus erythematosus nephritis by administering a plasma kallikrein binding protein (e.g., a therapeutically effective amount of a plasma kallikrein binding protein) to a subject having or suspected of having systemic lupus erythematosus nephritis. Additionally provided are methods of treating systemic lupus erythematosus nephritis by administering a plasma kallikrein binding protein (e.g., a therapeutically effective amount of a plasma kallikrein binding protein) in combination with a second therapy, e.g., steroid therapy (e.g., a corticosteroid), chemotherapy (e.g., cyclophosphamide, azathioprine, mycophenolate mofetil, and/or cyclosporine), and/or an immunosuppressant agent (e.g., mycophenolate mofetil and/or intravenous cyclophosphamide). The disclosure also provides methods of preventing systemic lupus erythematosus nephritis or a symptom thereof by administering a plasma kallikrein binding protein (e.g., a prophylactically effective amount of a plasma kallikrein binding protein) to a subject at risk of developing systemic lupus erythematosus nephritis (e.g., a subject that has been diagnosed with lupus or a subject having a family member with lupus or a genetic predisposition thereto).

Scales useful for assessing systemic lupus erythematosus nephritis and symptoms of systemic lupus erythematosus nephritis include, e.g., World Health Organization (WHO) classification based on the biopsy (Weening et al., *J. Am. Soc. Nephrol.* 15 (2): 241-50 (2004)) as well as other assessment tools known in the art.

Guidance for the determination of the dosage that delivers a therapeutically effective amount of a plasma kallikrein binding protein may be obtained from animal models of systemic lupus erythematosus nephritis, see, e.g., those described in U.S. Pat. No. 7,265,261, Peng, Methods Mol Med. 102:227-72 (2004), and references cited therein.

Burn Injury and Wound Healing

A burn injury is a type of injury that may be caused by heat, electricity, chemicals, light, radiation, or friction. Muscle, bone, blood vessel, dermal and epidermal tissue can all be damaged with subsequent pain due to profound injury to nerves. Depending on the location affected and the degree of severity, a burn victim may experience a wide number of potentially fatal complications including shock, infection, electrolyte imbalance and respiratory distress. In burn injuries, the damage to epidermis and dermal elements is the result of several key insults which can be divided into initial (e.g., heat injury, inflammatory mediator injury, ischemia induced injury) and delayed insults. Excess heat causes rapid protein denaturation and cell damage. Much of the tissue damage, e.g., in the perfused subsurface burn, can be caused by toxic mediators of inflammation (e.g., oxidants and/or proteases) which are activated with the burn. Consumption of wound oxygen by neutrophils can lead to tissue hypoxia. Instant surface vascular thrombosis occurs along with cell death from the heat insult and causes ischemia and further tissue damage. Delayed injury after the initial heat and mediator damage includes, e.g., inflammation caused by neurotic tissue, bacteria on surface, caustic topical agents, and surface exudate; and continued damage to viable cells and new tissue growth by excess wound proteolytic activity and oxidant release.

Treatments of burn injury include, e.g., intravenous fluids, dressings, pain management (e.g., analgesics (e.g., ibuprofen and acetaminophen), narcotics, and local anesthetics), inflammatory mediator inhibitors, and antibiotics.

The disclosure provides methods of treating (e.g., stabilizing, reducing, or eliminating one or more symptoms or stabilizing the subject's score on a burn scale) a burn injury and/or promoting wound healing by administering a plasma kallikrein binding protein (e.g., a therapeutically effective amount of a plasma kallikrein binding protein) to a subject having or suspected of having a burn injury. Additionally provided are methods of treating a burn injury by administering a plasma kallikrein binding protein (e.g., a therapeutically effective amount of a plasma kallikrein binding protein) in combination with a second therapy, e.g., intravenous fluid, a dressing, pain management (e.g., an analgesic (e.g., ibuprofen and acetaminophen), a narcotic, and a local anesthetic), an inflammatory mediator inhibitor, and an antibiotic. The disclosure also provides methods of preventing burn injuries or a symptom thereof by administering a plasma kallikrein binding protein (e.g., a prophylactically effective amount of a plasma kallikrein binding protein) to a subject at risk of developing burn injuries (e.g., a subject whose occupation creates a risk of a burn injury, e.g., firefighter or cook).

Scales useful for assessing burns and symptoms of burns include, e.g., burn scales by degrees, by thickness, and by total body surface area (TBSA) (Meek et al. *J Burn Care Rehabil.* 12(6):564-8 (1991)) as well as other assessment tools known in the art.

Guidance for the determination of the dosage that delivers a therapeutically effective amount of a plasma kallikrein binding protein may be obtained from animal models of burn, such as a porcine burn model (Singer and McClain, Methods Mol Med. 78:107-19 (2003), a sheep model of thermal injury (Jonkam et al., Shock, 28:704-709 (2007)), a rabbit model of thermal injury (Nwariaku et al., Burns, 22:324-327 (1996)), and a mouse model of burn wounding (Stevenson et al., Methods Mol Med. 78:95-105 (2003)).

Combination Therapies

A plasma kallikrein binding protein described herein, e.g., an anti-plasma kallikrein antibody, e.g., an anti-plasma kallikrein Fab or IgG, can be administered in combination with one or more of the other therapies for treating a disease or condition associated with plasma kallikrein activity, e.g., a disease or condition described herein. For example, a plasma kallikrein binding protein can be used therapeutically or prophylactically with surgery, another anti-plasma kallikrein Fab or IgG (e.g., another Fab or IgG described herein), another plasma kallikrein inhibitor, a peptide inhibitor, or small molecule inhibitor. Examples of plasma kallikrein inhibitors that can be used in combination therapy with a plasma kallikrein binding protein described herein include plasma kallikrein inhibitors described in, e.g., WO 95/21601 or WO 2003/103475.

One or more plasma kallikrein inhibitors can be used in combination with one or more plasma kallikrein binding proteins described herein. For example, the combination can result in a lower dose of the inhibitor being needed, such that side effects are reduced.

A plasma kallikrein binding protein described herein can be administered in combination with one or more current therapies for treating a plasma kallikrein associated disease or condition, including, but not limited to the current therapies for treating the disorder, e.g., a current therapy for rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, head trauma or peri-tumor brain edema, sepsis, acute middle cerebral artery (MCA) ischemic event (stroke), restenosis (e.g., after angioplasty), systemic lupus erythematosis nephritis, burn injury, or wound healing. For example, pKal inhibition is a novel mechanism of treating disease and therefore could provide effects that are synergistic or additive with other therapeutics. For example, a protein described herein that inhibits plasma kallikrein or that inhibits a downstream event of plasma kallikrein activity can also be used in combination with another treatment for a plasma kallikrein associated disease, such as surgery or administration of a second agent, e.g., as described herein. For example, the second agent can include ecallantide, a C1 esterase inhibitor (e.g., CINRYZE™), aprotinin (TRASYLOL®), a bradykinin B2 receptor inhibitor (e.g., icatibant (FIRAZYR®)).

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of a plasma kallikrein binding protein described herein can also be used to reduce the dosage of another therapy, e.g., to reduce the side effects associated with another agent that is being administered. Accordingly, a combination can include administering a second agent at a dosage at least 10, 20, 30, or 50% lower than would be used in the absence of the plasma kallikrein binding protein.

The second agent or therapy can also be another agent for a plasma kallikrein associated therapy. Non-limiting examples of another treatment for a plasma kallikrein associated disease or condition include, e.g., ecallantide, a C1 esterase inhibitor (e.g., CINRYZE™), aprotinin (TRASYLOL®), a bradykinin B2 receptor inhibitor (e.g., icatibant (FIRAZYR®)) or a second binding protein described herein.

A combination therapy can include administering an agent that reduces the side effects of other therapies. The agent can be an agent that reduces the side effects of a plasma kallikrein associated disease treatment. For example, for inflammatory diseases, a pKal inhibitor could be steroid sparring. Also, there could be synergism with a TNF-alpha inhibitor for treating inflammation or a VEGF blocker for treating cancer and/or angiogenesis.

Diagnostic Uses

A protein that binds to plasma kallikrein described herein can have in vitro and in vivo diagnostic utilities. A plasma kallikrein binding protein described herein (e.g., a protein that binds or binds and inhibits plasma kallikrein) can be used, e.g., for in vivo imaging, e.g., during a course of treatment for a disease or condition in which plasma kallikrein is active, e.g., a disease or condition described herein, or in diagnosing a disease or condition described herein.

In one aspect, the disclosure provides a diagnostic method for detecting the presence of plasma kallikrein, in vitro or in vivo (e.g., in vivo imaging in a subject). The method can include localizing plasma kallikrein within a subject or within a sample from a subject. With respect to sample evaluation, the method can include, for example: (i) contacting a sample with plasma kallikrein binding protein; and (ii) detecting the location of the plasma kallikrein binding protein in the sample.

A plasma kallikrein binding protein can also be used to determine the qualitative or quantitative level of expression of plasma kallikrein in a sample. The method can also include contacting a reference sample (e.g., a control sample, e.g., a negative control) with the binding protein, and determining a corresponding assessment of the reference sample. A difference (e.g., increase), e.g., a statistically significant difference, in the formation of the complex in the sample or subject relative to the control sample or subject can be indicative of the presence of plasma kallikrein in the sample. In one embodiment, the plasma kallikrein binding protein does not cross react with another kallikrein protein, such as tissue kallikrein and/or with plasma prekallikrein. E.g., the binding protein binds to another kallikrein protein or to prekallikrein 5- to 10-fold less well (or even less well) than it binds to plasma kallikrein. For example, the binding protein can bind to plasma kallikrein with a KD of ~10-50 pM, whereas it binds to tissue kallikrein and/or prekallikrein at ~10 nM.

The plasma kallikrein binding protein can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the plasma kallikrein binding protein and plasma kallikrein can be detected by evaluating the binding protein bound to the plasma kallikrein or unbound binding protein. Conventional detection assays can be used, e.g., an enzyme-linked immunosorbent assays (ELISA), a radioimmunoassay (RIA) or tissue immunohistochemistry. Further to labeling the plasma kallikrein binding protein, the presence of plasma kallikrein can be assayed in a sample by a competition immunoassay utilizing standards labeled with a detectable substance and an unlabeled plasma kallikrein binding protein. In one example of this assay, the biological sample, the labeled standards, and the plasma kallikrein binding protein are combined and the amount of labeled standard bound to the unlabeled binding protein is determined. The amount of plasma kallikrein in the sample is inversely proportional to the amount of labeled standard bound to the plasma kallikrein binding protein.

Fluorophore and chromophore labeled proteins can be prepared. Because antibodies and other proteins absorb light having wavelengths up to about 310 nm, the fluorescent moieties should be selected to have substantial absorption at wavelengths above 310 nm and preferably above 400 nm A variety of suitable fluorescers and chromophores are described by Stryer, 1968, Science 162:526 and Brand, L. et al., 1972, Annu. Rev. Biochem. 41:843-868. The proteins can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein can be used to detect the presence or localization of the plasma kallikrein in a sample, e.g., using fluorescent microscopy (such as confocal or deconvolution microscopy).

Histological Analysis. Immunohistochemistry can be performed using the proteins described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The plasma kallikrein binding protein can also be immobilized on a protein array. The protein array can be used as a diagnostic tool, e.g., to screen medical samples (such as isolated cells, blood, sera, biopsies, and the like). Of course, the protein array can also include other binding proteins, e.g., that bind to plasma kallikrein or to other target molecules.

Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, I-VII; MacBeath and Schreiber, 2000, Science 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the proteins can be grown on a filter in an arrayed format. Polypeptide production is induced, and the expressed polypeptides are immobilized to the filter at the location of the cell. A protein array can be contacted with a labeled target to determine the extent of binding of the target to each immobilized polypeptide. Information about the extent of binding at each address of the array can be stored as a profile, e.g., in a computer database. The protein array can be produced in replicates and used to compare binding profiles, e.g., of a target and a non-target.

FACS (Fluorescence Activated Cell Sorting). The plasma kallikrein binding protein can be used to label cells, e.g., cells in a sample (e.g., a patient sample). The binding protein is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the binding protein from those cells not bound by the binding protein. The separated cells can be cultured and/or characterized.

In vivo Imaging. Also featured is a method for detecting the presence of plasma kallikrein expressing tissues in vivo. The method includes (i) administering to a subject (e.g., a patient having, e.g., a plasma kallikrein associated disease or condition) an anti-plasma kallikrein antibody, conjugated to a detectable marker; (ii) exposing the subject to a means for detecting said detectable marker to the plasma kallikrein expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The protein can be labeled with such reagents; for example, see Wensel and Meares, 1983, Radioimmunoimaging and Radioimmunotherapy, Elsevier, New York for techniques relating to the radiolabeling of antibodies and D. Colcher et al., 1986, *Meth. Enzymol.* 121: 802-816.

The binding protein can be labeled with a radioactive isotope (such as $^{14}$C, $^{3}$H, $^{35}$S, $^{125}$I, $^{32}$P, $^{131}$I). A radiolabeled binding protein can be used for diagnostic tests, e.g., an in vitro assay. The specific activity of a isotopically-labeled binding protein depends upon the half life, the isotopic purity of the radioactive label, and how the label is incorporated into the antibody.

In the case of a radiolabeled binding protein, the binding protein is administered to the patient, is localized to cells bearing the antigen with which the binding protein reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments are used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The plasma kallikrein binding protein can also be labeled with an indicating group containing of the NMR active $^{19}F$ atom, or a plurality of such atoms inasmuch as (i) substantially all of naturally abundant fluorine atoms are the $^{19}F$ isotope and, thus, substantially all fluorine containing compounds are NMR active; (ii) many chemically active polyfluorinated compounds such as trifluoracetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing plasma kallikrein.

The following examples provide further illustration and are not limiting.

EXAMPLES

Example 1

We have discovered several antibody inhibitors and binders of plasma kallikrein (pKal). The most potent of these have been further characterized and shown to have apparent inhibition constants ($K_{i,app}$)<10 nM, to be specific pKal inhibitors with respect to other tested serine proteases, and to not bind prekallikrein. Amino acid sequences of the CDRs for the inhibitors and the binders are shown in Tables 1 and 2, respectively.

TABLE 1

CDR Amino Acid Sequences, ELISA Signal, and Apparent Inhibition Constant of Antibody Inhibitors of PKal

| Initial Name | Human pKal ELISA (T/B) | Human pKal (Ki, app nM) | LV-CDR1 | LV-CDR2 |
| --- | --- | --- | --- | --- |
| M6-D09 | 39.9 | 5.9 | RASQSIRNYLN | AASTLQS |
| M7-B04 | 4.1 | 54 | TGTNSDVGNYNLVS | EVNKRPSCS |
| M7-E07 | 45.7 | 36 | SGDKLGDKYAC | QDSKRPS |
| M8-A09 | 5.4 | 105 | SGDKLGNKYAY | QDNNRPS |
| M10-F10 | 39.2 | <100 nM | RASQSISVYLN | GASNLQF |
| M10-H05 | 42.2 | 18 | RASQSVSSSYLA | GASSRAT |
| M12-D05 | 48.5 | 5.2 | SGDQLGDKYVG | QDTKRPS |
| M27-E05 | 41.3 | 16 | SGDKLGDKYAC | QDSKRPS |
| M28-B11 | 33.3 | 5.5 | SGDQLGDKYVG | QDTKRPS |
| M29-D09 | 47.5 | 0.7 | SGNKLGDKYVA | QDTKRPS |
| M29-E09 | 28.8 | 11 | SGDNLGNKYNS | QDTKRPS |
| M35-G04 | 11.1 | 2.9 | RASQSVSSYLA | DASNRAT |
| M38-F02 | 33.5 | 14 | SGEKLGDKYVS | EDSRRPS |
| M41-A11 | 28.0 | 13 | SGDKLGDKYTS | QDIKRPS |
| M73-D06 | 4.0 | <100 nM | SGSSSNIGSNTVS | NDHRRPS |
| M76-D01 | 11.2 | <100 nM | RSSQSLSDDGNTYLD | TLSYRAS |
| M110-C12 | 2.4 | <100 nM | RSSLSLLHSNGYNYLD | LSSTRAS |
| M137-E12 | 4.5 | 79 | SGNNSNFGSNTVT | SDSRRPS |
| M142-H08 | 29.9 | 0.2 | RASQPIDNYLN | AASRLQS |
| M145-D01 | 6.2 | 1.1 | RASQSVSSYLA | DASNRAT |
| M145-D11 | 40.0 | 0.79 | SGDKLGDKYTS | QDIKRPS |
| M146-E12 | 49.6 | 2.2 | RASGDIGNALG | DASTLQS |

TABLE 1-continued

CDR Amino Acid Sequences, ELISA Signal, and Apparent Inhibition Constant of Antibody Inhibitors of PKal

| M152-A12 | 19. | <100 nM | RASQSISSYLS | AASSLQS |
| M160-G12 | 38.3 | 17 | RASQGISSYLA | AASTLQS |
| M161-C11 | 41.8 | 0.3 | SGDKLGDKYVS | QDTKRPS |
| M162-A04 | 11.4 | 4.8 | RASQSISSWLA | KASTLES |
| X67-B03 | nd | 2.1 | RASQPIDNYLN | AASRLQS |
| X67-C03 | nd | 0.7 | RASQPIDNYLN | AASRLQS |
| X67-C09 | nd | 8.6 | RASQPIDNYLN | AASRLQS |
| X67-D03 | nd | 0.1 | RASQPIDNYLN | AASRLQS |
| X67-E04 | nd | 1.3 | RASQPIDNYLN | AASRLQS |
| X67-F01 | nd | 0.9 | RASQPIDNYLN | AASRLQS |
| X67-F10 | nd | 1.3 | RASQPIDNYLN | AASRLQS |
| X67-G04 | nd | 0.35 | RASQPIDNYLN | AASRLQS |
| X67-H04 | nd | 3.6 | RASQPIDNYLN | AASRLQS |
| X81-B01 | nd | 0.2 | RTSQFVNSNYLA | GASSRAT |

| Initial Name | LV-CDR3 | HV-CDR1 | HV-CDR2 | HV-CDR3 |
| --- | --- | --- | --- | --- |
| M6-D09 | QQLSGYPHT | FYYMV | VIYPSGGITVYADSVKG | DKWAVMPPYYYYAMDV |
| M7-B04 | YAGNRNFYV | WYSMV | SISPSGGETNYADSVKG | HTAARPFYYYYMDV |
| M7-E07 | QAWDSSTGV | WYLMI | YIYPSGGFTYYADSVKG | TEGPLSWGYGMDV |
| M8-A09 | QAWDSRTVV | TYFML | SIYPSGGNTVYADSVKG | AASPVRNYYYYGMDV |
| M10-F10 | QQTFSLFT | FYNMN | SISPSGGETNYADSVKG | GGGAYRNNWWGGFDI |
| M10-H05 | QQYGSSPFT | PYNMY | SIRPSGGGTVYADSVKG | GFIAARWYYFDY |
| M12-D05 | QAWDTSTAG | WYTMV | RIYPSGGWTKYADSVKG | EGLLWFGENAFDI |
| M27-E05 | QAWDSSTGV | WYLMI | YIYPSGGFTYYADSVKG | TEGPLSWGYGMDV |
| M28-B11 | QAWDTSTAG | WYTMV | RIYPSGGWTKYADSVKG | EGLLWFGENAFDI |
| M29-D09 | QAWDSSIVI | WYTMV | YIYPSGGATFYADSVKG | GSYDYIWGFYSDH |
| M29-E09 | QAWDGNVV | WYEMG | SIYSSGGGTMYADSVKG | NPQYSGYDRSLSDGAFDI |
| M35-G04 | QQRSNWPRGFT | YYHMS | VISPSGGSTKYADSVKG | GGSSDYAWGSYRRPYYFDY |
| M38-F02 | QAWDSSTAI | YYMMV | YIYSSGGHTVYADSVKG | DLFLYDFWSKGAFDI |
| M41-A11 | QAWDSPNARV | HYRMS | SIYPSGGRTVYADSVKG | DKFEWRLLFRGIGNDAFDI |
| M73-D06 | SAWDDSLNGVV | RYEMY | SISSSGGPTAYADSVKG | GTPKWELLLRSIYIENAFDI |
| M76-D01 | MQGTHWPPT | FYAMH | GIVPSGGRTHYADSVKG | DSSGSPNPLFDY |
| M110-C12 | MQPLETPPT | YYEMD | GISSSGGHTAYADSVKG | ERRSSSRARYYYGMDV |
| M137-E12 | AAWDDSLNGV | DYRMQ | VIVPSGGNTMYADSVKG | GGPGSSIAARRAPTGYYGMDV |
| M142-H08 | QQSYTVPYT | AYSMI | YIRPSGGRTTYADSVKG | GGLLLWFRELKSNYFDY |
| M145-D01 | QQRSNWPRGFT | YYHMS | VISPSGGSTKYADSVKG | GGSSDYAWGSYRRPYYFDY |
| M145-D11 | QAWDSPNARV | HYRMS | SIYPSGGRTVYADSVKG | DKFEWRLLFRGIGNDAFDI |
| M146-E12 | LQGYNYPRT | RYIMH | SISPSGGLTSYADSVKG | EFENAYHYYYGMDV |
| M152-A12 | QQSISIPRT | PYFMG | GIGPSGGSTTYADSVKG | EGPPYSSGWYRGLRQYHFDY |

TABLE 1-continued

CDR Amino Acid Sequences, ELISA Signal, and Apparent Inhibition Constant of Antibody Inhibitors of PKal

| | | | | |
|---|---|---|---|---|
| M160-G12 | QQLNSYPLT | HYLMT | YISPSGGHTIYADSVKG | VARGIAARSRTSYFDY |
| M161-C11 | QAWDSSTYV | DYAMK | SISSSGGVTQYADSVKG | EEDYSSSWYSRRFDYYYGMDV |
| M162-A04 | QQYNTYWT | HYIMM | GIYSSGGITVYADSVKG | RRTGIPRRDAFDI |
| X67-B03 | QQSYTVPYT | AYSMI | YIRPSGGRTTYADSVKG | GGLLLWSRELKSNYFDY |
| X67-C03 | QQSYTVPYT | AYSMI | YIRPSGGRTTYADSVKG | GGLLLWFMELKSNYFDY |
| X67-C09 | QQSYTVPYT | AYSMI | YIRPSGGRTTYADSVKG | GGLLLWGRELKSNYFDY |
| X67-D03 | QQSYTVPYT | AYSMI | YIRPSGGRTTYADSVKG | GGLLLWNRELKSNYFDY |
| X67-E04 | QQSYTVPYT | AYSMI | YIRPSGGRTTYADSVKG | GGLLLWDRELKSNYFDY |
| X67-F01 | QQSYTVPYT | AYSMI | YIRPSGGRTTYADSVKG | GGLLLWQRELKSNYFDY |
| X67-F10 | QQSYTVPYT | AYSMI | YIRPSGGRTTYADSVKG | GGLLLWTRELKSNYFDY |
| X67-G04 | QQSYTVPYT | AYSMI | YIRPSGGRTTYADSVKG | GGLLLWARELKSNYFDY |
| X67-H04 | QQSYTVPYT | AYSMI | YIRPSGGRTTYADSVKG | GGLLLWERELKSNYFDY |
| X81-B01 | QQSSRTPWT | HYLMT | YISPSGGHTIYADSVKG | VARGIAARSRTSYFDY |

Abbreviations used: "T/B" is the ELISA signal obtained using of the "target" (biotinylated plasma kallikrein) divided by the ELISA signal of the "background" (streptavidin); both of which were coated on microtiter plates. "nd" is not determined. The symbol "q" refers to the amber suppressible stop codon (TAG), which is translated as glutamine (Q) in strains of E. coli such as the TG1 cells that were used to express the Fab fragments.

Amino Acid Sequences of Light Chain (LC) and Heavy Chain (HC) Variable Domain of pKal Antibody Inhibitors are Shown Below.

```
M6-D09 LC
QDIQMTQSPS SLSASVGDRV TITCRASQSI RNYLNWYQQK PGKAPNLLIY AASTLQSGVP    60

ARFSGSGSGT DFTLTISSLQ PEDFATYYCQ QLSGYPHTFG QGTKLEIK                108

M6-D09 HC
EVQLLESGGG LVQPGGSLRL SCAASGFTFS FYYMVWVRQA PGKGLEWVSV IYPSGGITVY    60

ADSVKGRFTI SRDNSKNTLY LQMNSLRAED TAVYYCARDK WAVMPPYYYY AMDVWGQGTT   120

VTVSSASTKG PSVFPLAPSS KS                                           142

M7-B04 LC
QSALTQPASV SGSPGQSITI SCTGTNSDVG NYNLVSWYQQ HPGEAPKLLI YEVNKRPSGV    60

SNRFSGSKSG NTASLTISGL QAEDEADYLC CSYAGNRNFY VFGAGTKVTV L            111

M7-B04 HC
EVQLLESGGG LVQPGGSLRL SCAASGFTFS WYSMVWVRQA PGKGLEWVSS ISPSGGLTNY    60

ADSVKGRFTI SRDNSKNTLY LQMNSLRAED TAVYYCARHT AARPFYYYYM DVWGKGTTVT   120

VSSASTKGPS VFPLAPSSKS                                              140

M7-E07 LC
QSELTQPPSV SVSPGQTASI TCSGDKLGDK YACWYQQKPG QSPVLVIYQD SKRPSGIPER    60

FSGSNSGNTA TLTISGTQAM DEADYYCQAW DSSTGVFGGG TKLTVL                  106

M7-E07 HC
EVQLLESGGG LVQPGGSLRL SCAASGFTFS WYLMIWVRQA PGKGLEWVSY IYPSGGFTYY    60

ADSVKGRFTI SRDNSKNTLY LQMNSLRAED MAVYYCARTE GPLSWGYGMD VWGQGTTVTV   120

SSASTKGPSV FPLAPSSKS                                               139
```

```
M8-A09 LC
QCELTQPPSE SVSPGQTANI TCSGDKLGNK YAYWYQQKPG QSPVLVIYQD NNRPSGIPER    60

FSGSNSGNTA TLTISGTQAI DEANYYCQAW DSRTVVFGGG TKLTVL                  106

M8-A09 HC
EVQLLESGGG LVQPGGSLRL SCAASGFTFS TYFMLWVRQA PGKGLEWVSS IYPSGGNTVY    60

ADSVKGRFTI SRDNSKNTLY LQMNSLRAED TAVYYCARAA SPVRNYYYYG MDVWGQGTTV   120

TVSSASTKGP SVFPLAPSSK S                                            141

M10-F10 LC
QDIQMTQSPS SLSASVGDRV TITCRASQSI SVYLNWYQHK PGKAPKLLIY GASNLQFGVP    60

SRFSGSGYGT DFTLTISSLQ PEDFATYHCQ QTFSLFTFGG GTKVEIK                 107

M10-F10 HC
EVQLLESGGG LVQPGGSLRL SCAASGFTFS FYNMNWVRQA PGKGLEWVSS ISPSGGETNY    60

ADSVKGRFTI SRDNSKNTLY LQMNSLRAED TAVYYCARGG GAYRNNWWGG FDIWGLGTMV   120

TVSSASTKGP SVFPLAPSSK S                                            141

M10-H05 LC
QDIQMTQSPG TLSLSPGERA TLSCRASQSV SSSYLAWYQQ KPGQAPRLLI YGASSRATGI    60

PDRFSGSGSG TDFTLTISRL EPEDFAVYYC QQYGSSPFTF GPGTKVDIK               109

M10-H05 HC
EVQLLESGGG LVQPGGSLRL SCAASGFTFS PYNMYWVRQA PGKGLEWVSS IRPSGGGTVY    60

ADSVKGRFTI SRDNSKNTLY LQMNSLRAED TAVYYCAGGF IAARWYYFDY WGQGTLVTVS   120

SASTKGPSVF PLAPSSKS                                                138

M12-D05 LC
QSVLTQPPSV SVSPGQTATI TCSGDQLGDK YVGWYQQKPG QSPILVIYQD TKRPSGIPER    60

FSGSNSGNTA TLTISGTHTV DEAHYYCQAW DTSTAGFGGG TKLTVL                  106

M12-D05 HC
EVQLLESGGG LVQPGGSLRL SCAASGFTFS WYTMVWVRQA PGKGLEWVSR IYPSGGWTKY    60

ADSVKGRFTI SRDNSKNTLY LQMNSLRAED TATYYCAREG LLWFGENAFD IWGQGTMVTV   120

SSASTKGPSV FPLAPSSKS                                               139

M27-E05 LC
QSELTQPPSV SVSPGQTASI TCSGDKLGDK YACWYQQKPG QSPVLVIYQD SKRPSGIPER    60

FSGSNSGNTA TLTISGTQAM DEADYYCQAW DSSTGVFGGG TKLTVL                  106

M27-E05 HC
EVQLLESGGG LVQPGGSLRL SCAASGFTFS WYLMIWVRQA PGKGLEWVSY IYPSGGFTYY    60

ADSVKGRFTI SRDNSKNTLY LQMNSLRAED MAVYYCARTE GPLSWGYGMD VWGQGTTVTV   120

SSASTKGPSV FPLAPSSKS                                               139

M28-B11 LC
QSVLTQPPSV SVSPGQTATI TCSGDQLGDK YVGWYQQKPG QSPILVIYQD TKRPSGIPER    60

FSGSNSGNTA TLTISGTHTV DEAHYYCQAW DTSTAGFGGG TKLTVL                  106

M28-B11 HC
EVQLLESGGG LVQPGGSLRL SCAASGFTFS WYTMVWVRQA PGKGLEWVSR IYPSGGWTKY    60

ADSVKGRFTI SRDNSKNTLY LQMNSLRAED TATYYCAREG LLWFGENAFD IWGQGTMVTV   120

SSASTKGPSV FPLAPSSKS                                               139

M29-D09 LC
QSALTQPPTV SVSPGQTARI TCSGNKLGDK YVAWYQQKPG QSPMLVIYQD TKRPSRVSER    60

FSGSNSANTA TLSISGTQAL DEADYYCQAW DSSIVIFGGG TRLTVL                  106
```

```
M29-D09 HC
EVQLLESGGG LVQPGGSLRL SCAASGFTFS WYTMVWVRQA PGKGLEWVSY IYPSGGATFY    60

ADSVKGRFTI SRDNSKNTLY LQMNSLRAED TAVYYCAMGS YDYIWGFYSD HWGQGTLVTV   120

SSASTKGPSV FPLAPSSKS                                                139

M29-E09 LC
QYELTQPPSV SVSPGQTATI TCSGDNLGNK YNSWYQQKPG QSPLLVIYQD TKRPSAIPER    60

FSGSNSGNTA TLTISGTQAM DEADYYCQAW DGNVVFGGGT KLTVL                   105

M29-E09 HC
EVQLLESGGG LVQPGGSLRL SCAASGFTFS WYEMGWVRQA PGKGLEWVSS IYSSGGGTMY    60

ADSVKGRFTI SRDNSKNTLY LQMNSLRAED TAVYYCARNP QYSGYDRSLS DGAFDIWGQG   120

TMVTVSSAST KGPSVFPLAP SSKS                                          144

M35-G04 LC
QDIQMTQSPA TLSLSPGERA TLSCRASQSV SSYLAWYQQK PGQAPRLLIY DASNRATGIP    60

ARFSGSGSGT DFTLTISSLE PEDFAVYYCQ QRSNWPRGFT FGPGTKVDIK              110

M35-G04 HC
EVQLLESGGG LVQPGGSLRL SCAASGFTFS YYHMSWVRQA PGKGLEWVSV ISPSGGSTKY    60

ADSVKGRFTI SRDNSKNTLY LQMNSLRAED TAVYYCARGG SSDYAWGSYR RPYYFDYWGQ   120

GTLVTVSSAS TKGPSVFPLA PSSKS                                         145

M38-F02 LC
QSVLTQPPSV SVSPGQTASI TCSGEKLGDK YVSWYQQKPG QSPSLVICED SRRPSGIPER    60

FSGSNSGNTA TLTISGAQPM DEADYYCQAW DSSTAIFGPG TKVTVL                  106

M38-F02 HC
EVQLLESGGG LVQPGGSLRL SCAASGFTFS YYMMVWVRQA PGKGLEWVSY IYSSGGHTVY    60

ADSVKGRFTI SRDNSKNTLY LQMNSLRAED TAVYYCARDL FLYDFWSKGA FDIWGQGTMV   120

TVSSASTKGP SVFPLAPSSK S                                             141

M41-A11 LC
QSVLTQPPSV SVSPGQTASI TCSGDKLGDK YTSWYQQRPG QSPVLVIYQD IKRPSGIPER    60

FSGSNSGNTA TLTISGTQAM DEADYYCQAW DSPNARVFGS GTKVTVL                 107

M41-A11 HC
EVQLLESGGG LVQPGGSLRL SCAASGFTFS HYRMSWVRQA PGKGLEWVSS IYPSGGRTVY    60

ADSVKGRFTI SRDNSKNTLY LQMNSLRAED TAVYYCAKDK FEWRLLFRGI GNDAFDIWGQ   120

GTMVTVSSAS TKGPSVFPLA PSSKS                                         145

M73-D06  LC
QSELTQPPSA SETPGQRVTI SCSGSSSNIG SNTVSWFQQL PGSAPRLLIY NDHRRPSGVP    60

DRFSGSKSGT SASLVISGLQ SQDEADYYCS AWDDSLNGVV FGGGTKLTVL              110

M73-D06 HC
EVQLLESGGG LVQPGGSLRL SCAASGFTFS RYEMYWVRQA PGKGLEWVSS ISSSGGPTAY    60

ADSVKGRFTI SRDNSKNTLY LQMNSLRAED TAMYYCAKGT PKWELLLRSI YIENAFDIWG   120

QGTMVTVSSA STKGPSVFPL APSSKS                                        146

M76-D01  LC
QDIVMTQTPP SLPVNPGEPA SISCRSSQSL SDDGNTYLDW YLQRPGQSPQ LLIHTLSYRA    60

SGVPDRFSGS GSGTDFTLKI SRVEAEDVGV YYCMQGTHWP PTFGQGTKVE IK           112

M76-D01 HC
EVQLLESGGG LVQPGGSLRL SCAASGFTFS FYAMHWVRQA PGKGLEWVSG IVPSGGRTHY    60

ADSVKGRFTI SRDNSKNTLY LQMNSLRAED TAVYYCATDS SGSPNPLFDY WGQGTLVTVS   120

SASTKGPSVF PLAPSPKS                                                 138
```

```
M110-C12 LC
QDIQMTQSPL SLSVTPGEPA SISCRSSLSL LHSNGYNYLD WYVQRPGQSP QLLMYLSSTR    60

ASGVPDRFSG SGSGTDFTLE ISRVEAEDVG VYYCMQPLET PPTFGGGTKV EIK          113

M110-C12 HC
EVQLLESGGG LVQPGGSLRL SCAASGFTFS YYEMDWVRQA PGKGLEWVSG ISSSGGHTAY    60

ADSVKGRFTI SRDNSKNTLY LQMNSLRAED TATYYCARER RSSSRARYYY GMDVWGQGTT   120

VTVSSASTKG PSVFPLAPSS KS                                            142

M137-E12 LC
QSVLIQPPSV SGIPGQRVTI SCSGNNSNFG SNTVTWYQQL PGTAPKLLIY SDSRRPSGVP    60

DRFSGSRSDT SASLAISGLQ SEDEAEYHCA AWDDSLNGVF GGGTKLTVL               109

M137-E12 HC
EVQLLESGGG LVQPGGSLRL SCAASGFTFS DYRMQWVRQA PGKGLEWVSV IVPSGGNTMY    60

ADSVKGRFTI SRDNSKNTLY LQMNSLRAED TAVYYCARGG PGSSIAARRA PTGYYGMDVW   120

GQGTTVTVSS ASTKGPSVFP LAPSSKS                                       147

M142-H08 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

M142-H08 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRELKS NYFDYWGQGT   120

LVTVSSASTK GPSVFPLAPS SKS                                           143

M145-D01 LC
QDIQMTQSPA TLSLSPGERA TLSCRASQSV SSYLAWYQQK PGQAPRLLIY DASNRATGIP    60

ARFSGSGSGT DFTLTISSLE PEDFAVYYCQ QRSNWPRGFT FGPGTKVDIK              110

M145-D01 HC
EVQLLESGGG LVQPGGSLRL SCAASGFTFS YYHMSWVRQA PGKGLEWVSV ISPSGGSTKY    60

ADSVKGRFTI SRDNSKNTLY LQMNSLRAED TAVYYCARGG SSDYAWGSYR RPYYFDYWGQ   120

GTLVTVSSAS TKGPSVFPLA PSSKS                                         145

M145-D11 LC
QSVLTQPPSV SVSPGQTASI TCSGDKLGDK YTSWYQQRPG QSPVLVIYQD IKRPSGIPER    60

FSGSNSGNTA TLTISGTQAM DEADYYCQAW DSPNARVFGS GTKVTVL                 107

M145-D11 HC
EVQLLESGGG LVQPGGSLRL SCAASGFTFS HYRMSWVRQA PGKGLEWVSS IYPSGGRTVY    60

ADSVKGRFTI SRDNSKNTLY LQMNSLRAED TAVYYCAKDK FEWRLLFRGI GNDAFDIWGQ   120

GTMVTVSSAS TKGPSVFPLA PSSKS                                         145

M146-E12 LC
QDIQMTQSPS SLSASVGDRV TITCRASGDI GNALGWYQQK PGKAPRLLIS DASTLQSGVP    60

LRFSGSGSGT EFTLTISSLQ PEDFATYYCL QGYNYPRTFG QGTKLEIR                108

M146-E12 HC
EVQLLESGGG LVQPGGSLRL SCAASGFTFS RYIMHWVRQA PGKGLEWVSS ISPSGGLTSY    60

ADSVKGRFTI SRDNSKNTLY LQMNSLRAED TAVYYCAREF ENAYHYYYYG MDVWGQGTTV   120

TVSSASTKGP SVFPLAPSSK S                                             141

M152-A12 LC
QDIQMTQSPS SLSASVGDRV TITCRASQSI SSYLSWYQQR PGKAPNLLIY AASSLQSGVP    60

SRFSGSGSGT DFTLTISSLQ PEDFATYYCQ QSISIPRTFG QGTKVEVK                108
```

```
M152-A12 HC
EVQLLESGGG LVQPGGSLRL SCAASGFTFS PYFMGWVRQA PGKGLEWVSG IGPSGGSTTY        60

ADSVKGRFTI SRDNSKNTLY LQMNSLRAED TAVYYCAREG PPYSSGWYRG LRQYHFDYWG       120

QGTLVTVSSA STKGPSVFPL APSSKS                                            146

M160-G12 LC
QDIQMTQSPS FLSASVGDRV TITCRASQGI SSYLAWYQQK PGKAPKLLIY AASTLQSGVP        60

SRFSGSGSGT EFTLTISSLQ PEDFATYYCQ QLNSYPLTFG GGTKVEIK                    108

M160-G12 HC
EVQLLESGGG LVQPGGSLRL SCAASGFTFS HYLMTWVRQA PGKGLEWVSY ISPSGGHTIY        60

ADSVKGRFTI SRDNSKNTLY LQMNSLRAED TAVYYCARVA RGIAARSRTS YFDYWGQGTL       120

VTVSSASTKG PSVFPLAPSS KS                                                142

M161-C11 LC
QSALTQPPSV SVSPGQTASI TCSGDKLGDK YVSWYQQRPG QSPVLVIYQD TKRPSGIPER        60

FSGSNSGNTA TLTISGTQAV DEADYYCQAW DSSTYVFGGG TKVTVL                      106

M161-C11 HC
EVQLLESGGG LVQPGGSLRL SCAASGFTFS DYAMKWVRQA PGKGLEWVSS ISSSGGVTQY        60

ADSVKGRFTI SRDNSKNTLY LQMNSLRAED TAVYYCAREE DYSSSWYSRR FDYYYGMDVW       120

GQGTTVTVSS ASTKGPSVFP LAPSSKS                                           147

M162-A04 LC
QDIQMTQSPS TLSASVGDRV TITCRASQSI SSWLAWYQQK PGKAPNLLIY KASTLESGVP        60

SRFSGSGSGT EFTLTISSLQ PDDFATYYCQ QYNTYWTFGQ GTKVEIK                     107

M162-A04 HC
EVQLLESGGG LVQPGGSLRL SCAASGFTFS HYIMMWVRQA PGKGLEWVSG IYSSGGITVY        60

ADSVKGRFTI SRDNSKNTLY LQMNSLRAED TAVYYCAYRR TGIPRRDAFD IWGQGTMVTV       120

SSASTKGPSV FPLAPSSKS                                                    139

X67-B03 LC
QDIQMTQSPS SLSAFVGDRV TITCRASQPI DNYLNWYHQK PGKAPKLLIY AASRLQSGVP        60

SRLSGSGFGT DFTLTISSLQ PEDFGNYYCQ QSYTVPYTFG GGTKVEIR                    108

X67-B03 HC
EVQLLESGGG LVQPGGSLRL SCAASGFTFS AYSMIWVRQA PGKGLEWVSY IRPSGGRTTY        60

ADSVKGRFTI SRDNSKNTLY LQMNSLRAED TAVYYCARGG LLLWSRELKS NYFDYWGQGT       120

LVTVSSASTK GPSVFPLAPS SKS                                               143

X67-C03 LC
QDIQMTQSPS SLSAFVGDRV TITCRASQPI DNYLNWYHQK PGKAPKLLIY AASRLQSGVP        60

SRLSGSGFGT DFTLTISSLQ PEDFGNYYCQ QSYTVPYTFG GGTKVEIR                    108

X67-C03 HC
EVQLLESGGG LVQPGGSLRL SCAASGFTFS AYSMIWVRQA PGKGLEWVSY IRPSGGRTTY        60

ADSVKGRFTI SRDNSKNTLY LQMNSLRAED TAVYYCARGG LLLWMRELKS NYFDYWGQGT       120

LVTVSSASTK GPSVFPLAPS SKS                                               143

X67-C09 LC
QDIQMTQSPS SLSAFVGDRV TITCRASQPI DNYLNWYHQK PGKAPKLLIY AASRLQSGVP        60

SRLSGSGFGT DFTLTISSLQ PEDFGNYYCQ QSYTVPYTFG GGTKVEIR                    108

X67-C09 HC
EVQLLESGGG LVQPGGSLRL SCAASGFTFS AYSMIWVRQA PGKGLEWVSY IRPSGGRTTY        60

ADSVKGRFTI SRDNSKNTLY LQMNSLRAED TAVYYCARGG LLLWGRELKS NYFDYWGQGT       120

LVTVSSASTK GPSVFPLAPS SKS                                               143
```

-continued

```
X67-D03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-D03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWNRELKS NYFDYWGQGT   120

LVTVSSASTK GPSVFPLAPS SKS                                           143

X67-E04 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X67-E04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWDRELKS NYFDYWGQGT   120

LVTVSSASTK GPSVFPLAPS SKS                                           143

X67-F01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-F01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWQRELKS NYFDYWGQGT   120

LVTVSSASTK GPSVFPLAPS SKS                                           143

X67-F10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-F10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWTRELKS NYFDYWGQGT   120

LVTVSSASTK GPSVFPLAPS SKS                                           143

X67-G04 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-G04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWARELKS NYFDYWGQGT   120

LVTVSSASTK GPSVFPLAPS SKS                                           143

X67-H04 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-H04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWERELKS NYFDYWGQGT   120

LVTVSSASTK GPSVFPLAPS SKS                                           143
Note:
X81-B01 is a germilined IgG derived from X63-G06 which is shown in Table 7.
```

TABLE 2

CDR Amino Acid Sequences and ELISA Signal of Antibody Binders of PKal

| Initial Name | Human pKal ELISA (T/B) | LV-CDR1 | LV-CDR2 | LV-CDR3 | HV-CDR1 | HV-CDR2 | HV-CDR3 |
|---|---|---|---|---|---|---|---|
| M6-A06 | 11.7 | RASQSISMYLN | GTSSLQS | QQSYSAPWT | LYQMT | GIWPSGGFTDYADSVKG | VSTAVADNDY |
| M6-A08 | 23.4 | RASQRISFYLN | GASSLQS | QQTFSTPNT | PYPMQ | SISSSGGMTEYADSVKG | DDYGGKGGAFDI |
| M6-D03 | 15.5 | RASQSISIYVN | AASSLQS | QQSYSTLWT | KYFMG | VIGSGGWTSYADSVKG | VSTAVADNDY |
| M6-D08 | 16 | RASQSISIYVN | GASSLQS | QQSYTRWT | RYHMV | SISPSGGWTNYADSVKG | EMATIAGQFDP |
| M6-G05 | 18.5 | RASQSISTYLN | NAFSMER | QQSYTTPTT | RYRMV | SIYPSGGMTAYADSVKG | DAVGIGDAFDI |
| M8-C04 | 44.7 | SGDKLGDKYTS | QDSKRPS | QAWDSSTV | YYPMQ | YIYPSGGLTSYADSVKG | LFYGSGSVGFEY |
| M8-D05 | 11.9 | RASQDISSWLV | DASNLQS | QQADGFPLT | LYNMN | SISPSGGFTDYADSVKG | DLDLGILDY |
| M8-E06 | 8.8 | RASQSISIYVN | AASSLQS | QQSYSTLMYT | HYFMT | SIVPSGGMTQYADSVKG | DSYSSSWFDI |
| M8-G09 | 28.2 | RASQGVSYYLA | GASSLQS | QQYNTYPPT | LYEML | VIYPSGGYTDYADSVKG | SFSGFGEIDY |
| M8-H04 | 3.3 | RASQYISTYLN | GTSSLQS | QQSFTTPFT | GYWMG | SISSSGGWTQYADSVKG | DDEIAAGGAFDI |
| M9-A03 | 14.4 | RASQNIDIYLN | GAYNLQS | QQSYGTPV | GYFMM | SIYSSGGYTDYADSVKG | EVAGTYAFDI |
| M9-A08 | 5.5 | RASQRISTYLN | GASSLQS | QQSYNTPRT | AYEMW | YIGSSGGSTSYADSVKG | GNSSSFDAFDI |
| M9-C08 | 10.9 | RASQSISIYVN | AASSLQR | QQSFSTPWT | HYGMV | YIVPSGGLTYYADSVKG | VDYTGDGLGY |
| M9-C10 | 7.8 | RASQGISSYLN | GASSLQS | QESYSTLFT | LYPMQ | SIGSSGGMTFYADSVKG | EVGAAGFAFDI |
| M9-D08 | 35.9 | RASRTISFYLN | GGSSLHS | QQSFSSPWT | WYKMM | SIYPSGGWTNYADSVKG | GSPWGDDAFDI |
| M9-E04 | 18.8 | RASQSISIYVN | AASNLQT | QQSHTPPKT | EYDMM | SIGSSGGMTYYADSVKG | DQVAAAAIDY |
| M9-F08 | 10.9 | RASQSISIYVN | AASSLQS | QQSYSTPPYT | PYAMT | VIYPSGGFTDYADSVKG | ASGSYLDAFDI |
| M9-F09 | 7 | RASQSISIYVN | AASSLQS | QQTYTTPWT | SYPMG | RISSSGGMTIYADSVKG | DDWNVGMDV |
| M9-F10 | 8.4 | RASQSINTYLN | AASTLES | QQSYSTPYT | DYDME | SISPSGGSTIYADSVKG | QGLLTAFDI |
| M9-G08 | 4.8 | RASQSISIYVN | AASSLQS | QQSYSTPIT | YYTML | SIYPSGGFTMYADSVKG | VDTAMAMIDY |
| M9-H02 | 3.5 | RASRSIATYLN | GASTLQS | QQSFSDPYT | AYMMI | VIYPSGGVTMYADSVKG | GTVGASDAFDI |
| M9-H03 | 4.4 | SGDKLGNRYTS | QDNKRPS | QALDSNTYV | WYSMG | YIVPSGGYTMYADSVKG | DPGVSYYYYGMDV |
| M9-H04 | 16.1 | RASQSISIYVN | AASSLQS | QQSYSTPPT | AYTMW | SIWPSGGSTFYADSVKG | TYDSSAGEVDY |
| M10-A03 | 33.7 | RASQRISFYLN | GASSLQS | QQTFSTPNT | PYPMQ | SISSSGGMTEYADSVKG | DDYGGKGGAFDI |
| M10-A12 | 20.8 | RASRDISVYLN | GASSLQS | QQSYSIPFT | LYLMH | SIYSSGGFTTYADSVKG | DTDYGMDV |
| M10-B09 | 14.1 | RASQSISTYLN | GASSLQS | QQSFSTPWT | WYEMS | RIWPSGGVTMYADSVKG | TSITTVGMDV |
| M10-C11 | 5.3 | RASQSISIYVN | AASTLQS | QQSHSIPPT | MYPMM | YISPSGGMTDYADSVKG | VAGSSDAFDI |
| M10-D11 | 6.4 | RSSQSLLHSNGYNYLD | LGSNRAS | MQALQTPLT | AYPMN | RISSSGGNTSYADSVKG | GYLGY |
| M10-E06 | 32.8 | RASQSISTYLN | GASSLQS | QQSYSDPYT | LYRMF | SIWSSGGPTMYADSVKG | EYPSTYYFDY |
| M28-E11 | 29.3 | RASQDISNWLA | AASSLQT | QQSYSSPWT | LYDMT | GISSSGGVTIYADSVKG | TYYYDSSGYADAFDI |
| M28-F01 | 1.5 | RASQSINTYLN | AASTLES | QQSYSTPPT | VYLMH | GISPSGGYTQYADSVKG | PGGLDAFDI |
| M28-F05 | 31.4 | RASQSISSYLN | AASSLQS | QQSYSTPPT | RYIMW | GIYSSGGYTQYADSVKG | ELEGLGGFDY |
| M28-F07 | 33 | RASQGISSWLA | ATSGLQS | QQAKSFPLT | DYTMY | SIVPSGGHTSYADSVKG | DHLSSWYGGFFDY |
| M29-C07 | 5.2 | RASQSISSYLN | AASSLQS | QQSYSTRYT | GYDMM | VISSSGGNTAYADSVKG | ESSGLYYFDY |
| M29-D10 | 23.6 | RASQSITIYLN | GASNLHS | QQSYDTPLT | WYPMY | SIGSSGGPTPYADSVKG | WADYGGSLDY |
| M29-E02 | 2 | SGSSSNIGNNAVS | YDDLLPS | AAWDDSLNGFV | RYPMM | VIYPSGGDTFYADSVKG | GDDYLWEAAVY |
| M29-G08 | 40.4 | RASQNIGNDVA | HASTRAY | QQFYDWPAHT | YYHMW | GISPSGGFTFYADSVKG | DYYYDSSGYSPLGY |
| M29-G10 | 16.4 | RASQSISIYLN | GASQLES | QQSYNVPYT | FYKMI | SISSSGGSTQYADSVKG | DRVDLGYLDY |

TABLE 2-continued

CDR Amino Acid Sequences and ELISA Signal of Antibody Binders of PKal

| Initial Name | Human pKal ELISA (T/B) | LV-CDR1 | LV-CDR2 | LV-CDR3 | HV-CDR1 | HV-CDR2 | HV-CDR3 |
|---|---|---|---|---|---|---|---|
| M74-A07 | 8.6 | RTSQNINTYLN | GVSSLHR | QQSYSSPWT | QYLMM | SIYPSGGYTSYADSVKG | VSTAVADNDY |
| M76-F02 | 6.4 | RASQTIDNYLH | DASSLQS | QQSYDTPQYT | LYDMN | GISPSGGQTMYADSVKG | QPMISAFDI |
| M76-G02 | 10.3 | RASQSISSYLN | AASSLQS | QQSYSTPPWT | LYAMW | YISSSGGFTSYADSVKG | YRVGVAATDY |
| M76-G06 | 11.8 | RASQSISTYLN | AASSLQS | QQSYSTPHT | GYIMH | WIYPSGGWTEYADSVKG | DAPGVGAIDY |
| M76-H02 | 13.4 | RASQDISVYLN | GGASLQS | QQSYSLPFT | MYWMQ | YIYPSGGPTKYADSVKG | PSGSYGDAFDI |
| M77-C07 | 16.1 | RASQNISSYLN | AASSLQS | QQSYSTPRT | LYIMG | GIYPSGGFTMYADSVKG | ESSGVAAPDY |
| M77-H04 | 7.6 | RSSQSLLHSRGYNYLD | LGSNRAS | MQALQRRT | YYTMI | GIRSSGGGTRYADSVKG | DGSRYSYGSIYYYYGMDA |

Abbreviations used: "T/B" is the ELISA signal obtained using of the "target" (biotinylated plasma kallikrein) divided by the ELISA signal of the "background" (streptavidin); both of which were coated on microtiter plates. "nd" is not determined. The symbol "q" refers to the amber suppressible stop codon (TAG), which is translated as glutamine (Q) in strains of E. coli such as the TG1 cells that were used to express the Fab fragments.

Amino Acid Sequences of Light Chain (LC) and Heavy Chain (HC) Variable Domain of pKal Antibody Binders are Shown Below.

```
M6-A06              LC
QDIQMTQSPS SLSASVGDSV TISCRASQSI SMYLNWYQHK PGKAPKLLIY GTSSLQSGVP    60

SRFSGSGPGG TDFTLTISSL QPEDFATYYC QQSYSAPWTF GQGTKVEIK              109

M6-A06              HC
EVQLLESGGG LVQPGGSLRL SCAASGFTFS LYQMTWVRQA PGKGLEWVSG IWPSGGFTDY    60

ADSVKGRFTI SRDNSKNTLY LQMNSLRAED TAVYYCARVS TAVADNDYWG QGTLVTVSSA   120

STKGPSVFPL APSSKS                                                  136

M6-A08              LC
QDIQMTQSPS SLSASVGDRV TITCRASQRI SFYLNWFQQK PGKAPNLLIY GASSLQSGVP    60

SRFSGSGSGT DFTLTISSLQ PKDFGTYYCQ QTFSTPNTFG QGTKLEIK               108

M6-A08              HC
EVQLLESGGG LVQPGGSLRL SCAASGFTFS PYPMQWVRQA PGKGLEWVSS ISSSGGMTEY    60

ADSVKGRFTI SRDNSKNTLY LQMNSLRAED TAVYYCARDD YGGKGGAFDI WGQGTMVTVS   120

SASTKGPSVF PLAPSSKS                                                138

M6-D03              LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTLWTFG QGTKVEIK               108

M6-D03              HC
EVQLLESGGG LVQPGGSLRL SCAASGFTFS KYFMGWVRQA PGKGLEWVSV IGSSGGWTSY    60

ADSVKGRFTI SRDNSKNTLY LQMNSLRAED TAVYYCARVS TAVADNDYWG QGTLVTVSSA   120

STKGPSVFPL APSSKS                                                  136

M6-D08              LC
QDIQMTQSPS SLSASVGDRV TITCRASQSI SSYLNWYqQK PGKAPKLLIY GASSLQSGVP    60

SRFSGSGSGT DFTLTISSLQ PEDSATYYCQ QSYTRWTFGQ GTKVEIK                107

M6-D08              HC
EVQLLESGGG LVQPGGSLRL SCAASGFTFS RYHMVWVRQA PGKGLEWVSS ISPSGGWTNY    60

ADSVKGRFTI SRDNSKNTLY LQMNSLRAED TAMYYCAREM ATIAGQFDPW GQGTLVTVSS   120

ASTKGPSVFP LAPSSKS                                                 137
```

```
M6-G05                  LC
QDIQMTQSPS SLSASVGDRV TITCRASQSI STYLNWYQLK PGKAPKLLIY NAFSMERGVP      60

STISGSGSGT DFTLTISSLQ PEDFATYYCQ QSYTTPTTFG QGTKVEIK                  108

M6-G05                  HC
EVQLLESGGG LVQPGGSLRL SCAASGFTFS RYRMVWVRQA PGKGLEWVSS IYPSGGMTAY      60

ADSVKGRFTI SRDNSKNTLY LQMNSLRAED TAVYYCARDA VGIGDAFDIW GQGTMVTVSS     120

ASTKGPSVFP LAPSSKS                                                   137

M8-C04                  LC
QSALTQPPSV SVSPGQTASI TCSGDKLGDK YTSWHQQKPG QSPVLVIYQD SKRPSGIPER      60

FSGSNSGNTA TLTISGTQAM DEADYYCQAW DSSTVFGGGT RLTVL                    105

M8-C04                  HC
EVQLLESGGG LVQPGGSLRL SCAASGFTFS YYPMQWVRQA PGKGLEWVSY IYPSGGLTSY      60

ADSVKGRFTI SRDNSKNTLY LQMNSLRAED TAVYYCARLF YGSGSVGFEY WGQGTLVTVS     120

SASTKGPSVF PLAPSSKS                                                  138

M8-D05                  LC
QDIQMTQSPS FVSASVGDRV TITCRASQDI SSWLVWYQQK PGKGPKLLIY DASNLQSGVP      60

SRFSGGGSGT HFTLTISSLQ PEDFATYYCQ QADGFPLTFG GGTKVEMK                 108

M8-D05                  HC
EVQLLESGGG LVQPGGSLRL SCAASGFTFS LYNMNWVRQA PGKGLEWVSS ISPSGGFTDY      60

ADSVKGRFTI SRDNSKNTLY LQMNSLRAED TAVYYCARDL DLGILDYWGQ GTLVTVSSAS    120

TKGPSVFPLA PSSKS                                                    135

M8-E06                  LC
QDIQMTQSPS SLSASVGDRV TITCRASQSI SSYLNWYQQK PGKAPKLLIY AASSLQSGVP      60

SRFSGSGSGT DFTLTISSLQ PEDFATYYCQ QSYSTLMYTF GQGTKLEIK                109

M8-E06                  HC
EVQLLESGGG LVQPGGSLRL SCAASGFTFS HYFMTWVRQA PGKGLEWVSS IVPSGGMTQY      60

ADSVKGRFTI SRDNSKNTLY LQMNSLRAED TAVYYCARDS YSSSWFDIWG QGTMVTVSSA    120

STKGPSVFPL APSSKS                                                   136

M8-G09                  LC
QDIQMTQSPS SLSASVGDTV TITCRASQGV SYYLAWFQQK PGKAPKSLIY GASSLQSGVP      60

SKFSGSGSGT VFTLTISSLQ PDDFATYYCQ QYNTYPPTFG QGTRLDIK                 108

M8-G09                  HC
EVQLLESGGG LVQPGGSLRL SCAASGFTFS LYEMLWVRQA PGKGLEWVSV IYPSGGYTDY      60

ADSVKGRFTI SRDNSKNTLY LQMNSLRAED MAVYYCARSF SGFGEIDYWG QGTLVTVSSA    120

STKGPSVFPL APSSKS                                                   136

M8-H04                  LC
QDIQMTQSPS SLSASIGDRV TITCRASQYI STYLNWYEQK PGKAPKLLIY GTSSLQSGVP      60

SRFSGSGSGT EFSLTISSLQ PEDFATYYCQ QSFTTPFTFG QGTKLEIK                 108

M8-H04                  HC
EVQLLESGGG LVQPGGSLRL SCAASGFTFS GYWMGWVRQA PGKGLEWVSS ISSSGGWTQY      60

ADSVKGRFTI SRDNSKNTLY LQMNSLRAED TATYYCARDD EIAAGGAFDI WGQGAMVTVS    120

SASTKGPSVF PLAPSSKS                                                 138

M9-A03                  LC
QDIQMTQSPS SLSASLGDRV TITCRASQNI DIYLNWYQQT PGKAPKLLIY GAYNLQSGVP      60

SRFSGSGSGT DFTLTISSLQ PEDFGTYYCQ QSYGTPVFGQ GTKLEIK                  107
```

```
M9-A03                    HC
EVQLLESGGG LVQPGGSLRL SCAASGFTFS GYFMMWVRQA PGKGLEWVSS IYSSGGYTDY    60

ADSVKGRFTI SRDNSKNTLY LQMNSLRAED TAVYYCAREV AGTYAFDIWG QGTMVTVSSA   120

STKGPSVFPL APSSKS                                                  136

M9-A08                    LC
QDIQMTQSPS SLSASVGDRV TVTCRASQRI STYLNWYQQK PGKAPKLLIS GASSLQSGVP    60

SRFSGSGSGT DFTLTISSLQ PDDFATYYCQ QSYNTPRTFG QGTKVEIR                108

M9-A08                    HC
EVQLLESGGG LVQPGGSLRL SCAASGFTFS AYEMWWVRQA PGKGLEWVSY IGSSGGSTSY    60

ADSVKGRFTI SRDNSKNTLY LQMNSLRAED TAVYYCTGGN SSSFDAFDIW GQGTMVTVSS   120

ASTKGPSVFP LAPSSKS                                                 137

M9-C08                    LC
QDIQMTQSPS SLSASVGDRV TITCRASQSI SIYVNWYQQK PGKAPNLLIF AASSLQRGVP    60

SRFSGSGSGA DFTLTISSLQ PEDFATYYCQ QSFSTPLTFG GGTKVEIK                108

M9-C08                    HC
EVQLLESGGG LVQPGGSLRL SCAASGFTFS HYGMWVRQA PGKGLEWVSY IVPSGGLTYY    60

ADSVKGRFTI SRDNSKNTLY LQMNSLRAED TAVYYCARVD YTGDGLGYWG QGTLVTVSSA   120

STKGPSVFPL APSSKS                                                  136

M9-C10                    LC
QDIQMTQSPS SLSASVGDRV TITCRASQGI SSYLNWYQQK PGNAPNLLIY GASSLQSGVP    60

SRFSGSGSGT DFTLTISSLQ PEDFATYYCQ ESYSTLFTFG PGTTVEIK                108

M9-C10                    HC
EVQLLESGGG LVQPGGSLRL SCAASGFTFS LYPMQWVRQA PGKGLEWVSS IGSSGGMTFY    60

ADSVKGRFTI SRDNSKNTLY LQMNSLRAED TAVYYCTREV GAAGFAFDIW GQGTMVTVSS   120

ASTKGPSVFP LAPSSKS                                                 137

M9-D08                    LC
QDIQMTQSPS SLSASVGDRV TLTCRASRTI SFYLNWYQQK AGKAPELLIY GGSSLHSGVP    60

SRFSGSGSGT DFSLTISNLQ PEDIAVYYCQ QSFSSPWTFG QGTKVEIK                108

M9-D08                    HC
EVQLLESGGG LVQPGGSLRL SCAASGFTFS WYKMMWVRQA PGKGLEWVSS IYPSGGWTNY    60

ADSVKGRFTI SRDNSKNTLY LQMNSLRAED TAVYYCTRGS PWGDDAFDIW GQGTMVTVSS   120

ASTKGPSVFP LAPSSKS                                                 137

M9-E04                    LC
QDIQMIQSPS SLSASVGDRV TITCRASQSI SGYLNWYQQR SGKAPKLLIF AASNLQTGVP    60

SRFSGSGSGT DFTLTINNLQ PEDFATYYCQ QSHTPPKTFG PGTKVDIK                108

M9-E04                    HC
EVQLLESGGG LVQPGGSLRL SCAASGFTFS EYDMWVRQA PGKGLEWVSS IGSSGGMTYY    60

ADSVKGRFTI SRDNSKNTLY LQMNSLRAED TAVYYCARDQ VAAAAIDYWG QGTLVTVSSA   120

STKGPSVFPL APSSKS                                                  136

M9-F08                    LC
QDIQMTqSPS SLSASVGDRV TITCRASQSI SSYLNWYQQK PGKAPKLLIY AASSLQSGVP    60

SRFSGSGSGT DFTLTISSLQ PEDFATYYCQ QSYSTPPYTF GQGTKLEIK               109

M9-F08                    HC
EVQLLESGGG LVQPGGSLRL SCAASGFTFS PYAMTWVRQA PGKGLEWVSV IYPSGGFTDY    60

ADSVKGRFTI SRDNSKNTLY LQMNSLRAED TAMYYCARAS GSYLDAFDIW GQGTMVTVSS   120

ASTKGPSVFP LAPSSKS                                                 137
```

-continued

```
M9-F09                  LC
QDIQMTQSPS SLSASVGDRV TITCRASQSI SSYLNWYQQK PGKAPKLLIY AASSLQSGVP    60

SKFSGSGSGT DYTLTISSLQ PEDFATYYCQ QTYTTPWTFG QGTKVEIK                108

M9-F09                  HC
EVQLLESGGG LVQPGGSLRL SCAASGFTFS SYPMGWVRQA PGKGLEWVSR ISSSGGMTIY    60

ADSVKGRFTI SRDNSKNTLY LQMNSLRAED TAVYYCARDD WNVGMDVWGQ GTTVTVSSAS   120

TKGPSVFPLA PSSKS                                                   135

M9-F10                  LC
QDIQMTQSPS SLSASVGDRV TITCRASQSI NTYLNWYQQK PGKAPKVLIH AASTLESGVP    60

SRFSGSGSGT DFTLTISSLQ PEDFATYYCQ QSYSTPYTFG QGTKLEVR                108

M9-F10                  HC
EVQLLESGGG LVQPGGSLRL SCAASGFTFS DYDMEWVRQA PGKGLEWVSS ISPSGGSTIY    60

ADSVKGRFTI SRDNSKNTLY LQMNSLRAED TAVYYCARQG LLTAFDIWGQ GTMVTVSSAS   120

TKGPSVFPLAPSSKS                                                    135

M9-G08                  LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPITFG GGTKVEIK                108

M9-G08                  HC
EVQLLESGGG LVQPGGSLRL SCAASGFTFS YYTMLWVRQA PGKGLEWVSS IYPSGGFTMY    60

ADSVKGRFTI SRDNSKNTLY LQMNSLRAED TAVYYCARVD TAMAMIDYWG QGTLVTVSSA   120

STKGPSVFPLAPSSKS                                                   136

M9-H02                  LC
QDIQMTQSPS SLSASVGDRV IITCRASRSI ATYLNWYQQK PGKAPNLLIF GASTLQSGVP    60

SRFSGSGSGT DFTLTISDLQ PEDFATYYCQ QSFSDPYTFG QGTNLEMK                108

M9-H02                  HC
EVQLLESGGG LVQPGGSLRL SCAASGFTFS AYMMIWVRQA PGKGLEWVSV IYPSGGVTMY    60

ADSVKGRFTI SRDNSKNTLY LQMNSLRAED TAVYYCARGT VGASDAFDIW GQGTMVTVSS   120

ASTKGPSVFP LAPSSKS                                                 137

M9-H03                  LC
QYELTQAPSV SVAPGQTASI TCSGDKLGNR YTSWYQQKPG QSPVLVIFQD NKRPSGIPER    60

FSGSNSGNTA TLTISGTQAM DEADYYCQAL DSNTYVFGTG TKVTVL                  106

M9-H03                  HC
EVQLLESGGG LVQPGGSLRL SCAASGFTFS WYSMGWVRQA PGKGLEWVSY IVPSGGYTMY    60

ADSVKGRFTI SRDNSKNTLY LQMNSLRAED TAVYYCARDP GVSYYYYGMD VWGQGTTVTV   120

SSASTKGPSVFPLAPSSKS                                                139

M9-H04                  LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPPTFG QGTRLEIK                108

M9-H04                  HC
EVQLLESGGG LVQPGGSLRL SCAASGFTFS AYTMWWVRQA PGKGLEWVSS IWPSGGSTFY    60

ADSVKGRFTI SRDNSKNTLY LQMNSLRAED TAVYYCARTY DSSAGEVDYW GQGTLVTVSS   120

ASTKGPSVFP LAPSSKS                                                 137

M10-A03                 LC
QDIQMTQSPS SLSASVGDRV TITCRASQRI SFYLNWFQQK PGKAPNLLIY GASSLQSGVP    60

SRFSGSGSGT DFTLTISSLQ PKDFGTYYCQ QTFSTPNTFG QGTKLEIK                108
```

```
M10-A03              HC
EVQLLESGGG LVQPGGSLRL SCAASGFTFS PYPMQWVRQA PGKGLEWVSS ISSSGGMTEY    60

ADSVKGRFTI SRDNSKNTLY LQMNSLRAED TAVYYCARDD YGGKGGAFDI WGQGTMVTVS   120

SASTKGPSVF PLAPSSKS                                                 138

M10-A12              LC
QDIQMTQSPL SLSAFVGDRV TITCRASRDI SVYLNWYQLK SGKAPKLLIY GASSLQSGVP    60

SRFSGSGSGT DFTLTITSLQ PEDFATYYCQ QSYSIPFTFG GGTKVETK                108

M10-A12              HC
EVQLLESGGG LVQPGGSLRL SCAASGFTFS LYLMHWVRQA PGKGLEWVSS IYSSGGFTTY    60

ADSVKGRFTI SRDNSKNTLY LQMNSLRAED TAVYYCARDT DYGMDVWGQG TTVTVSSAST   120

KGPSVFPLAP SSKS                                                     134

M10-B09              LC
QDIQMTQSPS SLSASVGDGV TITCRASQSI STYLNWYQQR PGKAPKLLIY GASSLQSGVP    60

SRFSGSGSGT DFTLTISSLQ REDFATYYCQ QSFSTPWTFG QGTRVEIK                108

M10-B09              HC
EVQLLESGGG LVQPGGSLRL SCAASGFTFS WYEMSWVRQA PGKGLEWVSR IWPSGGVTMY    60

ADSVKGRFTI SRDNSKNTLY LqMNSLRAED TAVYYCTRTS ITTVGMDVWG QGTTVTVSSA   120

STKGPSVFPL APSSKS                                                   136

M10-C11              LC
QDIQMTQSPS SLSASVGDRV TITCRASQSI SIYLNWYQQK PEKAPKLLIF AASTLQSGVP    60

SRFSGSGSGT DFTLTISNLQ PEDFATYYCQ QSHSIPPTFG LGTKVEVK                108

M10-C11              HC
EVQLLESGGG LVQPGGSLRL SCAASGFTFS MYPMMWVRQA PGKGLEWVSY ISPSGGMTDY    60

ADSVKGRFTI SRDNSKNTLY LQMNSLRAED MAVYYCARVA GSSDAFDIWG QGTMVTVSSA   120

STKGPSVFPL APSSKS                                                   136

M10-D11              LC
QDIQMTQSPL SLPVTPGEPA SISCRSSQSL LHSNGYNYLD WYLQKPGQSP QLLIYLGSNR    60

ASGVPDRFSG SGSGTDFTLK ISRVEAEDVG VYYCMQALQT PLTFGPGTKV HIK          113

M10-D11              HC
EVQLLESGGG LVQPGGSLRL SCAASGFTFS AYPMNWVRQA PGKGLEWVSR ISSSGGNTSY    60

ADSVKGRFTI SRDNSKNTLY LQMNSLRAED TAVYYCALGY LGYWGQGTLV TVSSASTKGP   120

SVFPLAPSSK S                                                        131

M10-E06              LC
QDIQMTQSPS SLSASVGDRV TITCRASQSI STYLNWYQQK PGKAPKLLIY GASSLQSGVP    60

SRFSGSGSGT DFTLTISSLQ PEDFTIYYCQ QSYSDPYTFG QGTKLDIK                108

M10-E06              HC
EVQLLESGGG LVQPGGSLRL SCAASGFTFS LYRMFWVRQA PGKGLEWVSS IWSSGGPTMY    60

ADSVKGRFTI SRDNSKNTLY LQMNSLRAED TAVYYCAREY PSTYYFDYWG QGTLVTVSSA   120

STKGPSVFPL APSSKS                                                   136

M10-F09              LC
QDIQMTQSPS SLSASVGDRV TITCRASQTI DDDLIWYQQK PGRAPKLLIY AASSLQSGVP    60

SRFSGSGSGT DFTLTITSLQ PEDFATYYCQ QSYNIPRTFG QGTKLESK                108

M10-F09              HC
EVQLLESGGG LVQPGGSLRL SCAASGFTFS NYDMMWVRQA PGKGLEWVSY ISPSGGFTRY    60

ADSVKGRFTI SRDNSKNTLY LQMNSLRAED TATYYCAKDI YYYNWGPSHY FDSWGQGTLV   120

TVSSASTKGP SVFPLAPSSK S                                             141
```

-continued

```
M10-G09                 LC
QDIQMTQSPS SLSASVGDSV TITCRASQSI SGYINWYQQK AGKAPKLLIY AASSLQSGVP    60

SRFSGSGSGT HFTLTISSLQ PEDFATYYCQ QYVSYPFTFG PGTKVDIK                108

M10-G09                 HC
EVQLLESGGG LVQPGGSLRL SCAASGFTFS QYGMQWVRQA PGKGLEWVSS IRSSGGATRY    60

ADSVKGRFTI SRDNSKNTLY LQMNSLRAED TAVYYCARDG YYDSSGYPDY WGQGTLVTVS   120

SASTKGPSVF PLAPSSKS                                                 138

M11-A10                 LC
QDIQMTQSPS SLSASVGDRV AITCRASQSI DTYLNWYQQK PGKAPKLLIY DASNLEIGVP    60

SRFSGSGSGT DFTFIINSLQ PEDVATYYCQ HYLYAPYSFG QGTKLEIK                108

M11-A10                 HC
EVQLLESGGG LVQPGGSLRL SCAASGFTFS NYWMMWVRQA PGKGLEWVSG IGSSGGFTSY    60

ADSVKGRFTI SRDNSKNTLY LQMNSLRAED TAVYYCAKGS YSDYGVFESW GQGTLVTVSS   120

ASTKGPSVFP LAPSSKS                                                  137

M11-E01                 LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPPTFG QGTKVEIK                108

M11-E01                 HC
EVQLLESGGG LVQPGGSLRL SCAASGFTFS TYEMYWVRQA PGKGLEWVSG IGSSGGMTMY    60

ADSVKGRFTI SRDNSKNTLY LQMNSLRAED TAMYYCAREQ PGIAALQFWG QGTLVTVSSA   120

STKGPSVFPL APSSKS                                                   136

M11-E04                 LC
QDIQMTQSPS SLSASVGDRV TITCRASQSI SIYLTWYQHR PGKAPNLLIY GAATLQTGVP    60

SRFSGSGSGT DFTLTIRGLQ PEDFATYYCQ QTFSLPRTFG QGTKLEIK                108

M11-E04                 HC
EVQLLESGGG LVQPGGSLRL SCAASGFTFS MYHMNWVRQA PGKGLEWVSG IVSSGGVTFY    60

ADSVKGRFTI SRDNSKNTLY LQMNSLRAED TAVYYCARIT TVTTGGAFDI WGQGTMVTVS   120

SASTKGPSVF PLAPSSKS                                                 138

M11-E05                 LC
QDIQMTQSPS SLSASVGDTV TITCRTSQTI NNYLNWYQQR PGEAPKVLIY ATHTLESGVP    60

SRFSGSGSGT DFTLTIGSLQ PEDFATYYCQ QSFAFPYTFG QGTKVEIT                108

M11-E05                 HC
EVQLLESGGG LVQPGGSLRL SCAASGFTFS WYTMGWVRQA PGKGLEWVSW IYFGGLTTYA    60

DSVKGRFTIS RDNSKNTLYL QMNSLRAEDT AVYYCARLGG PLDAFDIWGQ GTMVTVSSAS   120

TKGPSVFPLA PSSKS                                                    135

M11-E06                 LC
QDIQMTQSPS SLSASIGDRV TISCRASRGI GTYLNWYQQH AGKAPKLLIR AASSLETGVP    60

PRFSGSGSGT DFTLTISSLQ SDDFATYYCQ ESFTNVYNFG QGTKLEIK                108

M11-E06                 HC
EVQLLESGGG LVQPGGSLRL SCAASGFTFS QYAMHWVRQA PGKGLEWVSS IYPSGGFTLY    60

ADSVKGRFTI SRDNSKNTLY LQMNSLRAED TAMYYCARGG WLAGGELLNW GQGTLVTVSS   120

ASTKGPSVFP LAPSSKS                                                  137

M11-G09                 LC
QDIQMTQSPS SLSASVGDRV TITCRTSQGI NHYLNWYQQK PGKAPKILVF AASELQTGVP    60

SRFSGTGSGT SYTLTITSLQ PEDVATYYCQ QTYTSPYTFG QGTKLEVK                108
```

```
M11-G09                HC
EVQLLESGGG LVQPGGSLRL SCAASGFTFS LYNMTWVRQA PGKGLEWVSY IYPSGGGTHY    60

ADSVKGRFTI SRDNSKNTLY LQMNSLRAED TAVYYCARDT GFWSADAFDI WGQGTMVTVS   120

SASTKGPSVF PLAPSSKS                                                 138

M11-G12                LC
QDIQMTQSPS SLSAFVGDRV SITCRASQTI SVYVNWYQHK SGQAPKLLIY GASSLQSGVP    60

SRFSGSGSGT DFTLTISSLQ PEDFATYFCQ QSYSIPFTFG GGTDVQIR                108

M11-G12                HC
EVQLLESGGG LVQPGGSLRL SCAASGFTFS QYPMNWVRQA PGKGLEWVSS ISSSGGFTTY    60

ADSVKGRFTI SRDNSKNTLY LQMNSLRAED TAVYYCAREE QQGGFDYWGQ GTLVTVSSAS   120

TKGPSVFPLA PSSKS                                                    135

M12-A08                LC
QDIQMTQSPS SLSASVGDRV TITCRASQSI SRYLNWYQQK PGKAPKLLIY AASTLETGVP    60

SRFSGSGSGT DFTLTITTLQ PEDFVIYYCQ QSYSTPYTFG QGTKLEIK                108

M12-A08                HC
EVQLLESGGG LVQPGGSLRL SCAASGFTFS WYYMGWVRQA PGKGLEWVSW IVSSGGLTLY    60

ADSVKGRFTI SRDNSKNTLY LQMNSLRAED TAMYYCARTT VTTGDAFDIW GQGTMVTVSS   120

ASTKGPSVFP LAPSSKS                                                  137

M12-B04                LC
QDIQMTQSPS SLSASVGDRV TITCRASQGI RNDLGWYQHK PGKAPKLLIY AASILQSGVP    60

SRFSGTASGT DFTLTISSLQ PEDFATYFCL QDYEYPLTFG GGTKLDIK                108

M12-B04                HC
EVQLLESGGG LVQPGGSLRL SCAASGFTFS LYSMYWVRQA PGKGLEWVSR IRPSGGGTVY    60

ADSVKGRFTI SRDNSKNTLY LQMNSLRAED TAVYYCARDP LYSSGDVWGQ GTTVTVSSAS   120

TKGPSVFPLA PSSKS                                                    135

M12-C09                LC
QDIQMTQSPS SLSASVGDRV TITCRASQSI GIYLNWYHQK PGKAPNLLIY GASSLQSGVP    60

SRFSGSGSGT DFTLTISSLQ PGDFATYYCQ HSYSTPFTFG GGTKVEIK                108

M12-C09                HC
EVQLLESGGG LVQPGGSLRL SCAASGFTFS SYAMVWVRQA PGKGLEWVSS IGSSGGFTLY    60

ADSVKGRFTI SRDNSKNTLY LQMNSLRAED TAVYYCASMN LGGGDAFDIW GQGTMVTVSS   120

ASTKGPSVFP LAPSSKS                                                  137

M12-C10                LC
QSALTQPPSV SVSPGQTASI TCSGDKLGEK YVSWYQQKPG QSPVVIYQD NKRPSGIPER     60

FSGSNSGNTA TLTISGTQAV DEADYYCQAW DSYTVVFGGG SKLTVLGQPK              110

M12-C10                HC
EVQLLESGGG LVQPGGSLRL SCAASGFTFS DYEMHWVRQA PGKGLEWVSG ISPSGGKTQY    60

ADSVKGRFTI SRDNSKNTLY LQMNSLRAED TAVYYCARDL KWGGRGSPDW YFDLWGRGTL   120

VTVSSASTKG PSVFPLAPSS KS                                            142

M12-D10                LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPPTFG GGTKVEIK                108

M12-D10                HC
EVQLLESGGG LVQPGGSLRL SCAASGFTFS NYPMDWVRQA PGKGLEWVSS ISSSGGWTNY    60

ADSVKGRFTI SRDNSKNTLY LQMNSLRAED TAVYYCATDT SGSYLGFDYW GQGTLVTVSS   120

ASTKGPSVFP LAPSSKS                                                  137
```

```
M12-E06                    LC
QDIQMTQSPS SLSASVGDRV SITCRASQSI STYLNWYQHK PGKAPTLLIY GAFSLQSGVP    60

SRFSGSGSGT DFALTISSLQ PEDFATYYCQ QSHSTPPTFG QGTRVEIK               108

M12-E06                    HC
EVQLLESGGG LVQPGGSLRL SCAASGFTFS QYKMLWVRQA PGKGLEWVSG IGPSGGLTAY    60

ADSVKGRFTI SRDNSKNTLY LQMNSLRAED TAVYYCARAP WFGELGMDVW GQGTTVTVSS   120

ASTKGPSVFP LAPSSKS                                                 137

M27-A10                    LC
QDIQMTQSPS SLSASVGDRV TITCRASQSI SAYLNWYQQK PGKAPQLLMY GVGSLQSGVP    60

SRFSGSGSGT DFTLTISSLQ PEDFATYFCQ QGYTTPVTFG GGTKVEIK               108

M27-A10                    HC
EVQLLESGGG LVQPGGSLRL SCAASGFTFS WYRMDWVRQA PGKGLEWVSS IWPSGGLTSY    60

ADSVKGRFTI SRDNSKNTLY LQMNSLRAED TAVYYCARGW APGGDAFDIW GQGTMVTVSS   120

ASTKGPSVFP LAPSSKS                                                 137

M27-B01                    LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPYTFG QGTKLEIK               108

M27-B01                    HC
EVQLLESGGG LVQPGGSLRL SCAASGFTFS DYTMWWVRQA PGKGLEWVSS ISSSGGITFY    60

ADSVKGRFTI SRDNSKNTLY LQMNSLRAED TAVYYCARSA DTAMGGAFDI WGQGTMVTVS   120

SASTKGPSVF PLAPSSKS                                                138

M27-B12                    LC
QYELTQPPAV SVSPGQTATI TCSGDKLGDE YAAWYQQKPG QSPVLVIYQD RKRPSGIPER    60

FSGSNFGNTA TLTITGTQVM DEADYYCQAW GKRNVVFGGG TKLTVL                 106

M27-B12                    HC
EVQLLESGGG LVQPGGSLRL SCAASGFTFS WYQMMWVRQA PGKGLEWVSS ISPSGGITEY    60

ADSVKGRFTI SRDNSKNTLY LQMNSLRAED TAVYYCARDR SSGWYYYGMD VWGQGTTVTV   120

SSASTKGPSV FPLAPSSKS                                               139

M27-E03                    LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPRTFG QGTKVEIK               108

M27-E03                    HC
EVQLLESGGG LVQPGGSLRL SCAASGFTFS SYMMHWVRQA PGKGLEWVSG IYPSGGWTDY    60

ADSVKGRFTI SRDNSKNTLY LQMNSLRAED TATYYCARLV AGLDAFDIWG QGTMVTVSSA   120

STKGPSVFPL APSSKS                                                  136

M27-F04                    LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPPTFG QGTKVEIK               108

M27-F04                    HC
EVQLLESGGG LVQPGGSLRL SCAASGFTFS WYPMTWVRQA PGKGLEWVSS IGPSGGQTIY    60

ADSVKGRFTI SRDNSKNTLY LQMNSLRAED TAVYYCTTEY GDYGGGFDPW GQGTLVTVSS   120

ASTKGPSVFP LAPSSKS                                                 137

M27-F11                    LC
QDIQMTQSPS FLSASVGDRV TITCRASQGI SSYLAWYQQK PGKAPKLLIY AASSLQSGVP    60

SRFSGSGSGT DFTLTISSLQ PEDFATYYCQ QSYNTLRTFG PGTKVDLK               108
```

```
M27-F11          HC
EVQLLESGGG LVQPGGSLRL SCAASGFTFS SYHMMWVRQA PGKGLEWVSS IYPSGGATMY    60

ADSVKGRFTI SRDNSKNTLY LQMNSLRAED TAMYYCARDG YHYGDYTYFQ HWGQGTLVTV   120

SSASTKGPSV FPLAPSSKS                                                139

M27-G01          LC
QDIQMTQSPS SLSASVGDRV TITCRASQSI STYLNWYQQK PGKAPKLLIY GASSLQSGVP    60

SRFSGSGSGT DFTLTISSLQ PEDFTIYYCQ QSYSDPYTFG QGTKLDIK                108

M27-G01          HC
EVQLLESGGG LVQPGGSLRL SCAASGFTFS LYRMFWVRQA PGKGLEWVSS IWSSGGPTMY    60

ADSVKGRFTI SRDNSKNTLY LQMNSLRAED TAVYYCAREY PSTYYFDYWG QGTLVTVSSA   120

STKGPSVFPL APSSKS                                                   136

M27-G04          LC
QDIQMTQSPS SLSASVGDRV TITCRASQRI SYYLTWYQQK PGKVPKLLIY AASSLESGVP    60

SRFSGSGSGT DFTLTISNLQ PEDFATYYCQ QAFSTPFTFG GGTKVEIK                108

M27-G04          HC
EVQLLESGGG LVQPGGSLRL SCAASGFTFS AYYMVWVRQA PGKGLEWVSY ISPSGGQTQY    60

ADSVKGRFTI SRDNSKNTLY LQMNSLRAED TAVYYCAREA ISSSSFDYWG QGTLVTVSSA   120

STKGPSVFPL APSSKS                                                   136

M27-G09          LC
QDIQMTQSPS SVSASVGDRI TITCRTRQSI SNYLNWYQQK PGEPPKLLIF AASSLQSGVP    60

SRFSGSGTGT EFTLTISSLQ PEDLAIYYCQ QSYDIPFTFG QGTKLEIK                108

M27-G09 HC
EVQLLESGGG LVQPGGSLRL SCAASGFTFS EYDMAWVRQA PGKGLEWVSY IVSSGGFTSY    60

ADSVKGRFTI SRDNSKNTLY LQMNSLRAED TAVYYCTTWA GWIAAADYWG QGTLVTVSSA   120

STKGPSVFPL APSSKS                                                   136

M27-H10          LC
QDIQMTQSPS SLSASVGDRV TITCRASQSI SNYLNWYQQK PGKAPKFLIY AASSLQSGVP    60

SRFSGSGSGT DFTLSISSLQ PEDFATYYCQ QSYSTPQTFG QGTKVEMK                108

M27-H10          HC
EVQLLESGGG LVQPGGSLRL SCAASGFTFS AYQMAWVRQA PGKGLEWVSV IYSSGGYTDY    60

ADSVKGRFTI SRDNSKNTLY LQMNSLRAED TAVYYCARHN WNDGAFDIWG QGTMVTVSSA   120

STKGPSVFPL APSSKS                                                   136

M28-A01          LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTLTFGG GTKVEIK                 107

M28-A01          HC
EVQLLESGGG LVQPGGSLRL SCAASGFTFS WYAMHWVRQA PGKGLEWVSG IYSSGGYTKY    60

ADSVKGRFTI SRDNSKNTLY LQMNSLRAED TAVYYCARDL SNGDDVFDIW GQGTMVTVSS   120

ASTKGPSVFP LAPSSKS                                                  137

M28-C03          LC
QDIQMTQSPS SLSASVGDRV TITCRASQSI NFYLNWYQQK PGKAPKLLIY VASSLESGVP    60

SRFSGSASGT EFTLTISSLQ PEDFATYYCL QSYSAPYTFG QGTKVEIT                108

M28-C03          HC
EVQLLESGGG LVQPGGSLRL SCAASGFTFS YYQMGWVRQA PGKGLEWVSS IYPSGGMTDY    60

ADSVKGRFTI SRDNSKNTLY LQMNSLRAED TAVYYCTRGS PWGDDAFDIW GQGTMVTVSS   120

ASTKGPSVFP LAPSSKS                                                  137
```

```
-continued
M28-D02                    LC
QDIqMTQSPS SLSASEGDMV TITCRTSRRI GTYLNWYQQK PGKAPKLLIY GASSLQSGVP    60

SRFSGSGSGT DFTLTVSSLQ PEDVGTYYCQ QSFSSPWTFG PGTKVEIK                108

M28-D02                    HC
EVQLLESGGG LVQPGGSLRL SCAASGFTFS WYPMQWVRQA PGKGLEWVSY IYPSGGGTDY    60

ADSVKGRFTI SRDNSKNTLY LQMNSLRAED TATYYCATSS GWLGDAFDIW GQGTMVTVSS   120

ASTKGPSVFP LAPSSKS                                                  137

M28-D12                    LC
QDIQMTQSPS SLSASVGDRV TITCRASQSI ATYLNWYQQK PGRAPKLLIY AASSLQSGVP    60

SRFVGGGSGS GTHFTLTISS LQPEDFATYY CQQSYSTRET FGQGTKVEIK              110

M28-D12                    HC
EVQLLESGGG LVQPGGSLRL SCAASGFTFS WYTMHWVRQA PGKGLEWVSV IYPSGGPTSY    60

ADSVKGRFTI SRDNSKNTLY LQMNSLRAED TATYYCARDG SGSYLGFDYW GQGTLVTVSS   120

ASTKGPSVFP LAPSSKS                                                  137

M28-E01                    LC
QDIQMTQSPS SLSASVGDRV TITCRASQSI SSYLNWYQQK PGKAPKLLIY AASSLQSGVP    60

SKFSGSGSGT DYTLTISSLQ PEDFATYYCQ QTYTTPWTFG QGTKVEIK                108

M28-E01                    HC
EVQLLESGGG LVQPGGSLRL SCAASGFTFS SYPMGWVRQA PGKGLEWVSR ISSSGGMTIY    60

ADSVKGRFTI SRDNSKNTLY LQMNSLRAED TAVYYCARDD WNVGMDVWGQ GTTVTVSSAS   120

TKGPSVFPLAPSSKS                                                     135

M28-E11                    LC
QDIQMTQSPS SVSASVGDRV TINCRASQDI SNWLAWYQQK PGKAPNLLIY AASSLQTGAP    60

SRFSGSGSGT DFTLTISSLQ PEDFGTYVCQ QSYSLPWTFG LGTKVEVR                108

M28-E11                    HC
EVQLLESGGG LVQPGGSLRL SCAASGFTFS LYDMTWVRQA PGKGLEWVSG ISSSGGVTIY    60

ADSVKGRFTI SRDNSKNTLY LQMNSLRAED TAVYYCARTY YDSSGYADA FDIWGQGTMV   120

TVSSASTKGP SVFPLAPSSK S                                             141

M28-F01                    LC
QDIQMTQSPS SLSASVGDRV TITCRASQSI NTYLNWYQQK PGKAPKVLIH AASTLESGVP    60

SRFSGSGSGT DFTLTISSLQ PEDFATYYCQ QSYSTPPTFG QGTKVEIK                108

M28-F01                    HC
EVQLLESGGG LVQPGGSLRL SCAASGFTFS VYLMHWVRQA PGKGLEWVSG ISPSGGYTQY    60

ADSVKGRFTI SRDNSKNTLY LQMNSLRAED TAVYYCARPG GLDAFDIWGQ GTMVTVSSAS   120

TKGPSVFPLA PSSKS                                                    135

M28-F05                    LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPLTFG GGTKVEIK                108

M28-F05                    HC
EVQLLESGGG LVQPGGSLRL SCAASGFTFS RYIMWWVRQA PGKGLEWVSG IYSSGGYTQY    60

ADSVKGRFTI SRDNSKNTLY LQMNSLRAED TAMYYCAREL EGLGGFDYWG QGTLVTVSSA   120

STKGPSVFPL APSSKS                                                   136

M28-F07                    LC
QDIQMTQSPS SVSASVGDRV TITCRASQGI SSWLAWYQQK PGKAPKLLIY ATSGLQSGVP    60

SRFSGSGSGT DFTLTISSLQ PEDFATYYCQ QAKSFPLTFG GGTRVEIK                108
```

```
M28-F07              HC
EVQLLESGGG LVQPGGSLRL SCAASGFTFS DYTMYWVRQA PGKGLEWVSS IVPSGGHTLY    60

ADSVKGRFTI SRDNSKNTLY LQMNSLRAED TAVYYCAKDH LSSWYGGFFD YWGQGTLVTV   120

SSASTKGPSV FPLAPSSKS                                                139

M29-C07              LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTRYTFG QGTKLEIK                108

M29-C07              HC
EVQLLESGGG LVQPGGSLRL SCAASGFTFS GYDMMWVRQA PGKGLEWVSV ISSSGGNTAY    60

ADSVKGRFTI SRDNSKNTLY LQMNSLRAED TAVYYCARES SGLYYFDYWG QGTLVTVSSA   120

STKGPSVFPL APSSKS                                                   136

M29-D10              LC
QDIQMTQSPS SLSASVGDTV SITCRASQSI TIYLNWYQHK PGKAPNLLIY GASNLHSGVP    60

SRFSGSGSGT DFTLTISSLQ PEDFATYYCQ QSYDTPLTFG GGTKVEIK                108

M29-D10              HC
EVQLLESGGG LVQPGGSLRL SCAASGFTFS WYPMYWVRQA PGKGLEWVSS IGSSGGPTPY    60

ADSVKGRFTI SRDNSKNTLY LQMNSLRAED TAVYYCARWA DYGGSLDYWG QGTLVTVSSA   120

STKGPSVFPL APSSKS                                                   136

M29-E02              LC
QSVLTQPPSV SEAPRQRVTI SCSGSSSNIG NNAVSWYQQL PGKAPKLLIY YDDLLPSGVS    60

DRFSGSKSGT SASLAISGLR SEDEADYYCA AWDDSLNGFV FGTGTKVTVL              110

M29-E02              HC
EVQLLESGGG LVQPGGSLRL SCAASGFTFS RYPMMWVRQA PGKGLEWVSV IYPSGGDTFY    60

ADSVKGRFTI SRDNSKNTLY LQMNSLRAED TAVYYCASGD DYLWEAAVYW GQGTLVTVSS   120

ASTKGPSVFP LAPSSKS                                                  137

M29-G08              LC
QDIQMTQSPA TLSASPGETV TLSCRASQNI GNDVAWYRQR PGQAPRLLIH HASTRAYGIP    60

ARLRGSGSAT EFTLTITSLE PEDFAIYYCQ QFYDWPAHTF ALGTRLEIKR              110

M29-G08              HC
EVQLLESGGG LVQPGGSLRL SCAASGFTFS YYHMWVRQA PGKGLEWVSG ISPSGGFTFY     60

ADSVKGRFTI SRDNSKNTLY LQMNSLRAED TAVYYCARDY YDSSGYSPL GYWGQGTLVT    120

VSSASTKGPS VFPLAPSSKS                                               140

M29-G10              LC
QDIQMTQSPS SLSSSVGDSA TITCRASQSI SIYLNWYQQK PGKAPKILIY GASQLESGVP    60

SRFSGSGSGT DFTLTVSGLQ PEDFATYWCQ QSYNVPYTFG QGTKLEIK                108

M29-G10              HC
EVQLLESGGG LVQPGGSLRL SCAASGFTFS FYKMIWVRQA PGKGLEWVSS ISSSGGSTQY    60

ADSVKGRFTI SRDNSKNTLY LQMNSLRAED TAVYYCARDR VDLGYLDYWG QGTLVTVSSA   120

STKGPSVFPL APSSKS                                                   136

M74-A07              LC
QDIQMTQSPS SLSASVRDRV TITCRTSQNI NTYLNWYYQA PGRAPKLLIF GVSSLHRGVS    60

SRFSGSGDGT EFTLTISSLQ PEDIGTYFCQ QSYSSPWTFG QGTKVEIK                108

M74-A07              HC
EVQLLESGGG LVQPGGSLRL SCAASGFTFS QYLMMWVRQA PGKGLEWVSS IYPSGGYTSY    60

ADSVKGRFTI SRDNSKNTLY LQMNSLRAED TAVYYCARVS TAVADNDYWG QGTLVTVSSA   120

STKGPSVFPL APSSKS                                                   136
```

```
-continued
M76-F02                 LC
QDIQMTQSPS SLSASVGDRV TITCRASQTI DNYLHWYQQK PGKAPKVLIH DASSLQSGVP    60

PRFSGSGSGT DFTLTISSLQ PEDFATYYCQ QSYDTPQYTF GQGTKLEIK               109

M76-F02                 HC
EVQLLESGGG LVQPGGSLRL SCAASGFTFS LYDMNWVRQA PGKGLEWVSG ISPSGGQTMY    60

ADSVKGRFTI SRDNSKNTLY LQMNSLRAED TAVYYCARQP MISAFDIWGQ GTMVTVSSAS   120

TKGPSVFPLA PSSKS                                                   135

M76-G02                 LC
QDIQMTQSPS SLSASVGDRV TITCRASQSI SSYLNWYQQK PGKAPKLLIY AASSLQSGVP    60

SRFSGSGSGT DFTLTISSLQ PEDFATYYCQ QSYSTPPWTF GQGTKVEIK               109

M76-G02                 HC
EVQLLESGGG LVQPGGSLRL SCAASGFTFS LYAMWWVRQA PGKGLEWVSY ISSSGGFTSY    60

ADSVKGRFTI SRDNSKNTLY LQMNSLRAED TAVYYCARYR VGVAATDYWG QGTLVTVSSA   120

STKGPSVFPL APSSKS                                                  136

M76-G06                 LC
QDIQMTQSPS SLSASVRDRV TITCRASQSI STYLNWYQQK PGEAPKLLVF AASSLQSGVP    60

SRFSGSGSGT DFTLSISSLQ PEDFATYYCQ QSYSTPHTFG QGAKVEIK                108

M76-G06                 HC
EVQLLESGGG LVQPGGSLRL SCAASGFTFS GYIMHWVRQA PGKGLEWVSW IYPSGGWTEY    60

ADSVKGRFTI SRDNSKNTLY LQMNSLRAED TAVYYCARDA PGVGAIDYWG QGTLVTVSSA   120

STKGPSVFPL APSSKS                                                  136

M76-H02                 LC
QDIQMTQSPS SLSASEGDRV TITCRASQDI SVYLNWYQMK SGKAPKLLIY GGASLQSGVP    60

ARFSGSGYGT DFTLTITDLR PEDFATYYCQ QSYSLPFTFG GGTKVEIK                108

M76-H02                 HC
EVQLLESGGG LVQPGGSLRL SCAASGFTFS MYWMQWVRQA PGKGLEWVSY IYPSGGPTKY    60

ADSVKGRFTI SRDNSKNTLY LQMNSLRAED TAVYYCARPS GSYGDAFDIW GQGTMVTVSS   120

ASTKGPSVFP LAPSSKS                                                 137

M77-C07                 LC
QDIQMTQSPS TLSASVGDRV TITCRASQNI SSYLNWYQQK PGKAPKLLIY AASSLQSGVP    60

SRFSGSGSGT DFTLTISSLQ PEDFATYSCQ QSYSTPRTFG QGTKVEIK                108

M77-C07                 HC
EVQLLESGGG LVQPGGSLRL SCAASGFTFS LYIMGWVRQA PGKGLEWVSG IYPSGGFTMY    60

ADSVKGRFTI SRDNSKNTLY LQMNSLRAED TAVYYCARES SGVAAPDYWG QGTLVTVSSA   120

STKGPSVFPL APSSKS                                                  136

M77-H04                 LC
QDIQMTQSPL SLPVTPGEPA SISCRSSQSL LHSRGYNYLD WYLQKPGQSP QLLIYLGSNR    60

ASGVPDRFSG SGSGTDFTLK ISRVEAEDVG VYYCMQALQR RTFGQGTKLE IK           112

M77-H04                 HC
EVQLLESGGG LVQPGGSLRL SCAASGFTFS YYTMIWVRQA PGKGLEWVSG IRSSGGGTRY    60

ADSVKGRFTI SRDNSKNTLY LQMNSLRAED TAVYYCAKDG SRYSYGSIYY YYGMDAWGQG   120

TTVTVSSAST KGPSVFPPLAP SSKS                                        144
```

Example 2

Lead Antibody Inhibitors

Antibodies were selected as lead plasma kallikrein inhibitors on the basis of apparent inhibition constant ($K_{i,app}$), specificity with respect to lack of inhibition of other serine proteases, inhibition of bradykinin generation, and lack of binding to plasma prekallikrein (Table 3). Plasma kallikrein circulates in the plasma as an inactive zymogen (prekallikrein) at a concentration of approximately 500 nM. Antibodies that bound prekallikrein may be rendered inaccessible towards active plasma kallikrein inhibition and could substantially increase the in vivo dose required for efficacy. Therefore, a surface plasmon resonance (SPR) assay was used to identify antibodies that do not bind prekallikrein (data not shown). Specifically, human IgGs (X81-B01, M162-A04 (R84-H05); M160-G12 (R84-D02); and M142-H08) were captured on a CM5 chip using an anti-human Fc surface and 100 nM of plasma kallikrein or 100 nM or 500 nM prekallikrein. The prekallikrein was treated with aprotinin-Sepharose to remove active plasma kallikrein. The prekallikrein used for X81-B01 was buffer exchanged into the exact preparation of SPR running buffer (HEPES buffered saline) to avoid the refractive index shift that was observed with three other antibodies that were tested: M162-A04 (R84-H05); M160-G12 (R84-D02); and M142-H08.

Of the antibodies listed in Table 3, only M142-H08 inhibits human plasma kallikrein with a subnanomolar $K_{i,app}$. However, when M142-H08 was produced as an IgG it was found to be cleaved in the CDR3 of the heavy chain. Consequently, we decided to undertake two approaches to improve the affinity: 1) affinity maturation of M162-A04 and M160-G12 using a novel form of light chain shuffling called ROLIC (Rapid Optimization of Light Chains) (see, e.g., WO 2009/102927 and U.S. 2009-0215119); and 2) sequence optimization of M142-H08 in order to prevent the cleavage of the IgG that occurs while retaining the binding and inhibitor properties of M142-H08.

TABLE 3

Top Ranking Antibody Inhibitors of PKal Before Affinity Maturation or Sequence Optimization

| Criteria | M162-A04 | M160-G12 | M142-H08[a] |
|---|---|---|---|
| $K_{i,app}$ human pKal | 2 nM (as an IgG) | 5.6 nM (as an IgG) | 0.6 nM (as a Fab) |
| $K_{i,app}$ rodent pKal | 2 nM (mouse and rat) | <1 nM (mouse) | ~1 nM (mouse and rat) |
| Binds prekallikrein? | No | No | No |
| Specific inhibitor with respect to fXIa, plasmin, and trypsin | Yes | Yes | Yes |
| Inhibits bradykinin generation | Yes | Yes | Yes |

[a]When M142-H08 was produced as an IgG it was determined to be cleaved in the CDR3 of its heavy chain (GGLLLWFR-ELKSNYFDY).

Example 3

Sequence Optimization of M142-H08

Of the antibodies listed in Table 3, only M142-H08 inhibits human pKal with a subnanomolar $K_{i,app}$. However, when M142-H08 was produced as an IgG it was found to be cleaved in the CDR3 of the heavy chain. M142-H08 was found by mass spectrometry to be cleaved after the arginine in the "WFR" sequence of the HC-CDR3 sequence (GGLLLWFRELKSNYFDY). This cleavage suggests that a protease from the cells used to express the antibody (both CHO and 293T human kidney cells) is enzymatically cleaving the antibody at a single specific site. We mutated the HC-CDR3 sequence of M142-H08 in order to identify amino acid substitutions that prevent the cleavage of the IgG that occurs while retaining the binding and inhibitor properties of M142-H08. Previous experience with similarly "clipped" antibodies suggested that focusing simply on the putative P1 position (protease subsite 1, see Table 4) may not be sufficient to identify antibodies that retain potent inhibition of the target enzyme while not being clipped by a host cell protease. Therefore, we created a small library of single point mutations in the region around the cleavage site in order to identify variants of M142-H08 that are not clipped but are still potent pKal inhibitors. We refer to this library as the "CDR3 by Design" library. The small library was constructed using a PCR primer that contains the randomized codon NNK at either the P3, the P2, the P1, or the P1' site. This results in a small library where each of the 4 positions may contain any of the 20 amino acids (20+20+20+20=80 members). Using PCR, this library was cloned into the M142-H08 Fab sequence in the pMid21 vector, which is a standard phagemid vector.

TABLE 4

Primer sequences

| Primer Name | Sequence | N |
|---|---|---|
| | P3 P2 P1 P1' P2'<br>G G L L L W F R E L K S N Y | |
| 559A.P1.top | GGC GGT CTA TTA CTA TGG TTC NNK GAG CTG AAG TCT AAC TAC | 20 |
| 559A.P2.top | GGC GGT CTA TTA CTA TGG NNK AGG GAG CTG AAG TCT AAC TAC | 20 |
| 559A.P3.top | GGC GGT CTA TTA CTA NNK TTC AGG GAG CTG AAG TCT AAC TAC | 20 |
| 559A.P1p.top | GGC GGT CTA TTA CTA TGG TTC AGG NNK CTG AAG TCT AAC TAC | 20 |

By DNA sequencing, we recovered 61 of the possible 80 antibodies (Table 5). These antibodies were produced as Fab fragments in small scale (~20 µg) and tested for inhibition against human pKal in an in vitro protease cleavage assay using Pro-Phe-Arg-aminomethylcoumarin as the synthetic peptide substrate. The Fabs that were found to be inhibitors of human pKal were subcloned into our pBRH1f vector (a vector for transient expression of IgGs in 293T cells) for conversion to full length human IgG1 antibodies. Five antibodies were then expressed in 293T cells and purified by protein A sepharose chromatography. The antibodies were analyzed by SDS-PAGE to determine which of the inhibitory mutants are not cleaved by the host cell protease(s) (data not shown). The cleaved antibodies (559A-X67-G05, 559A-X67-H01, 559A-X67-G09) had an extra band that migrated between the 38 and the 49 kDa molecular weight marker. This band is absent in the 559A-X67-H04 and 559A-X67-D03 antibodies, which indicates that these antibodies are intact.

$K_{i,app}$ values were determined by steady state enzyme kinetics for those that were shown by SDS-PAGE to be not cleaved (Table 5). Interestingly, the P2 position was the only position where amino acid substitutions yielded intact antibody inhibitors of pKal. Of the 14 different mutations that were recovered at the P3 position (Table 5), only one mutant (W to L) was found to be a pKal inhibitor as a Fab but it was subsequently shown to be clipped as an IgG. None of the 16 different mutations at the P1 position (Table 5) were found to be pKal inhibitors. Eight of the 15 different mutations at the P1' position were found to be inhibitors of pKal as a Fab but all were clipped as an IgG. Consequently, only mutations at the P2 position led to antibody inhibitors that were not clipped during expression. Of the 16 different mutations that were recovered at the P2 position (Table 5), eight mutants were found to be a pKal inhibitor as a Fab but it was subsequently shown to be clipped as an IgG. Four mutants at the P2 position were found to have subnanomolar $K_{i,app}$ values: X67-G04 (F to A), X67-C03 (F to M), X67-F01 (F to Q) and X67-D03 (F to N). The antibody with the highest potency is X67-D03 ($K_{i,app}$=0.1 nM). The two antibodies shown in Table 6 were not cleaved when expressed as IgGs and were found to inhibit pKal with a subnanomolar $K_{i,app}$.

DNA and amino acid sequence alignments of the light chains of nongermlined (X63-G06) and germlined, codon optimized (X81-B01) versions of the same antibody discovered using ROLIC affinity maturation are shown in FIGS. 4 and 5, respectively. DNA and amino acid sequence alignments of the heavy chains of nongermlined (X63-G06) and germlined, codon optimized (X81-B01) versions of the same antibody discovered using ROLIC affinity maturation are shown in FIGS. 6 and 7, respectively.

TABLE 5

HV-CDR3 Sequences Obtained from "CDR3 by Design" Library*

| Mutation Site | Antibody I.D. | HV-CDR3 | Inhibit as a Fab? | Intact as an IgG? | Ki, app as an IgG (nM) |
|---|---|---|---|---|---|
| Parental | X69-C09 | GGLLLWFRELKSNYFDY | Yes | No | 0.2 |
| P3 | X68-E07 | GGLLLAFRELKSNYFDY | No | n/a | n/a |
| P3 | X68-E12 | GGLLLCFRELKSNYFDY | No | n/a | n/a |
| P3 | X68-A03 | GGLLLDFRELKSNYFDY | No | n/a | n/a |
| P3 | X68-E03 | GGLLLEFRELKSNYFDY | No | n/a | n/a |
| P3 | X68-A12 | GGLLLGFRELKSNYFDY | No | n/a | n/a |
| P3 | X68-D11 | GGLLLKFRELKSNYFDY | No | n/a | n/a |
| P3 | X68-E01 | GGLLLLFRELKSNYFDY | Yes | No | n/a |
| P3 | X68-F05 | GGLLLMFRELKSNYFDY | No | n/a | n/a |
| P3 | X68-D10 | GGLLLPFRELKSNYFDY | No | n/a | n/a |
| P3 | X68-F10 | GGLLLQFRELKSNYFDY | No | n/a | n/a |
| P3 | X68-G01 | GGLLLRFRELKSNYFDY | No | n/a | n/a |
| P3 | X68-G05 | GGLLLSFRELKSNYFDY | No | n/a | n/a |
| P3 | X68-F12 | GGLLLTFRELKSNYFDY | No | n/a | n/a |
| P3 | X68-H04 | GGLLLVFRELKSNYFDY | No | n/a | n/a |
| P2 | X67-G04 | GGLLLWARELKSNYFDY | Yes | Yes | 0.35 |
| P2 | X67-G01 | GGLLLWCRELKSNYFDY | No | n/a | n/a |
| P2 | X67-E04 | GGLLLWDRELKSNYFDY | Yes | Yes | 1.3 |
| P2 | X67-H04 | GGLLLWERELKSNYFDY | Yes | Yes | 3.6 |
| P2 | X67-C09 | GGLLLWGRELKSNYFDY | Yes | Yes | 8.6 |

TABLE 5-continued HV-CDR3 Sequences Obtained from "CDR3 by Design" Library*

| Mutation Site | Antibody I.D. | HV-CDR3 | Inhibit as a Fab? | Intact as an IgG? | Ki, app as an IgG (nM) |
|---|---|---|---|---|---|
| P2 | X67-B04 | GGLLLWKRELKSNYFDY | Yes | No | n/a |
| P2 | X67-G09 | GGLLLWLRELKSNYFDY | Yes | No | n/a |
| P2 | X67-C03 | GGLLLWMRELKSNYFDY | Yes | Yes | 0.7 |
| P2 | X67-D03 | GGLLLWNRELKSNYFDY | Yes | Yes | 0.1 |
| P2 | X67-B05 | GGLLLWPRELKSNYFDY | No | n/a | n/a |
| P2 | X67-F01 | GGLLLWQRELKSNYFDY | Yes | Yes | 0.9 |
| P2 | X67-G05 | GGLLLWRRELKSNYFDY | Yes | No | n/a |
| P2 | X67-B03 | GGLLLWSRELKSNYFDY | Yes | Yes | 2.1 |
| P2 | X67-F10 | GGLLLWTRELKSNYFDY | Yes | Yes | 1.3 |
| P2 | X67-H01 | GGLLLWWRELKSNYFDY | Yes | No | n/a |
| P2 | X67-F08 | GGLLLWYRELKSNYFDY | Yes | No | n/a |
| P1 | X66-E09 | GGLLLWFAELKSNYFDY | No | n/a | n/a |
| P1 | X66-B05 | GGLLLWFCELKSNYFDY | No | n/a | n/a |
| P1 | X66-D03 | GGLLLWFEELKSNYFDY | No | n/a | n/a |
| P1 | X66-H04 | GGLLLWFFELKSNYFDY | No | n/a | n/a |
| P1 | X66-H02 | GGLLLWFGELKSNYFDY | No | n/a | n/a |
| P1 | X66-C11 | GGLLLWFHELKSNYFDY | No | n/a | n/a |
| P1 | X66-A07 | GGLLLWFKELKSNYFDY | No | n/a | n/a |
| P1 | X66-C03 | GGLLLWFLELKSNYFDY | No | n/a | n/a |
| P1 | X66-G05 | GGLLLWFMELKSNYFDY | No | n/a | n/a |
| P1 | X66-F10 | GGLLLWFPELKSNYFDY | No | n/a | n/a |
| P1 | X66-E04 | GGLLLWFQELKSNYFDY | No | n/a | n/a |
| P1 | X66-F01 | GGLLLWFSELKSNYFDY | No | n/a | n/a |
| P1 | X66-H11 | GGLLLWFTELKSNYFDY | No | n/a | n/a |
| P1 | X66-C02 | GGLLLWFVELKSNYFDY | No | n/a | n/a |
| P1 | X66-F09 | GGLLLWFWELKSNYFDY | No | n/a | n/a |
| P1 | X66-G08 | GGLLLWFYELKSNYFDY | No | n/a | n/a |
| P1' | X69-D08 | GGLLLWFRALKSNYFDY | No | n/a | n/a |
| P1' | X69-B02 | GGLLLWFRCLKSNYFDY | No | n/a | n/a |
| P1' | X69-D09 | GGLLLWFRGLKSNYFDY | Yes | No | n/a |
| P1' | X69-D02 | GGLLLWFRHLKSNYFDY | No | n/a | n/a |
| P1' | X69-A12 | GGLLLWFRKLKSNYFDY | No | n/a | n/a |
| P1' | X69-F05 | GGLLLWFRLLKSNYFDY | Yes | No | n/a |
| P1' | X69-B08 | GGLLLWFRNLKSNYFDY | Yes | No | n/a |
| P1' | X69-A10 | GGLLLWFRPLKSNYFDY | No | n/a | n/a |
| P1' | X69-A09 | GGLLLWFRQLKSNYFDY | Yes | No | n/a |
| P1' | X69-E05 | GGLLLWFRRLKSNYFDY | No | n/a | n/a |

TABLE 5-continued

HV-CDR3 Sequences Obtained from "CDR3 by Design" Library*

| Mutation Site | Antibody I.D. | HV-CDR3 | Inhibit as a Fab? | Intact as an IgG? | Ki, app as an IgG (nM) |
|---|---|---|---|---|---|
| P1' | X69-F09 | GGLLLWFRSLKSNYFDY | Yes | No | n/a |
| P1' | X69-F01 | GGLLLWFRTLKSNYFDY | Yes | No | n/a |
| P1' | X69-C12 | GGLLLWFRVLKSNYFDY | Yes | No | n/a |
| P1' | X69-E01 | GGLLLWFRWLKSNYFDY | Yes | No | n/a |
| P1' | X69-H10 | GGLLLWFRYLKSNYFDY | No | n/a | n/a |

*All of these antibodies are single point mutations of the M142-H08 sequence.

Amino Acid Sequences of Light Chain (LC) and Heavy Chain (HC) Variable Domain of pKal Antibodies with Designed HC CDR3s are Shown Below.

```
X68-E07 LC
QDIQMTQSPS SLSAFVGDRV TITCRASQPI DNYLNWYHQK PGKAPKLLIY AASRLQSGVP      60

SRLSGSGFGT DFTLTISSLQ PEDFGNYYCQ QSYTVPYTFG GGTKVEIR                  108

X68-E07 HC
EVQLLESGGG LVQPGGSLRL SCAASGFTFS AYSMIWVRQA PGKGLEWVSY IRPSGGRTTY      60

ADSVKGRFTI SRDNSKNTLY LQMNSLRAED TAVYYCARGG LLLAFRELKS NYFDYWGQGT    120

LVTVSSASTK GPSVFPLAPS SKS                                            143

X68-E12 LC
QDIQMTQSPS SLSAFVGDRV TITCRASQPI DNYLNWYHQK PGKAPKLLIY AASRLQSGVP      60

SRLSGSGFGT DFTLTISSLQ PEDFGNYYCQ QSYTVPYTFG GGTKVEIR                  108

X68-E12 HC
EVQLLESGGG LVQPGGSLRL SCAASGFTFS AYSMIWVRQA PGKGLEWVSY IRPSGGRTTY      60

ADSVKGRFTI SRDNSKNTLY LQMNSLRAED TAVYYCARGG LLLCFRELKS NYFDYWGQGT    120

LVTVSSASTK GPSVFPLAPS SKS                                            143

X68-A03 LC
QDIQMTQSPS SLSAFVGDRV TITCRASQPI DNYLNWYHQK PGKAPKLLIY AASRLQSGVP      60

SRLSGSGFGT DFTLTISSLQ PEDFGNYYCQ QSYTVPYTFG GGTKVEIR                  108

X68-A03 HC
EVQLLESGGG LVQPGGSLRL SCAASGFTFS AYSMIWVRQA PGKGLEWVSY IRPSGGRTTY      60

ADSVKGRFTI SRDNSKNTLY LQMNSLRAED TAVYYCARGG LLLDFRELKS NYFDYWGQGT    120

LVTVSSASTK GPSVFPLAPS SKS                                            143

X68-E03 LC
QDIQMTQSPS SLSAFVGDRV TITCRASQPI DNYLNWYHQK PGKAPKLLIY AASRLQSGVP      60

SRLSGSGFGT DFTLTISSLQ PEDFGNYYCQ QSYTVPYTFG GGTKVEIR                  108

X68-E03 HC
EVQLLESGGG LVQPGGSLRL SCAASGFTFS AYSMIWVRQA PGKGLEWVSY IRPSGGRTTY      60

ADSVKGRFTI SRDNSKNTLY LQMNSLRAED TAVYYCARGG LLLEFRELKS NYFDYWGQGT    120

LVTVSSASTK GPSVFPLAPS SKS                                            143

X68-A12 LC
QDIQMTQSPS SLSAFVGDRV TITCRASQPI DNYLNWYHQK PGKAPKLLIY AASRLQSGVP      60

SRLSGSGFGT DFTLTISSLQ PEDFGNYYCQ QSYTVPYTFG GGTKVEIR                  108
```

```
X68-A12 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLGFRELKS NYFDYWGQGT   120

LVTVSSASTK GPSVFPLAPS SKS                                          143

X68-D11 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-D11 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLKFRELKS NYFDYWGQGT   120

LVTVSSASTK GPSVFPLAPS SKS                                          143

X68-E01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-E01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLLFRELKS NYFDYWGQGT   120

LVTVSSASTK GPSVFPLAPS SKS                                          143

X68-F05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-F05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLMFRELKS NYFDYWGQGT   120

LVTVSSASTK GPSVFPLAPS SKS                                          143

X68-D10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-D10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLPFRELKS NYFDYWGQGT   120

LVTVSSASTK GPSVFPLAPS SKS                                          143

X68-F10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-F10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLQFRELKS NYFDYWGQGT   120

LVTVSSASTK GPSVFPLAPS SKS                                          143

X68-G01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X68-G01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLRFRELKS NYFDYWGQGT   120

LVTVSSASTK GPSVFPLAPS SKS                                          143
```

-continued

```
X68-G05 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X68-G05 HC
EVQLLESGGG LVQPGGSLRL SCAASGFTFS AYSMIWVRQA PGKGLEWVSY IRPSGGRTTY    60
ADSVKGRFTI SRDNSKNILY LQMNSLRAED TAVYYCARGG LLLSFRELKS NYFDYWGQGT   120
LVTVSSASTK GPSVFPLAPS SKS                                          143

X68-F12 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X68-F12 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLTFRELKS NYFDYWGQGT   120
LVTVSSASTK GPSVFPLAPS SKS                                          143

X68-H04 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X68-H04 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLVFRELKS NYFDYWGQGT   120
LVTVSSASTK GPSVFPLAPS SKS                                          143

X67-G04 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X67-G04 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWARELKS NYFDYWGQGT   120
LVTVSSASTK GPSVFPLAPS SKS                                          143

X67-G01 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X67-G01 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWCRELKS NYFDYWGQGT   120
LVTVSSASTK GPSVFPLAPS SKS                                          143

X67-E04 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108

X67-E04 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWDRELKS NYFDYWGQGT   120
LVTVSSASTK GPSVFPLAPS SKS                                          143

X67-H04 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR               108
```

```
-continued
X67-H04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWERELKS NYFDYWGQGT   120

LVTVSSASTK GPSVFPLAPS SKS                                          143

X66-E09 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-E09 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFAELKS NYFDYWGQGT   120

LVTVSSASTK GPSVFPLAPS SKS                                          143

X66-B05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-B05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFCELKS NYFDYWGQGT   120

LVTVSSASTK GPSVFPLAPS SKS                                          143

X66-D03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-D03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFEELKS NYFDYWGQGT   120

LVTVSSASTK GPSVFPLAPS SKS                                          143

X66-H04 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-H04 HC
EVQLLESGGG LVQPGGSLRL SCAASGFTFS AYSMIWVRQAPGKGLEWVSY IRPSGGRTTY     60

ADSVKGRFTI SRDNSKNTLY LQMNSLRAED TAVYYCARGGLLLWFFELKS NYFDYWGQGT    120

LVTVSSASTK GPSVFPLAPS SKS                                          143

X66-H02 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-H02 HC
EVQLLESGGG LVQPGGSLRL SCAASGFTFS AYSMIWVRQA PGKGLEWVSY IRPSGGRTTY    60

ADSVKGRFTI SRDNSKNTLY LQMHSLRAED TAVYYCARGG LLLWFGELKS NYFDYWGQGT   120

LVTVSSASTK GPSVFPLAPS SKS                                          143

X66-C11 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-C11 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFHELKS NYFDYWGQGT   120

LVTVSSASTK GPSVFPLAPS SKS                                          143
```

-continued

```
X66-A07 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X66-A07 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFKELKS NYFDYWGQGT   120

LVTVSSASTK GPSVFPLAPS SKS                                          143

X66-C03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X66-C03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFLELKS NYFDYWGQGT   120

LVTVSSASTK GPSVFPLAPS SKS                                          143

X66-G05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X66-G05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFMELKS NYFDYWGQGT   120

LVTVSSASTK GPSVFPLAPS SKS                                          143

X66-F10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X66-F10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFPELKS NYFDYWGQGT   120

LVTVSSASTK GPSVFPLAPS SKS                                          143

X66-E04 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X66-E04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFQELKS NYFDYWGQGT   120

LVTVSSASTK GPSVFPLAPS SKS                                          143

X69-D08 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X69-D08 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRALKS NYFDYWGQGT   120

LVTVSSASTK GPSVFPLAPS SKS                                          143

X69-B02 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108
```

```
X69-B02 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRCLKS NYFDYWGQGT   120

LVTVSSASTK GPSVFPLAPS SKS                                          143

X69-009 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-009 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRELKS NYFDYWGQGT   120

LVTVSSASTK GPSVFPLAPS SKS                                          143

X69-D09 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-D09 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRGLKS NYFDYWGQGT   120

LVTVSSASTK GPSVFPLAPS SKS                                          143

X69-D02 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-D02 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRHLKS NYFDYWGQGT   120

LVTVSSASTK GPSVFPLAPS SKS                                          143

X69-A12 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-A12 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRKLKS NYFDYWGQGT   120

LVTVSSASTK GPSVFPLAPS SKS                                          143

X69-F05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-F05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRLLKS NYFDYWGQGT   120

LVTVSSASTK GPSVFPLAPS SKS                                          143

X69-B08 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-B08 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRNLKS NYFDYWGQGT   120

LVTVSSASTK GPSVFPLAPS SKS                                          143
```

-continued

```
X69-A10 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-A10 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRPLKS NYFDYWGQGT   120
LVTVSSASTK GPSVFPLAPS SKS                                          143

X69-A09 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-A09 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRQLKS NYFDYWGQGT   120
LVTVSSASTK GPSVFPLAPS SKS                                          143

X69-E05 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-E05 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRRLKS NYFDYWGQGT   120
LVTVSSASTK GPSVFPLAPS SKS                                          143

X69-F09 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-F09 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRSLKS NYFDYWGQGT   120
LVTVSSASTK GPSVFPLAPS SKS                                          143

X69-F01 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-F01 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRTLKS NYFDYWGQGT   120
LVTVSSASTK GPSVFPLAPS SKS                                          143

X69-C12 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108

X69-C12 HC
EVQLLESGGG LVQPGGSLRL SCAASGFTFS AYSMIWVRQA PGKGLEWVSY IRPSGGRTTY    60
ADSVKGRFTI SRDNSKNTLY LQMNSLRAED TAVYYCARGG LLLWFRVLKS NYFDYWGQGT   120
LVTVSSASTK GPSVFPLAPS SKS                                          143

X69-E01 LC
QDIQMTQSPS SLSAFVGDRV TITCRASQPI DNYLNWYHQK PGKAPKLLIY AASRLQSGVP    60
SRLSGSGFGT DFTLTISSLQ PEDFGNYYCQ QSYTVPYTFG GGTKVEIR                108
```

```
-continued
X69-E01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRWLKS NYFDYWGQGT   120

LVTVSSASTK GPSVFPLAPS SKS                                          143

X69-H10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X69-H10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFRYLKS NYFDYWGQGT   120

LVTVSSASTK GPSVFPLAPS SKS                                          143

X66-F01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-F01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFSELKS NYFDYWGQGT   120

LVTVSSASTK GPSVFPLAPS SKS                                          143

X66-H11 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-H11 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFTELKS NYFDYWGQGT   120

LVTVSSASTK GPSVFPLAPS SKS                                          143

X66-C02 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-C02 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFVELKS NYFDYWGQGT   120

LVTVSSASTK GPSVFPLAPS SKS                                          143

X66-F09 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-F09 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFWELKS NYFDYWGQGT   120

LVTVSSASTK GPSVFPLAPS SKS                                          143

X66-G08 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X66-G08 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWFYELKS NYFDYWGQGT   120

LVTVSSASTK GPSVFPLAPS SKS                                          143
```

```
X67-C09 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-C09 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWGRELKS NYFDYWGQGT   120

LVTVSSASTK GPSVFPLAPS SKS                                          143

X67-B04 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-B04 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWKRELKS NYFDYWGQGT   120

LVTVSSASTK GPSVFPLAPS SKS                                          143

X67-G09 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-G09 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWLRELKS NYFDYWGQGT   120

LVTVSSASTK GPSVFPLAPS SKS                                          143

X67-C03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-C03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWMRELKS NYFDYWGQGT   120

LVTVSSASTK GPSVFPLAPS SKS                                          143

X67-D03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-D03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWNRELKS NYFDYWGQGT   120

LVTVSSASTK GPSVFPLAPS SKS                                          143

X67-B05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108

X67-B05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWPRELKS NYFDYWGQGT   120

LVTVSSASTK GPSVFPLAPS SKS                                          143

X67-F01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR               108
```

-continued

```
X67-F01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWQRELKS NYFDYWGQGT   120

LVTVSSASTK GPSVFPLAPS SKS                                          143

X67-G05 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-G05 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWRRELKS NYFDYWGQGT   120

LVTVSSASTK GPSVFPLAPS SKS                                          143

X67-B03 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-B03 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWSRELKS NYFDYWGQGT   120

LVTVSSASTK GPSVFPLAPS SKS                                          143

X67-F10 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-F10 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWTRELKS NYFDYWGQGT   120

LVTVSSASTK GPSVFPLAPS SKS                                          143

X67-H01 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-H01 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWWRELKS NYFDYWGQGT   120

LVTVSSASTK GPSVFPLAPS SKS                                          143

X67-F08 LC
QDIQMTQSPS SLSAFVGDRV TITCRASQPI DNYLNWYHQK PGKAPKLLIY AASRLQSGVP    60

SRLSGSGFGT DFTLTISSLQ PEDFGNYYCQ QSYTVPYTFG GGTKVEIR                108

X67-F08 HC
EVQLLESGGG LVQPGGSLRL SCAASGFTFS AYSMIWVRQA PGKGLEWVSY IRPSGGRTTY    60

ADSVKGRFTI SRDNSKNTLY LQMNSLRAED TAVYYCARGG LLLWYRELKS NYFDYWGQGT   120

LVTVSSASTK GPSVFPLAPS SKS                                          143
```

TABLE 6

CDR Amino Acid Sequences of Optimized Antibody Inhibitor of pKal Based on M142-H08

| Initial Name | Ki, app (nM) of IgG | LV-CDR1 | LV-CDR2 | LV-CDR3 | HV-CDR1 | HV-CDR2 | HV-CDR3[a] |
|---|---|---|---|---|---|---|---|
| X67-D03 | 0.1 | RASQPIDNYLN | AASRLQS | QQSYTVPYT | AYSMI | YIRPSGGRTTYADSVKG | GGLLLWNRELKSNYFDY |
| X67-G04 | 0.35 | RASQPIDNYLN | AASRLQS | QQSYTVPYT | AYSMI | YIRPSGGRTTYADSVKG | GGLLLWARELKSNYFDY |

[a]The F to N substitution (in bold) in the CDR3 of the M142-H08 gives X67-D03 an IgG that is not cleaved during expression and is a potent inhibitor of human Similarly, the F to A substitution gives X67-G04, which is also not cleaved.

TABLE 7

CDR Amino Acid Sequences of Affinity Matured Antibody Inhibitors of pKal Discovered using ROLIC

| Initial Name | Ki, app (nM) | LV-CDR1 | LV-CDR2 | LV-CDR3 | HV-CDR1 | HV-CDR2 | HV-CDR3 |
|---|---|---|---|---|---|---|---|
| X59-C07 | 6.1 | RAGRSISTYVN | AASSLQS | QQSQSTPYT | HYLMT | YISPSGGHTIYADSVKG | VARGIAARSRTSYFDY |
| X60-D01 | 2.0 | RASQIVSSRYLA | GAASRAT | QQTYSSPFT | HYLMT | YISPSGGHTIYADSVKG | VARGIAARSRTSYFDY |
| X63-G10 | 9.0 | RASQSISNYLN | AASSLQS | QQSYTSPYT | HYLMT | YISPSGGHTIYADSVKG | VARGIAARSRTSYFDY |
| X64-F04 | 1.9 | RASQIVSSNYLA | GASNRAT | QQSFNIPYT | HYLMT | YISPSGGHTIYADSVKG | VARGIAARSRTSYFDY |
| X63-G06 | 0.4 (Fab) | RTSQFVNSNYLA | GASSRAT | QQSSRTPWT | HYLMT | YISPSGGHTIYADSVKG | VARGIAARSRTSYFDY |
| X81-B01[a] | 0.2 (IgG) | RTSQFVNSNYLA | GASSRAT | QQSSRTPWT | HYLMT | YISPSGGHTIYADSVKG | VARGIAARSRTSYFDY |

[a]X81-B01 is the codon optimized and germlined version of X63-G06 as a full length human IgG produced in HEK 293T cells.

Amino Acid Sequences of Light Chain (LC) and Heavy Chain (HC) Variable Domain of Affinity Matured Antibody Inhibitors of pKal Discovered Using ROLIC are Shown Below.

```
X59-007 LC
QDIQMTQSPS SLSASVGDRV TVTCRAGRSI STYVNWYQQK PGKAPKLLIY AASSLQSGVP    60

SRFSGSRSGT DFTLTISSLQ PEDFATYYCQ QSQSTPYTFG QGTKLEVK               108

X59-007 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

X60-D01 LC
QDIQMTQSPG TLSLSPGERA TLSCRASQIV SSRYLAWYQQ RPGQAPRLLI YGAASRATGI    60

PDRFSGSGSG TDFTLTISSL QAEDFATYYC QQTYSSPFTF GQGTKMEIK              109

X60-D01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

X63-G06 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

X63-G06 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YFDYWGQGTL   120

VTVSSASTKG PSVFPLAPSS KS                                           142
```

```
X63-G10 LC
QDIQMTQSPD SLSASVGDRV TITCRASQSI SNYLNWYQQK PGKAPKLLIY AASSLQSGVP    60

SRFSGSGSGT DFTLTISGLQ PEDFASYYCQ QSYTSPYTFV QGTKLEIKRT             110

X63-G10 HC
EVQLLESGGG LVQPGGSLRL SCAASGFTFS HYLMTWVRQA PGKGLEWVSY ISPSGGHTIY   60

ADSVKGRFTI SRDNSKNTLY LQMNSLRAED TAVYYCARVA RGIAARSRTS YFDYWGQGTL  120

VTVSSASTKG PSVFPLAPSS KS                                           142

X64-F04 LC
QDIQMTQSPA TLSLSPGERA TLSCRASQIV SSNYLAWYQQ KPGQAPRLLI YGASNRATGI   60

PDRFSGSGSG TEFTLTISSL QSEDFAIYYC QQSFNIPYTF GQGTRVDIK              109

X64-F04 HC
EVQLLESGGG LVQPGGSLRL SCAASGFTFS HYLMTWVRQA PGKGLEWVSY ISPSGGHTIY   60

ADSVKGRFTI SRDNSKNTLY LQMNSLRAED TAVYYCARVA RGIAARSRTS YFDYWGQGTL  120

VTVSSASTKG PSVFPLAPSS KS                                           142
X81-B01 is the germlined IgG produced in HEK 293T cells version of the X63-G06 Fab, as
indicated above.
X101-A01 (aka DX-2922) is the germlined IgG produced in CHO cells version of the X63-G06
Fab
```

Example 4

Affinity Maturation

In addition to optimizing the sequence of the clipped antibody (M142-H08), we also performed affinity maturation on two of the antibodies identified by phage display (M162-A04 and M160-G12). Both of these antibodies inhibit human pKal with single digit nanomolar potency, appear specific to pKal, and do not bind prekallikrein (Table 3). We first performed a novel form of light chain shuffling called ROLIC (Rapid Optimization of Light Chains) on M162-A04 and M160-G12 (see, e.g., WO 2009/102927 and U.S. 2009-0215119). From the screening of the antibodies discovered by ROLIC we identified one antibody with subnamolar potency (X63-G06) that shared the same heavy chain as M160-G12. We then constructed HV-CDR3 spiking affinity maturation libraries based on CDR3 sequences in M162-A04 and X63-G06 (described below).

Affinity Maturation by ROLIC. We used ROLIC to affinity mature the two leads from Table 3 that were not cleaved (M162-A04 and M160-G12). This process identified one antibody that inhibits pKal with a subnanomolar $K_{i,app}$ (Table 7). X63-G06 inhibits pKal with a $K_{i,app}$ of approximately 0.4 nM as a Fab fragment. When this antibody was converted to an IgG that is germlined and sequenced optimized for CHO cell expression (X81-B01) it was found to inhibit pKal with a $K_{i,app}$ of approximately 0.2 nM.

Example 5

Affinity Maturation of Heavy Chain CDR1/2 and CDR3

We used two additional affinity maturation strategies to identify highly potent antibodies based on two different parental antibody inhibitor leads: M162-A04 and X63-G06. One approach was to generate libraries that shuffled the CDR1/2 of the HC of two different parental antibody inhibitor leads (M162-A04 and X63-G06) against additional CDR1/2 diversity. Another approach was to create heavy chain CDR3 spiking libraries based on these leads.

The 82 antibodies that were discovered based on improvements in M162-A04 due to modifications in either the CDR1/2 and CDR3 region are shown in Table 8. Inhibition screening with 10 nM antibody (as Fab fragments) revealed that there were 33 antibodies that inhibited pKal activity by over 90%. Several antibodies were shown to be subnanomolar inhibitors of human pKal.

The 62 antibodies that were discovered based on improvements in X63-G06 due to modifications in either the CDR1/2 and CDR3 region are shown in Table 9. Inhibition screening with 10 nM antibody (as Fab fragments) revealed that there were 24 antibodies that inhibited pKal activity by over 90%. Several antibodies were shown to be subnanomolar inhibitors of human pKal.

TABLE 8

Sequences of Antibodies Obtained from CDR1/2 and CDR3 Spiking Affinity Maturation Libraries Based on M162-A04

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
|---|---|---|---|---|---|---|---|---|
| M202-A12 | 97.5 | 0.2 | RASQSISSWLA | KASTLES | QQYNTYWT | HYIMM | GIYSSGGITVYADSVKG | QRTGVPRRDSFNI |
| M196-C06 | 97.2 | 0.1 | RASQSISSWLA | KASTLES | QQYNTYWT | IYSMH | SIYPSRGMTWYADSVKG | RRTGIPRRDAFDI |
| M198-F09 | 96.9 | 0.2 | RASQSISSWLA | KASTLES | QQYNTYWT | VYNMH | SIYPSGGMTYYADSVKG | RRTGIPRRDAFDI |

TABLE 8-continued

Sequences of Antibodies Obtained from CDR1/2 and CDR3 Spiking Affinity Maturation Libraries Based on M162-A04

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
| --- | --- | --- | --- | --- | --- | --- | --- | --- |
| M199-A08 | 96.4 | 0.06 | RASQSISSWLA | KASTLES | QQYNTYWT | HYIMM | GIYSSGGITVYADSVKG | RRIGVPRRDEFDI |
| M202-C01 | 96.3 | 0.1 | RASQSISSWLA | KASTLES | QQYNTYWT | HYIMM | GIYSSGGITVYADSVKG | RRTGVPRWDDFDI |
| M198-A06 | 96.1 | 0.4 | RASQSISSWLA | KASTLES | QQYNTYWT | IYSMH | SIYSSGGPTKYADSVKG | RRTGIPRRDAFDI |
| M200-D03 | 95.9 | 0.1 | RASQSISSWLA | KASTLES | QQYNTYWT | HYIMM | GIYSSGGITVYADSVKG | RRIGVPRRDSFDM |
| M202-H03 | 95.7 | 0.1 | RASQSISSWLA | KASTLES | QQYNTYWT | HYIMM | GIYSSGGITVYADSVKG | RRTGVPRWDDFDI |
| M201-A07 | 95.7 | 0.1 | RASQSISSWLA | KASTLES | QQYNTYWT | HYIMM | GIYSSGGITVYADSVKG | RRTGVPRRDEFDI |
| M197-A01 | 95.3 | | RASQSISSWLA | KASTLES | QQYNTYWT | IYDMI | SIYPSGGNTSYADSVKG | RRTGIPRRDAFDI |
| M202-D09 | 95.0 | 0.4 | RASQSISSWLA | KASTLES | QQYNTYWT | HYIMM | GIYSSGGITVYADSVKG | RRIGVPRRDSFDI |
| M197-A09 | 94.9 | 0.6 | RASQSISSWLA | KASTLES | QQYNTYWT | VYNMH | SIYPSGGMTTYADSVKG | RRTGIPRRDAFDI |
| M198-G07 | 94.9 | | RASQSISSWLA | KASTLES | QQYNTYWT | IYDMT | SIYPSGGQTIYADSVKG | RRTGIPRRDAFDI |
| M200-A10 | 94.3 | 0.3 | RASQSISSWLA | KASTLES | QQYNTYWT | HYIMM | GIYSSGGITVYADSVKG | RRTGVPRRDSFDI |
| M197-H10 | 94.1 | | RASQSISSWLA | KASTLES | QQYNTYWT | SYNMH | SIVPSGGKTNYADSVKG | RRTGIPRRDAFDI |
| M196-D12 | 94.1 | 0.2 | RASQSISSWLA | KASTLES | QQYNTYWT | RYSMR | VIYPSGGQTYYADSVKG | RRTGIPRRDAFDI |
| M197-A08 | 93.7 | | RASQSISSWLA | KASTLES | QQYNTYWT | IYSMQ | SIGSSGGKTLYADSVKG | RRTGIPRRDAFDI |
| M198-B09 | 93.5 | | RASQSISSWLA | KASTLES | QQYNTYWT | VYSMT | SIGSSGGSTTYADSVKG | RRTGIPRRDAFDI |
| M198-E09 | 93.1 | | RASQSISSWLA | KASTLES | QQYNTYWT | IYDMN | SIYPSGGRTRYADSVKG | RRTGIPRRDAFDI |
| M202-B03 | 93.1 | 0.3 | RASQSISSWLA | KASTLES | QQYNTYWT | HYIMM | GIYSSGGITVYADSVKG | RRTGVPRRDDFDI |
| M198-C10 | 93.0 | | RASQSISSWLA | KASTLES | QQYNTYWT | HYMGMN | SIVPSGGWTQYADSVKG | RRTGIPRRDAFDI |
| M197-E12 | 93.0 | | RASQSISSWLA | KASTLES | QQYNTYWT | TYTMR | SIYPSGGKTQYADSVKG | RRTGIPRRDAFDI |
| M198-F04 | 92.9 | | RASQSISSWLA | KASTLES | QQYNTYWT | IYDMW | SIRPSGGITKYADSVKG | RRTGIPRRDAFDI |
| M197-H11 | 92.9 | | RASQSISSWLA | KASTLES | QQYNTYWT | IYNMI | SIYPSGGWTTYADSVKG | RRTGIPRRDAFDI |
| M197-F01 | 92.6 | | RASQSISSWLA | KASTLES | QQYNTYWT | IYHMY | SIGPSGGPTGYADSVKG | RRTGIPRRDAFDI |
| M198-E11 | 92.5 | | RASQSISSWLA | KASTLES | QQYNTYWT | TYSMY | SIYPSGGLTWYADSVKG | RRTGIPRRDAFDI |
| M202-C09 | 92.3 | 0.3 | RASQSISSWLA | KASTLES | QQYNTYWT | HYIMM | GIYSSGGITVYADSVKG | RRIGVPRRDDFDI |
| M198-H08 | 92.3 | | RASQSISSWLA | KASTLES | QQYNTYWT | IYDMY | SIGPSGGPTAYADSVKG | RRTGIPRRDAFDI |
| M198-F08 | 91.8 | | RASQSISSWLA | KASTLES | QQYNTYWT | VYSMW | SISSSGGMTEYADSVKG | RRTGIPRRDAFDI |
| M202-E06 | 91.5 | | RASQSISSWLA | KASTLES | QQYNTYWT | HYIMM | GIYSSGGITVYADSVKG | RRRGVPRRDDFDI |
| M195-D12 | 90.8 | | RASQSISSWLA | KASTLES | QQYNTYWT | IYGMF | GIGPSGGPTKYADSVKG | RRTGIPRRDAFDI |
| M197-F03 | 90.7 | | RASQSISSWLA | KASTLES | QQYNTYWT | IYSMF | SIGPSGGVTHYADSVKG | RRTGIPRRDAFDI |
| M198-E02 | 90.3 | | RASQSISSWLA | KASTLES | QQYNTYWT | IYSMY | YIRPSGGNTKYADSVKG | RRTGIPRRDAFDI |
| M198-A02 | 89.1 | | RASQSISSWLA | KASTLES | QQYNTYWT | RYSMI | SIWSSGGATEYADSVKG | RRTGIPRRDAFDI |
| M202-A01 | 88.9 | | RASQSISSWLA | KASTLES | QQYNTYWT | HYIMM | GIYSSGGITVYADSVKG | RRIGVPRRDAFDI |
| M202-G03 | 88.3 | | RASQSISSWLA | KASTLES | QQYNTYWT | HYIMM | GIYSSGGITVYADSVKG | RRTGVPRRDSFEI |
| M195-B12 | 87.7 | | RASQSISSWLA | KASTLES | QQYNTYWT | KYWMY | YIRPSGGQTYYADSVKG | RRTGIPRRDAFDI |
| M198-A07 | 86.1 | | RASQSISSWLA | KASTLES | QQYNTYWT | RYQMH | WISPSGGITGYADSVKG | RRTGIPRRDAFDI |

TABLE 8-continued

Sequences of Antibodies Obtained from CDR1/2 and CDR3 Spiking Affinity Maturation Libraries Based on M162-A04

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
| --- | --- | --- | --- | --- | --- | --- | --- | --- |
| M198-H02 | 85.8 | | RASQSISSWLA | KASTLES | QQYNTYWT | PYNMY | WIVPGGVTKYADSVKG | RRTGIPRRDAFDI |
| M200-H07 | 85.4 | | RASQSISSWLA | KASTLES | QQYNTYWT | HYIMM | GIYSSGGITVYADSVKG | RRTGVPRRNAFDN |
| M201-H06 | 84.6 | | RASQSISSWLA | KASTLES | QQYNTYWT | HYIMM | GIYSSGGITVYADSVKG | RRTGVPRRDAFDI |
| M202-F06 | 84.2 | | RASQSISSWLA | KASTLES | QQYNTYWT | HYIMM | GIYSSGGITVYADSVKG | RRTGVPRWDAFDI |
| M195-C12 | 84.2 | | RASQSISSWLA | KASTLES | QQYNTYWT | MYQMF | SISPGGGTQYADSVKG | RRTGIPRRDAFDI |
| M202-H05 | 84.0 | | RASQSISSWLA | KASTLES | QQYNTYWT | HYIMM | GIYSSGGITVYADSVKG | RRTGVPRRDVFDI |
| M198-C05 | 83.9 | | RASQSISSWLA | KASTLES | QQYNTYWT | RYKMY | VIGPSGGATFYADSVKG | RRTGIPRRDAFDI |
| M196-H03 | 83.9 | | RASQSISSWLA | KASTLES | QQYNTYWT | RYVMW | SISPSGDTHYADSVKG | RRTGIPRRDAFDI |
| M200-E11 | 83.2 | | RASQSISSWLA | KASTLES | QQYNTYWT | HYIMM | GIYSSGGITVYADSVKG | RRTGVPRRDAFDI |
| M202-B04 | 81.9 | | RASQSISSWLA | KASTLES | QQYNTYWT | HYIMM | GIYSSGGITVYADSVKG | RRSGVPRRDDFDI |
| M202-A04 | 81.2 | | RASQSISSWLA | KASTLES | QQYNTYWT | HYIMM | GIYSSGGITVYADSVKG | RRKGIPRRDDFDI |
| M198-B12 | 80.7 | | RASQSISSWLA | KASTLES | QQYNTYWT | KYSMA | GIYPSGGRTLYADSVKG | RRTGIPRRDAFDI |
| M198-A09 | 77.3 | | RASQSISSWLA | KASTLES | QQYNTYWT | IYFMS | SIRSSGGPTWYADSVKG | RRTGIPRRDAFDI |
| M198-C06 | 76.5 | | RASQSISSWLA | KASTLES | QQYNTYWT | QYFMH | YIYPSGGMTEYADSVKG | RRTGIPRRDAFDI |
| M198-C09 | 75.4 | | RASQSISSWLA | KASTLES | QQYNTYWT | IYTMY | SISPSGGWTYYADSVKG | RRTGIPRRDAFDI |
| M195-B02 | 75.1 | | RASQSISSWLA | KASTLES | QQYNTYWT | PYLMW | YIGPSGGPTHYADSVKG | RRTGIPRRDAFDI |
| M198-F12 | 74.6 | | RASQSISSWLA | KASTLES | QQYNTYWT | IYTMM | SIWSSGGQTKYADSVKG | RRTGIPRRDAFDI |
| M201-H08 | 74.5 | | RASQSISSWLA | KASTLES | QQYNTYWT | HYIMM | GIYSSGGITVYADSVKG | RRTGVPRRDALDN |
| M202-C02 | 74.3 | | RASQSISSWLA | KASTLES | QQYNTYWT | HYIMM | GIYSSGGITVYADSVKG | RRPGVPRRDAFDI |
| M198-C03 | 72.4 | | RASQSISSWLA | KASTLES | QQYNTYWT | RYSMS | GISPSGGETSYADSVKG | RRTGIPRRDAFDI |
| M198-A08 | 72.3 | | RASQSISSWLA | KASTLES | QQYNTYWT | WYMMQ | RISPSGGTTYADSVKG | RRTGIPRRDAFDI |
| M195-A02 | 71.3 | | RASQSISSWLA | KASTLES | QQYNTYWT | QYMMM | GISSSGGHTDYADSVKG | RRTGIPRRDAFDI |
| M197-G10 | 67.6 | | RASQSISSWLA | KASTLES | QQYNTYWT | VYAMR | SIYPSGGKTWYADSVKG | RRTGIPRRDAFDI |
| M195-G02 | 67.5 | | RASQSISSWLA | KASTLES | QQYNTYWT | PYNMM | SIWPSGGTTDYADSVKG | RRTGIPRRDAFDI |
| M196-D02 | 66.2 | | RASQSISSWLA | KASTLES | QQYNTYWT | VYSMH | VIGPSGGITLYADSVKG | RRTGIPRRDAFDI |
| M199-A11 | 65.4 | | RASQSISSWLA | KASTLES | QQYNTYWT | HYIMM | GIYSSGGITVYADSVKG | RRRGIPRRDAFDI |
| M200-F01 | 65.1 | | RASQSISSWLA | KASTLES | QQYNTYWT | HYIMM | GIYSSGGITVYADSVKG | RRMGIPRRNAFDI |
| M198-D12 | 63.5 | 0.7 | RASQSISSWLA | KASTLES | QQYNTYWT | LYVMY | YIVPSGGPTAYADSVKG | RRTGIPRRDAFDI |
| M197-C12 | 56.4 | | RASQSISSWLA | KASTLES | QQYNTYWT | PYDML | YIVSSGGLTKYADSVKG | RRTGIPRRDAFDI |
| M198-G03 | 53.8 | | RASQSISSWLA | KASTLES | QQYNTYWT | QYTMV | WIYSSRANYADSVKG | RRTGIPRRDAFDI |
| M199-B01 | 53.4 | | RASQSISSWLA | KASTLES | QQYNTYWT | HYIMM | GIYSSGGITVYADSVKG | RRTGIPRRDAFDN |
| M202-A08 | 52.9 | | RASQSISSWLA | KASTLES | QQYNTYWT | HYIMM | GIYSSGGITVYADSVKG | RRTGVPRWDAFDI |
| M195-A12 | 51.7 | | RASQSISSWLA | KASTLES | QQYNTYWT | PYMMM | GIYPSGGYTVYADSVKG | RRTGIPRRDAFDI |
| M202-E03 | 51.4 | | RASQSISSWLA | KASTLES | QQYNTYWT | HYIMM | GIYSSGGITVYADSVKG | RRTGIPRRDAFEI |
| M196-G12 | 51.1 | | RASQSISSWLA | KASTLES | QQYNTYWT | NYSMD | RIYSGGGTIYADSVKG | RRTGIPRRDAFDI |
| M195-F12 | 45.5 | | RASQSISSWLA | KASTLES | QQYNTYWT | HYVMM | YIVPSGGVTAYADSVKG | RRTGIPRRDAFDI |

TABLE 8-continued

Sequences of Antibodies Obtained from CDR1/2 and CDR3 Spiking Affinity Maturation Libraries Based on M162-A04

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
|---|---|---|---|---|---|---|---|---|
| M200-B01 | 42.6 | | RASQSISSWLA | KASTLES | QQYNTYWT | HYIMM | GIYSSGGITVYADSVKG | RRTGIPRRDAFDS |
| M198-H09 | 41.1 | | RASQSISSWLA | KASTLES | QQYNTYWT | IYLMI | YIGPSGGPTEYADSVKG | RRTGIPRRDAFDI |
| M195-E12 | 38.0 | | RASQSISSWLA | KASTLES | QQYNTYWT | YYIMF | YISPSGGYTHYADSVKG | RRTGIPRRDAFDI |
| M201-A06 | 36.8 | | RASQSISSWLA | KASTLES | QQYNTYWT | HYIMM | GIYSSGGITVYADSVKG | RRTGIPRRDVFDI |
| M202-A10 | 36.3 | | RASQSISSWLA | KASTLES | QQYNTYWT | HYIMM | GIYSSGGITVYADSVKG | RRTGIPRRDSFDI |
| M197-G11 | 19.2 | | RASQSISSWLA | KASTLES | QQYNTYWT | TYAMV | SIYPSGGITTYADSVKG | RRTGIPRRDAFDI |
| M201-F11 | 15.7 | | RASQSISSWLA | KASTLES | QQYNTYWT | HYIMM | GIYSSGGITVYADSVKG | RRSGIPRRDAFDI |
| M198-A01 | 13.8 | | RASQSISSWLA | KASTLES | QQYNTYWT | PYTMI | SISSSGGMTPYADSVKG | RRTGIPRRDAFDI |

Amino Acid Sequences of Light Chain (LC) and Heavy Chain (HC) Variable Domain of pKal Antibodies Obtained from CDR1/2 and CDR3 Spiking Affinity Maturation Libraries Based on M162-A04.

```
M195-A02 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M195-A02 HC
EVQLLESGGG LVQPGGSLRL SCAASGFTFS QYMMMWVRQA PGKGLEWVSG ISSSGGHTDY      60

ADSVKGRFTI SRDNSKNTLY LQMNSLRAED TAVYYCAYRR TGIPRRDAFD IWGQGTMVTV     120

SSASTKGPSV FPLAPSSKS                                                  139

M195-A12 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M195-A12 HC
EVQLLESGGG LVQPGGSLRL SCAASGFTFS PYMMMWVRQA PGKGLEWVSG IYPSGGYTVY      60

ADSVKGRFTI SRDNSKNTLY LQMNSLRAED TAVYYCAYRR TGIPRRDAFD IWGQGTMVTV     120

SSASTKGPSV FPLAPSSKS                                                  139

M195-B02 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M195-B02 HC
EVQLLESGGG LVQPGGSLRL SCAASGFTFS PYLMWVRQA PGKGLEWVSY IGPSGGPTHY       60

ADSVKGRFTI SRDNSKNTLY LQMNSLRAED TAVYYCAYRR TGIPRRDAFD IWGQGTMVTV     120

SSASTKGPSV FPLAPSSKS                                                  139

M195-B12 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107
```

-continued

```
M195-B12 HC
EVQLLESGGG LVQPGGSLRL SCAASGFTFS KYWMYWVRQA PGKGLEWVSY IRPSGGQTYY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M195-C12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M195-C12 HC
EVQLLESGGG LVQPGGSLRL SCAASGFTFS MYQMFWVRQA PGKGLEWVSS ISPGGGTQYA    60

DSVKGRFTIS RDNSKNTLYL QMNSLRAEDT AVYYCAYRRT GIPRRDAFDI WGQGTMVTVS   120

SASTKGPSVF PLAPSSKS                                                 138

M195-D12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M195-D12 HC
EVQLLESGGG LVQPGGSLRL SCAASGFTFS IYGMFWVRQA PGKGLEWVSG IGPSGGPTKY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M195-E12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M195-E12 HC
EVQLLESGGG LVQPGGSLRL SCAASGFTFS YYIMFWVRQA PGKGLEWVSY ISPSGGYTHY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M195-F12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M195-F12 HC
EVQLLESGGG LVQPGGSLRL SCAASGFTFS HYVMMWVRQA PGKGLEWVSY IVPSGGVTAY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M0195-G02 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M195-G02 HC
EVQLLESGGG LVQPGGSLRL SCAASGFTFS PYNMMWVRQA PGKGLEWVSS IWPSGGTTDY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M196-C06 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M196-C06 HC
EVQLLESGGG LVQPGGSLRL SCAASGFTFS IYSMHWVRQA PGKGLEWVSS IYPSRGMTWY    60

ADSVKGRFTI SRDNSKNTLY LQMNSLRAED TAVYYCAYRR TGIPRRDAFD IWGQGTMVTV   120

SSASTKGPSV FPLAPSSKS                                                139
```

```
M196-D02 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M196-D02 HC
EVQLLESGGG LVQPGGSLRL SCAASGFTFS VYSMHWVRQA PGKGLEWVSV IGPSGGITLY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M196-D12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M196-D12 HC
EVQLLESGGG LVQPGGSLRL SCAASGFTFS RYSMRWVRQA PGKGLEWVSV IYPSGGQTYY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M196-G12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M196-G12 HC
EVQLLESGGG LVQPGGSLRL SCAASGFTFS NYSMDWVRQA PGKGLEWVSR IYSSGGGTIY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M196-H03 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M196-H03 HC
EVQLLESGGG LVQPGGSLRL SCAASGFTFS RYVMWWVRQA PGKGLEWVSS ISPSGDTHYA    60

DSVKGRFTIS RDNSKNTLYL QMNSLRAEDT AVYYCAYRRT GIPRRDAFDI WGQGTMVTVS   120

SASTKGPSVF PLAPSSKS                                                 138

M197-A01 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-A01 HC
EVQLLESGGG LVQPGGSLRL SCAASGFTFS IYDMIWVRQA PGKGLEWVSS IYPSGGNTSY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-A08 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-A08 HC
EVQLLESGGG LVQPGGSLRL SCAASGFTFS IYSMQWVRQA PGKGLEWVSS IGSSGGKTLY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-A09 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107
```

```
M197-A09 HC
EVQLLESGGG LVQPGGSLRL SCAASGFTFS VYNMHWVRQA PGKGLEWVSS IYPSGGMTTY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-C12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-C12 HC
EVQLLESGGG LVQPGGSLRL SCAASGFTFS PYDMLWVRQA PGKGLEWVSY IVSSGGLTKY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-E12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-E12 HC
EVQLLESGGG LVQPGGSLRL SCAASGFTFS TYTMRWVRQA PGKGLEWVSS IYPSGGKTQY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-F01 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-F01 HC
EVQLLESGGG LVQPGGSLRL SCAASGFTFS IYHMWVRQA PGKGLEWVSS IGPSGGPTGY     60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-F03 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-F03 HC
EVQLLESGGG LVQPGGSLRL SCAASGFTFS IYSMFWVRQA PGKGLEWVSS IGPSGGVTHY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-G10 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-G10 HC
EVQLLESGGG LVQPGGSLRL SCAASGFTFS VYAMRWVRQA PGKGLEWVSS IYPSGGKTWY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M197-G11 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-G11 HC
EVQLLESGGG LVQPGGSLRL SCAASGFTFS TYAMVWVRQA PGKGLEWVSS IYPSGGITTY    60

ADSVKGRFTI SRDNSKNTLY LQMNSLRAED TAVYYCAYRR TGIPRRDAFD IWGQGTMVTV   120

SSASTKGPSV FPLAPSSKS                                                139
```

```
-continued
M197-H10 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-H10 HC
EVQLLESGGG LVQPGGSLRL SCAASGFTFS SYNMHWVRQA PGKGLEWVSS IVPSGGKTNY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M197-H11 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M197-H11 HC
EVQLLESGGG LVQPGGSLRL SCAASGFTFS IYNMIWVRQA PGKGLEWVSS IYPSGGWTTY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-A01 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-A01 HC
EVQLLESGGG LVQPGGSLRL SCAASGFTFS PYTMIWVRQA PGKGLEWVSS ISSSGGMTPY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-A02 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-A02 HC
EVQLLESGGG LVQPGGSLRL SCAASGFTFS RYSMIWVRQA PGKGLEWVSS IWSSGGATEY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-A06 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-A06 HC
EVQLLESGGG LVQPGGSLRL SCAASGFTFS IYSMHWVRQA PGKGLEWVSS IYSSGGPTKY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-A07 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-A07 HC
EVQLLESGGG LVQPGGSLRL SCAASGFTFS RYQMHWVRQA PGKGLEWVSW ISPSGGITGY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-A08 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107
```

```
M198-A08 HC
EVQLLESGGG LVQPGGSLRL SCAASGFTFS WYMMQWVRQA PGKGLEWVSR ISPSGGTTYA    60

DSVKGRFTIS RDNSKNTLYL QMNSLRAEDT AVYYCAYRRT GIPRRDAFDI WGQGTMVTVS   120

SASTKGPSVF PLAPSSKS                                                 138

M198-A09 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-A09 HC
EVQLLESGGG LVQPGGSLRL SCAASGFTFS IYFMSWVRQA PGKGLEWVSS IRSSGGPTWY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-B09 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-B09 HC
EVQLLESGGG LVQPGGSLRL SCAASGFTFS VYSMTWVRQA PGKGLEWVSS IGSSGGSTTY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-B12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-B12 HC
EVQLLESGGG LVQPGGSLRL SCAASGFTFS KYSMAWVRQA PGKGLEWVSG IYPSGGRTLY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-C03 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-C03 HC
EVQLLESGGG LVQPGGSLRL SCAASGFTFS RYSMSWVRQA PGKGLEWVSG ISPSGGETSY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-C05 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-C05 HC
EVQLLESGGG LVQPGGSLRL SCAASGFTFS RYKMYWVRQA PGKGLEWVSV IGPSGGATFY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-C06 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-C06 HC
EVQLLESGGG LVQPGGSLRL SCAASGFTFS QYFMHWVRQA PGKGLEWVSY IYPSGGMTEY    60

ADSVKGRFTI SRDNSKNTLY LQMNSLRAED TAVYYCAYRR TGIPRRDAFD IWGQGTMVTV   120

SSASTKGPSV FPLAPSSKS                                                139
```

-continued

```
M198-C09 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                  107

M198-C09 HC
EVQLLESGGG LVQPGGSLRL SCAASGFTFS IYTMYWVRQA PGKGLEWVSS ISPSGGWTYY     60

ADSVKGRFTI SRDNSKNTLY LQMNSLRAED TAVYYCAYRR TGIPRRDAFD IWGQGTMVTV    120

SSASTKGPSV FPLAPSSKS                                                 139

M198-C10 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M198-C10 HC
EVQLLESGGG LVQPGGSLRL SCAASGFTFS HYMGMNWVRQ APGKGLEWVS SIVPSGGWTQ     60

YADSVKGRFT ISRDNSKNTL YLQMNSLRAE DTAVYYCAYR RTGIPRRDAF DIWGQGTMVT    120

VSSASTKGPS VFPLAPSSKS                                                140

M198-D12 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M198-D12 HC
EVQLLESGGG LVQPGGSLRL SCAASGFTFS LYVMYWVRQA PGKGLEWVSY IVPSGGPTAY     60

ADSVKGRFTI SRDNSKNTLY LQMNSLRAED TAVYYCAYRR TGIPRRDAFD IWGQGTMVTV    120

SSASTKGPSV FPLAPSSKS                                                 139

M198-E02 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M198-E02 HC
EVQLLESGGG LVQPGGSLRL SCAASGFTFS IYSMYWVRQA PGKGLEWVSY IRPSGGNTKY     60

ADSVKGRFTI SRDNSKNTLY LQMNSLRAED TAVYYCAYRR TGIPRRDAFD IWGQGTMVTV    120

SSASTKGPSV FPLAPSSKS                                                 139

M198-E09 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M198-E09 HC
EVQLLESGGG LVQPGGSLRL SCAASGFTFS IYDMNWVRQA PGKGLEWVSS IYPSGGRTRY     60

ADSVKGRFTI SRDNSKNTLY LQMNSLRAED TAVYYCAYRR TGIPRRDAFD IWGQGTMVTV    120

SSASTKGPSV FPLAPSSKS                                                 139

M198-E11 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M198-E11 HC
EVQLLESGGG LVQPGGSLRL SCAASGFTFS TYSMYWVRQA PGKGLEWVSS IYPSGGLTWY     60

ADSVKGRFTI SRDNSKNTLY LQMNSLRAED TAVYYCAYRR TGIPRRDAFD IWGQGTMVTV    120

SSASTKGPSV FPLAPSSKS                                                 139

M198-F04 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107
```

```
M198-F04 HC
EVQLLESGGG LVQPGGSLRL SCAASGFTFS IYDMWWVRQA PGKGLEWVSS IRPSGGITKY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-F08 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-F08 HC
EVQLLESGGG LVQPGGSLRL SCAASGFTFS VYSMWWVRQA PGKGLEWVSS ISSSGGMTEY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-F09 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-F09 HC
EVQLLESGGG LVQPGGSLRL SCAASGFTFS VYNMHWVRQA PGKGLEWVSS IYPSGGMTYY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-F12 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-F12 HC
EVQLLESGGG LVQPGGSLRL SCAASGFTFS IYTMWWVRQA PGKGLEWVSS IWSSGGQTKY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-G03 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-G03 HC
EVQLLESGGG LVQPGGSLRL SCAASGFTFS QYTMWVRQA PGKGLEWVSW IYSSRANYAD     60

SVKGRFTISR DNSKNTLYLQ MNSLRAEDTA VYYCAYRRTG IPRRDAFDIW GQGTMVTVSS   120

ASTKGPSVFP LAPSSKS                                                  137

M198-G07 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-G07 HC
EVQLLESGGG LVQPGGSLRL SCAASGFTFS IYDMTWVRQA PGKGLEWVSS IYPSGGQTIY    60

ADSVKGRFTI SRDNSKNTLY LQMNSLRAED TAVYYCAYRR TGIPRRDAFD IWGQGTMVTV   120

SSASTKGPSV FPLAPSSKS                                                139

M198-H02 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                 107

M198-H02 HC
EVQLLESGGG LVQPGGSLRL SCAASGFTFS PYNMYWVRQA PGKGLEWVSW IVPGGVTKYA    60

DSVKGRFTIS RDNSKNTLYL QMNSLRAEDT AVYYCAYRRT GIPRRDAFDI WGQGTMVTVS   120

SASTKGPSVF PLAPSSKS                                                 138
```

-continued

M198-H08 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M198-H08 HC
EVQLLESGGG LVQPGGSLRL SCAASGFTFS IYDMYWVRQA PGKGLEWVSS IGPSGGPTAY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M198-H09 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M198-H09 HC
EVQLLESGGG LVQPGGSLRL SCAASGFTFS IYLMIWVRQA PGKGLEWVSY IGPSGGPTEY    60

ADSVKGRFTI SRDNSKNTLY LQMNSLRAED TAVYYCAYRR TGIPRRDAFD IWGQGTMVTV   120

SSASTKGPSV FPLAPSSKS                                               139

M199-A08 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M199-A08 HC
EVQLLESGGG LVQPGGSLRL SCAASGFTFS HYIMMWVRQA PGKGLEWVSG IYSSGGITVY    60

ADSVKGRFTI SRDNSKNTLY LQMNSLRAED TAVYYCAYRR IGVPRRDEFD IWGQGTMVTV   120

SSASTKGPSV FPLAPSSKS                                               139

M199-A11 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M199-A11 HC
EVQLLESGGG LVQPGGSLRL SCAASGFTFS HYIMMWVRQA PGKGLEWVSG IYSSGGITVY    60

ADSVKGRFTI SRDNSKNTLY LQMNSLRAED TAVYYCAYRR RGIPRRDAFD IWGQGTMVTV   120

SSASTKGPSV FPLAPSSKS                                               139

M199-B01 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M199-B01 HC
EVQLLESGGG LVQPGGSLRL SCAASGFTFS HYIMMWVRQA PGKGLEWVSG IYSSGGITVY    60

ADSVKGRFTI SRDNSKNTLY LQMNSLRAED TAVYYCAFRR TGIPRRDAFD NWGQGTMVTV   120

SSASTKGPSV FPLAPSSKS                                               139

M200-A10 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

M200-A10 HC
EVQLLESGGG LVQPGGSLRL SCAASGFTFS HYIMMWVRQA PGKGLEWVSG IYSSGGITVY    60

ADSVKGRFTI SRDNSKNTLY LQMNSLRAED TAVYYCAYRR TGVPRRDSFD IWGQGTMVTV   120

SSASTKGPSV FPLAPSSKS                                               139

M200-B01 LC
QDIQMTQSPS TLSASVGDRV TITCRASQSI SSWLAWYQQK PGKAPNLLIY KASTLESGVP    60

SRFSGSGSGT EFTLTISSLQ PDDFATYYCQ QYNTYWTFGQ GTKVEIK                107

```
-continued
M200-B01 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR TGIPRRDAFD SWGQGTMVTV     120

SSASTKGPSV FPLAPSSKS                                                  139

M200-D03 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M200-D03 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAWRR IGVPRRDSFD MWGQGTMVTV     120

SSASTKGPSV FPLAPSSKS                                                  139

M200-E11 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M200-E11 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR TGVPRRDAFD NWGQGTMVTV     120

SSASTKGPSV FPLAPSSKS                                                  139

M200-F01 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M200-F01 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR MGIPRRNAFD IWGQGTMVTV     120

SSASTKGPSV FPLAPSSKS                                                  139

M200-H07 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M200-H07 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR TGVPRRNAFD NWGQGTMVTV     120

SSASTKGPSV FPLAPSSKS                                                  139

M201-A06 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M201-A06 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR TGIPRRDVFD IWGQGTMVTV     120

SSASTKGPSV FPLAPSSKS                                                  139

M201-A07 LC
QDIQMTQSPS TLSASVGDRV TITCRASQSI SSWLAWYQQK PGKAPNLLIY KASTLESGVP      60

SRFSGSGSGT EFTLTISSLQ PDDFATYYCQ QYNTYWTFGQ GTKVEIK                   107

M201-A07 HC
EVQLLESGGG LVQPGGSLRL SCAASGFTFS HYIMMWVRQA PGKGLEWVSG IYSSGGITVY      60

ADSVKGRFTI SRDNSKNTLY LQMNSLRAED TAVYYCAYRR TGVPRRDEFD IWGQGTMVTV     120

SSASTKGPSV FPLAPSSKS                                                  139
```

```
M201-F11 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M201-F11 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR SGIPRRDAFD IWGQGTMVTV   120
SSASTKGPSV FPLAPSSKS                                                139

M201-H06 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M201-H06 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR TGVPRRDAFD IWGQGTMVTV   120
SSASTKGPSV FPLAPSSKS                                                139

M201-H08 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M201-H08 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR TGVPRRDALD NWGQGTMVTV   120
SSASTKGPSV FPLAPSSKS                                                139

M202-A01 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-A01 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR IGVPRRDAFD IWGQGTMVTV   120
SSASTKGPSV FPLAPSSKS                                                139

M202-A04 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-A04 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR KGIPRRDDFD IWGQGTMVTV   120
SSASTKGPSV FPLAPSSKS                                                139

M202-A08 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-A08 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR TGIPRWDAFD IWGQGTMVTV   120
SSASTKGPSV FPLAPSSKS                                                139

M202-A10 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107
```

```
M202-A10 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAFRR TGIPRRDSFD IWGQGTMVTV    120

SSASTKGPSV FPLAPSSKS                                                 139

M202-A12 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M202-A12 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYQR TGVPRRDSFN IWGQGTMVTV    120

SSASTKGPSV FPLAPSSKS                                                 139

M202-B03 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M202-B03 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYRR TGVPRRDDFD IWGQGTMVTV    120

SSASTKGPSV FPLAPSSKS                                                 139

M202-B04 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M202-B04 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYRR SGVPRRDDFD IWGQGTMVTV    120

SSASTKGPSV FPLAPSSKS                                                 139

M202-C01 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M202-C01 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYRR TGVPRWDDFD IWGQGTMVTV    120

SSASTKGPSV FPLAPSSKS                                                 139

M202-C02 LC
QDIQMTQSPS TLSASVGDRV TITCRASQSI SSWLAWYQQK PGKAPNLLIY KASTLESGVP     60

SRFSGSGSGT EFTLTISSLQ PDDFATYYCQ QYNTYWTFGQ GTKVEIK                  107

M202-C02 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYRR PGVPRRDAFD IWGQGTMVTV    120

SSASTKGPSV FPLAPSSKS                                                 139

M202-C09 LC
QDIQMTQSPS TLSASVGDRV TITCRASQSI SSWLAWYQQKP GKAPNLLIYK ASTLESGVP     60

SRFSGSGSGT EFTLTISSLQ PDDFATYYCQ QYNTYWTFGQ GTKVEIK                  107

M202-C09 HC
EVQLLESGGG LVQPGGSLRL SCAASGFTFS HYIMMWVRQA PGKGLEWVSG IYSSGGITVY     60

ADSVKGRFTI SRDNSKNTLY LQMNSLRAED TAVYYCAYRR IGVPRRDDFD IWGQGTMVTV    120

SSASTKGPSV FPLAPSSKS                                                 139
```

```
M202-D09 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-D09 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR IGVPRRDSFD IWGQGTMVTV   120
SSASTKGPSV FPLAPSSKS                                               139

M202-E03 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-E03 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR TGIPRRDAFE IWGQGTMVTV   120
SSASTKGPSV FPLAPSSKS                                               139

M202-E06 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-E06 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR RGVPRRDDFD IWGQGTMVTV   120
SSASTKGPSV FPLAPSSKS                                               139

M202-F06 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-F06 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAYRR TGVPRWDAFD IWGQGTMVTV   120
SSASTKGPSV FPLAPSSKS                                               139

M202-G03 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-G03 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAFRR TGVPRRDSFE IWGQGTMVTV   120
SSASTKGPSV FPLAPSSKS                                               139

M202-H03 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107

M202-H03 HC
EVQLLESGGG LVQPGGSLRL SCAASGFTFS HYIMMWVRQA PGKGLEWVSG IYSSGGITVY    60
ADSVKGRFTI SRDNSKNTLY LQMNSLRAED TAVYYCAFRR TGVPRWDDFD IWGQGTMVTV   120
SSASTKGPSV FPLAPSSKS                                               139

M202-H05 LC
QDIQMTQSPS TLSASVGDRV TITCRASQSI SSWLAWYQQK PGKAPNLLIY KASTLESGVP    60
SRFSGSGSGT EFTLTISSLQ PDDFATYYCQ QYNTYWTFGQ GTKVEIK                 107
```

-continued

M202-H05 HC
```
EVQLLESGGG LVQPGGSLRL SCAASGFTFS HYIMMWVRQA PGKGLEWVSG IYSSGGITVY    60

ADSVKGRFTI SRDNSKNTLY LQMNSLRAED TAVYYCAFRR TGVPRRDVFD IWGQGTMVTV   120

SSASTKGPSV FPLAPSSKS                                                139
```

TABLE 9

Sequences of Antibodies Obtained from CDR1/2 and CDR3 Spiking Affinity Maturation Libraries Based on X63-G06

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
|---|---|---|---|---|---|---|---|---|
| M209-F04 | 97.6 | 0.09 | RTSQFVNSNYLA | GASSRAT | QQSSRTPWT | HYLMT | YISPSGGHTIYADSVKG | VARGIAARSRTSYLDq |
| M209-C11 | 96.2 | 0.14 | RTSQFVNSNYLA | GASSRAT | QQSSRTPWT | HYLMT | YISPSGGHTIYADSVKG | VGQGIRGRSRTSYFAq |
| M206-H08 | 96.0 | 0.17 | RTSQFVNSNYLA | GASSRAT | QQSSRTPWT | DYMMA | SIVPSGGHTHYADSVKG | VARGIAARSRTSYFDY |
| M210-C12 | 95.6 | 0.16 | RTSQFVNSNYLA | GASSRAT | QQSSRTPWT | HYLMT | YISPSGGHTIYADSVKG | VAQGIAARSRTSSVDq |
| M208-F04 | 95.4 | 0.2 | RTSQFVNSNYLA | GASSRAT | QQSSRTPWT | HYLMT | YISPSGGHTIYADSVKG | VARGIAARSRTSFFDY |
| M206-B10 | 94.7 | 0.3 | RTSQFVNSNYLA | GASSRAT | QQSSRTPWT | qYLMA | SIYPSGGWTKYADSVKG | VARGIAARSRTSYFDY |
| M208-H02 | 94.4 | 0.2 | RTSQFVNSNYLA | GASSRAT | QQSSRTPWT | HYLMT | YISPSGGHTIYADSVKG | VARGIASRSRTRYCDY |
| M210-G04 | 94.2 | 0.3 | RTSQFVNSNYLA | GASSRAT | QQSSRTPWT | HYLMT | YISPSGGHTIYADSVKG | VATGIVARSRTRYFDq |
| M210-H06 | 93.8 | 0.2 | RTSQFVNSNYLA | GASSRAT | QQSSRTPWT | HYLMT | YISPSGGHTIYADSVKG | VARGIAARSRTRYFDY |
| M208-E10 | 93.7 | 0.09 | RTSQFVNSNYLA | GASSRAT | QQSSRTPWT | HYLMT | YISPSGGHTIYADSVKG | VAQGISARSRTSYFDY |
| M209-B09 | 93.5 | 0.2 | RTSQFVNSNYLA | GASSRAT | QQSSRTPWT | HYLMT | YISPSGGHTIYADSVKG | VAQGIVARSRTSYLHq |
| M209-C12 | 93.4 |  | RTSQFVNSNYLA | GASSRAT | QQSSRTPWT | HYLMT | YISPSGGHTIYADSVKG | VGRGIAARSRTSqLDY |
| M208-G03 | 93.4 | 0.3 | RTSQFVNSNYLA | GASSRAT | QQSSRTPWT | HYLMT | YISPSGGHTIYADSVKG | VARGIAARSRTSYLDY |
| M206-A06 | 93.0 |  | RTSQFVNSNYLA | GASSRAT | QQSSRTPWT | NYMMG | SISPSGGLTKYADSVKG | VARGIAARSRTSYFDY |
| M210-H07 | 92.8 | 0.4 | RTSQFVNSNYLA | GASSRAT | QQSSRTPWT | HYLMT | YISPSGGHTIYADSVKG | VARGIAARSRTRYFDq |
| M206-F01 | 92.6 | 0.2 | RTSQFVNSNYLA | GASSRAT | QQSSRTPWT | GYMMV | RISPSGGPTIYADSVKG | VARGIAARSRTSYFDY |
| M208-F10 | 92.5 | 0.2 | RTSQFVNSNYLA | GASSRAT | QQSSRTPWT | HYLMT | YISPSGGHTIYADSVKG | VARGIAARSRTSYFDq |
| M209-E02 | 92.4 | 0.3 | RTSQFVNSNYLA | GASSRAT | QQSSRTPWT | HYLMT | YISPSGGHTIYADSVKG | VARGIAARSRTILLDq |
| M208-C06 | 91.7 | 0.4 | RTSQFVNSNYLA | GASSRAT | QQSSRTPWT | HYLMT | YISPSGGHTIYADSVKG | VARGIAARSRTSFIDY |
| M205-D04 | 91.5 | 0.4 | RTSQFVNSNYLA | GASSRAT | QQSSRTPWT | TYKMq | SISPSGGPTNYADSVKG | VARGIAARSRTSYFDY |
| M210-G10 | 91.2 | 0.4 | RTSQFVNSNYLA | GASSRAT | QQSSRTPWT | HYLMT | YISPSGGHTIYADSVKG | VARGIAARSRTSYLDF |
| M207-A04 | 90.9 |  | RTSQFVNSNYLA | GASSRAT | QQSSRTPWT | HYLMT | YISPSGGHTIYADSVKG | VARGIAARSRTRSFDY |
| M210-B02 | 90.9 | 0.2 | RTSQFVNSNYLA | GASSRAT | QQSSRTPWT | HYLMT | YISPSGGHTIYADSVKG | VARGIAARSRTSYFNq |
| M208-B01 | 90.1 |  | RTSQFVNSNYLA | GASSRAT | QQSSRTPWT | HYLMT | YISPSGGHTIYADSVKG | VARGIAARSRTSFFDq |
| M209-G07 | 89.8 |  | RTSQFVNSNYLA | GASSRAT | QQSSRTPWT | HYLMT | YISPSGGHTIYADSVKG | VARGIAARSRTSYFDT |
| M204-A02 | 89.5 |  | RTSQFVNSNYLA | GASSRAT | QQSSRTPWT | DYMMT | YISPSGGLTSYADSVKG | VARGIAARSRTSYFDY |
| M206-H01 | 87.6 |  | RTSQFVNSNYLA | GASSRAT | QQSSRTPWT | EYMMV | RISPSGGTTEYADSVKG | VARGIAARSRTSYFDY |
| M209-B11 | 87.3 |  | RTSQFVNSNYLA | GASSRAT | QQSSRTPWT | HYLMT | YISPSGGHTIYADSVKG | VARGIAARSRTRYIDq |
| M206-F09 | 86.8 |  | RTSQFVNSNYLA | GASSRAT | QQSSRTPWT | VYMMS | SIVPSGGTTYADSVKG | VARGIAARSRTSYFDY |
| M209-C02 | 86.8 |  | RTSQFVNSNYLA | GASSRAT | QQSSRTPWT | HYLMT | YISPSGGHTIYADSVKG | VARGIAYRRRTSYFDY |
| M208-G02 | 86.7 |  | RTSQFVNSNYLA | GASSRAT | QQSSRTPWT | HYLMT | YISPSGGHTIYADSVKG | VARGIADRSRTSYSDY |

TABLE 9-continued

Sequences of Antibodies Obtained from CDR1/2 and CDR3 Spiking Affinity Maturation Libraries Based on X63-G06

| Antibody I.D. | % inhibition at 10 nM | human pKal Ki, app (nM) | LV-CDR1 | LV-CDR2 | LV-CDR3 | HV-CDR1 | HV-CDR2 | HV-CDR3 |
|---|---|---|---|---|---|---|---|---|
| M205-C11 | 86.5 | | RTSQFVNSNYLA | GASSRAT | QQSSRTPWT | QYMMM | RISPSGGSTLYADSVKG | VARGIAARSRTSYFDY |
| M205-H08 | 85.9 | | RTSQFVNSNYLA | GASSRAT | QQSSRTPWT | DYMMM | SIVPSGGHTqYADSVKG | VARGIAARSRTSYFDY |
| M210-H01 | 85.5 | | RTSQFVNSNYLA | GASSRAT | QQSSRTPWT | HYLMT | YISPSGGHTIYADSVKG | VARGIAARSRNSqQDY |
| M209-D12 | 85.4 | | RTSQFVNSNYLA | GASSRAT | QQSSRTPWT | HYLMT | YISPSGGHTIYADSVKG | VARGIAARSRTSYFDq |
| M209-H09 | 85.3 | | RTSQFVNSNYLA | GASSRAT | QQSSRTPWT | HYLMT | YISPSGGHTIYADSVKG | VARGIAARSRTVYFDH |
| M204-E12 | 84.1 | | RTSQFVNSNYLA | GASSRAT | QQSSRTPWT | TYMMq | YIGPSGGKTDYADSVKG | VARGIAARSRTSYFDY |
| M209-H03 | 82.6 | | RTSQFVNSNYLA | GASSRAT | QQSSRTPWT | HYLMT | YISPSGGHTIYADSVKG | VAQGIAARSRTTqFDY |
| M206-H05 | 82.5 | | RTSQFVNSNYLA | GASSRAT | QQSSRTPWT | GYKMq | SISPSGGITMYADSVKG | VARGIAARSRTSYFDY |
| M209-D03 | 80.4 | | RTSQFVNSNYLA | GASSRAT | QQSSRTPWT | HYLMT | YISPSGGHTIYADSVKG | VGRGIAARSRTSFFDq |
| M205-A02 | 80.3 | | RTSQFVNSNYLA | GASSRAT | QQSSRTPWT | TYLMA | GIVSSGGRTLYADSVKG | VARGIAARSRTSYFDY |
| M208-A10 | 78.5 | | RTSQFVNSNYLA | GASSRAT | QQSSRTPWT | HYLMT | YISPSGGHTIYADSVKG | VARGIAARSRTSqFDH |
| M205-E11 | 78.2 | | RTSQFVNSNYLA | GASSRAT | QQSSRTPWT | NYTMG | SISPSGGKTDYADSVKG | VARGIAARSRTSYFDY |
| M206-E02 | 77.6 | | RTSQFVNSNYLA | GASSRAT | QQSSRTPWT | EYMMM | VISPSGGQTHYADSVKG | VARGIAARSRTSYFDY |
| M205-H01 | 77.1 | | RTSQFVNSNYLA | GASSRAT | QQSSRTPWT | NYTMQ | YISPSGGYTGYADSVKG | VARGIAARSRTSYFDY |
| M207-A02 | 76.6 | | RTSQFVNSNYLA | GASSRAT | QQSSRTPWT | HYLMT | YISPSGGHTIYADSVKG | VARGIAARSRTINLDY |
| M209-H07 | 76.1 | | RTSQFVNSNYLA | GASSRAT | QQSSRTPWT | HYLMT | YISPSGGHTIYADSVKG | VARGIAARqRTSYYDY |
| M209-G01 | 74.8 | | RTSQFVNSNYLA | GASSRAT | QQSSRTPWT | HYLMT | YISPSGGHTIYADSVKG | VAgGISGRSRLSYVDY |
| M210-A06 | 74.8 | | RTSQFVNSNYLA | GASSRAT | QQSSRTPWT | HYLMT | YISPSGGHTIYADSVKG | VARGIAARSRTSqFDY |
| M209-D02 | 74.7 | | RTSQFVNSNYLA | GASSRAT | QQSSRTPWT | HYLMT | YISPSGGHTIYADSVKG | VARGITARSRTSYFDD |
| M205-B04 | 71.1 | | RTSQFVNSNYLA | GASSRAT | QQSSRTPWT | NYDMI | SISSSGGTTKYADSVKG | VARGIAARSRTSYFDY |
| M203-A03 | 69.1 | | RTSQFVNSNYLA | GASSRAT | QQSSRTPWT | VYMMI | SISPSGGQTTYADSVKG | VARGIAARSRTSYFDY |
| M209-E03 | 68.8 | | RTSQFVNSNYLA | GASSRAT | QQSSRTPWT | HYLMT | YISPSGGHTIYADSVKG | qARGIAARSRTSYFDY |
| M207-A01 | 67.2 | | RTSQFVNSNYLA | GASSRAT | QQSSRTPWT | HYLMT | YISPSGGHTIYADSVKG | VARGISARSRTSCFDY |
| M206-C03 | 65.5 | | RTSQFVNSNYLA | GASSRAT | QQSSRTPWT | qYMMV | SIYSSGGNTPYADSVKG | VARGIAARSRTSYFDY |
| M207-505 | 61.4 | | RTSQFVNSNYLA | GASSRAT | QQSSRTPWT | HYLMT | YISPSGGHTIYADSVKG | VGRGIAARSRTSYFDK |
| M205-A12 | 58.8 | | RTSQFVNSNYLA | GASSRAT | QQSSRTPWT | QYDMI | YISSSGGFTRYADSVKG | VARGIAARSRTSYFDY |
| M205-F03 | 58.6 | | RTSQFVNSNYLA | GASSRAT | QQSSRTPWT | SqQMV | YISPSGGNTYYADSVKG | VARGIAARSRTSYFDY |
| M203-A01 | 51.4 | | RTSQFVNSNYLA | GASSRAT | QQSSRTPWT | NYLMA | WIVPSGGYTEYADSVKG | VARGIAARSRTSYFDY |
| M209-B01 | 47.0 | | RTSQFVNSNYLA | GASSRAT | QQSSRTPWT | HYLMT | YISPSGGHTIYADSVKG | VARGIVARSRTSNFDq |
| M208-D12 | 43.7 | | RTSQFVNSNYLA | GASSRAT | QQSSRTPWT | HYLMT | YISPSGGHTIYADSVKG | LARGIAARSRTSYqDI |
| M206-H04 | 19.0 | | RTSQFVNSNYLA | GASSRAT | QQSSRTPWT | SYMMV | SISPSGGYTIqADSVKG | VARGIAARSRTSYFDY |

Amino Acid Sequences of Light Chain (LC) and Heavy Chain (HC) Variable Domain of pKal Antibodies Obtained from CDR1/2 and CDR3 Spiking Affinity Maturation Libraries Based on X63-G06.

```
M203-A01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M203-A01 HC
EVQLLESGGG LVQPGGSLRL SCAASGFTFS NYLMAWVRQA PGKGLEWVSW IVPSGGYTEY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M203-A03 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M203-A03 HC
EVQLLESGGG LVQPGGSLRL SCAASGFTFS VYMMIWVRQA PGKGLEWVSS ISPSGGQTTY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M204-A02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M204-A02 HC
EVQLLESGGG LVQPGGSLRL SCAASGFTFS DYMMTWVRQA PGKGLqWVSY ISPSGGLTSY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M204-E12 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M204-E12 HC
EVQLLESGGG LVQPGGSLRL SCAASGFTFS TYMMqWVRQA PGKGLEWVSY IGPSGGKTDY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-A02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M205-A02 HC
EVQLLESGGG LVQPGGSLRL SCAASGFTFS TYLMAWVRQA PGKGLEWVSG VSSGGRTLY     60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-A12 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M205-A12 HC
EVQLLESGGG LVQPGGSLRL SCAASGFTFS QYDMIWVRQA PGKGLEWVSY ISSSGGFTRY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-B04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109
```

```
M205-B04 HC
EVQLLESGGG LVQPGGSLRL SCAASGFTFS NYDMIWVRQA PGKGLEWVSS ISSSGGTTKY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-C11 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-C11 HC
EVQLLESGGG LVQPGGSLRL SCAASGFTFS QYMMMWVRQA PGKGLEWVSR ISPSGGSTLY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-D04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-D04 HC
EVQLLESGGG LVQPGGSLRL SCAASGFTFS TYKMqWVRQA PGKGLEWVSS ISPSGGPTNY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-E11 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-E11 HC
EVQLLESGGG LVQPGGSLRL SCAASGFTFS NYTMGWVRQA PGKGLEWVSS ISPSGGKTDY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-F03 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-F03 HC
EVQLLESGGG LVQPGGSLRL SCAASGFTFS SqQMVWVRQA PGKGLEWVSY ISPSGGNTYY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-H01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-H01 HC
EVQLLESGGG LVQPGGSLRL SCAASGFTFS NYTMQWVRQA PGKGLqWVSY ISPSGGYTGY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M205-H08 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M205-H08 HC
EVQLLESGGG LVQPGGSLRL SCAASGFTFS DYMMMWVRQA PGKGLEWVSS IVPSGGHTqY    60

ADSVKGRFTI SRDNSKNTLY LQMNSLRAED TAVYYCARVA RGIAARSRTS YFDYWGQGTL   120

VTVSSASTKG PSVFPLAPSS KS                                           142
```

```
M206-A06 LC
QDIQMTQSPG TLSLSPGERA TLSCRTSQFV NSNYLAWYQQ TPGQAPRLLI YGASSRATGI      60

PDRFSGTGYG TDFTLTISRL EPEDYGTYYC QQSSRTPWTF GQGTRVEIK                109

M206-A06 HC
EVQLLESGGG LVQPGGSLRL SCAASGFTFS NYMMGWVRQA PGKGLqWVSS ISPSGGLTKY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-B10 LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109

M206-B10 HC
EVQLLESGGG LVQPGGSLRL SCAASGFTFS qYLMAWVRQA PGKGLEWVSS IYPSGGWTKY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-C03                                                              LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109

M206-C03                                                              HC
EVQLLESGGG LVQPGGSLRL SCAASGFTFS qYMMVWVRQA PGKGLEWVSS IYSSGGNTPY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-E02 LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109

M206-E02 HC
EVQLLESGGG LVQPGGSLRL SCAASGFTFS EYMMMWVRQA PGKGLEWVSV ISPSGGQTHY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-F01 LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109

M206-F01 HC
EVQLLESGGG LVQPGGSLRL SCAASGFTFS GYMMVWVRQA PGKGLEWVSR ISPSGGPTIY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-F09 LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109

M206-F09 HC
EVQLLESGGG LVQPGGSLRL SCAASGFTFS VYMMSWVRQA PGKGLEWVSS IVPSGGSTTY     60

ADSVKGRFTI SRDNSKNTLY LQMNSLRAED TAVYYCARVA RGIAARSRTS YFDYWGQGTL    120

VTVSSASTKG PSVFPLAPSS KS                                             142

M206-H01 LC
QDIQMTQSPG TLSLSPGERA TLSCRTSQFV NSNYLAWYQQ TPGQAPRLLI YGASSRATGI     60

PDRFSGTGYG TDFTLTISRL EPEDYGTYYC QQSSRTPWTF GQGTRVEIK                109
```

```
M206-H01 HC
EVQLLESGGG LVQPGGSLRL SCAASGFTFS EYMMVWVRQA PGKGLEWVSR ISPSGGTTEY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M206-H04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M206-H04 HC
EVQLLESGGG LVQPGGSLRL SCAASGFTFS SYMMVWVRQA PGKGLEWVSS ISPSGGYTIq    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M206-H05 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M206-H05 HC
EVQLLESGGG LVQPGGSLRL SCAASGFTFS GYKMqWVRQA PGKGLEWVSS ISPSGGITMY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M206-H08 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M206-H08 HC
EVQLLESGGG LVQPGGSLRL SCAASGFTFS DYMMAWVRQA PGKGLEWVSS IVPSGGHTHY    60

ADSVKGRFTI SRDNSKNTLY LQMNSLRAED TAVYYCARVA RGIAARSRTS YFDYWGQGTL   120

VTVSSASTKG PSVFPLAPSS KS                                           142

M207-A01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M207-A01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGISARSRTS CFDYWGQGTL   120

VTVSSASTKG PSVFPLAPSS KS                                           142

M207-A02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M207-A02 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TALYYCARVA RGIAARSRTI NLDYWGQGTL   120

VTVSSASTKG PSVFPLAPSS KS                                           142

M207-A04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M207-A04 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTR SFDYWGQGTL   120

VTVSSASTKG PSVFPLAPSS KS                                           142
```

```
M207-C05 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

R0121-D02 = M0207-005 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVG RGIAARSRTS YFDKWGQGTL   120

VTVSSASTKG PSVFPLAPSS KS                                           142

M208-A10 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M208-A10 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS qFDHWGQGTL   120

VTVSSASTKG PSVFPLAPSS KS                                           142

M208-B01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M208-B01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS FFDqWGQGTL   120

VTVSSASTKG PSVFPLAPSS KS                                           142

M208-C06 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M208-C06 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS FIDYWGQGTL   120

VTVSSASTKG PSVFPLAPSS KS                                           142

M208-D12 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M208-D12 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARLA RGIAARSRTS YqDIWGQGTL   120

VTVSSASTKG PSVFPLAPSS KS                                           142

M208-E10 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M208-E10 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA QGISARSRTS YFDYWGQGTL   120

VTVSSASTKG PSVFPLAPSS KS                                           142

M208-F04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109
```

```
M208-F04 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS FFDYWGQGTL   120

VTVSSASTKG PSVFPLAPSS KS                                            142

M208-F10 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M208-F10 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YFDqWGQGTL   120

VTVSSASTKG PSVFPLAPSS KS                                            142

M208-G02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M208-G02 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIADRSRTS YSDYWGQGTL   120

VTVSSASTKG PSVFPLAPSS KS                                            142

M208-G03 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M208-G03 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YLDYWGQGTL   120

VTVSSASTKG PSVFPLAPSS KS                                            142

M208-H02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M208-H02 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIASRSRTR YCDYWGQGTL   120

VTVSSASTKG PSVFPLAPSS KS                                            142

M209-B01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M209-B01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIVARSRTS NFDqWGQGTL   120

VTVSSASTKG PSVFPLAPSS KS                                            142

M209-B09 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M209-B09 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA QGIVARSRTS YLHqWGQGTL   120

VTVSSASTKG PSVFPLAPSS KS                                            142
```

```
M209-B11 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-B11 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCARVA RGIAARSRTR YIDqWGQGTL       120
VTVSSASTKG PSVFPLAPSS KS                                                142

M209-C02 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-C02 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCARVA RGIAYRRRTS YFDYWGQGTL       120
VTVSSASTKG PSVFPLAPSS KS                                                142

M209-C11 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-C11 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCAMVG QGIRGRSRTS YFAqWGQGTL       120
VTVSSASTKG PSVFPLAPSS KS                                                142

M209-C12 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-C12 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCARVG RGIAARSRTS qLDYWGQGTL       120
VTVSSASTKG PSVFPLAPSS KS                                                142

M0209-D02 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-D02 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCARVA RGITARSRTS YFDDWGQGTL       120
VTVSSASTKG PSVFPLAPSS KS                                                142

M209-D03 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109

M209-D03 HC
EVQLLESGGG LVQPGGSLRL SCAASGFTFS HYLMTWVRQA PGKGLEWVSY ISPSGGHTIY        60
ADSVKGRFTI SRDNSKNTLY LQMNSLRAED TAVYYCARVG RGIAARSRTS FFDqWGQGTL       120
VTVSSASTKG PSVFPLAPSS KS                                                142

M209-D12 LC
QDIQMTQSPG TLSLSPGERA TLSCRTSQFV NSNYLAWYQQ TPGQAPRLLI YGASSRATGI        60
PDRFSGTGYG TDFTLTISRL EPEDYGTYYC QQSSRTPWTF GQGTRVEIK                   109
```

```
M209-D12 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCATVA RGIAARSRTS YFDqWGQGTL   120

VTVSSASTKG PSVFPLAPSS KS                                           142

M209-E02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-E02 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTI LLDqWGQGTL   120

VTVSSASTKG PSVFPLAPSS KS                                           142

M209-E03 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-E03 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARqA RGIAARSRTS YFDYWGQGTL   120

VTVSSASTKG PSVFPLAPSS KS                                           142

M209-F04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-F04 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YLDqWSQGTL   120

VTVSSASTKG PSVFPLAPSS KS                                           142

M209-G01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-G01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA qGISGRSRLS YVDYWGQGTL   120

VTVSSASTKG PSVFPLAPSS KS                                           142

M209-G07 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-G07 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YFDTWGQGTL   120

VTVSSASTKG PSVFPLAPSS KS                                           142

M209-H03 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK              109

M209-H03 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA QGIAARSRTT qFDY-       120
WGQGTL

VTVSSASTKG PSVFPLAPSS KS                                           142
```

```
M209-H07 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M209-H07 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARqRTS YYDYWGQGTL   120

VTVSSASTKG PSVFPLAPSS KS                                           142

M209-H09 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M209-H09 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTV YFDHWGQGTL   120

VTVSSASTKG PSVFPLAPSS KS                                           142

M210-A06 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-A06 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS qFDYWGQGTL   120

VTVSSASTKG PSVFPLAPSS KS                                           142

M210-B02 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-B02 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCASVA RGIAARSRTS YFNqWGQGTL   120

VTVSSASTKG PSVFPLAPSS KS                                           142

M210-C12 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-C12 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA QGIAARSRTS SVDqWGQGTL   120

VTVSSASTKG PSVFPLAPSS KS                                           142

M210-G04 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-G04 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA TGIVARSRTR YFDqWGQGTL   120

VTVSSASTKG PSVFPLAPSS KS                                           142

M210-G10 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109
```

-continued

```
M210-G10 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTS YLDFWGQGTL   120

VTVSSASTKG PSVFPLAPSS KS                                           142

M210-H01 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-H01 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRNS qQDYWGQGTL   120

VTVSSASTKG PSVFPLAPSS KS                                           142

M210-H06 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-H06 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTR YFDYWGQGTL   120

VTVSSASTKG PSVFPLAPSS KS                                           142

M210-H07 LC
QDIQMTQSPG TLSLSPGERA TLSCRTSQFV NSNYLAWYQQ TPGQAPRLLI YGASSRATGI    60

PDRFSGTGYG TDFTLTISRL EPEDYGTYYC QQSSRTPWTF GQGTRVEIK               109

M210-H07 HC
EVQLLESGGG LVQPGGSLRL SCAASGFTFS HYLMTWVRQA PGKGLEWVSY ISPSGGHTIY    60

ADSVKGRFTI SRDNSKNTLY LQMNSLRAED TAVYYCARVA RGIAARSRTR YFDqWGQGTL   120

VTVSSASTKG PSVFPLAPSS KS                                           142
```

Example 6

In Vivo Testing of M162-A04 (IgG) and X101-A01

Figure 2:
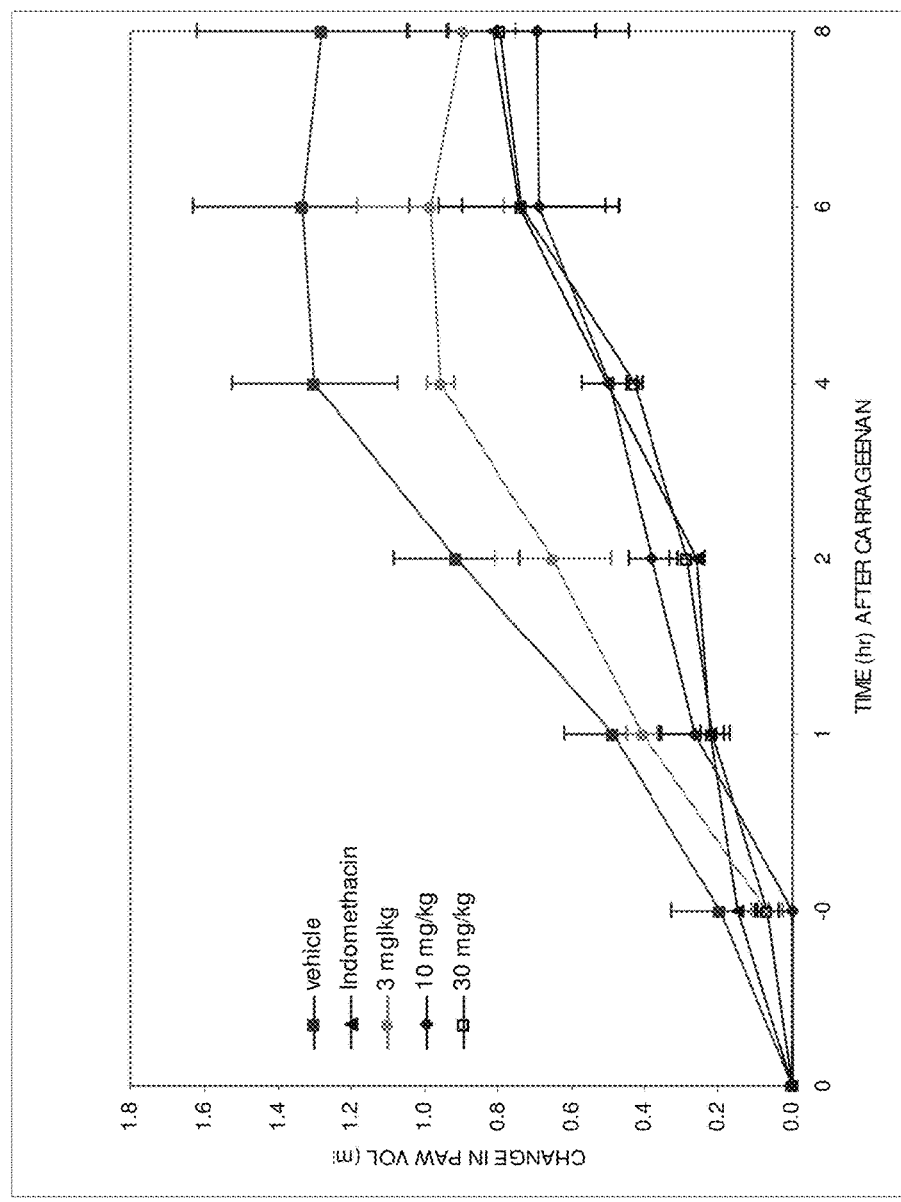
FIG. 2 depicts the effect of M162-A04 on carrageenan-induced rat paw edema. Paw swelling was measured by water displacement.
Figure 3:
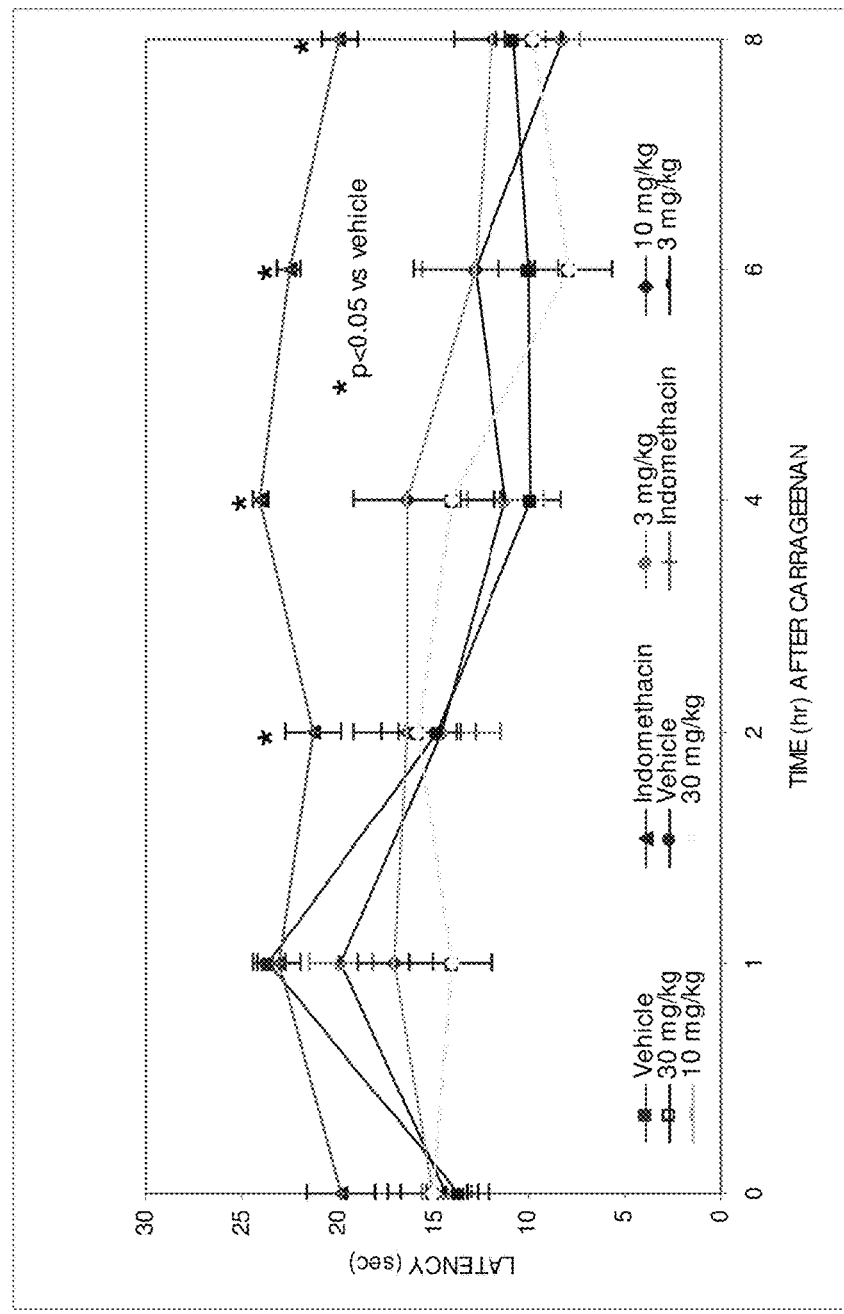
FIG. 3 depicts the effect of M162-A04 on carrageenan-induced thermal hyperalgesia. Pain latency was measured by the Hargreaves method after carrageenan injection.

Bradykinin and other bioactive kinins have been previously implicated in carrageenan-induced edema and inflammatory pain (Sharma J. N. et al. (1998) Inflammopharmacology 6, 9-17; Asano M. et al. (1997) Br J Pharmacol 122, 1436-1440; De Campos R. O. et al. (1996) Eur J Pharmacol 316, 277-286). Plasma kallikrein and tissue kallikrein 1 are the two primary kininogenases in mammals (Schmaier A. H. (2008) Int Immunopharmacol 8, 161-165). M162-A04 (M162-A4) (IgG), a specific plasma kallikrein inhibitor, was tested to determine whether it would be effective in carrageenan induced edema. The study design is outlined in Table 10. The route of administration (ROA) for the vehicle (PBS), the antibody, and the positive control (indomethacin) was intra-peritoneal (IP) and was given 30 minutes prior to carrageenan injection (0.1 mL of a 2% carrageenan solution). It is evident from FIG. 2 that antibody doses at 10 mg/kg and above were equally effective in reducing carrageenan-induced edema as the positive control (indomethacin). However, the antibody was not effective in reducing carrageenan-induced thermal hyperalgesia (FIG. 3). The reason for the dissociation between effectiveness in edema and hyperalgesia are not obvious but may be due to differences in the bioactivity of different kinin metabolites. Lys-desArg9-bradykinin is the most potent agonist of the B1 receptor, which is believed to be primarily involved in pain hypersensitivity (Leeb-Lundberg L. M et al. (2005) Pharmacol Rev 57, 27-77). This kinin metabolite is generated by tissue kallikrein 1, not plasma kallikrein (Schmaier A. H. (2008) Int Immunopharmacol 8,161-165). This difference in kinin generation and resulting bradykinin receptor activation may account for the unexpected decoupling of edema and hyperalgesia in this model.

Figure 14:
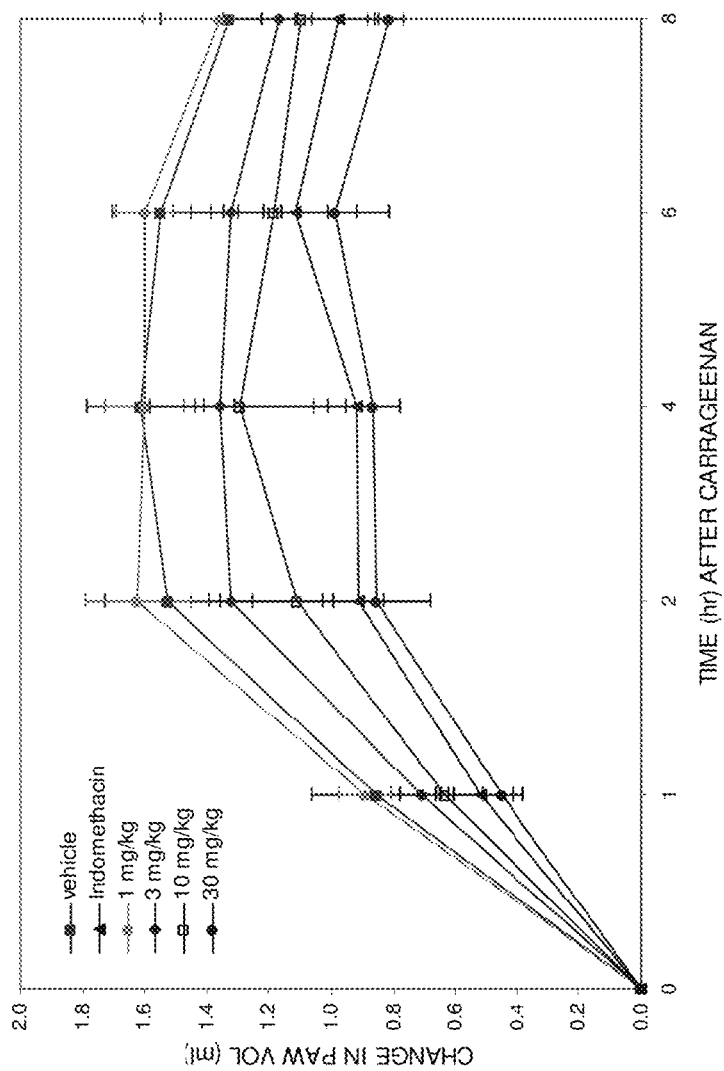
FIG. 14 depicts a graph showing dose dependent inhibition of edema by X101-A01 in carrageenan-induced paw edema (CPE) in rats.
Figure 15:
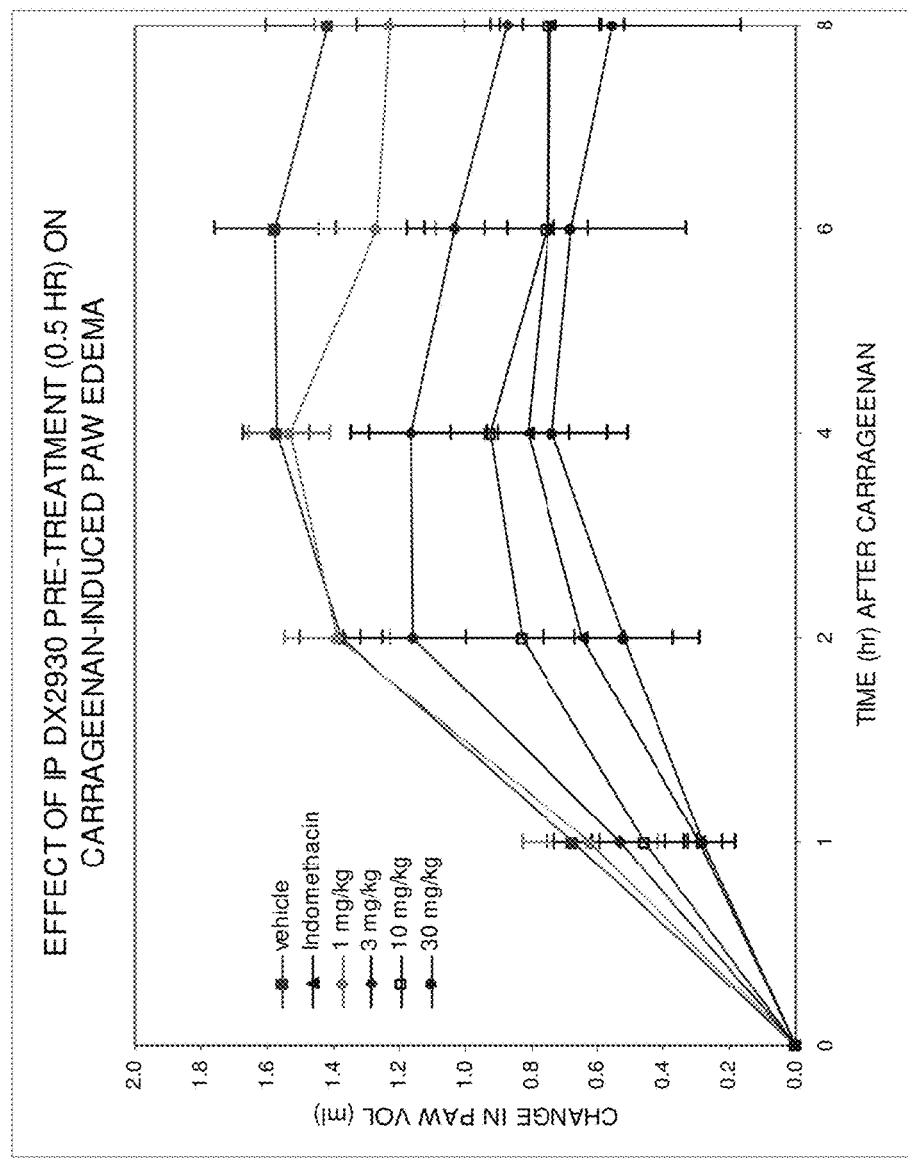
FIG. 15 depicts a graph showing dose dependent inhibition of edema by intraperitoneal administration DX-2930 in carrageenan-induced paw edema in the rat.
Figure 16:
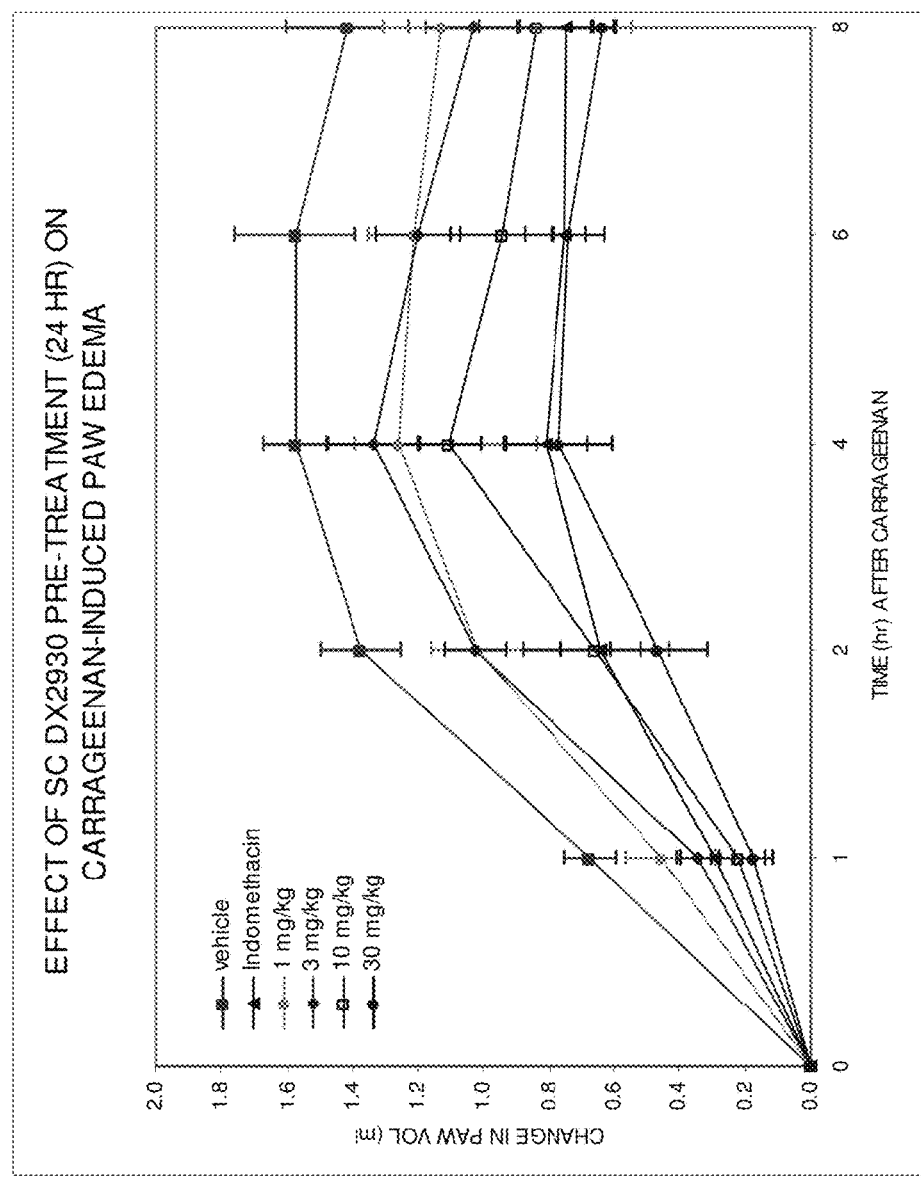
FIG. 16 depicts a graph showing dose dependent inhibition of edema by subcutaneous administration DX-2930 in carrageenan-induced paw edema in the rat.

Another pKal antibody inhibitor X101-A01 was also tested in the CPE model using the study design shown in Table 10B. The data obtained in FIG. 14 shows that X101-A01 inhibited edema in a dose-dependent manner to an extent that is comparable to that of the positive control (indomethacin).

TABLE 10A

Carrageenan-Induced Paw Edema Study Design to test M162-A04

| Group # | Number of Rats | Treatment | Dose (mg/kg) | ROA | Timing relative to carrageenan | Dose Volume (mL/kg) |
|---|---|---|---|---|---|---|
| 1 | 6 | Vehicle | N/A | IP | T −30 minutes | 20 |
| 2 | 6 | 559A-M162-A4 | 3 | IP | T −30 minutes | 20 |
| 3 | 6 | 559A-M162-A4 | 10 | IP | T −30 minutes | 20 |
| 4 | 6 | 559A-M162-A4 | 30 | IP | T −30 minutes | 20 |
| 5 | 6 | Indomethacin | 5 | IP | T −30 minutes | 20 |

TABLE 10B

Carrageenan-Induced Paw Edema Study Design to Test X101-A01

| Group | Treatment | n | Dose (mg/Kg) | ROA | Timing* | Vol (mL/Kg) |
|---|---|---|---|---|---|---|
| 1 | Vehicle | 10 | N/A | IP | −30 min | 20 |
| 2 | X101-A01 | 10 | 1 | IP | −30 min | 20 |
| 3 | X101-A01 | 10 | 3 | IP | −30 min | 20 |
| 4 | X101-A01 | 10 | 10 | IP | −30 min | 20 |
| 5 | X101-A01 | 10 | 30 | IP | −30 min | 20 |
| 6 | Indomethacin | 10 | 5 | IP | −30 min | 20 |

Example 7

Evaluation of Selected Antibody Inhibitors of Plasma Kallikrein

Evaluation of selected optimized antibodies (X81-B01 and X67-D03) is shown in Table 11. Neither antibody has any putative deamidation, isomerization, or oxidation sites.

TABLE 11

| Criteria | X81-B01 (IgG) | X67-D03 (IgG) |
|---|---|---|
| < nM Ki, app against human pKal | 0.2 nM | 0.1 nM |
| < nM Ki, app against rodent pKal | mouse - 11 pM<br>rat - 0.14 nM | mouse - 0.7 nM<br>rat - 0.34 nM |
| prekallikrein binding | no | no |
| Specific inhibitor with respect to fXIa, plasmin, and trypsin | yes | yes |
| Inhibits bradykinin generation | yes | yes |
| Inhibits pKal in presence of prekallikrein | yes | yes |
| Competition for binding with aprotinin | yes | yes |
| Stability in human serum | yes | nd* |

*not done; a parental form of this antibody was shown to be stable in serum

Example 8

Epitope Mapping

The region of pKal bound by selected anti-pKal antibodies was investigated using several methods. First, competition assays were used to determine whether the antibodies competed for binding to pKal with known active site-directed inhibitors. Second, antibodies were grouped according to whether they were inhibitors or just binders to pKal. Third, epitopes were investigated using synthetic peptides and peptidic structures based on the sequence and 3-dimensional structure of pKal. These peptidic structures are called "CLIPS" (Chemically Linked Peptides on Scaffolds) and the testing was performed by a fee for service company called Pepscan.

Fourth, antibodies were tested for their ability to inhibit pKal from other species, besides human, where the amino acid sequence of pKal has been determined in order to identify amino acids that may account for the differences in inhibition.

Competition Assays

Using a BIACORE® SPR assay antibodies of interest were tested for competition with a known active site inhibitor of pKal. EPI-KAL2 is potent ($K_{i,app}$=0.1 nM) active site inhibitor of pKal and a Kunitz domain inhibitor based on the first domain of tissue factor pathway inhibitor (Markland (1996) *Iterative optimization of high-affinity protease inhibitors using phage display. 2. Plasma kallikrein and thrombin.* Biochemistry. 35(24):8058-67). Kunitz domains are known active site inhibitors of serine proteases, such as pKal.

The sequence of EPI-KAL2 is:

EAMHSFCAFKA*DDGP*CR*AAHPRW*FFNIFTRQCEEF*SY*GGCGGN*Q*NRFES
LEECKKMCTRD
(amino acids in italics are those that differ from TFPI)

Figure 8A:
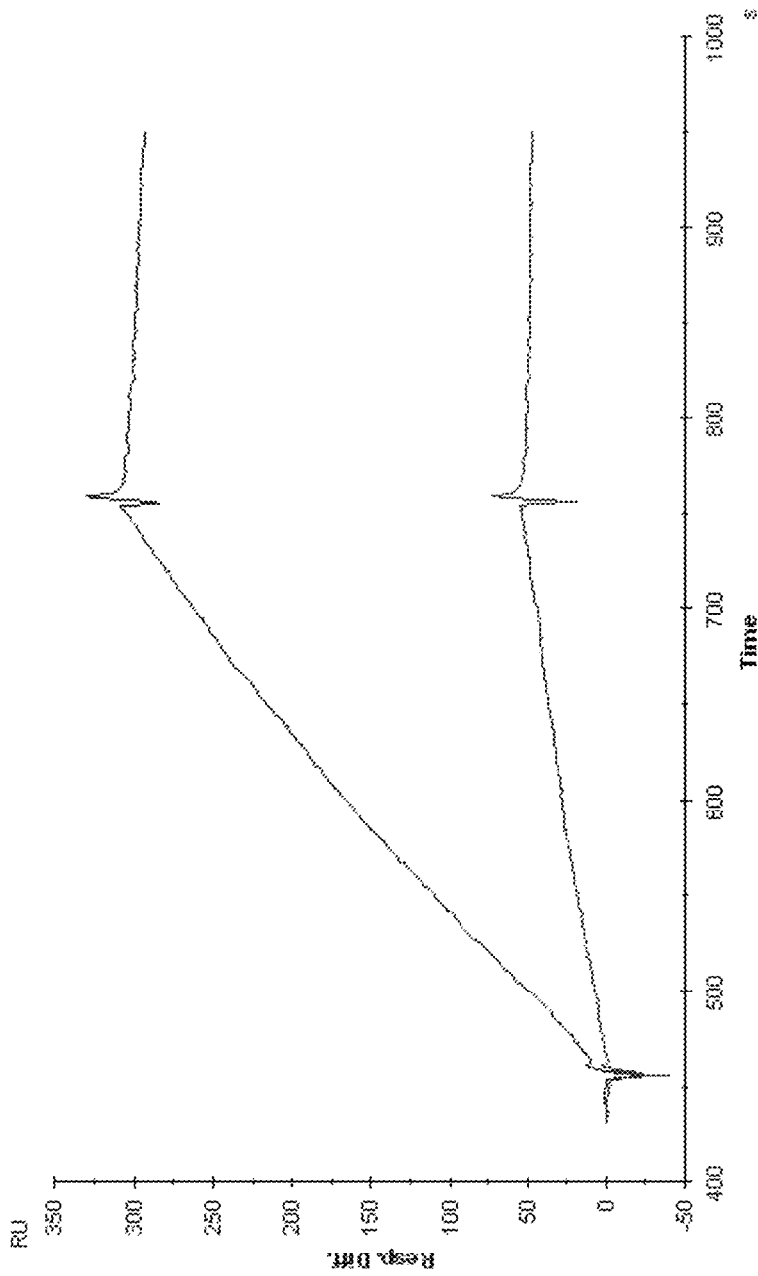
FIG. 8A depicts the EPI-KAL2 competition for X81-B01 binding pKal. X81-B01 (IgG) was captured on an anti-human Fc fragment specific surface of a CM5 BIACORE® chip. pKal (100 nM) was flowed over the surface in the presence (lower sensorgram in the figure) or absence of 1 µM EPI-KAL2 (upper sensorgram in the figure).
Figure 8B:
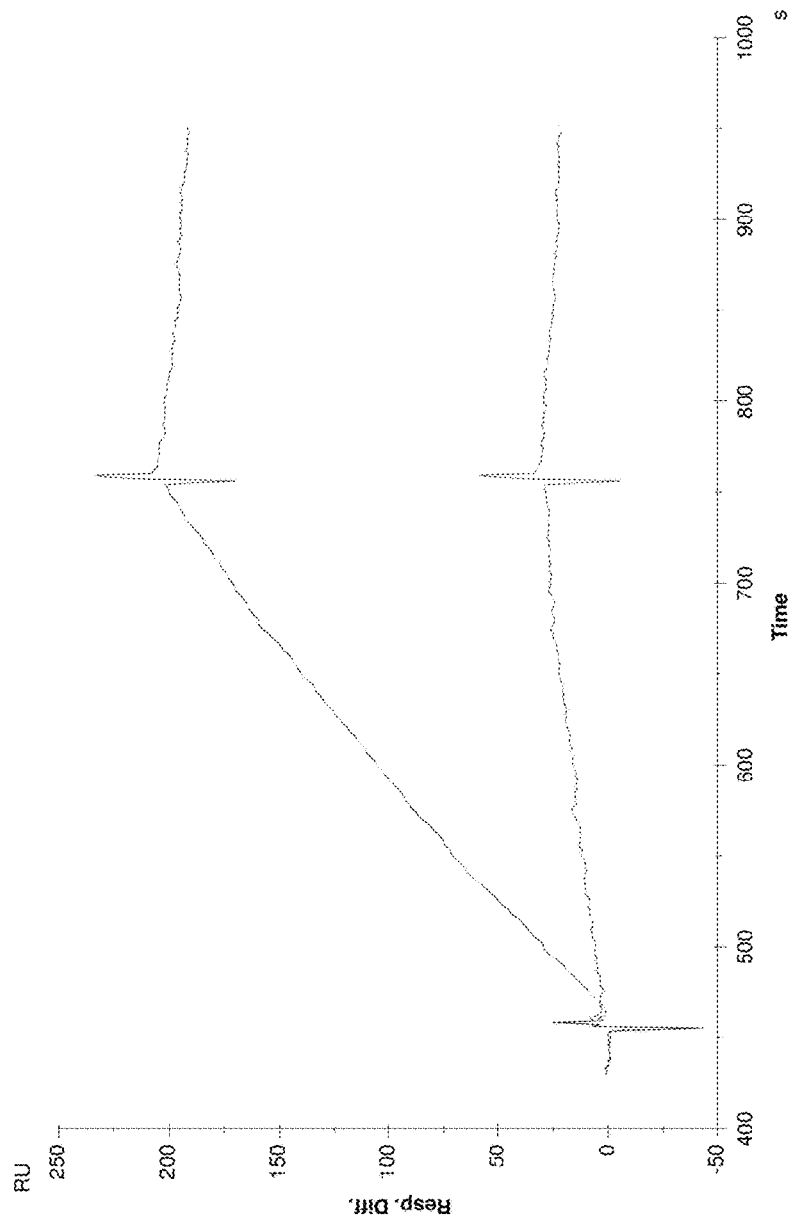
FIG. 8B depicts the EPI-KAL2 competition for X67-D03 binding pKal. X67-D03 (IgG) was captured on an anti-human Fc fragment specific surface of a CM5 Biacore chip. pKal (100 nM) was flowed over the surface in the presence (lower sensorgram in the figure) or absence of 1 µM EPI-KAL2 (upper sensorgram in the figure).

As shown in FIGS. 8A-8B, the antibodies X81-B01 and X67-D03 were competed for binding to pKal in the presence or EPI-KAL2. This result indicates that these antibodies either bind in vicinity of the active site or allosteric changes in the conformation of the pKal-EPI-KAL2 complex prevent antibody binding.

Antibody Binders vs Inhibitors

As shown in Tables 1 and 2, all the unique antibodies discovered by phage display were characterized as being either pKal inhibitors or binders but not inhibitors. Antibodies that inhibit the activity of pKal either bind near the active site and preclude substrate interactions (competitive inhibitors) or that bind away from the active site and induce allosteric changes in the structure of the active site (non-competitive inhibitors). Antibodies that bind but do not inhibit pKal are unlikely to bind near the active site and may bind the non-catalytic domain (i.e. the apple domain). Table 12 categorizes selected antibodies as being either inhibitors or binders of pKal. Also shown in Table 12 for the listed antibodies, is a demonstration of whether they cross-react with mouse pKal as inhibitors and whether they bind prekallikrein.

TABLE 12

Binding Properties of Selected Anti-pKal Antibodies

| Number | Antibody | Binding Category | human Ki, app (nM) | mouse Ki, app (nM) | CLIPS Peptide(s) Identified |
|---|---|---|---|---|---|
| 1 | M6-A06 | 1) Binder only | no | no | C4 |
| 2 | M6-D09 | 2) inhibitor, prekallikrein binder, inhibits mouse and human pKal | 5.9 | 3.9 | C1, C5 |
| 3 | M8-C04 | 1) Binder only | no | no | |
| 4 | M8-G09 | 1) Binder only | no | no | C1, C4, C6, C7 |
| 5 | M29-D09 | 3) inhibitor, does not bind prekallikrein, does not inhibit mouse pKal | 0.7 | no | C1, C4, C7 |
| 6 | M35-G04 | 2) inhibitor, prekallikrein binder, inhibits mouse and human pKal | 2.9 | 8 | C1, C4 |
| 7 | M145-D11 | 3) inhibitor, does not bind prekallikrein, weak inhibitor of mouse pKal | 0.79 | 800 | C1, C4 |
| 8 | M160-G12 | 4) inhibitor of both mouse and human pKal, does not bind prekallikrein | 5 | 0.2 | C2 |
| 9 | X55-F01 | 4) inhibitor of both mouse and human pKal, does not bind prekallikrein | 0.4 | 2 | C2, C3 |
| 10 | X73-H09 | 4) inhibitor, does not bind prekallikrein, weak inhibitor of human and mouse pKal | 20 | 70 | C6 |

TABLE 12-continued

Binding Properties of Selected Anti-pKal Antibodies

| Number | Antibody | Binding Category | human Ki, app (nM) | mouse Ki, app (nM) | CLIPS Peptide(s) Identified |
|---|---|---|---|---|---|
| 11 | X81-B01 | 4) inhibitor of both mouse and human pKal, does not bind prekallikrein | 0.1 | 0.011 | C2, C3, C5, C6 |
| 12 | A2 | 5) Negative control, does not bind pKal, binds streptavidin | No binding | No binding | No binding |

C1-C7: peptides in pKal identified by CLIPS epitope mapping (see FIGS. 9 and 10A-10C). C1 corresponds to positions 55-67 of the catalytic domain, C2 to positions 81-94, C3 to positions 101-108, C4 to positions 137-151, C5 to positions 162-178, C6 to positions 186-197, and C7 to positions 214-217.

Epitope Mapping Using CLIPS

The 11 anti-pKal antibodies listed in Table 12, plus one negative control (A2) were tested for binding to 5000 different synthetic CLIPS (Chemically Linked Peptides on Scaffolds) by Pepscan as described below in the CLIP METHODS sections. This analysis led to the identification of peptide regions in pKal that are likely to be a part of the antibody epitope for each of the tested antibodies (FIG. 9).

Clips Methods

The linear and CLIPS peptides were synthesized based on the amino acid sequence of the target protein using standard Fmoc-chemistry and deprotected using trifluoric acid with scavengers. The constrained peptides were synthesized on chemical scaffolds in order to reconstruct conformational epitopes, using Chemically Linked Peptides on Scaffolds (CLIPS) technology (Timmerman et al. (2007). For example, the single looped peptides were synthesized containing a dicysteine, which was cyclized by treating with alpha, alpha'-dibromoxylene and the size of the loop was varied by introducing cysteine residues at variable spacing. If other cysteines besides the newly introduced cysteines were present, they were replaced by alanine. The side-chains of the multiple cysteines in the peptides were coupled to CLIPS templates by reacting onto credit-card format polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1(v/v)). The cards were gently shaken in the solution for 30 to 60 minutes while completely covered in solution. Finally, the cards were washed extensively with excess of $H_2O$ and sonicated in distrupt-buffer containing 1 percent SDS/0.1 percent beta-mercaptoethanol in PBS (pH 7.2) at 70° C. for 30 minutes, followed by sonication in $H_2O$ for another 45 minutes. The binding of antibody to each peptide were tested in a PEPSCAN-based ELISA. The 455-well credit card format polypropylene cards containing the covalently linked peptides were incubated with primary antibody solution for example consisting of 1 micrograms/mL diluted in blocking solution called SQ (4% horse serum, 5% ovalbumin (w/v) in PBS/1% Tween or diluted in PBS e.g., 20% SQ) overnight. After washing, the peptides were incubated with a 1/1000 dilution of rabbit anti-human antibody peroxidase or goat-anti-human FAB peroxidase for one hour at 25° C. After washing, the peroxidase substrate 2,2'-azino-di-3-ethylbenzthiazoline sulfonate (ABTS) and 2 microliters of 3 percent $H_2O_2$ were added. After one hour, the color development was measured. The color development was quantified with a charge coupled device (CCD)—camera and an image processing system (as firstly described in Slootstra et al., 1996).

Data Calculation

Raw Data: Optical density (Arbitrary OD units)

The raw data are optical values obtained by a CCD-camera. The values mostly range from 0 to 3000, a log scale similar to 1 to 3 of a standard 96-well plate elisa-reader. First the CCD-camera makes a picture of the card before peroxidase coloring and then again a picture after the peroxidase coloring. These two pictures are subtracted from each other which results in the data which is called raw-data. This is copied into the Peplab™ database. Then the values are copied to excel and this file is labeled as raw-data file. One follow-up manipulation is allowed. Sometimes a well contains an air-bubble resulting in a false-positive value, the cards are manually inspected and any values caused by an air-bubble are scored as 0.

Normally assays are not done in replicate (only upon request client request). Replicate tests are usually very similar. In addition, the dataset of thousands of peptides contains many peptides that are similar, thus results are never based on recognition of one peptide but on families of similar peptides. If one or a few peptides do not bind, or exhibit lower binding, in a replicate experiment, a different epitope mapping is not normally attributed.

Timmerman et al. (2007). Functional reconstruction and synthetic mimicry of a conformational epitope using CLIPS™ technology. *J. Mol. Recognit.* 20:283-99

Slootstra et al. (1996). Structural aspects of antibody-antigen interaction revealed through small random peptide libraries, *Molecular Diversity*, 1, 87-96.

Example 9

Analysis of pKal Sequences from Different Species

Figure 10A:
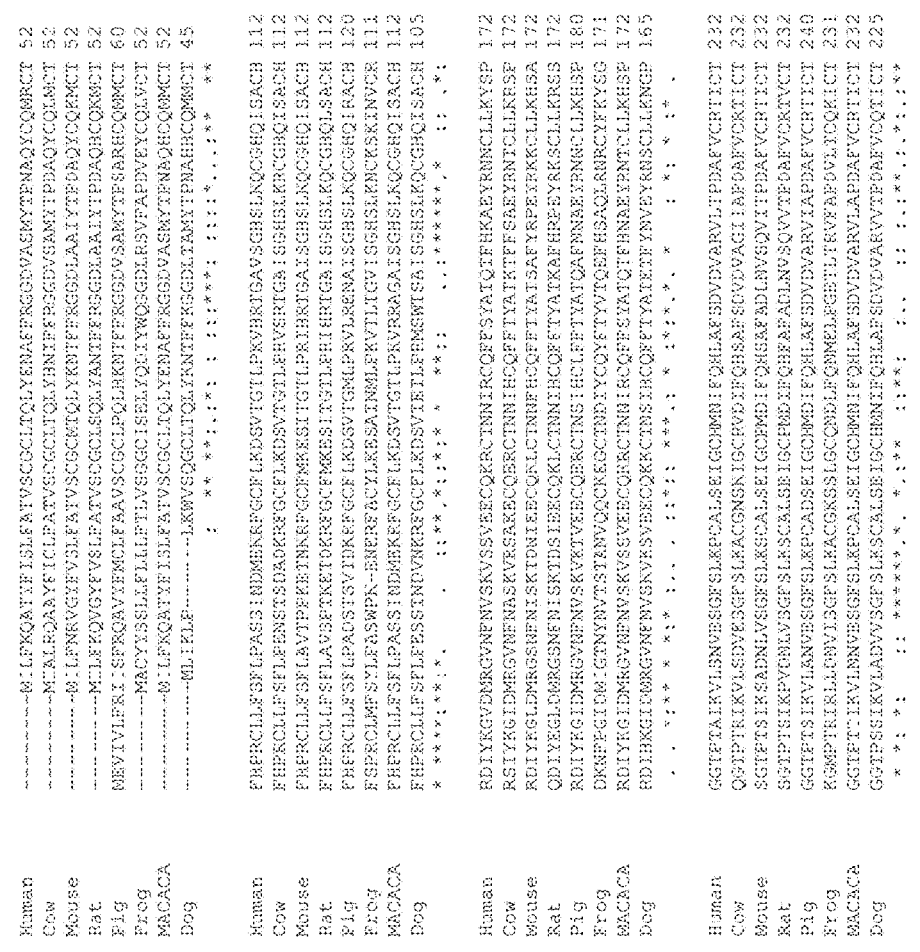
Figure 10B:
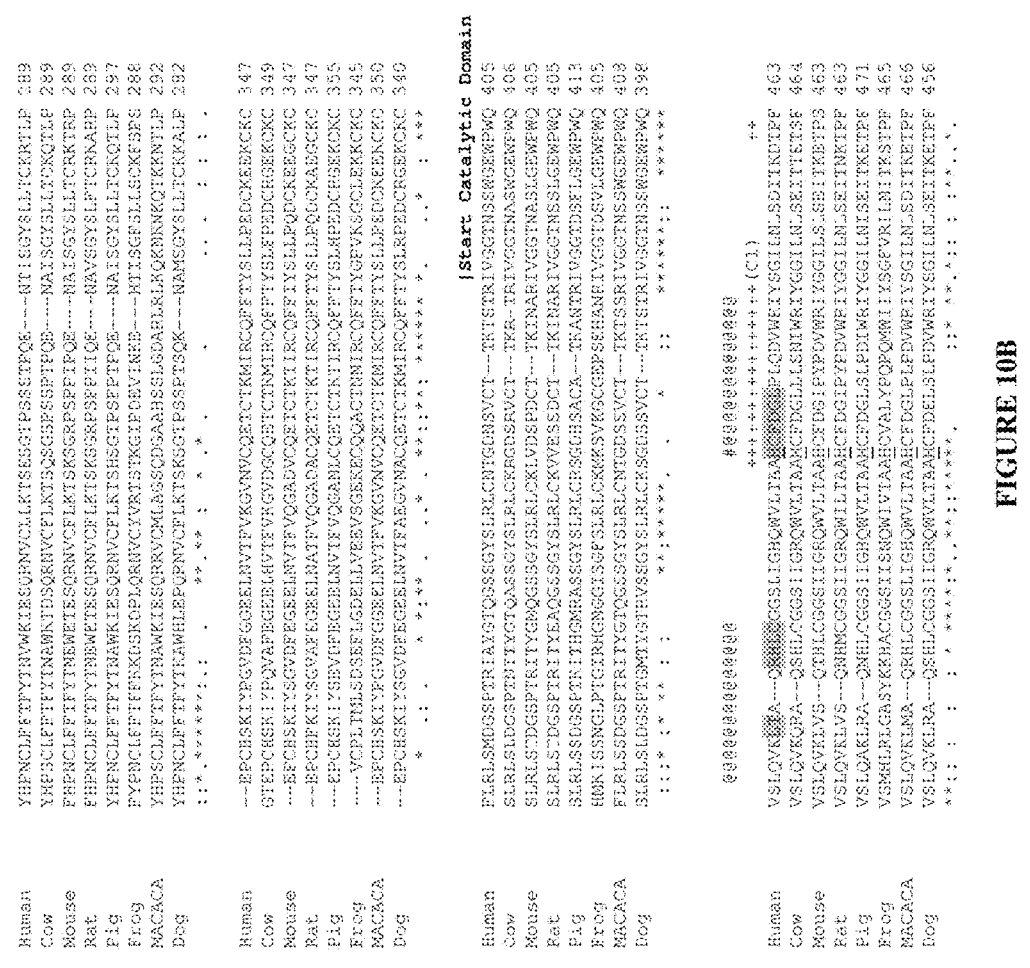

All available sequence of pKal were obtained from public databases and aligned using ClustalW and regions were highlighted based on solvent accessibility, contact with an active site Kunitz inhibitor, and those peptides identified by CLIPS analysis (FIGS. 10A-10C). Citrated plasma from each of these species was obtained and activated using a commercially available prekallikrein activator (from Enzyme Research Laboratories) according to the instructions of the manufacturer. Kallikrein activity was then measured in each of the samples in the presence or absence of X81-B01.

It was found that X81-B01 inhibited pKal from all the species except for pig pKal. Since the CLIPS analysis identified four peptides of pKal that X81-B01 binds to—C2 (positions 81-94), C3 (positions 101-108), C5 (positions 162-178) and C6 (positions 186-197)—differences in the pig pKal sequence that correspond to these peptides were examined to identify potential amino acids changes that account for the lack of inhibition of pig pKal by X81-B01. Peptides C2 and C3 are close in the sequence and are both highly similar in sequence among the different species. However, there is a difference at position 479. All the species except pig, frog, and dog have a serine at position 479. The frog and dog pKal sequence has an alanine and a threonine at position 479, respectively; both of which are considered conservative substitutions for a serine. In contrast, the pig pKal sequence has a leucine at position 479, which is a considerably less conservative substitution for a serine. Peptide C5 in pig pKal is highly similar to the sequences from the other species. However, at position 563, only in the pig pKal is a histidine present (bold in FIG. 10C). This position in all the other species, except frog, is a tyrosine. In the frog pKal, which is inhibited by X81-B01, this position is a threonine. Peptide C6 in pig pKal is again highly similar to the other sequences. However, only in the pig pKal sequence is position 585 a glutamate (in bold in FIG. 10C). In all the other species this position is an aspartate. This analysis may indicate potentially critical residues in pKal that interact with X81-B01.

Example 10

In Vitro and In Vivo Assays to Assess Efficacy of a Plasma Kallikrein Binding Protein Binding to prekallikrein vs. kallikrein: The advantage of an antibody inhibitor of pKal that does not bind prekallikrein over an antibody that binds prekallikrein can be demonstrated experimentally. For example, an in vitro experiment can be designed to compare the potency of a pKal antibody inhibitor that does not bind prekallikrein (e.g. DX-2922 or DX-2930) with one that binds prekallikrein (e.g. M6-D09) using an activated partial thromboplastin time (APTT) plasma clotting time assay. The APTT assay induces clotting in plasma by the addition of a reagent that specifically activates the contact system component of the intrinsic coagulation pathway, of which the activity of pKal is involved. It is well known in the literature that the inhibition of pKal or that a genetic deficiency in pKal leads to prolonged aPPT (see e.g., Morishita, H., et al., Thromb Res, 1994. 73(3-4): p. 193-204; Wynne Jones, D., et al., Br J Haematol, 2004. 127(2): p. 220-3). An in vitro experiment can be performed to measure the effect of spiking citrated human plasma with different concentrations of either M6-D09 or DX-2922 or DX-2930 on observed clotting times induced using commercially available APTT reagents and a coagulation analyzer (Table 13). It is expected that the observed EC50 for APTT prolongation of M6-D09 will be significantly higher than that of DX-2922 and DX-2930 due to the binding of M6-D09 to the high concentration prekallikrein (~500 nM) in the normal plasma sample. Efficacy of the antibody inhibitor of pKal as demonstrated by prolonging APTT supports the potential therapeutic use of the antibody in treating or preventing cardiovascular disease associated with aberrant clot formation, such as may be observed in atherosclerosis, stroke, vasculitis, aneurism, and patients implanted with ventricular assist devices.

TABLE 13

Study Design to Measure Effect of Antibody Inhibitors of pKal on APTT

| Condition | Observed Effect on APPT |
| --- | --- |
| No treatment, just plasma | Normal |
| Prekallikrein depleted plasma control (commercially available) | Maximum prolongation |
| M6-D09 at low concentration | Normal |
| M6-D09 at middle concentration | Normal |
| M6-D09 at high concentration | Prolonged APTT |
| DX-2922 at low concentration | Prolonged APTT |
| DX-2922 at middle concentration | Prolonged APTT |
| DX-2922 at high concentration | Maximum prolongation |

Efficacy in a rat model of edema: An in vivo experiment can also be conducted to demonstrate the increased potency of an antibody inhibitor of pKal that does not bind prekallikrein. The carrageenan-induced paw edema (CPE) model of edema in rats is a common pharmacology model. A group of rats will be treated with escalating doses of M6-D09 and DX-2922 by intraperitoneal (IP) injection prior to injecting carrageenan (e.g. 0.1 mL of a 10% w/v solution) in the paws of the rats (Table 14). It is expected that DX-2922 will be more effective in reducing the observed paw swelling than M6-D09. Efficacy of the antibody supports the therapeutic use of the antibody in various inflammatory diseases that are associated with either swelling (e.g. hereditary angioedema, stroke induced edema, brain edema) or bradykinin mediated inflammation and pain (e.g. rheumatoid arthritis, inflammatory bowel disease).

TABLE 14

Study Design to Observe Effect of Antibody Inhibitors on CPE

| Group | Treatment | Example Dose (mg/Kg) | Effect Expected |
| --- | --- | --- | --- |
| 1 | Vehicle | N/A | Maximum swelling |
| 2 | Indomethacin (positive control) | 5 | Maximum reduction of swelling |
| 3 | M6-D09 | 1 | No effect on swelling |
| 4 | M6-D09 | 3 | No effect on swelling |
| 5 | M6-D09 | 10 | Intermediate reduction of swelling |
| 6 | DX-2922 | 1 | No effect on swelling |
| 7 | DX-2922 | 3 | Intermediate reduction of swelling |
| 8 | DX-2922 | 10 | Maximum reduction of swelling |

An in vivo experiment was conducted to demonstrate the anti-inflammatory potency and efficacy of a plasma kallikrein binding protein, DX-2930 after intraperitoneal and subcutaneous injection in the CPE model of edema in rats.

A group of rats where treated with escalating doses of DX-2930 by intraperitoneal (IP) injection prior to injecting carrageenan (e g 0.1 mL of a 1% w/v solution) in the paws of the rats. Paw swelling was measured by plethysmography according fluid displacement using established procedures. Indomethacin, the positive control for this experiment, was administered IP at 5 mg/Kg 30 minutes prior to carrageenan injection. The dose of DX-2930 was varied from 1, 3, 10, and 30 mg/Kg. Injection of 0.1 ml 1% carrageenan into the right hind paw resulted in a maximum 2-fold increase in paw volume four hours after challenge. Pretreatment with 5 mg/kg indomethacin inhibited this response by ~50% for the duration of the study. Intraperitoneal injection of DX-2930 thirty minutes prior to carrageenan challenge resulted in a dose-dependent inhibition of the carrageenan-induced response such that no amelioratory effect was observed at the 1 mg/kg dose, but that at the 30 mg/kg dose effects similar to indomethacin were measured.

DX-2930 was administered SC to rats 24 hours prior to the injection of a 0.1 mL 1% carrageenan solution into the right hind paw. Paw swelling was measured by plethysmography according fluid displacement using established procedures. Indomethacin, the positive control for this experiment, was administered IP at 5 mg/Kg 30 minutes prior to carrageenan injection. The dose of DX-2930 was varied from 1, 3, 10, and 30 mg/Kg. In contrast, subcutaneous injection of DX-2930 twenty-four hours prior to carrageenan challenge not only dose-dependently inhibited the carrageenan response, this treatment regimen yielded a significant improvement over indomethacin, delayed the development of the carrageenan-induced edema and significantly inhibited the carrageenan response at all doses throughout the time course of the study.

Measuring half-life: The pharmacokinetic properties of DX-2922 and DX-2930 were determined in rats and the pharmacokinetic properties of DX-2930 was determined in cynomolgus monkeys. Serum was collected at the times indicated below. The concentration of DX-2922 and DX-2930 was determined by ELISA and plotted versus time in order to obtain pharmacokinetic parameters (clearance, half life, volume of distribution, etc).

Pharmacokinetics of DX-2922 and DX-2930 Following Single Intravenous, Subcutaneous or Intraperitoneal Administration in Rats The objective of this study was to evaluate the pharmacokinetics of DX-2922 and DX-2930, antibody inhibitors of plasma kallikrein, following a single intravenous (IV), subcutaneous (SC), or intraperitoneal (IP) injection to male Sprague-Dawley rats.

Forty two male Sprague-Dawley rats were assigned to 7 dose groups each consisting of 6 animals. All animals were dosed on Day 0. Groups 1 through 3 received a single IV injection of 1 mg/kg, 10 mg/kg, or 20 mg/kg DX-2922, respectively. Groups 4 and 5 received a single SC or IP injection of 20 mg/kg DX-2922, respectively. Groups 6 and 7 received a single IV or SC injection of 20 mg/kg DX-2930, respectively. On Day 0, blood was collected from 3 animals/group (Cohort 1) approximately 5 minutes and 4 hours post-dose. The 3 remaining animals/group (Cohort 2), were bled approximately 1 hour post-dose. All animals from each group were bled on Days 1, 2, 4, 7, 10, 14, 18, and 21. Serum samples were analyzed using a qualified ELISA method. Pharmacokinetic parameters were calculated using WinNonlin Professional Version 5.3 (Pharsight Inc., Cary, N.C.). All data were analyzed noncompartmentally. The study design is summarized in Table 15.

TABLE 15

Study Design

| Group | Test Article | Dose Level (mg/kg/day) | Route | Dose Concentration (mg/mL) | Dose Volume (mL/kg) | # Animals |
|---|---|---|---|---|---|---|
| 1 | DX-2922 | 1 | V | 0.5 | 2 | 6 |
| 2 | DX-2922 | 10 | V | 5 | 2 | 6 |
| 3 | DX-2922 | 20 | V | 10 | 2 | 6 |
| 4 | DX-2922 | 20 | C | 10 | 2 | 6 |
| 5 | DX-2922 | 20 | P | 10 | 2 | 6 |
| 6 | DX-2930 | 20 | V | 10 | 2 | 6 |
| 7 | DX-2930 | 20 | C | 10 | 2 | 6 |

The pharmacokinetic parameter estimates are summarized in Table 16.

TABLE 16

Summary of Mean Pharmacokinetic Parameters

| Group | $C_{max}$ (µg/mL) | $AUC_{last}$ (hr*µg/mL) | CL (mL/hr/Kg) | Vss (mL/Kg) | $t^{1/2}$ (hr) | F (%) |
|---|---|---|---|---|---|---|
| 1 | 18.2 | 459.4 | 1.79 | 461.6 | 267.5 | n/a |
| 2 | 204.5 | 5178.5 | 1.72 | 314.2 | 204.6 | n/a |
| 3 | 384.4 | 9683.0 | 1.91 | 279.6 | 156.4 | n/a |
| 4 | 14.3 | 1912.4 | 10.23* | n/a | 115.4 | 20% |
| 5 | 0.12 | 26.12 | 629.93* | n/a | 200.53 | 0.3% |
| 6 | 414.6 | 39556.6 | 0.41 | 120.0 | 219.8 | n/a |
| 7 | 91.8 | 20421.3 | 0.97* | n/a | 57.7 | 52% | n/a: not applicable
*CL/F

DX-2922 serum concentrations were detected from 5 minutes post-dose to 504 hours (21 Days) post-dose in all dose groups. Mean $C_{max}$ and $AUC_{last}$ values following IV dosing were proportional to dose and increased in a linear fashion with increasing dose. IV clearance was rapid and independent of dose with mean values ranging from 1.72 mL/hr/Kg to 1.91 mL/hr/Kg across dose groups. Mean elimination half-life values decreased with increasing dose and ranged from 268 hours in the 1 mg/kg IV dose group to 156 hours in the 20 mg/kg dose group. Volume of distribution was greater than serum volume suggesting extravascular distribution. Following SC and IP dosing, the mean elimination half-life was 115 hours and 201 hours, respectively. The relative bioavailability when administered by the SC and IP routes were approximately 20% and 0.3%, respectively.

DX-2930 serum concentrations were detected from 5 minutes post-dose to 504 hours (21 Days) post-dose in all dose groups. Following IV dosing, mean $C_{max}$ and $AUC_{last}$ values were 415 µg/mL and 39557 µg/mL*hr, respectively. Mean clearance and elimination half-life values were 0.41 mL/hr/kg and 220 hours, respectively. Volume of distribution was consistent with serum volume suggesting limited extravascular distribution. The relative bioavailability when administered by the SC route was approximately 52%.

Figure 17:
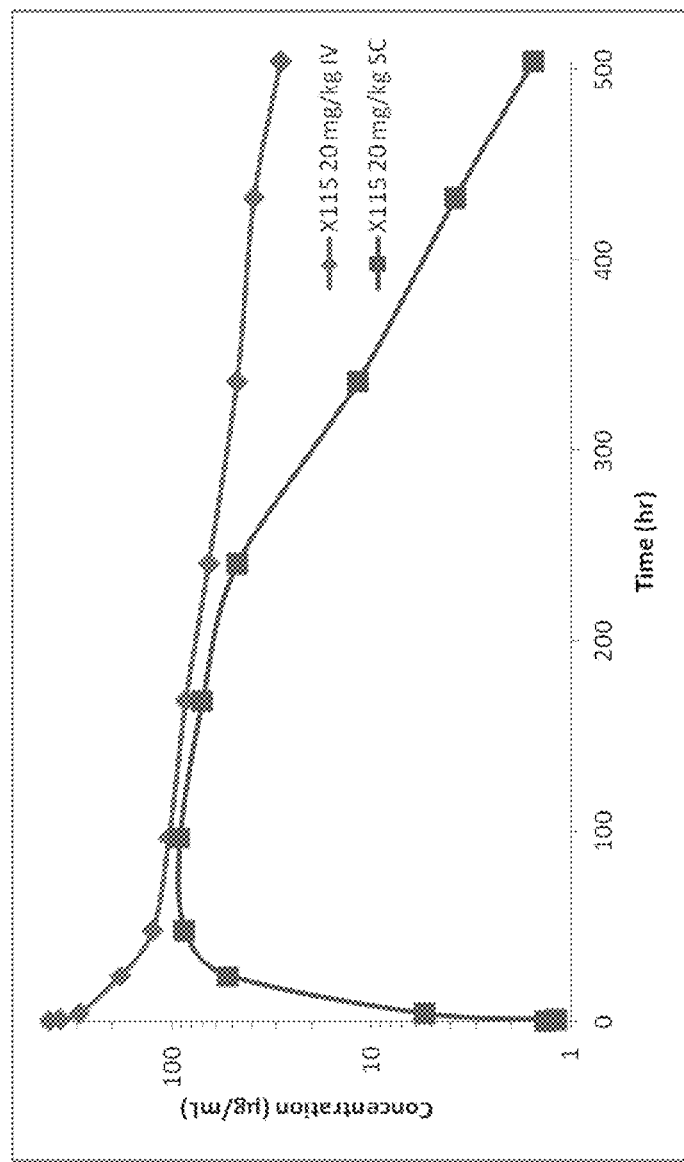
FIG. 17 depicts a graph showing mean DX-2930 serum concentrations following IV and SC administration to Sprague-Dawley rats for pharmacokinetic assessments.
Figure 18:
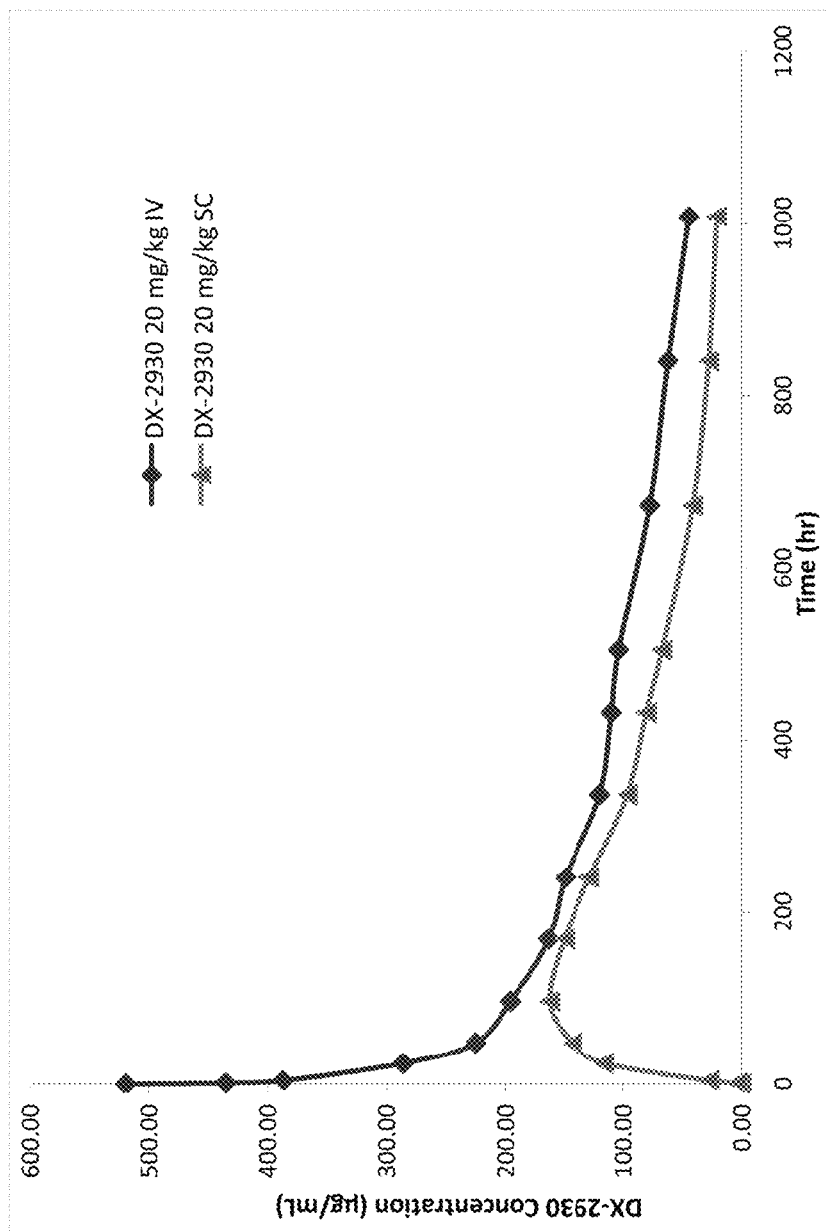
FIG. 18 depicts a graph showing mean DX-2930 serum concentrations following IV and SC administration to cynomolgus monkeys for pharmacokinetic assessments.

The mean serum concentration data for DX-2930 are shown graphically in FIG. 17 and FIG. 18.

Example 11

Epitope Mapping Using Amino Acid Mutations of pKal

Based on the epitope mapping studies described herein in Example 8, we inspected the published 3 dimensional model in the RCSB Protein Data Bank (available on the world wide web at rcsb.org; pdb code 2ANY) and identified a collection of sets of amino acids in surface accessible loops near the enzyme active site that we reasoned could interact with the antibody binding resulting in enzyme inhibition. These amino acids were substituted for alanine and the catalytic domain of each of the mutant was expressed in *Pichia pastoris* with a His tag fusion and purified by IMAC. Four different mutant pKal mutants were synthesized and tested:

Mutant 1: Amino acids S478, N481, S525, and K526 of the human kallikrein sequence (Accession No. NP_00883.2) were mutated to alanine. These amino acids were determined to be involved in substrate recognition (S3 subsite).

Mutant 2: Amino acid residues R551, Q553, Y555, T558 and R560 of the human kallikrein sequence (Accession No. NP_00883.2) were mutated to alanine. It was determined that these residues are involved in the active site substrate recognition (S1' subsite).

Mutant 3: Amino acids D572, K575, and D577 of the human kallikrein sequence (Accession No. NP_00883.2) were mutated to alanine. These amino acid residues are involved in substrate recognition (S1' subsite)

Mutant 4: Amino acids N395, 5397 and 5398 of the human kallikrein sequence (Accession No. NP_00883.2) were mutated to alanine. These residues are distal from the active site of plasma kallikrein.

Three of the 4 mutants (Mutant 1, 2, and 4) have similar activity to that of the wildtype catalytic domain of pKal. The amino acid substitutions in Mutant 3 yielded an inactive protein that was not recognized in SPR (Biacore) binding assays by any of the tested anti-pKal antibodies.

The antibodies tested for inhibition of mutants 1, 2 and 4 are shown herein in Table 17. Based on the measured $K_{i,app}$ values for the antibodies in Group 1 (i.e., antibodies that inhibit human and mouse pKal but do not bind prekallikrein) it is evident that this group of antibodies binds an epitope on pKal that contains the amino acids that were mutated in Mutant 2 but were not dependent on residues mutated in Mutants 1 or 4. In addition, the interaction of plasma kallikrein binding proteins X81-B01/X101-A01/DX-2922 and affinity matured derivative X115-B07 to kallikrein is adversely affected by the substitutions in Mutant 1. For an example of the differences in the ability of the antibodies to bind prekallikrein see e.g., FIGS. 11A and 11B, which compares prekallikrein the binding of DX-2922 (Group 1) to that of M6-D09 (Group 3).

The antibodies in Group 2 (i.e., those that inhibit human pKal not mouse pkal and do not bind prekallikrein) were not significantly affected by the mutated amino acids indicating that they make contact with alternate amino acids. The Group 2 antibodies are likely to bind near the active site, as they were unable to bind pKal complexed with a Kunitz domain (EPI-KAL2), which are known to bind at the active site of a serine protease. Furthermore, one of the antibodies in Group 2 (M145-D11) is similar to those in Group 1 in that it is unable to bind pKal in a Biacore assay that is inactivated with the suicide inhibitor AEBSF (4-(2-Aminoethyl) benzenesulfonyl fluoride hydrochloride), which is a small molecule covalent inhibitor of trypsin-like serine proteases (FIG. 12). However, the other antibody (M29-D09) assigned to Group 2 was able to bind AEBSF inactivated pKal, indicating that it may bind a different epitope than M145-D11 despite sharing similar binding properties.

The antibodies in Group 3 inhibited human and mouse pKal but bound prekallikrein. One of these antibodies, M6-D09, was unable to bind pKal inactivated by either EPI-KAL2 or AEBSF, indicating that this group of pKal inhibitors interacts with alternative amino acids near the active site. The $K_{i,app}$ for M6-D09 increased approximately 5-fold towards Mutant 2 (i.e., decreased potency of M6-D09).

Example 12

Affinity Maturation

In addition to the affinity maturation described herein in Examples 4 and 5, which involved optimization of the light chain we attempted to further optimize affinity with libraries that vary amino acids in the CDR1, CDR2, and CDR3 regions of the variable heavy chain of two different parental anti-pKal antibodies. Both of the antibodies selected for further optimization (X63-G06 and M162-A04) exhibit desirable properties for further development as a therapeutic antibody inhibitor of plasma kallikrein; properties which include: a) complete inhibition of human and rodent plasma kallikrein and b) no binding to prekallikrein. In some embodiments, complete inhibition of human pKal is essential to block the activity of plasma kallikrein in disease uses. Inhibition of rodent pKal facilitates preclinical development including toxicity assessment. The lack of binding to prekallikrein is a highly desirable property for an antibody inhibitor of pKal to maximize the bioavailability of the antibody therapeutic towards active pKal target and to potentially reduce the dose required for efficacy.

Affinity maturation was performed using 4 different phage display libraries. For each parental antibody (e.g., I62-A04), a library was constructed that contained varied amino acid positions in both the CDR1 and the CDR2 of the heavy chain. An additional library was constructed for each of the two parental antibodies wherein positions in the CDR3 of the heavy chain were varied. Each of these 4 phage display libraries were selected (panned) with decreasing amounts of active pKal in each subsequent round in order to obtain high affinity antibodies. To minimize the appearance of prekallikrein binding in the selected antibody output libraries were initially depleted against immobilized prekallikrein. After screening as Fab fragments, we discovered the affinity matured antibodies shown in Table 16 (i.e. the antibodies with the identification number starting with "X115").

Four discovered antibodies (X115-B07, X115-D05, X115-E09, and X115-H06) are derived from the DX-2922 parental antibody (also known as X63-G06 as a Fab fragment, X81-B01 as an IgG produced in 293T cells, or X101-A01 as an IgG produced in CHO cells) were found to be potent pKal inhibitors. For comparison the amino acid sequence of DX-2922 is shown. It is evident that three of the affinity matured antibodies (X115-B07, X115-E09, and X115-H06) contain mutations in Hv-CDR3; whereas X115-D05 has a different Hv-CDR1/CDR2. Four other discovered antibodies (X115-F02, X115-A03, X115-D01, and X115-G04) are derived from the M162-A04 parental antibody. All 8 affinity matured antibodies do not bind prekallikrein.

TABLE 17

Summary of Affinity Matured Anti-pKal Antibodies Inhibition Constants (Ki, app) on Wild Type pKal Catalytic Domain and Mutants 1, 2, and 4[a].

| Isolate | WT cat. Domain Ki, app (nM) | Mutant 1 Ki, app (nM) | Mutant 2 Ki, app (nM) | Mutant 4 Ki, app (nM) | Competes with AEBSF | Competes with epi-kal2 | Characteristics |
|---|---|---|---|---|---|---|---|
| DX-2922 | 0.22 | 14 | 20 | 0.25 | y | y | inhibits human and mouse pKal; does not bind pre-kallikrein |
| 559A-X115-B07 (aff mat; X101-A01 parent) | 0.13 | 4.7 | 47 | 0.14 | y | nd | inhibits human and mouse pKal; does not bind pre-kallikrein |
| 559A-X115-D05 (aff mat; X101-A01 parent) | nd | nd | nd | nd | y | nd | inhibits human and mouse pKal; does not bind pre-kallikrein |
| 559A-X115-E09 (aff mat; X101-A01 parent) | nd | nd | nd | nd | y | nd | inhibits human and mouse pKal; does not bind pre-kallikrein |
| 559A-X115-H06 (aff mat; X101-A01 parent) | nd | nd | nd | nd | y | nd | inhibits human and mouse pKal; does not bind pre-kallikrein |
| 559A-X115-A03 (aff mat; M162-A04 parent) | 0.16 | 0.23 | 3.7 | 0.13 | y | nd | inhibits human and mouse pKal; does not bind pre-kallikrein |

TABLE 17-continued Summary of Affinity Matured Anti-pKal Antibodies Inhibition Constants
(Ki, app) on Wild Type pKal Catalytic Domain and Mutants 1, 2, and 4[a].

| Isolate | WT cat. Domain Ki, app (nM) | Mutant 1 Ki, app (nM) | Mutant 2 Ki, app (nM) | Mutant 4 Ki, app (nM) | Competes with AEBSF | Competes with epi-kal2 | Characteristics |
|---|---|---|---|---|---|---|---|
| 559A-X115-D01 (aff mat; M162-A04 parent) | 0.18 | 0.26 | 2.5 | 0.12 | y | nd | inhibits human and mouse pKal; does not bind pre-kallikrein |
| 559A-X115-F02 (aff mat; M162-A04 parent) | 0.09 | 0.14 | 5.9 | 0.1 | y | y | inhibits human and mouse pKal; does not bind pre-kallikrein |
| 559A-X115-G04 (aff mat; M162-A04 parent) | 0.3 | 0.4 | 2.2 | 0.3 | y | y | inhibits human and mouse pKal; does not bind pre-kallikrein |
| 559A-M29-D09 (sFab)) | 0.24 | 0.27 | 0.34 | 0.39 | nd | y | inhibits human and mouse pKal; does not inhibit mouse pKal; does not bind pre-kallikrein |
| 559A-M145-D11 (sFab)) | 0.16 | 0.23 | 0.1 | 0.21 | y | y | inhibits human and mouse pKal; weakly inhibits mouse pKal; does not bind pre-kallikrein |
| 559A-M06-D09 | 2.5 | 3.4 | 13.5 | 2.9 | y | y | inhibits human and mouse pKal; binds pre-kallikrein |
| 559A-M35-G04 | 0.8 | 0.09 | 1.1 | 0.8 | nd | nd | inhibits human and mouse pKal; binds pre-kallikrein |

[a]Antibodies were obtained from HV-CDR1/2 and HV- CDR3 affinity maturation, purified and tested for inhibition of either wildtype pKal catalytic domain
(Note,
the antibodies inhibited full length wild type pKal approximately equal to that of the wild type catalytic domain).

TABLE 18

| Isolate | LV-CDR1 | LV-CDR2 | LV-CDR3 | HV -CDR1 | HV-CDR2 | HV-CDR3 |
|---|---|---|---|---|---|---|
| DX-2922 | RTSQFVNSNYLA | GASSRAT | QQSSRTPWT | HYLMT | YISPSGGHTIYADSVKG | VARGIAARSRTSYFDY |
| X115-B07 | RTSQFVNSNYLA | GASSRAT | QQSSRTPWT | HYLMT | YISPSGGHTIYADSVKG | VGQGIRGRSRTSYFAQ |
| X115-D05 | RTSQFVNSNYLA | GASSRAT | QQSSRTPWT | DYMMA | SIVPSGGHTHYADSVKG | VARGIAARSRTSYFDY |
| X115-E09 | RTSQFVNSNYLA | GASSRAT | QQSSRTPWT | HYLMT | YISPSGGHTIYADSVKG | VAQGIAARSRTSSVDQ |
| X115-H06 | RTSQFVNSNYLA | GASSRAT | QQSSRTPWT | HYLMT | YISPSGGHTIYADSVKG | VAQGISARSRTSYFDY |
| M162-A04 | RASQSISSWLA | KASTLES | QQYNTYWT | HYIMM | GIYSSGGITVYADSVKG | RRTGIPRRDADDI |
| X115-A03 | RASQSISSWLA | KASTLES | QQYNTYWT | HYIMM | GIYSSGGITVYADSVKG | RRIGVPRRDSFDM |
| X115-D01 | RASQSISSWLA | KASTLES | QQYNTYWT | IYSMH | SIYPSRGMTWYADSVKG | RRTGIPRRDADDI |
| X115-F02 | RASQSISSWLA | KASTLES | QQYNTYWT | HYIMM | GIYSSGGITVYADSVKG | RRIGVPRRDEFDI |
| X115-G04 | RASQSISSWLA | KASTLES | QQYNTYWT | HYIMM | GIYSSGGITVYADSVKG | RRTGVPRRDEFDI |
| M29-D09 | SGNKLGDKYVA | QDTKRPS | QAWDSSIVI | WYTMV | YIYPSGGATFYADSVKG | GSYDYIWGFYSDH |
| M145-D11 | SGDKLGDKYTS | QDIKRPS | QAWDSPNARV | HYRMS | SIYPSGGRTVYADSVKG | DKFEWRLLFRGIGNDAFDI |
| M06-D09 | RASQSIRNYLN | AASTLQS | QQLSGYPHT | FYYMV | VIYPSGGITVYADSVKG | DKWAVMPPYYYYAMDV |
| M35-G04 | RASQSVSSYLA | DASNRAT | QQRSNWPRGFT | YYHMS | VISPSGGSTKYADSVKG | GGSSDYAWGSYRRPYYFDY |

| Isolate | Full length pKal Ki, app (nM) | WT cat. Domain Ki, app (nM) | Mutant 1 Ki, app (nM) | Mutant 2 Ki, app (nM) | Mutant 4 Ki, app (nM) | competes with AEBSF | competes with epi-kal2 | Group |
|---|---|---|---|---|---|---|---|---|
| DX-2922 | 0.2 | 0.22 | 14 | 20 | 0.25 | y | y | 1 |
| X115-B07 | 0.33 | | 4.7 | 47 | 0.14 | y | nd | 1 |
| X115-D05 | 0.25 | nd | nd | nd | nd | y | nd | 1 |
| X115-E09 | 0.34 | nd | nd | nd | nd | y | nd | 1 |

TABLE 18-continued

| | | | | | | | | |
|---|---|---|---|---|---|---|---|---|
| X115-H06 | 0.35 | nd | nd | nd | nd | y | nd | 1 |
| M162-A04 | | nd | nd | nd | nd | y | y | 1 |
| X115-A03 | 0.16 | 0.16 | 0.23 | 3.7 | 0.13 | y | nd | 1 |
| X115-D01 | 0.18 | 0.18 | 0.26 | 2.5 | 0.12 | y | nd | 1 |
| X115-F02 | 0.089 | 0.09 | 0.14 | 5.9 | 0.1 | y | y | 1 |
| X115-G04 | 0.6 | 0.3 | 0.4 | 2.2 | 0.3 | y | y | 1 |
| M29-D09 | 0.7 | 0.24 | 0.27 | 0.34 | 0.39 | n | y | 2 |
| M145-D11 | 0.79 | 0.16 | 0.23 | 0.1 | 0.21 | y | y | 2 |
| M06-D09 | 5.9 | 2.5 | 3.4 | 13.5 | 2.9 | y | y | 3 |
| M35-G04 | 2.9 | 0.8 | 0.09 | 1.1 | 0.8 | nd | nd | 3 |

Equilibrium $K_{i,app}$ measurements. Apparent Inhibition constants ($K_{i,app}$ values) were measured by pre-incubating enzyme and inhibitor solutions prior to initiating the reactions with substrate. Enzyme and inhibitor were pre-incubated for 2 hours at 30° C. in a 96-well plate by adding 10 µL of a 10× enzyme solution and 10 µL of 10× inhibitor solutions to 70 µL of reaction buffer. Reactions were initiated by the addition of 10 µL of a 10× concentrated stock of substrate, and were monitored at 30° C. in a fluorescence plate reader with the excitation and emission wavelengths set at 360 nm/460 nm, respectively. Kinetic data were acquired by the increase in fluorescence, and initial rates for each condition were plotted against the total inhibitor concentration. The data was fit to the following equation for tight binding inhibitors:

$$A = A_0 - A_{inh} \left( \frac{(K_{i,app} + Inh + E) - \sqrt{(K_{i,app} + Inh + E)^2 - 4 \cdot Inh \cdot E}}{2 \cdot E} \right) \quad \text{Eqn. 1}$$

Where A=initial rate observed at each inhibitor concentration; $A_o$=initial rate observed in the absence of inhibitor; $A_{inh}$=initial rate observed for the enzyme inhibitor complex; Inh=concentration of inhibitor; E=total enzyme concentration (treated as a floated parameter); and $K_{i,app}$=apparent equilibrium inhibition constant.

Groups of antibody inhibitors. Antibodies in Group 1 inhibit human and mouse pKal but do not bind prekallikrein. Antibodies in Group 2 inhibit human but not mouse pKal and do not bind prekallikrein. Antibodies in Group 3 inhibit human and mouse pKal but bind prekallikrein.

Biacore Competition Analysis with an Exemplary Kallikrein Antibody, Epi-Kal2.

Epi-Kal2 is an antibody inhibitor of kallikrein that acts by binding to the active site of kallikrein (for sequence see Example 8). The Biacore competition analysis is used herein as an assay to determine whether a test kallikrein antibody binds to the same site as epi-Kal2 and is assessed by measuring the competition (e.g., displacement) between epi-Kal2 and the test antibody for binding to the active site.

Figure 11A:
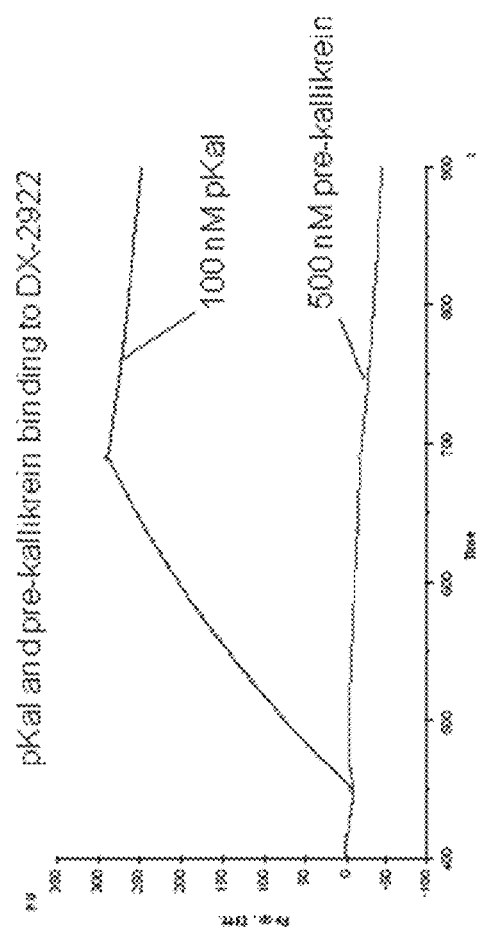
FIGS. 11A and 11B depict a Biacore competition analysis with epi-kal2, as described herein in Example 12, for (i) DX-2922, and (ii) M6-D09 antibodies.
Figure 11B:
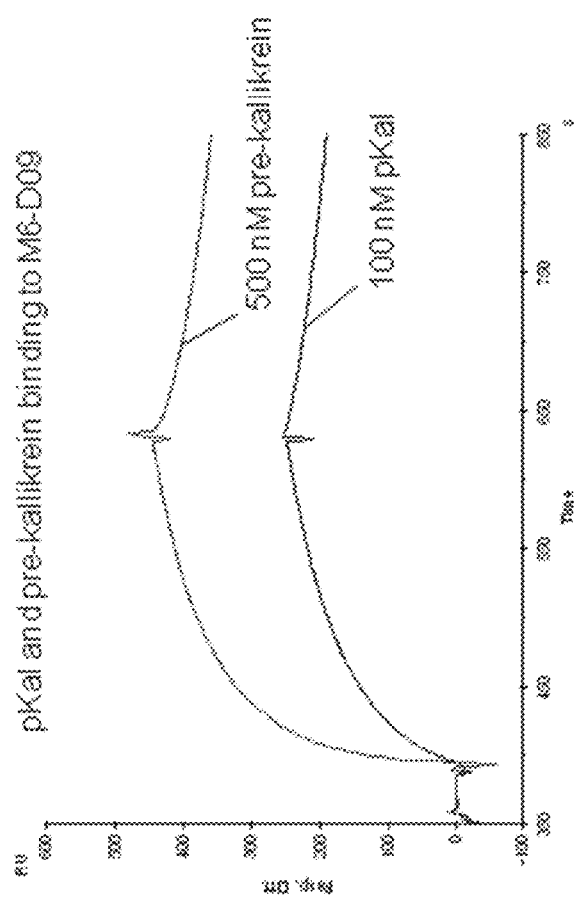

Goat anti-human Fc fragment specific IgG or anti-human Fab IgG was immobilized by amine coupling on a CM5 sensor chip at immobilization densities of approximately 5000 RU. Anti-pKal antibodies or sFabs were captured on their respective surfaces by injecting a 50 nM solution of IgG/sFab for 1-2 minutes at 5 at µl/min Human pKal (100 nM) or human pKal-ep-kal2 complex (100 nM hpKal that had been pre-incubated with 1 µM epi-kal2 for 1 hour at room temperature) were injected over the captured IgGs or sFabs for 5 minutes at 20-50 µl/min followed by a 5-10 minute dissociation phase. Binding responses were recorded at the end of the association phase. Anti-pKal IgGs or sFabs were considered to compete with epi-kal2 for binding to human pKal if binding of the pKal-epi-kal2 complex to anti-pKal antibodies was significantly reduced (>70%) as compared to an injection of hpKal only. The sensor chip surface was regenerated with a pulse of 10 mM glycine pH 1.5 at a flow rate of 100 µl/min Measurements were performed at 25° C. using HBS-P (10 mM HEPES pH 7.4, 150 mM NaCl and 0.005% surfactant P20) as the running buffer. Results from the Biacore competition analysis for epi-Kal2 are shown herein in FIGS. 11A and 11B.

Biacore Competition Analysis with the Small Molecule Kallikrein Inhibitor, AEBSF.

AEBSF (i.e., 4-(2-aminoethyl)benzene sulfonyl fluoride hydrochloride) is a small molecule inhibitor of kallikrein. The Biacore competition analysis is used herein to determine whether a test antibody binds to the same site (or an overlapping site) utilized by AEBSF for kallikrein inhibition.

Figure 12:
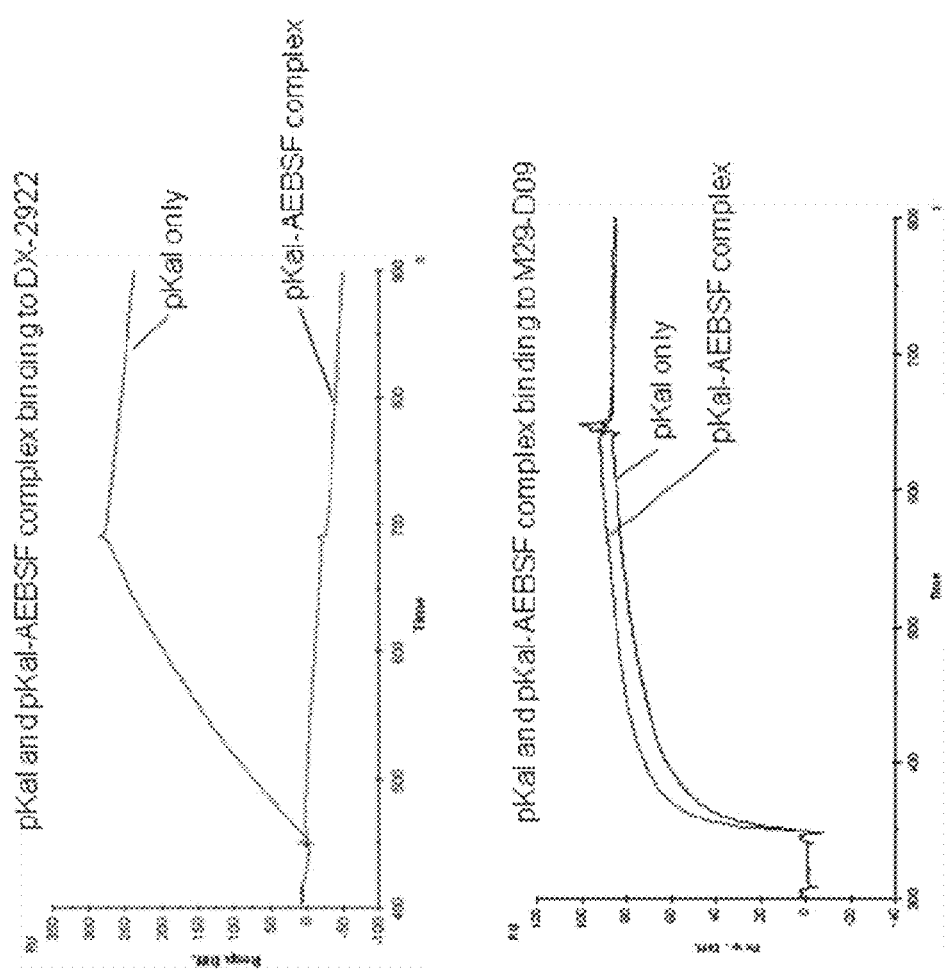
FIG. 12 depicts a Biacore competition analysis with AEBSF, as described herein in Example 12, for (i) DX-2911, and (ii) M6-D09 antibodies.
Figure 13:
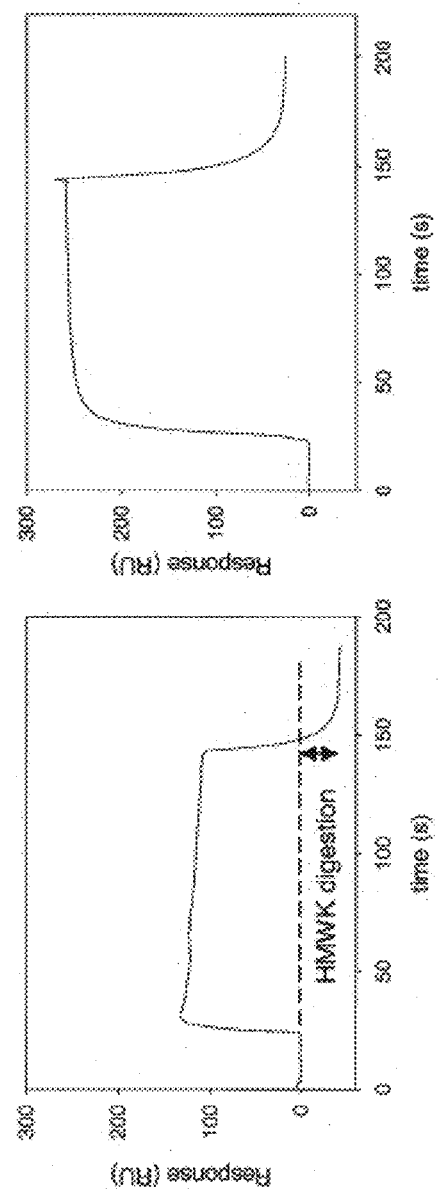
FIG. 13 depicts a Biocore analysis showing that DX-2922 binds to plasma kallikrein that bound to hign molecular weight kininogen (HMWK).

Goat anti-human Fc fragment specific IgG or anti-human Fab IgG was immobilized by amine coupling on a CM5 sensor chip at immobilization densities of approximately 5000 RU. Anti-pKal IgGs or sFabs were captured on their respective surfaces by injecting a 50 nM solution of IgG/sFab for 1-2 minutes at 5 at µl/min Human pKal (100 nM) or human pKal-AEBSF complex (100 nM hpKal that had been pre-treated with 1 mM AEBSF for 1 hour at room temperature) were injected over the captured IgGs or sFabs for 5 minutes at 20-50 µl/min followed by a 5-10 minute dissociation phase. Binding responses were recorded at the end of the association phase. Anti-pKal IgGs or sFabs were considered to compete with AEBSF for binding to human pKal if binding of the pKal-AEBSF complex to anti-pKal antibodies was significantly reduced (>70%) as compared to an injection of hpKal only. The sensor chip surface was regenerated with a pulse of 10 mM glycine pH 1.5 at a flow rate of 100 gmin Measurements were performed at 25° C. using HBS-P (10 mM HEPES pH 7.4, 150 mM NaCl and 0.005% surfactant P20) as the running buffer. Results from the Biacore competition analysis for AEBSF are shown herein in FIG. 12.

The Following are Sequences for the Light Chain Variable Regions (LV), and Heavy Chain Variable Regions (HV) Regions for 8 Exemplary Affinity Matured Anti-pKal Antibodies:

559A-M0029-D09-LV
QSALTQPPTVSVSPGQTARITCSGNKLGDKYVAWYQQKPGQSPMLVIYQ
DTKRPSRVSERFSGSNSANTATLSISGTQALDEADYYCQAWDSSIVIFG
GGTRLTVL

559A-M0145-D11-LV
QSVLTQPPSVSVSPGQTASITCSGDKLGDKYTSWYQQRPGQSPVLVIYQ
DIKRPSGIPERFSGSNSGNTATLTISGTQAMDEADYYCQAWDSPNARVF
GSGTKVTVL

559A-M0162-A04-LV
DIQMTQSPSTLSASVGDRVTITCRASQSISSWLAWYQQKPGKAPNLLIY
KASTLESGVPSRFSGSGSGTEFTLTISSLQPDDFATYYCQQYNTYWTFG
QGTKVEIK

559A-X0101-A01-LV
EIVLTQSPGTLSLSPGERATLSCRTSQFVNSNYLAWYQQKPGQAPRLLI
YGASSRATGIPDRFSGSGSGTDFTLTISRLEPEDFAVYYCQQSSRTPWT
FGQGTKVEIK

559A-X0115-A03-LV
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEIK

559A-X0115-B07-LV
EIVLTQSPGTLSLSPGERATLSCRTSQFVNSNYLAWYQQKPGQAPRLLI
YGASSRATGIPDRFSGSGSGTDFTLTISRLEPEDFAVYYCQQSSRTPWT
FGQGTKVEIK

559A-X0115-D01-LV
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEIK

559A-X0115-D05-LV
EIVLTQSPGTLSLSPGERATLSCRTSQFVNSNYLAWYQQKPGQAPRLLI
YGASSRATGIPDRFSGSGSGTDFTLTISRLEPEDFAVYYCQQSSRTPWT
FGQGTKVEIK

559A-X0115-E09-LV
EIVLTQSPGTLSLSPGERATLSCRTSQFVNSNYLAWYQQKPGQAPRLLI
YGASSRATGIPDRFSGSGSGTDFTLTISRLEPEDFAVYYCQQSSRTPWT
FGQGTKVEIK

559A-X0115-F02-LV
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEIK

559A-X0124-G01-LV
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEI

559A-X0115-G04-LV
DIQMTQSPSTLSASVGDRVTITCRASQSISSWLAWYQQKPGKAPKLLIY
KASTLESGVPSRFSGSGSGTEFTLTISSLQPDDFATYYCQQYNTYWTFG
QGTKVEIK

559A-X0115-H06-LV
EIVLTQSPGTLSLSPGERATLSCRTSQFVNSNYLAWYQQKPGQAPRLLI
YGASSRATGIPDRFSGSGSGTDFTLTISRLEPEDFAVYYCQQSSRTPWT
FGQGTKVEIK

559A-M0006-D09-LV
DIQMTQSPSSLSASVGDRVTITCRASQSIRNYLNWYQQKPGKAPNLLIY
AASTLQSGVPARFSGSGSGTDFTLTISSLQPEDFATYYCQQLSGYPHTF
GQGTKLEIK

559A-M0035-G04-LV
QDIQMTQSPATLSLSPGERATLSCRASQSVSSYLAWYQQKPGQAPRLLI
YDASNRATGIPARFSGSGSGTDFTLTISSLEPEDFAVYYCQQRSNWPRG
FTFGPGTKVDIK

559A-M0029-D09-HV
EVQLLESGGGLVQPGGSLRLSCAASGFTFSWYTMVWVRQAPGKGLEWVS
YIYPSGGATFYADSVKGRFTISRDNSKNTLYLQMNSLRAEDTAVYYCAM
GSYDYIWGFYSDHWGQGTLVTVSS

559A-M0145-D11-HV
EVQLLESGGGLVQPGGSLRLSCAASGFTFSHYRMSWVRQAPGKGLEWVS
SIYPSGGRTVYADSVKGRFTISRDNSKNTLYLQMNSLRAEDTAVYYCAK
DKFEWRLLFRGIGNDAFDIWGQGTMVTVSS

559A-M0162-A04-HV
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAY
RRTGIPRRDAFDIWGQGTMVTVSS

559A-X0101-A01-HV
EVQLLESGGGLVQPGGSLRLSCAASGFTFSHYLMTWVRQAPGKGLEWVS
YISPSGGHTIYADSVKGRFTISRDNSKNTLYLQMNSLRAEDTAVYYCAR
VARGIAARSRTSYFDYWGQGTLVTVSS

559A-X0115-A03-HV
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAW
RRIGVPRRDSFDMWGQGTMVTVSS

559A-X0115-B07-HV
EVQLLESGGGLVQPGGSLRLSCAASGFTFSHYLMTWVRQAPGKGLEWVS
YISPSGGHTIYADSVKGRFTISRDNSKNTLYLQMNSLRAEDTAVYYCAM
VGQGIRGRSRTSYFAQWGQGTLVTVSS

559A-X0115-D01-HV
EVQLLESGGGLVQPGGSLRLSCAASGFTFSIYSMHWVRQAPGKGLEWVS
SIYPSRGMTWYADSVKGRFTISRDNSKNTLYLQMNSLRAEDTAVYYCAY
RRTGIPRRDAFDIWGQGTMVTVSS

559A-X0115-D05-HV
EVQLLESGGGLVQPGGSLRLSCAASGFTFSDYMMAWVRQAPGKGLEWVS
SIVPSGGHTHYADSVKGRFTISRDNSKNTLYLQMNSLRAEDTAVYYCAR
VARGIAARSRTSYFDYWGQGTLVTVSS

559A-X0115-E09-HV
EVQLLESGGGLVQPGGSLRLSCAASGFTFSHYLMTWVRQAPGKGLEWVS
YISPSGGHTIYADSVKGRFTISRDNSKNTLYLQMNSLRAEDTAVYYCAR
VAQGIAARSRTSSVDQWGQGTLVTVSS

559A-X0115-F02-HV
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAY
RRIGVPRRDEFDIWGQGTMVTVSS

559A-X0124-G01-HV
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAY
RRIGVPRRDEFDIWGQGTMVTVSS

559A-X0115-G04-HV
EVQLLESGGGLVQPGGSLRLSCAASGFTFSHYIMMWVRQAPGKGLEWVS
GIYSSGGITVYADSVKGRFTISRDNSKNTLYLQMNSLRAEDTAVYYCAY
RRTGVPRRDEFDIWGQGTMVTVSS

559A-X0115-H06-HV
EVQLLESGGGLVQPGGSLRLSCAASGFTFSHYLMTWVRQAPGKGLEWVS
YISPSGGHTIYADSVKGRFTISRDNSKNTLYLQMNSLRAEDTAVYYCAR
VAQGISARSRTSYFDYWGQGTLVTVSS

559A-M0006-D09-HV
EVQLLESGGGLVQPGGSLRLSCAASGFTFSFYYMVWVRQAPGKGLEWVS
VIYPSGGITVYADSVKGRFTISRDNSKNTLYLQMNSLRAEDTAVYYCAR
DKWAVMPPYYYYAMDVWGQGTTVTVSS

559A-M0035-G04-HV
EVQLLESGGGLVQPGGSLRLSCAASGFTFSYYHMSWVRQAPGKGLEWVS
VISPSGGSTKYADSVKGRFTISRDNSKNTLYLQMNSLRAEDTAVYYCAR
GGSSDYAWGSYRRPYYFDYWGQGTLVTVSS

-continued

559A-M0029-D09 LV
CAGAGCGCTTTGACTCAGCCACCCACAGTGTCTGTGTCCCCAGGACAGA

CAGCCAGGATCACCTGCTCTGGAAATAAATTGGGGGATAAATATGTTGC

CTGGTATCAGCAGAAGCCAGGCCAGTCCCCTATGTTGGTCATCTATCAA

GATACTAAGCGCCCCTCAAGAGTTTCTGAGCGATTCTCTGGCTCCAACT

CTGCGAATACAGCCACTCTGTCCATCAGCGGGACCCAGGCTCTGGATGA

GGCTGACTATTACTGTCAGGCGTGGGACAGCAGCATTGTGATCTTCGGC

GGAGGGACCAGGCTGACCGTCCTA

559A-M0145-D11 LV
CAGAGCGTCTTGACTCAGCCACCCTCAGTGTCCGTGTCTCCAGGACAGA

CAGCCAGCATCACCTGCTCTGGAGATAAATTGGGGGATAAATATACTTC

CTGGTATCAGCAGAGGCCAGGCCAGTCCCCTGTATTGGTCATCTATCAA

GATATCAAGCGGCCCTCAGGGATCCCTGAGCGATTCTCTGGCTCCAACT

CTGGGAACACAGCCACTCTGACCATCAGCGGGACCCAGGCTATGGATGA

GGCTGACTATTACTGTCAGGCGTGGGACAGTCCCAATGCGAGGGTCTTC

GGATCTGGGACCAAGGTCACCGTCCTA

559A-M0162-A04 LV
GACATCCAGATGACCCAGTCTCCTTCCACCCTGTCTGCATCTGTAGGAG

ACAGAGTCACCATCACTTGCCGGGCCAGTCAGAGTATCAGTAGTTGGTT

GGCCTGGTATCAGCAGAAACCAGGGAAAGCCCCTAACCTCCTGATCTAT

AAGGCGTCTACTTTAGAAAGTGGGGTCCCATCAAGGTTCAGCGGCAGTG

GATCTGGGACAGAATTCACTCTCACCATCAGCAGCCTGCAGCCTGATGA

TTTTGCAACTTATTACTGCCAACAGTATAATACTTATTGGACGTTCGGC

CAAGGGACCAAGGTGGAAATCAAA

559A-X0101-A01 LV
GAGATCGTGCTGACCCAGTCCCCTGGCACCCTGTCTCTGTCTCCCGGCG

AGAGAGCCACCCTGTCCTGCCGGACCTCCCAGTTCGTGAACTCCAACTA

CCTGGCTTGGTATCAGCAGAAGCCAGGCCAGGCCCCTAGACTGCTGATC

TACGGCGCCTCTTCCAGAGCCACCGGCATCCCTGACCGGTTCTCCGGCT

CTGGCTCCGGCACCGACTTCACCCTGACCATCTCCCGGCTGGAACCTGA

GGACTTCGCCGTGTACTACTGCCAGCAGTCCTCCCGGACCCCTTGGACC

TTTGGCCAGGGCACCAAGGTGGAGATCAAG

559A-X0115-A03 LV
GACATCCAGATGACCCAGTCCCCCTCCACCCTGTCCGCCTCTGTGGGCG

ACAGAGTGACCATCACCTGTCGGGCCTCCCAGTCCATCTCCAGCTGGCT

GGCCTGGTATCAGCAGAAGCCCGGCAAGGCCCCCAAGCTGCTGATCTAC

AAGGCCAGCACCCTGGAATCCGGCGTGCCCTCCAGATTCTCCGGCTCTG

GCTCCGGCACCGAGTTCACCCTGACCATCAGCTCCCTGCAGCCCGACGA

CTTCGCCACCTACTACTGCCAGCAGTACAACACCTACTGGACCTTCGGC

CAGGGCACCAAGGTGGAAATCAAG

559A-X0115-B07 LV
GAGATCGTGCTGACCCAGTCCCCTGGCACCCTGTCTCTGTCTCCCGGCG

AGAGAGCCACCCTGTCCTGCCGGACCTCCCAGTTCGTGAACTCCAACTA

CCTGGCTTGGTATCAGCAGAAGCCAGGCCAGGCCCCTAGACTGCTGATC

TACGGCGCCTCTTCCAGAGCCACCGGCATCCCTGACCGGTTCTCCGGCT

CTGGCTCCGGCACCGACTTCACCCTGACCATCTCCCGGCTGGAACCTGA

GGACTTCGCCGTGTACTACTGCCAGCAGTCCTCCCGGACCCCTTGGACC

TTTGGCCAGGGCACCAAGGTGGAGATCAAG

559A-X0115-D01 LV
GACATCCAGATGACCCAGTCCCCCTCCACCCTGTCCGCCTCTGTGGGCG

ACAGAGTGACCATCACCTGTCGGGCCTCCCAGTCCATCTCCAGCTGGCT

GGCCTGGTATCAGCAGAAGCCCGGCAAGGCCCCCAAGCTGCTGATCTAC

AAGGCCAGCACCCTGGAATCCGGCGTGCCCTCCAGATTCTCCGGCTCTG

GCTCCGGCACCGAGTTCACCCTGACCATCAGCTCCCTGCAGCCCGACGA

CTTCGCCACCTACTACTGCCAGCAGTACAACACCTACTGGACCTTCGGC

CAGGGCACCAAGGTGGAAATCAAG

559A-X0115-D05 LV
GAGATCGTGCTGACCCAGTCCCCTGGCACCCTGTCTCTGTCTCCCGGCG

AGAGAGCCACCCTGTCCTGCCGGACCTCCCAGTTCGTGAACTCCAACTA

CCTGGCTTGGTATCAGCAGAAGCCAGGCCAGGCCCCTAGACTGCTGATC

TACGGCGCCTCTTCCAGAGCCACCGGCATCCCTGACCGGTTCTCCGGCT

CTGGCTCCGGCACCGACTTCACCCTGACCATCTCCCGGCTGGAACCTGA

GGACTTCGCCGTGTACTACTGCCAGCAGTCCTCCCGGACCCCTTGGACC

TTTGGCCAGGGCACCAAGGTGGAGATCAAG

559A-X0115-E09 LV
GAGATCGTGCTGACCCAGTCCCCTGGCACCCTGTCTCTGTCTCCCGGCG

AGAGAGCCACCCTGTCCTGCCGGACCTCCCAGTTCGTGAACTCCAACTA

CCTGGCTTGGTATCAGCAGAAGCCAGGCCAGGCCCCTAGACTGCTGATC

TACGGCGCCTCTTCCAGAGCCACCGGCATCCCTGACCGGTTCTCCGGCT

CTGGCTCCGGCACCGACTTCACCCTGACCATCTCCCGGCTGGAACCTGA

GGACTTCGCCGTGTACTACTGCCAGCAGTCCTCCCGGACCCCTTGGACC

TTTGGCCAGGGCACCAAGGTGGAGATCAAG

559A-X0115-F02 LV
GACATCCAGATGACCCAGTCCCCCTCCACCCTGTCCGCCTCTGTGGGCG

ACAGAGTGACCATCACCTGTCGGGCCTCCCAGTCCATCTCCAGCTGGCT

GGCCTGGTATCAGCAGAAGCCCGGCAAGGCCCCCAAGCTGCTGATCTAC

AAGGCCAGCACCCTGGAATCCGGCGTGCCCTCCAGATTCTCCGGCTCTG

GCTCCGGCACCGAGTTCACCCTGACCATCAGCTCCCTGCAGCCCGACGA

CTTCGCCACCTACTACTGCCAGCAGTACAACACCTACTGGACCTTCGGC

CAGGGCACCAAGGTGGAAATCAAG

559A-X0115-G04 LV
GACATCCAGATGACCCAGTCCCCCTCCACCCTGTCCGCCTCTGTGGGCG

ACAGAGTGACCATCACCTGTCGGGCCTCCCAGTCCATCTCCAGCTGGCT

GGCCTGGTATCAGCAGAAGCCCGGCAAGGCCCCCAAGCTGCTGATCTAC

AAGGCCAGCACCCTGGAATCCGGCGTGCCCTCCAGATTCTCCGGCTCTG

GCTCCGGCACCGAGTTCACCCTGACCATCAGCTCCCTGCAGCCCGACGA

-continued

CTTCGCCACCTACTACTGCCAGCAGTACAACACCTACTGGACCTTCGGC
CAGGGCACCAAGGTGGAAATCAAG

559A-X0115-H06 LV
GAGATCGTGCTGACCCAGTCCCCTGGCACCCTGTCTCTGTCTCCCGCG
AGAGAGCCACCCTGTCCTGCCGGACCTCCCAGTTCGTGAACTCCAACTA
CCTGGCTTGGTATCAGCAGAAGCCAGGCCAGGCCCCTAGACTGCTGATC
TACGGCGCCTCTTCCAGAGCCACCGGCATCCCTGACCGGTTCTCCGGCT
CTGGCTCCGGCACCGACTTCACCCTGACCATCTCCCGGCTGGAACCTGA
GGACTTCGCCGTGTACTACTGCCAGCAGTCCTCCCGGACCCCTTGGACC
TTTGGCCAGGGCACCAAGGTGGAGATCAAG

559A-M0006-D09 LV
GACATCCAGATGACCCAGTCTCCATCCTCCCTGTCTGCATCTGTAGGAG
ACAGAGTCACCATCACTTGCCGGGCAAGTCAGAGTATTCGCAACTATTT
AAATTGGTATCAGCAGAAACCAGGGAAAGCCCCTAACCTCCTGATCTAT
GCTGCATCCACTTTGCAAAGTGGGGTCCCAGCAAGGTTCAGTGGCAGTG
GATCTGGGACAGATTTCACTCTCACTATCAGCAGTCTGCAGCCTGAAGA
TTTTGCAACTTATTACTGTCAACAGCTTAGTGGTTACCCCCACACTTTT
GGCCAGGGGACCAAGCTGGAGATCAAA

559A-M0035-G04 LV
CAAGACATCCAGATGACCCAGTCTCCAGCCACCCTGTCTTTGTCTCCAG
GGGAAAGAGCCACCCTCTCCTGCAGGGCCAGTCAGAGTGTTAGCAGCTA
CTTAGCCTGGTACCAACAGAAACCTGGCCAGGCTCCCAGGCTCCTCATC
TATGATGCATCCAACAGGGCCACTGGCATCCCAGCCAGGTTCAGTGGCA
GTGGGTCTGGGACAGACTTCACTCTCACCATCAGCAGCCTAGAGCCTGA
AGATTTTGCAGTTTATTACTGTCAGCAGCGTAGCAACTGGCCTCGCGGA
TTCACTTTCGGCCCTGGGACCAAAGTGGATATCAAA

559A-M0029-D09 HV
GAAGTTCAATTGTTAGAGTCTGGTGGCGGTCTTGTTCAGCCTGGTGGTT
CTTTACGTCTTTCTTGCGCTGCTTCCGGATTCACTTTCTCTTGGTACAC
TATGGTTTGGGTTCGCCAAGCTCCTGGTAAAGGTTTGGAGTGGGTTTCT
TATATCTATCCTTCTGGTGGCGCTACTTTTTATGCTGACTCCGTTAAAG
GTCGCTTCACTATCTCTAGAGACAACTCTAAGAATACTCTCTACTTGCA
GATGAACAGCTTAAGGGCTGAGGACACGGCCGTGTATTACTGTGCGATG
GGTTCATATGATTACATTTGGGGATTTTATAGTGACCACTGGGGCCAGG
GAACCCTGGTCACCGTCTCAAGC

559A-M0145-D11 HV
GAAGTTCAATTGTTAGAGTCTGGTGGCGGTCTTGTTCAGCCTGGTGGTT
CTTTACGTCTTTCTTGCGCTGCTTCCGGATTCACTTTCTCTCATTACCG
TATGTCTTGGGTTCGCCAAGCTCCTGGTAAAGGTTTGGAGTGGGTTTCT
TCTATCTATCCTTCTGGTGGCCGTACTGTTTATGCTGACTCCGTTAAAG
GTCGCTTCACTATCTCTAGAGACAACTCTAAGAATACTCTCTACTTGCA
GATGAACAGCTTAAGGGCTGAGGACACGGCCGTGTATTACTGTGCGAAA

GATAAGTTCGAGTGGAGGTTATTATTTCGCGGGATTGGAAATGATGCTT
TTGATATCTGGGGCCAAGGGACAATGGTCACCGTCTCAAGC

559A-M0162-A04 HV
GAAGTTCAATTGTTAGAGTCTGGTGGCGGTCTTGTTCAGCCTGGTGGTT
CTTTACGTCTTTCTTGCGCTGCTTCCGGATTCACTTTCTCTCATTACAT
TATGATGTGGGTTCGCCAAGCTCCTGGTAAAGGTTTGGAGTGGGTTTCT
GGTATCTATTCTTCTGGTGGCATTACTGTTTATGCTGACTCCGTTAAAG
GTCGCTTCACTATCTCTAGAGACAACTCTAAGAATACTCTCTACTTGCA
GATGAACAGCTTAAGGGCTGAGGACACGGCCGTGTATTACTGTGCGTAC
CGCCGGACTGGGATTCCAAGAAGAGATGCTTTTGATATCTGGGGCCAAG
GGACAATGGTCACCGTCTCAAGC

559A-X0101-A01 HV
GAGGTGCAATTGCTGGAATCCGGCGGAGGTCTGGTCAGCCTGGCGGCT
CCCTGAGACTGTCTTGCGCCGCCTCCGGCTTCACCTTCTCCCACTACCT
GATGACCTGGGTGCGCCAGGCTCCTGGCAAGGGCCTCGAATGGGTGTCC
TACATCTCCCCCTCTGGCGGCCACACCATCTACGCCGACTCCGTGAAGG
GCCGGTTCACCATCTCCCGGGACAACTCCAAGAACACCCTGTATCTGCA
GATGAACTCCCTGAGGGCCGAGGACACCGCCGTGTACTACTGCGCCAGG
GTGGCCAGAGGAATCGCCGCCAGGTCCCGGACCTCCTACTTCGACTACT
GGGGCCAGGGCACCCTGGTGACCGTGTCCTCC

559A-X0115-A03 HV
GAGGTGCAATTGCTGGAATCCGGCGGAGGACTGGTCAGCCTGGCGGCT
CCCTGAGACTGTCTTGCGCCGCCTCCGGCTTTACCTTCTCCCACTACAT
CATGATGTGGGTGCGACAGGCTCCAGGCAAGGGCCTGGAATGGGTGTCC
GGCATCTACTCCTCCGGCGGCATCACCGTGTACGCCGACTCCGTGAAGG
GCCGGTTCACCATCTCCCGGGACAACTCCAAGAACACCCTGTACCTGCA
GATGAACTCCCTGCGGGCCGAGGACACCGCCGTGTACTACTGTGCCTGG
CGGAGAATCGGCGTGCCCAGACGGGACTCCTTCGACATGTGGGGACAGG
GCACCATGGTGACAGTGTCCTCC

559A-X0115-B07 HV
GAGGTGCAATTGCTGGAATCCGGCGGAGGACTGGTCAGCCTGGCGGCT
CCCTGAGACTGTCTTGCGCCGCCTCCGGCTTCACCTTCTCCCACTACCT
GATGACCTGGGTGCGACAGGCTCCTGGCAAAGGCCTGGAATGGGTGTCC
TACATCTCCCCCTCTGGCGGCCACACCATCTACGCCGACTCCGTGAAGG
GCCGGTTTACCATCTCCCGGGACAACTCCAAGAACACCCTGTACCTGCA
GATGAACTCCCTGCGGGCCGAGGACACCGCCGTGTACTACTGTGCCATG
GTCGGCCAGGGAATCCGGGGCAGATCCCGGACCTCCTACTTCGCCCAGT
GGGGCCAGGGCACCCTGGTGACAGTGTCCTCT

559A-X0115-D01 HV
GAGGTGCAATTGCTGGAATCCGGCGGAGGACTGGTCAGCCTGGCGGCT
CCCTGAGACTGTCTTGCGCCGCCTCCGGCTTCACCTTCTCCATCTACTC
CATGCACTGGGTGCGACAGGCTCCAGGCAAGGGCCTGGAATGGGTGTCC
TCCATCTACCCCTCCCGGGGCATGACTTGGTACGCCGACTCCGTGAAGG

-continued

GCCGGTTCACAATCTCCCGGGACAACTCCAAGAACACCCTGTACCTGCA

GATGAACTCCCTGCGGGCCGAGGACACCGCCGTGTACTACTGCGCCTAC

CGGCGGACCGGCATCCCTAGACGGGACGCCTTCGACATCTGGGGCAGG

GCACCATGGTGACAGTGTCCTCC

559A-X0115-D05 HV
GAGGTGCAATTGCTGGAATCCGGCGGTGGACTGGTGCAGCCTGGCGGCT

CCCTGAGACTGTCTTGCGCCGCCTCCGGCTTCACCTTCTCCGACTACAT

GATGGCCTGGGTGCGACAGGCCCCTGGCAAGGGACTGGAATGGGTGTCC

TCCATCGTGCCCTCTGGCGGCCACACCCACTACGCCGACTCCGTGAAGG

GCCGGTTCACCATCTCCCGGGACAACTCCAAGAACACCCTGTACCTGCA

GATGAACTCCCTGCGGGCCGAGGACACCGCCGTGTACTACTGCGCCAGA

GTGGCCAGAGGAATCGCCGCCAGATCCCGGACCTCCTACTTCGACTACT

GGGGCCAGGGCACCCTGGTGACAGTGTCCTCC

559A-X0115-E09 HV
GAGGTGCAATTGCTGGAATCCGGCGGAGGACTGGTGCAGCCTGGCGGCT

CCCTGAGACTGTCTTGCGCCGCCTCCGGCTTCACCTTCTCCCACTACCT

GATGACCTGGGTGCGACAGGCTCCTGGCAAAGGCCTGGAATGGGTGTCC

TACATCTCCCCCTCTGGCGGCCACACCATCTACGCCGACTCCGTGAAGG

GCCGGTTTACCATCTCCCGGGACAACTCCAAGAACACCCTGTACCTGCA

GATGAACTCCCTGCGGGCCGAGGACACCGCCGTGTACTACTGTGCCCGG

GTGGCCCAGGGAATCGCCGCCAGATCCCGGACCTCCTCTGTGGATCAGT

GGGGCCAGGGCACCCTGGTGACAGTGTCCTCT

559A-X0115-F02 HV
GAGGTGCAATTGCTGGAATCCGGCGGAGGACTGGTGCAGCCTGGCGGCT

CCCTGAGACTGTCTTGCGCCGCCTCCGGCTTCACCTTCTCCCACTACAT

CATGATGTGGGTGCGACAGGCTCCTGGCAAGGGGCTGGAATGGGTGTCC

GGCATCTACTCCTCCGGCGGCATCACCGTGTACGCCGACTCCGTGAAGG

GCCGGTTCACCATCTCTCGGGACAACTCCAAGAACACCCTGTACCTGCA

GATGAACTCCCTGCGGGCCGAGGACACCGCCGTGTACTACTGCGCCTAC

CGGCGGATCGGCGTGCCCAGACGGGACGAGTTCGACATCTGGGGCAGG

GCACCATGGTGACAGTGTCCTCC

559A-X0115-G04 HV
GAGGTGCAATTGCTGGAATCCGGCGGAGGACTGGTGCAGCCTGGCGGCT

CCCTGAGACTGTCTTGCGCCGCCTCCGGCTTCACCTTCTCTCACTACAT

TATGATGTGGGTGCGACAGGCTCCTGGCAAAGGCCTGGAATGGGTGTCC

GGCATCTACTCCTCCGGCGGCATCACCGTGTACGCCGACTCCGTGAAGG

GCCGGTTCACCATCTCCCGGGACAACTCCAAGAACACCCTGTACCTGCA

GATGAACTCCCTGCGGGCCGAGGACACCGCCGTGTACTACTGCGCCTAC

AGACGGACCGGCGTGCCCAGACGGGACGAGTTCGATATCTGGGGCAGG

GCACCATGGTGACAGTGTCCTCC

559A-X0115-H06 HV
GAGGTGCAATTGCTGGAATCCGGCGGAGGACTGGTGCAGCCTGGCGGCT

CCCTGAGACTGTCTTGCGCCGCCTCCGGCTTCACCTTCTCCCACTACCT

GATGACCTGGGTGCGACAGGCTCCTGGCAAAGGCCTGGAATGGGTGTCC

TACATCTCCCCCTCTGGCGGCCACACCATCTACGCCGACTCCGTGAAGG

GCCGGTTTACCATCTCCCGGGACAACTCCAAGAACACCCTGTACCTGCA

GATGAACTCCCTGCGGGCCGAGGACACCGCCGTGTACTACTGTGCCCGG

GTGGCCCAGGGAATCTCCGCCAGATCCCGGACCTCCTACTTCGATTACT

CCCTGGTGACAGTGTCCTCTGGGGCCAGGGCA

559A-M0006-D09 HV
GAAGTTCAATTGTTAGAGTCTGGTGGCGGTCTTGTTCAGCCTGGTGGTT

CTTTACGTCTTTCTTGCGCTGCTTCCGGATTCACTTTCTCTTTTTACTA

TATGGTTTGGGTTCGCCAAGCTCCTGGTAAAGGTTTGGAGTGGGTTTCT

GTTATCTATCCTTCTGGTGGCATTACTGTTTATGCTGACTCCGTTAAAG

GTCGCTTCACTATCTCTAGAGACAACTCTAAGAATACTCTCTACTTGCA

GATGAACAGCTTAAGGGCTGAGGACACGGCCGTGTATTACTGTGCGAGA

GATAAATGGCGGTGATGCCCCCCTACTACTACTACGCTATGGACGTCT

GGGGCCAAGGGACCACGGTCACCGTCTCAAGC

559A-M0035-G04 HV
GAAGTTCAATTGTTAGAGTCTGGTGGCGGTCTTGTTCAGCCTGGTGGTT

CTTTACGTCTTTCTTGCGCTGCTTCCGGATTCACTTTCTCTTATTACCA

TATGTCTTGGGTTCGCCAAGCTCCTGGTAAAGGTTTGGAGTGGGTTTCT

GTTATCTCTCCTTCTGGTGGCTCTACTAAGTATGCTGACTCCGTTAAAG

GTCGCTTCACTATCTCTAGAGACAACTCTAAGAATACTCTCTACTTGCA

GATGAACAGCTTAAGGGCTGAGGACACTGCAGTCTACTATTGTGCGAGA

GGCGGTTCGAGCGATTACGCTTGGGGAGTTATCGTCGACCCTACTACT

TTGACTACTGGGGCCAGGGAACCCTGGTCACCGTCTCAAGC

Example 13

URP Fusion Proteins of Plasma Kallikrein Binding Proteins

Table 19 shows an annotated sequence of the vector pM160G12URP12 that, in *E. coli*, can cause the secretion of the light chain (LC) of M160-G12 fused to URP1 and the heavy chain (HC) of M160-G12 fused to URP2. In Table 19, the numbered DNA sequence is accompanied with comments, which are denoted on each line following an exclamation point (!). The URPs have no secondary structure in the amino-acid sequence. These sequences are derived from the digits of pi.

URP1 is derived from the first 420 digits of pi. If I is a digit in pi and J is the next digit, then IM=1+integer ((10*I+j)/16). If IM is 1 or 7, the next AA is Gly, IM=2 gives Ala, 3 gives Ser, 4 gives Thr, 5 gives Glu, and 6 gives Pro. URP2 uses digits 421-840. Table 20 contains the unannotated sequence of pM160G12URP12. Table 21 gives the amino-acid sequence of LC(M160-G12)::URP1. Table 22 shows DNA that encodes HC(M160-G12)::URP2. Table 23 shows the amino-acid sequence of HC(M160-G12)::URP2.

Tables 19-23 all show the plasma kallikrein inhibiting Fab of M160-G12, an exemplary plasma kallikrein. It is contemplated herein that any of the antibodies described herein can be put into this or a similar construction. In addition, other sequences could be used for the URPs. In particular, the antibodies M162-A04, M142-H08, X63-G06, X81-B01, X67-D03, and X67-G04 could be substituted for M160-G12. Sequences from U.S. Pat. No. 7,846,445 (herein incorporated by reference in its entirety) can also be used with the plasma kallikrein binding proteins described herein.

TABLE 19

| pM160G12URP12, annotated |
| --- |

```
559A-M160-G12_0III 5932 bp DNA circular
Input=F:\pKal_Ab\559a-m160-g12_LCHC_03_urpv2.ibi
559A-M160-G12::URP 5932 CIRCULAR
Ngene = 5932

Useful REs (cut MAnoLI fewer than 3 times) 2003.02.04

Non-cutters
AfeI  AGCgct                    AvrII  Cctagg              BamHI  Ggatcc BclI  Tgatca                    BglII  Agatct              BmgBI  CACgtc BsaBI GATNNnnatc                BsiWI  Cgtacg              BsmI   NGcattc BspDI ATcgat                    BspMI  Nnnnnnnnngcaggt     BsrGI  Tgtaca BstAPI GCANNNNntgc              BstBI  TTcgaa              BstZ17I GTAtac BtrI  CACgtg                    Ecl136I GAGctc             EcoRV  GATatc FseI  GGCCGGcc                  HpaI   GTTaac              NdeI   CAtatg NsiI  ATGCAt                    PacI   TTAATtaa            PmeI   GTTTaaac PmlI  CACgtg                    PshAI  GACNNnngtc          RsrII  CGgwccg SacI  GAGCTc                    SacII  CCGCgg              SalI   Gtcgac SbfI  CCTGCAgg                  SgfI   GCGATcgc            SnaBI  TACgta SphI  GCATGc                    Sse8387I CCTGCAgg          StuI   AGGcct SwaI  ATTTaaat                  TliI   Ctcgag              XcmI   CCANNNNNnnnntgg XhoI  Ctcgag cutters
Enzymes that cut more than     5 times.

AgeI  Accggt                    6

BsiHKAI GWGCWc                  9

BsrFI Rccggy                    15

EarI  CTCTTCNnnn                6

Eco57I CTGAAG                   7

Eco0109I RGgnccy                7

FauI  nNNNNNNGCGGG              10

HgiAI GWGCWc                    9

Enzymes that cut from 1 to     5 times.

$ = DAM site, * = DCM site,& = both

BssSI Ctcgtg                   1            12

-"-   Cacgag                   1          1703

BspHI Tcatga                   4            43      148     1156    3665$

AatII GACGTc                   1            65

BciVI GTATCCNNNNNN              2           140     1667

AvaI  Cycgrg                   3           319     4010    5628

BcgI  gcannnnnntcg             2           461     4021$
```

TABLE 19-continued pM160G12URP12, annotated

| | | | | | |
|---|---|---|---|---|---|
| ScaI AGTact | 4 | 505 | 3232 | 3529 | 4573 |
| PvuI CGATcg | 3 | 616$ | 4027$ | 5176$ | |
| FspI TGCgca | 2 | 763 | 5196 | | |
| BglI GCCNNNNnggc | 5 | 864 | 3538 | 3694 | 4945 | 5202 |
| BpmI CTGGAG | 1 | 898 | | | |
| BsaI GGTCTCNnnnn | 1 | 916 | | | |
| -"- nnnnngagacc | 2 | 3386 | | | |
| AhdI GACNNNnngtc | 2 | 983 | 5019* | | |
| Eam1105I GACNNNnngtc | 2 | 983 | 5019* | | |
| AlwNI CAGNNNctg | 2 | 1462 | 2923 | | |
| DrdI GACNNNNnngtc | 3 | 1768 | 5562 | 5831 | |
| PciI Acatgt | 1 | 1876 | | | |
| SapI gaagagc | 1 | 1998 | | | |
| PvuII CAGctg | 2 | 2054 | 5146 | | |
| PflMI CCANNNNntgg | 1 | 2233 | | | |
| HindIII Aagctt | 2 | 2235 | 3655 | | |
| ApaLI Gtgcac | 1 | 2321 | | | |
| PflFI GACNnngtc | 3 | 2340 | 2377 | 4197 | |
| Tth111I GACNnngtc | 3 | 2340 | 2377 | 4197 | |
| BsmFI Nnnnnnnnnnnnnngtccc | 1 | 2485 | | | |
| -"- GGGACNNNNNNNNNNnn | 2 | 2530 | | | |
| PpuMI RGgwccy | 3 | 2498 | 3024 | 4587 | |
| SanDI GGgwccc | 1 | 2498 | | | |
| EcoRI Gaattc | 2 | 2536 | 5056 | | |
| PstI CTGCAg | 1 | 2560 | | | |
| HincII GTYrac | 1 | 2591 | | | |
| StyI Ccwwgg | 4 | 2633 | 3704 | 4094 | 4361 |
| BsgI ctgcac | 1 | 2660 | | | |
| -"- GTGCAG | 1 | 5751 | | | |
| BbsI gtcttc | 2 | 2671 | 4108 | | |
| BlpI GCtnagc | 1 | 2868 | | | |
| EspI GCtnagc | 1 | 2868 | | | |
| AccI GTmkac | 1 | 2899 | | | |
| SgrAI CRccggyg | 2 | 2936 | 3585 | | |
| Acc65I Ggtacc | 1 | 2971 | | | |
| KpnI GGTACc | 1 | 2971 | | | |
| BsmBI CGTCTCNnnnn | 3 | 3104 | 4077 | 5877 | |
| -"- Nnnnnngagacg | 1 | 5925 | | | |
| Bsu36I CCtnagg | 3 | 3121 | 3310 | 4657* | |

TABLE 19-continued

| pM160G12URP12, annotated | | | | | |
|---|---|---|---|---|---|
| NaeI GCCggc | 3 | 3148 | 3699 | 5416 | |
| NgoMIV Gccggc | 3 | 3148 | 3699 | 5416 | |
| EagI Cggccg | 4 | 3284 | 3983 | 4397 | 4805 |
| BspEI Tccgga | 4 | 3453* | 3784 | 4905 | 4959 |
| SexAI Accwggt | 2 | 3459* | 4665* | | |
| BseRI NNnnnnnnnnctcctc | 4 | 3466* | 4115 | 4634 | 4960* |
| EcoNI CCTNNnnnagg | 3 | 3604 | 3832* | 4167* | |
| AscI GGcgcgcc | 1 | 3613 | | | |
| BssHII Gcgcgc | 1 | 3614 | | | |
| SfiI GGCCNNNNnggcc | 1 | 3693 | | | |
| BtgI Ccrygg | 1 | 3704 | | | |
| DsaI Ccrygg | 1 | 3704 | | | |
| NcoI Ccatgg | 1 | 3704 | | | |
| MfeI Caattg | 1 | 3718 | | | |
| BstXI CCANNNNNntgg | 1 | 3825* | | | |
| MscI TGGcca | 1 | 3876 | | | |
| XbaI Tctaga | 1 | 3922 | | | |
| AflII Cttaag | 1 | 3966 | | | |
| XmaI Cccggg | 1 | 4010 | | | |
| NruI TCGcga | 1 | 4030$ | | | |
| BstEII Ggtnacc | 1 | 4071* | | | |
| ApaI GGGCCc | 1 | 4098 | | | |
| BanII GRGCYc | 4 | 4098 | 4381 | 4602 | 5446 |
| Bsp120I Gggccc | 1 | 4098 | | | |
| PspOMI Gggccc | 1 | 4098 | | | |
| NheI Gctagc | 1 | 4116 | | | |
| KasI Ggcgcc | 3 | 4216 | 4465 | 5217 | |
| NotI GCggccgc | 1 | 4396 | | | |
| SpeI Actagt | 1 | 5020* | | | |
| MluI Acgcgt | 1 | 5045 | | | |
| BsaAI YACgtr | 1 | 5519 | | | |
| DraIII CACNNNgtg | 1 | 5519 | | | |
| PsiI TTAtaa | 1 | 5647 | | | |

```
  1    gacgaaaggg cctcgtgata cgcctatttt tataggttaa tgtcatgata ataatggttt 61    cttaGACGTC aggtggcact tttcggggaa atgtgcgcgg aaccccctatt tgtttatttt
          AatII.

121    tctaaataca ttcaaatatg tatccgctca tgagacaata accctgataa atgcttcaat 181    aatattgaaa aaggaagagt atgagtattc aacatttccg tgtcgccctt attcccttttt 241    ttgcggcatt ttgccttcct gttttttgctc acccagaaac gctggtgaaa gtaaaagatg 301    ctgaagatca gttgggtgcc cgagtgggtt acatcgaact ggatctcaac agcggtaaga
```

TABLE 19-continued pM160G12URP12, annotated

```
 361   tccttgagag ttttcgcccc gaagaacgtt ttccaatgat gagcacttttt aaagttctgc
 421   tatgtggcgc ggtattatcc cgtattgacg ccgggcaaga gcaactcggt cgccgcatac
 481   actattctca gaatgacttg gttgagtact caccagtcac agaaaagcat cttacggatg
 541   gcatgacagt aagagaatta tgcagtgctg ccataaccat gagtgataac actgcggcca
 601   acttacttct gacaacgatc ggaggaccga aggagctaac cgcttttttg cacaacatgg
 661   gggatcatgt aactcgcctt gatcgttggg aaccggagct gaatgaagcc ataccaaacg
 721   acgagcgtga caccacgatg cctgtagcaa tggcaacaac gttgcgcaaa ctattaactg
 781   gcgaactact tactctagct tcccggcaac aattaataga ctggatggag gcggataaag
 841   ttgcaggacc acttctgcgc tcggcccttc cggctggctg gtttattgct gataaatCTG
                                                                    BpmI.
 901   GAGccggtga gcgtgggtct cgcggtatca ttgcagcact ggggccagat ggtaagccct
       BpmI.
 961   cccgtatcgt agttatctac acgacgggga gtcaggcaac tatggatgaa cgaaatagac
1021   agatcgctga gataggtgcc tcactgatta agcattggta actgtcagac caagtttact
1081   catatatact ttagattgat ttaaaacttc attttaatt taaaaggatc taggtgaaga
1141   tccttttgga taatctcatg accaaaatcc cttaacgtga gttttcgttc cactgagcgt
1201   cagaccccgt agaaaagatc aaaggatctt cttgagatcc ttttttttctg cgcgtaatct
1261   gctgcttgca acaaaaaaa ccaccgctac cagcggtggt ttgtttgccg gatcaagagc
1321   taccaactct ttttccgaag gtaactggct tcagcagagc gcagatacca aatactgttc
1381   ttctagtgta gccgtagtta ggccaccact tcaagaactc tgtagcaccg cctacatacc
1441   tcgctctgct aatcctgtta ccagtggctg ctgccagtgg cgataagtcg tgtcttaccg
1501   ggttggactc aagacgatag ttaccggata aggcgcagcg gtcgggctga acgggggggtt
1561   cgtgcataca gcccagcttg gagcgaacga cctacaccga actgagatac ctacagcgtg
1621   agctatgaga aagcgccacg cttcccgaag ggagaaaggc ggacaggtat ccggtaagcg
1681   gcagggtcgg aacaggagag cgcacgaggg agcttccagg gggaaacgcc tggtatcttt
1741   atagtcctgt cgggtttcgc caccctctgac ttgagcgtcg atttttgtga tgctcgtcag
1801   gggggcggag cctatggaaa aacgccagca acgcggcctt tttacggttc ctggccttt
1861   gctggccttt tgctcACATG Ttctttcctg cgttatcccc tgattctgtg gataaccgta
                          PciI...
1921   ttaccgcctt tgagtgagct gataccgctc gccgcagccg aacgaccgag cgcagcgagt
1981   cagtgagcga ggaagcgGAA GAGCgcccaa tacgcaaacc gcctctcccc gcgcgttggc
                                SapI....
2041   cgattcatta atgcagctgg cacgacaggt ttcccgactg gaaagcgggc agtgagcgca
2101   acgcaattaa tgtgagttag ctcactcatt aggcacccca ggctttacac tttatgcttc
2161   cggctcgtat gttgtgtgga attgtgagcg gataacaatt tcacacagga aacagctatg
2221   accatgatta cgccaagctt tggagccttt ttttttggaga ttttcaac
```

TABLE 19-continued pM160G12URP12, annotated

M160-G12 LC
QDIQMTQSPS FLSASVGDRV TITCRASQGI SSYLAWYQQK PGKAPKLLIY AASTLQSGVP    60

SRFSGSGSGT EFTLTISSLQ PEDFATYYCQ QLNSYPLTFG GGTKVEIK                108

```
           LC signal sequence----------------------------------
            1   2   3   4   5   6   7   8   9   10  11  12  13  14  15
            M   K   K   L   L   F   A   I   P   L   V   V   P   F   Y
      2269  atg aaa aaa tta tta ttc gca att cct tta gtt gtt cct ttc tat Signal-----      | LC Vkappa-------------------------------
            16  17  18  19  20  21  22  23  24  25  26  27  28  29  30
            S   H   S   A   Q   D   I   Q   M   T   Q   S   P   S   F
      2314  tct cac aGT GCA Caa gac atc cag atg acc cag tct cca tcc ttc
                          ApaLI...

LC Vkappa--------------------------------------------------
            31  32  33  34  35  36  37  38  39  40  41  42  43  44  45
            L   S   A   S   V   G   D   R   V   T   I   T   C   R   A
      2359  ctg tct gca tct gta gga gac aga gtc acc atc act tgc cgg gcc LC Vkappa--------------------------------------------------
            46  47  48  49  50  51  52  53  54  55  56  57  58  59  60
            S   Q   G   I   S   S   Y   L   A   W   Y   Q   Q   K   P
      2404  agt cag ggc att agc agt tat tta gcc tgg tat cag caa aaa cca LC Vkappa--------------------------------------------------
            61  62  63  64  65  66  67  68  69  70  71  72  73  74  75
            G   K   A   P   K   L   L   I   Y   A   A   S   T   L   Q
      2449  ggg aaa gcc cct aag ctc ctg atc tat gct gca tcc act ttg caa LC Vkappa--------------------------------------------------
            76  77  78  79  80  81  82  83  84  85  86  87  88  89  90
            S   G   V   P   S   R   F   S   G   S   G   S   G   T   E
      2494  agt gGG GTC CCa tca agg ttc agc ggc agt gga tct ggg aca gaa
                   SanDI....

LC Vkappa--------------------------------------------------
            91  92  93  94  95  96  97  98  99  100 101 102 103 104 105
            F   T   L   T   I   S   S   L   Q   P   E   D   F   A   T
      2539  ttc act ctc aca atc agc agc CTG CAG cct gaa gat ttt gca act
                                        PstI...

LC Vkappa--------------------------------------------------
            106 107 108 109 110 111 112 113 114 115 116 117 118 119 120
            Y   Y   C   Q   Q   L   N   S   Y   P   L   T   F   G   G
      2584  tat tac tGT CAA Cag ctt aat agt tac cct ctc act ttc ggc gga
                          HincII..

LC Vkappa-----------------  | Ckappa-----------------------
            121 122 123 124 125 126 127 128 129 130 131 132 133 134 135
            G   T   K   V   E   I   K   R   T   V   A   A   P   S   V
      2629  ggg acc aag gtg gag atc aaa cga act gtg gct gca cca tct gtc Ckappa----------------------------------------------------
            136 137 138 139 140 141 142 143 144 145 146 147 148 149 150
            F   I   F   P   P   S   D   E   Q   L   K   S   G   T   A
      2674  ttc atc ttc ccg cca tct gat gag cag ttg aaa tct gga act gcc Ckappa----------------------------------------------------
            151 152 153 154 155 156 157 158 159 160 161 162 163 164 165
            S   V   V   C   L   L   N   N   F   Y   P   R   E   A   K
      2719  tct gtt gtg tgc ctg ctg aat aac ttc tat ccc aga gag gcc aaa Ckappa----------------------------------------------------
            166 167 168 169 170 171 172 173 174 175 176 177 178 179 180
            V   Q   W   K   V   D   N   A   L   Q   S   G   N   S   Q
      2764  gta cag tgg aag gtg gat aac gcc ctc caa tcg ggt aac tcc cag Ckappa----------------------------------------------------
            181 182 183 184 185 186 187 188 189 190 191 192 193 194 195
            E   S   V   T   E   Q   D   S   K   D   S   T   Y   S   L
      2809  gag agt gtc aca gag cag gac agc aag gac agc acc tac agc ctc
```

TABLE 19-continued pM160G12URP12, annotated

```
      Ckappa----------------------------------------------------
      196 197 198 199 200 201 202 203 204 205 206 207 208 209 210
       S   S   T   L   T   L   S   K   A   D   Y   E   K   H   K
2854  agc agc acc ctg acG CTG AGC aaa gca gac tac gag aaa cac aaa
                          BlpI Ckappa----------------------------------------------------
      211 212 213 214 215 216 217 218 219 220 221 222 223 224 225
       V   Y   A   C   E   V   T   H   Q   G   L   S   S   P   V
2899  GTC TAC gcc tgc gaa gtc acc cat cag ggc ctg agt tca ccg gtg
      AccI...

Ckappa------------------------- ! URP------------------
      226 227 228 229 230 231 232 233 234 235 236 237 238 239 240
       T   K   S   F   N   R   G   E   C   G   T   A   S   T   A
2944  aca aag agc ttc aac agg gga gag tgt GGT ACC gct tct act gcc
                                              KpnI...

URP-------------------------------------------------------
      241 242 243 244 245 246 247 248 249 250 251 252 253 254 255
       T   T   G   P   A   P   T   E   S   P   A   P   G   P   S
2989  acc act ggt cct gct cct act gaa tcc cct gct ccg ggt cct tct URP-------------------------------------------------------
      256 257 258 259 260 261 262 263 264 265 266 267 268 269 270
       G   A   P   G   S   T   G   P   G   E   P   S   P   S   E
3034  ggt gct cct ggc tct act ggt cct ggt gag ccg agt cct agt gaa URP-------------------------------------------------------
      271 272 273 274 275 276 277 278 279 280 281 282 283 284 285
       A   T   T   P   A   P   G   T   P   S   P   T   S   G   P
3079  gcc acc act cct gct cct ggt act ccg tct cct act tcc ggc cct URP-------------------------------------------------------
      286 287 288 289 290 291 292 293 294 295 296 297 298 299 300
       E   G   A   T   G   E   G   A   A   G   E   P   P   P   S
3124  gag ggt gct acc ggt gaa ggt gct gcc ggc gag cct ccg cct tct URP-------------------------------------------------------
      301 302 303 304 305 306 307 308 309 310 311 312 313 314 315
       G   T   G   P   A   A   A   S   P   G   G   P   P   G   E
3169  ggt act ggt cct gct gct gct tct cct ggt ggc ccg cct ggt gaa URP-------------------------------------------------------
      316 317 318 319 320 321 322 323 324 325 326 327 328 329 330
       T   A   S   G   P   A   S   T   G   G   T   G   S   T   A
3214  act gcc agt ggt cct gct agt act ggt ggc acc ggt tct act gct URP-------------------------------------------------------
      331 332 333 334 335 336 337 338 339 340 341 342 343 344 345
       T   P   T   S   S   A   E   S   P   A   G   T   E   P   S
3259  act cct act tcc tct gct gag tct ccg gcc ggt act gaa cct agt URP-------------------------------------------------------
      346 347 348 349 350 351 352 353 354 355 356 357 358 359 360
       S   G   P   E   E   P   S   E   E   P   A   T   E   A   A
3304  agt ggt cct gag gaa cct tct gag gaa ccg gct act gag gct gct URP-------------------------------------------------------
      361 362 363 364 365 366 367 368 369 370 371 372 373 374 375
       G   G   T   T   T   E   A   S   G   T   T   G   T   S   E
3349  ggc ggt act act acc gaa gcc tcc ggt act act ggt act tct gag URP-------------------------------------------------------
      376 377 378 379 380 381 382 383 384 385 386 387 388 389 390
       T   A   S   P   E   E   E   A   P   S   A   S   A   T   P
3394  acc gct tct cct gaa gag gaa gct cct agt gct agt gcc act cct URP-------------------------------------------------------
      391 392 393 394 395 396 397 398 399 400 401 402 403 404 405
       G   E   T   G   T   P   E   P   G   A   P   G   T   P   P
3439  ggc gag act ggt act ccg gaa cct ggt gct cct ggt act cct ccg URP-------------------------------------------------------
      406 407 408 409 410 411 412 413 414 415 416 417 418 419 420
       T   G   A   G   S   S   E   P   A   G   S   G   G   S   G
3484  act ggc gct ggt tct tcc gag cct gct ggt tct ggt ggc tct ggt
```

TABLE 19-continued pM160G12URP12, annotated

```
        URP------------------------------------------------------------
        421 422 423 424 425 426 427 428 429 430 431 432 433 434 435
         S   T   P   A   S   E   A   S   S   S   P   A   S   T   A
3529    agt act cct gcc agt gag gct tct tcc tct cct gct tct act gct URP----------------------------------------
        436 437 438 439 440 441 442 443 444 445 446 447 448
         G   S   S   T   A   G   E   E   P   P   P   .   .
3574    ggt agt agt acc gcc ggt gag gaa ccg cct cct taa taa 3613    GGCG CGCCtaacca tctatttcaa
        AscI.....
         BssHII 3637    ggaacagtct ta M160-G12 HC
EVQLLESGGG LVQPGGSLRL SCAASGFTFS HYLMTWVRQA PGKGLEWVSY ISPSGGHTIY       60

ADSVKGRFTI SRDNSKNTLY LQMNSLRAED TAVYYCARVA RGIAARSRTS YFDYWGQGTL      120

VTVSSASTKG PSVFPLAPSS KS                                               142

HC signal sequence---------------------------------------
          1   2   3   4   5   6   7   8   9  10  11  12  13  14  15
          M   K   K   L   L   F   M   I   P   L   V   V   P   F   V
3649    atg aaa aag ctt tta ttc atg atc ccg tta gtt gtt ccg ttc gtG
                                                                SfiI signal sequence--------|--- VH----------------------------
         16  17  18  19  20  21  22  23  24  25  26  27  28  29  30
          A   Q   P   A   M   A   E   V   Q   L   L   E   S   G   G
3694    GCC CAG CCG GCC atg gcc gaa gtt CAA TTG tta gag tct ggt ggc
        SfiI...........             MfeI...
            NcoI....

VH--------------------------------------------------------
         31  32  33  34  35  36  37  38  39  40  41  42  43  44  45
          G   L   V   Q   P   G   G   S   L   R   L   S   C   A   A
3739    ggt ctt gtt cag cct ggt ggt tct tta cgt ctt tct tgc gct gct VH--------------------------------------------------------
         46  47  48  49  50  51  52  53  54  55  56  57  58  59  60
          S   G   F   T   F   S   H   Y   L   M   T   W   V   R   Q
3784    tcc gga ttc act ttc tct cat tac ctt atg act tgg gtt cgc caa 61  62  63  64  65  66  67  68  69  70  71  72  73  74  75
          A   P   G   K   G   L   E   W   V   S   Y   I   S   P   S
3829    gct cct ggt aaa ggt ttg gag tgg gtt tct tat atc tct cct tct VH--------------------------------------------------------
         76  77  78  79  80  81  82  83  84  85  86  87  88  89  90
          G   G   H   T   I   Y   A   D   S   V   K   G   R   F   T
3874    ggt ggc cat act att tat gct gac tcc gtt aaa ggt cgc ttc act VH--------------------------------------------------------
         91  92  93  94  95  96  97  98  99 100 101 102 103 104 105
          I   S   R   D   N   S   K   N   T   L   Y   L   Q   M   N
3919    atc TCT AGA gac aac tct aag aat act ctc tac ttg cag atg aac
            XbaI...

VH--------------------------------------------------------
        106 107 108 109 110 111 112 113 114 115 116 117 118 119 120
          S   L   R   A   E   D   T   A   V   Y   Y   C   A   R   V
3964    agc tta agg gct gag gac acg gcc gtg tat tac tgt gcg aga gtg VH--------------------------------------------------------
        121 122 123 124 125 126 127 128 129 130 131 132 133 134 135
          A   R   G   I   A   A   R   S   R   T   S   Y   F   D   Y
4009    gCC CGG Ggg ata gca gct cga TCG CGA acc agc tac ttt gac tac
        XmaI....                    NruI...

VH--------------------------------------------------------
        136 137 138 139 140 141 142 143 144 145 146 147 148 149 150
          W   G   Q   G   T   L   V   T   V   S   S   A   S   T   K
4054    tgg ggc cag gga acc ctG GTC ACC gtc tca agc gcc tcc acc aaG
                                BstEII...                   Bsp120I .
```

TABLE 19-continued pM160G12URP12, annotated

```
      151 152 153 154 155 156 157 158 159 160 161 162 163 164 165
       G   P   S   V   F   P   L   A   P   S   S   K   S   T   S
4099  GGC CCa tcg gtc ttc ccG CTA GCa ccc tcc tcc aag agc acc tct
      Bsp120I.              NheI....

166 167 168 169 170 171 172 173 174 175 176 177 178 179 180
       G   G   T   A   A   L   G   C   L   V   K   D   Y   F   P
4144  ggg ggc aca gcg gcc ctg ggc tgc ctg gtc aag gac tac ttc ccc 181 182 183 184 185 186 187 188 189 190 191 192 193 194 195
       E   P   V   T   V   S   W   N   S   G   A   L   T   S   G
4189  gaa ccg gtg acg gtg tcg tgg aac tca ggc gcc ctg acc agc ggc 196 197 198 199 200 201 202 203 204 205 206 207 208 209 210
       V   H   T   F   P   A   V   L   Q   S   S   G   L   Y   S
4234  gtc cac acc ttc ccg gct gtc cta cag tct agc gga ctc tac tcc 211 212 213 214 215 216 217 218 219 220 221 222 223 224 225
       L  S   S   V   V   T   V   P   S   S   S   L   G   T   Q
4279  ctc agc agc gta gtg acc gtg ccc tct tct agc ttg ggc acc cag 226 227 228 229 230 231 232 233 234 235 236 237 238 239 240
       T   Y   I   C   N   V   N   H   K   P   S   N   T   K   V
4324  acc tac atc tgc aac gtg aat cac aag ccc agc aac acc aag gtg URP------------------>
      241 242 243 244 245 246 247 248 249 250 251 252 253 254 255
       D   K   K   V   E   P   K   S   C   A   A   A   S   P   A
4369  gac aag aaa gtt gag ccc aaa tct tgt GCG GCC GCt tct cct gct
                                              NotI 256 257 258 259 260 261 262 263 264 265 266 267 268 269 270
       T   A   S   A   S   T   A   P   A   T   A   T   P   E   S
4414  act gct tcc gct tct act gcc ccg gct act gct acc cct gag tct 271 272 273 274 275 276 277 278 279 280 281 282 283 284 285
       A   E   G   A   T   T   E   T   P   T   T   E   T   P   A
4459  gct gaa ggc gcc act act gag act cct acc act gaa act cct gct 286 287 288 289 290 291 292 293 294 295 296 297 298 299 300
       E   S   A   S   G   P   P   A   P   S   E   S   A   T   E
4504  gag agt gct agt ggt ccg cct gct cct tct gaa tcc gcc act gag 301 302 303 304 305 306 307 308 309 310 311 312 313 314 315
       E   S   G   E   A   S   T   S   S   T   A   E   G   P
4549  gaa tct ggt gag gct tct acc agt agt act gct gaa gag ggt cct 316 317 318 319 320 321 322 323 324 325 326 327 328 329 330
       A   E   P   G   S   P   A   P   T   P   A   A   T   P   A
4594  gct gaa ccg ggc tct cct gcc cct act cct gct gct act ccg gct 331 332 333 334 335 336 337 338 339 340 341 342 343 344 345
       E   T   S   S   E   P   P   E   E   P   G   G   A   G   T
4639  gag acc tcc tct gaa cct cct gag gaa cct ggt ggt gcc ggt act 346 347 348 349 350 351 352 353 354 355 356 357 358 359 360
       P   A   G   T   T   T   G   A   E   T   E   S   A   T   E
4684  ccg gct ggc act act acc ggt gct gag act gaa tct gct act gag 361 362 363 364 365 366 367 368 369 370 371 372 373 374 375
       G   G   A   S   S   A   P   A   S   P   T   G   G   A   P
4729  ggt ggt gcc agt agt gct cct gct tct cct act ggc ggt gct cct 376 377 378 379 380 381 382 383 384 385 386 387 388 389 390
       S   S   G   E   T   T   T   E   G   G   P   A   G   P   A
4774  tcc tct ggt gaa acc act act gag ggt ggc ccg gcc ggt cct gct 391 392 393 394 395 396 397 398 399 400 401 402 403 404 405
       P   A   T   A   A   P   T   G   G   G   A   G   G   E   G
4819  cct gct act gct gcc cct acc ggt ggt ggc gct ggt ggt gaa ggt 406 407 408 409 410 411 412 413 414 415 416 417 418 419 420
       S   A   G   G   G   T   G   E   E   G   G   G   G   A   P
4864  tct gct ggc ggt ggt act ggt gag gaa ggc ggt ggt ggt gct ccg
```

TABLE 19-continued pM160G12URP12, annotated

```
       421 422 423 424 425 426 427 428 429 430 431 432 433 434 435
        E   G   S   G   G   G   P   E   G   P   T   P   A   T   E
4909   gag ggc agt ggt ggt ggt cct gaa ggc cct act cct gcc act gag 436 437 438 439 440 441 442 443 444 445 446 447 448 449 450
        A   S   P   E   G   A   P   P   G   S   T   S   T   S   G
4954   gct agt ccg gaa ggt gct cct cct ggt tct acc tcc act tct ggt 451 452 453 454 455 456 457 458 459 460 461 462 463
        P   G   E   A   A   S   P   T   S   S   P   G   .
4999   cct ggc gag gct gcc tct ccg ACT AGT agt cct ggt taa
                                  SpeI...

5038   tga taa 5044   aACGC GTgatgaga attcactggc cgtcgtttta caacgtcgtg actgggaaaa
       MluI...

5098   ccctggcgtt acccaactta atcgccttgc agcacatccc cctttcgcca gctggcgtaa 5158   tagcgaagag gcccgcaccg atcgccttc ccaacagttg cgcagcctga atggcgaatg 5218   gcgcctgatg cggtattttc tccttacgca tctgtgcggt atttcacacc gcatacgtca 5278   aagcaaccat agtacgcgcc ctgtagcggc gcattaagcg cggcgggtgt ggtggttacg 5338   cgcagcgtga ccgctacact tgccagcgcc ttagcgcccg ctcctttcgc tttcttccct 5398   tcctttctcg ccacgttcgc cggctttccc cgtcaagctc taaatcgggg gctcccttta 5458   gggttccgat ttagtgcttt acggcacctc gaccccaaaa aacttgattt gggtgatggt 5518   tCACGTAgtg ggccatcgcc ctgatagacg gttttcgcc ctttgacgtt ggagtccacg
       BsaAI.
       DraIII...

5578   ttctttaata gtggactctt gttccaaact ggaacaacac tcaactctat ctcgggctat 5638   tcttttgatT TATAAgggat tttgccgatt tcggtctatt ggttaaaaaa tgagctgatt
                    PsiI...

5698   taacaaaaat ttaacgcgaa ttttaacaaa atattaacgt ttacaatttt atggtgcagt 5758   ctcagtacaa tctgctctga tgccgcatag ttaagccagc cccgacaccc gccaacaccc 5818   gctgacgcgc cctgacgggc ttgtctgctc ccggcatccg cttacagaca agctgtgacc 5878   gtctccggga gctgcatgtg tcagaggttt tcaccgtcat caccgaaacg cgcga
```

TABLE 20 unannotated DNA sequence of pM160G12:URP12

```
LOCUS pM160G12 5932 CIRCULAR
M160-G12_URP1-2 5926 bp DNA circular
ORIGIN
     1  GACGAAAGGG CCTCGTGATA CGCCTATTTT TATAGGTTAA TGTCATGATA ATAATGGTTT

61  CTTAGACGTC AGGTGGCACT TTTCGGGGAA ATGTGCGCGG AACCCCTATT TGTTTATTTT

121  TCTAAATACA TTCAAATATG TATCCGCTCA TGAGACAATA ACCCTGATAA ATGCTTCAAT

181  AATATTGAAA AAGGAAGAGT ATGAGTATTC AACATTTCCG TGTCGCCCTT ATTCCCTTTT

241  TTGCGGCATT TGCCTTCCT GTTTTTGCTC ACCCAGAAAC GCTGGTGAAA GTAAAAGATG

301  CTGAAGATCA GTTGGGTGCC CGAGTGGGTT ACATCGAACT GGATCTCAAC AGCGGTAAGA

361  TCCTTGAGAG TTTTCGCCCC GAAGAACGTT TTCCAATGAT GAGCACTTTT AAAGTTCTGC

421  TATGTGGCGC GGTATTATCC CGTATTGACG CCGGGCAAGA GCAACTCGGT CGCCGCATAC

481  ACTATTCTCA GAATGACTTG GTTGAGTACT CACCAGTCAC AGAAAAGCAT CTTACGGATG
```

TABLE 20-continued

| unannotated DNA sequence of pM16OG12:URP12 |
|---|

```
 541  GCATGACAGT AAGAGAATTA TGCAGTGCTG CCATAACCAT GAGTGATAAC ACTGCGGCCA
 601  ACTTACTTCT GACAACGATC GGAGGACCGA AGGAGCTAAC CGCTTTTTTG CACAACATGG
 661  GGGATCATGT AACTCGCCTT GATCGTTGGG AACCGGAGCT GAATGAAGCC ATACCAAACG
 721  ACGAGCGTGA CACCACGATG CCTGTAGCAA TGGCAACAAC GTTGCGCAAA CTATTAACTG
 781  GCGAACTACT TACTCTAGCT TCCCGGCAAC AATTAATAGA CTGGATGGAG GCGGATAAAG
 841  TTGCAGGACC ACTTCTGCGC TCGGCCCTTC CGGCTGGCTG GTTTATTGCT GATAAATCTG
 901  GAGCCGGTGA GCGTGGGTCT CGCGGTATCA TTGCAGCACT GGGGCCAGAT GGTAAGCCCT
 961  CCCGTATCGT AGTTATCTAC ACGACGGGGA GTCAGGCAAC TATGGATGAA CGAAATAGAC
1021  AGATCGCTGA GATAGGTGCC TCACTGATTA AGCATTGGTA ACTGTCAGAC CAAGTTTACT
1081  CATATATACT TTAGATTGAT TTAAAACTTC ATTTTTAATT TAAAAGGATC TAGGTGAAGA
1141  TCCTTTTTGA TAATCTCATG ACCAAAATCC CTTAACGTGA GTTTTCGTTC CACTGAGCGT
1201  CAGACCCCGT AGAAAAGATC AAAGGATCTT CTTGAGATCC TTTTTTTCTG CGCGTAATCT
1261  GCTGCTTGCA AACAAAAAAA CCACCGCTAC CAGCGGTGGT TTGTTTGCCG GATCAAGAGC
1321  TACCAACTCT TTTTCCGAAG GTAACTGGCT TCAGCAGAGC GCAGATACCA AATACTGTTC
1381  TTCTAGTGTA GCCGTAGTTA GGCCACCACT TCAAGAACTC TGTAGCACCG CCTACATACC
1441  TCGCTCTGCT AATCCTGTTA CCAGTGGCTG CTGCCAGTGG CGATAAGTCG TGTCTTACCG
1501  GGTTGGACTC AAGACGATAG TTACCGGATA AGGCGCAGCG GTCGGGCTGA ACGGGGGGTT
1561  CGTGCATACA GCCCAGCTTG GAGCGAACGA CCTACACCGA ACTGAGATAC CTACAGCGTG
1621  AGCTATGAGA AAGCGCCACG CTTCCCGAAG GGAGAAAGGC GGACAGGTAT CCGGTAAGCG
1681  GCAGGGTCGG AACAGGAGAG CGCACGAGGG AGCTTCCAGG GGGAAACGCC TGGTATCTTT
1741  ATAGTCCTGT CGGGTTTCGC CACCTCTGAC TTGAGCGTCG ATTTTTGTGA TGCTCGTCAG
1801  GGGGGCGGAG CCTATGGAAA AACGCCAGCA ACGCGGCCTT TTTACGGTTC CTGGCCTTTT
1861  GCTGGCCTTT TGCTCACATG TTCTTTCCTG CGTTATCCCC TGATTCTGTG GATAACCGTA
1921  TTACCGCCTT TGAGTGAGCT GATACCGCTC GCCGCAGCCG AACGACCGAG CGCAGCGAGT
1981  CAGTGAGCGA GGAAGCGGAA GAGCGCCCAA TACGCAAACC GCCTCTCCCC GCGCGTTGGC
2041  CGATTCATTA ATGCAGCTGG CACGACAGGT TTCCCGACTG GAAAGCGGGC AGTGAGCGCA
2101  ACGCAATTAA TGTGAGTTAG CTCACTCATT AGGCACCCCA GGCTTTACAC TTTATGCTTC
2161  CGGCTCGTAT GTTGTGTGGA ATTGTGAGCG GATAACAATT TCACACAGGA AACAGCTATG
2221  ACCATGATTA CGCCAAGCTT TGGAGCCTTT TTTTTGGAGA TTTTCAACAT GAAAAAATTA
2281  TTATTCGCAA TTCCTTTAGT TGTTCCTTTC TATTCTCACA GTGCACAAGA CATCCAGATG
2341  ACCCAGTCTC CATCCTTCCT GTCTGCATCT GTAGGAGACA GAGTCACCAT CACTTGCCGG
2401  GCCAGTCAGG GCATTAGCAG TTATTTAGCC TGGTATCAGC AAAAACCAGG GAAAGCCCCT
2461  AAGCTCCTGA TCTATGCTGC ATCCACTTTG CAAAGTGGGG TCCCATCAAG GTTCAGCGGC
2521  AGTGGATCTG GGACAGAATT CACTCTCACA ATCAGCAGCC TGCAGCCTGA AGATTTTGCA
2581  ACTTATTACT GTCAACAGCT TAATAGTTAC CCTCTCACTT TCGGCGGAGG GACCAAGGTG
2641  GAGATCAAAC GAACTGTGGC TGCACCATCT GTCTTCATCT TCCCGCCATC TGATGAGCAG
2701  TTGAAATCTG GAACTGCCTC TGTTGTGTGC CTGCTGAATA ACTTCTATCC CAGAGAGGCC
2761  AAAGTACAGT GGAAGGTGGA TAACGCCCTC CAATCGGGTA ACTCCCAGGA GAGTGTCACA
2821  GAGCAGGACA GCAAGGACAG CACCTACAGC CTCAGCAGCA CCCTGACGCT GAGCAAAGCA
```

TABLE 20-continued unannotated DNA sequence of pM160G12:URP12

| | |
|---|---|
| 2881 | GACTACGAGA AACACAAAGT CTACGCCTGC GAAGTCACCC ATCAGGGCCT GAGTTCACCG |
| 2941 | GTGACAAAGA GCTTCAACAG GGGAGAGTGT GGTACCGCTT CTACTGCCAC CACTGGTCCT |
| 3001 | GCTCCTACTG AATCCCCTGC TCCGGGTCCT TCTGGTGCTC CTGGCTCTAC TGGTCCTGGT |
| 3061 | GAGCCGAGTC CTAGTGAAGC CACCACTCCT GCTCCTGGTA CTCCGTCTCC TACTTCCGGC |
| 3121 | CCTGAGGGTG CTACCGGTGA AGGTGCTGCC GGCGAGCCTC CGCCTTCTGG TACTGGTCCT |
| 3181 | GCTGCTGCTT CTCCTGGTGG CCCGCCTGGT GAAACTGCCA GTGGTCCTGC TAGTACTGGT |
| 3241 | GGCACCGGTT CTACTGCTAC TCCTACTTCC TCTGCTGAGT CTCCGGCCGG TACTGAACCT |
| 3301 | AGTAGTGGTC CTGAGGAACC TTCTGAGGAA CCGGCTACTG AGGCTGCTGG CGGTACTACT |
| 3361 | ACCGAAGCCT CCGGTACTAC TGGTACTTCT GAGACCGCTT CTCCTGAAGA GGAAGCTCCT |
| 3421 | AGTGCTAGTG CCACTCCTGG CGAGACTGGT ACTCCGGAAC CTGGTGCTCC TGGTACTCCT |
| 3481 | CCGACTGGCG CTGGTTCTTC CGAGCCTGCT GGTTCTGGTG CTCTGGTAG TACTCCTGCC |
| 3541 | AGTGAGGCTT CTTCCTCTCC TGCTTCTACT GCTGGTAGTA GTACCGCCGG TGAGGAACCG |
| 3601 | CCTCCTTAAT AAGGCGCGCC TAACCATCTA TTTCAAGGAA CAGTCTTAAT GAAAAAGCTT |
| 3661 | TTATTCATGA TCCCGTTAGT TGTACCGTTC GTGGCCCAGC CGGCCATGGC CGAAGTTCAA |
| 3721 | TTGTTAGAGT CTGGTGGCGG TCTTGTTCAG CCTGGTGGTT CTTTACGTCT TTCTTGCGCT |
| 3781 | GCTTCCGGAT TCACTTTCTC TCATTACCTT ATGACTTGGG TTCGCCAAGC TCCTGGTAAA |
| 3841 | GGTTTGGAGT GGGTTTCTTA TATCTCTCCT TCTGGTGGCC ATACTATTTA TGCTGACTCC |
| 3901 | GTTAAAGGTC GCTTCACTAT CTCTAGAGAC AACTCTAAGA ATACTCTCTA CTTGCAGATG |
| 3961 | AACAGCTTAA GGGCTGAGGA CACGGCCGTG TATTACTGTG CGAGAGTGGC CCGGGGGATA |
| 4021 | GCAGCTCGAT CGCGAACCAG CTACTTTGAC TACTGGGGCC AGGGAACCCT GGTCACCGTC |
| 4081 | TCAAGCGCCT CCACCAAGGG CCCATCGGTC TTCCCGCTAG CACCCTCCTC CAAGAGCACC |
| 4141 | TCTGGGGGCA CAGCGGCCCT GGGCTGCCTG GTCAAGGACT ACTTCCCCGA ACCGGTGACG |
| 4201 | GTGTCGTGGA ACTCAGGCGC CCTGACCAGC GGCGTCCACA CCTTCCCGGC TGTCCTACAG |
| 4261 | TCTAGCGGAC TCTACTCCCT CAGCAGCGTA GTGACCGTGC CCTCTTCTAG CTTGGGCACC |
| 4321 | CAGACCTACA TCTGCAACGT GAATCACAAG CCCAGCAACA CCAAGGTGGA CAAGAAAGTT |
| 4381 | GAGCCCAAAT CTTGTGCGGC CGCTTCTCCT GCTACTGCTT CCGCTTCTAC TGCCCCGGCT |
| 4441 | ACTGCTACCC CTGAGTCTGC TGAAGGCGCC ACTACTGAGA CTCCTACCAC TGAAACTCCT |
| 4501 | GCTGAGAGTG CTAGTGGTCC GCCTGCTCCT TCTGAATCCG CCACTGAGGA ATCTGGTGAG |
| 4561 | GCTTCTACCA GTAGTACTGC TGAAGAGGGT CCTGCTGAAC CGGGCTCTCC TGCCCCTACT |
| 4621 | CCTGCTGCTA CTCCGGCTGA GACCTCCTCT GAACCTCCTG AGGAACCTGG TGGTGCCGGT |
| 4681 | ACTCCGGCTG GCACTACTAC CGGTGCTGAG ACTGAATCTG CTACTGAGGG TGGTGCCAGT |
| 4741 | AGTGCTCCTG CTTCTCCTAC TGGCGGTGCT CCTTCCTCTG GTGAAACCAC TACTGAGGGT |
| 4801 | GGCCCGGCCG GTCCTGCTCC TGCTACTGCT GCCCCTACCG GTGGTGGCGC TGGTGGTGAA |
| 4861 | GGTTCTGCTG GCGGTGGTAC TGGTGAGGAA GGCGGTGGTG GTGCTCCGGA GGGCAGTGGT |
| 4921 | GGTGGTCCTG AAGGCCCTAC TCCTGCCACT GAGGCTAGTC CGGAAGGTGC TCCTCCTGGT |
| 4981 | TCTACCTCCA CTTCTGGTCC TGGCGAGGCT GCCTCTCCGA CTAGTAGTCC TGGTTAATGA |
| 5041 | TAAAACGCGT GATGAGAATT CACTGGCCGT CGTTTTACAA CGTCGTGACT GGGAAAACCC |
| 5101 | TGGCGTTACC CAACTTAATC GCCTTGCAGC ACATCCCCCT TTCGCCAGCT GGCGTAATAG |
| 5161 | CGAAGAGGCC CGCACCGATC GCCCTTCCCA ACAGTTGCGC AGCCTGAATG GCGAATGGCG |

TABLE 20-continued unannotated DNA sequence of pM160G12:URP12

```
5221  CCTGATGCGG TATTTTCTCC TTACGCATCT GTGCGGTATT TCACACCGCA TACGTCAAAG

5281  CAACCATAGT ACGCGCCCTG TAGCGGCGCA TTAAGCGCGG CGGGTGTGGT GGTTACGCGC

5341  AGCGTGACCG CTACACTTGC CAGCGCCTTA GCGCCCGCTC CTTTCGCTTT CTTCCCTTCC

5401  TTTCTCGCCA CGTTCGCCGG CTTTCCCCGT CAAGCTCTAA ATCGGGGCT  CCCTTTAGGG

5461  TTCCGATTTA GTGCTTTACG GCACCTCGAC CCCAAAAAAC TTGATTTGGG TGATGGTTCA

5521  CGTAGTGGGC CATCGCCCTG ATAGACGGTT TTTCGCCCTT TGACGTTGGA GTCCACGTTC

5581  TTTAATAGTG GACTCTTGTT CCAAACTGGA ACAACACTCA ACTCTATCTC GGGCTATTCT

5641  TTTGATTTAT AAGGGATTTT GCCGATTTCG GTCTATTGGT TAAAAAATGA GCTGATTTAA

5701  CAAAATTTA  ACGCGAATTT TAACAAAATA TTAACGTTTA CAATTTTATG GTGCAGTCTC

5761  AGTACAATCT GCTCTGATGC CGCATAGTTA AGCCAGCCCC GACACCCGCC AACACCCGCT

5821  GACGCGCCCT GACGGGCTTG TCTGCTCCCG GCATCCGCTT ACAGACAAGC TGTGACCGTC

5881  TCCGGGAGCT GCATGTGTCA GAGGTTTTCA CCGTCATCAC CGAAACGCGC GA
```

TABLE 21

Examples of human Glycine Rich Sequences (GRS) for use in designing human-specific URPs

| Accession | Gly (%) | GRS length | Gene length | Hydro-phobics | Predicted Function |
|---|---|---|---|---|---|
| NP_000217 | 62 | 135 | 622 | Yes | keratin 9 |
| NP_631961 | 61 | 73 | 592 | Yes | TBP-associated factor 15 isoform 1 |
| NP_476429 | 65 | 70 | 629 | Yes | keratin 3 |

TABLE 21-continued

Examples of human Glycine Rich Sequences (GRS) for use in designing human-specific URPs

| Accession | Gly (%) | GRS length | Gene length | Hydro-phobics | Predicted Function |
|---|---|---|---|---|---|
| NP_000418 | 70 | 66 | 316 | Yes | loricrin, cell envelope |
| NP_056932 | 60 | 66 | 638 | Yes | cytokeratin 2 |

TABLE 22

Additional examples of human Glycine Rich Sequences for use in designing human-specific URPs

| Accession | Sequences | Number of amino acids |
|---|---|---|
| NP_006228 | GPGGGGGPGGGGPGGGGPGGGGGGPGGGGGGPGGG | 37 |
| NP_787059 | GAGGGGGGGGGGGGGSGGGGGGGGAGAGGAGAG | 33 |
| NP_009060 | GGGSGSGGAGGGSGGGSGSGGGGGGAGGGGGG | 32 |
| NP_031393 | GDGGGAGGGGGGGSGGGGSGGGGGGG | 27 |
| NP_005850 | GSGSGSGGGGGGGGGGGSGGGGGG | 25 |
| NP_061856 | GGGRGGRGGGRGGGGRGGGRGGG | 22 |
| NP_787059 | GAGGGGGGGGGGGGGSGGGGGGGGAGAGGAGAG | 33 |
| NP_009060 | GGGSGSGGAGGGSGGGSGSGGGGGGAGGGGGG | 32 |
| NP_031393 | GDGGGAGGGGGGGSGGGGSGGGGGGG | 27 |
| NP_115818 | GSGGSGGSGGGPGPGPGGGGG | 21 |
| XP_376532 | GEGGGGGEGGGAGGGSG | 18 |
| NP_065104 | GGGGGGGGDGGG | 12 |

GGGSGSGGAGGGSGGGSGSGGGGGGAGGGGGGSSGGGSGTAGGHSG
POU domain, class 4, transcription factor 1 [Homo sapiens]

GPGGGGGPGGGGPGGGGPGGGGGGPGGGGGGPGGG
YEATS domain containing 2 [Homo sapiens]

TABLE 22-continued

Additional examples of human Glycine Rich Sequences for use in designing human-specific URPs GGSGAGGGGGGGGGGGSGSGGGGSTGGGGGTAGGG
AT rich interactive domain 1B (SWI1-like) isoform 3; BRG1-binding
protein ELD/OSA1; Eld (eyelid)/Osa protein [Homo sapiens]

GAGGGGGGGGGGGGGSGGGGGGGGGAGAGGAGAG
AT rich interactive domain 1B (SWI1-like) isoform 2; BRG1-binding
protein ELD/OSA1; Eld (eyelid)/Osa protein [Homo sapiens]

GAGGGGGGGGGGGGGSGGGGGGGGGAGAGGAGAG
AT rich interactive domain 1B (SWI1-like) isoform 1; BRG1-binding
protein ELD/OSA1; Eld (eyelid)/Osa protein [Homo sapiens]

GAGGGGGGGGGGGGGSGGGGGGGGGAGAGGAGAG
purine-rich element binding protein A; purine-rich single-stranded DNA-binding
protein alpha; transcriptional activator protein PUR-alpha [Homo sapiens]

GHPGSGSGSGGGGGGGGGGGSGGGGGGAPGG
regulatory factor X1; trans-acting regulatory factor 1; enhancer factor C;
MHC class II regulatory factor RFX [Homo sapiens]

GGGGSGGGGGGGGGGGGGSGSTGGGGS GAG
bromo domain-containing protein disrupted in leukemia [Homo sapiens]

GGRGRGGRGRGSRGRGGGGTRGRGRGRGGRG
unknown protein [Homo sapiens]

GSGGSGGSGGGPGPGPGGGGGPSGSGSGPG
PREDICTED: hypothetical protein XP_059256 [Homo sapiens]

GGGGGGGGGGGRGGGGRGGGRGGGGEGGG
zinc finger protein 281; ZNP-99 transcription factor [Homo sapiens]

GGGGTGSSGGSGSGGGGSGGGGGGSSG
RNA binding protein (autoantigenic, hnRNP-associated with lethal yellow)
short isoform; RNA-binding protein (autoantigenic); RNA-binding protein
(autoantigenic, hnRNP-associated with lethal yellow) [Homo sapiens]

GDGGGAGGGGGGGGSGGGGSGGGGGG
signal recognition particle 68 kDa [Homo sapiens]

GGGGGGGSGGGGGSGGGGSGGGRGAGG
KIAA0265 protein [Homo sapiens]

GGGAAGAGGGGSGAGGGSGGSGGRGTG
engrailed homolog 2; Engrailed-2 [Homo sapiens]

GAGGGRGGGAGGEGGASGAEGGGGAGG
RNA binding protein (autoantigenic, hnRNP-associated with lethal yellow)
long isoform; RNA-binding protein (autoantigenic);
RNA-binding protein (autoantigenic, hnRNP-associated with lethal yellow)
[Homo sapiens]

GDGGGAGGGGGGGSGGGGSGGGGGG
androgen receptor; dihydrotestosterone receptor [Homo sapiens]

GGGGGGGGGGGGGGGGGGGGGEAG
homeo box D11; homeo box 4F; Hox-4.6, mouse, homolog of; homeobox protein
Hox-D11 [Homo sapiens]

GGGGGGSAGGGSSGGGPGGGGGGAGG
frizzled 8; frizzled (Drosophila) homolog 8 [Homo sapiens]

GGGGGPGGGGGGGPGGGGGPGGGGG
ocular development-associated gene [Homo sapiens]

GRGGAGSGGAGSGAAGGTGSSGGGG
homeo box B3; homeo box 2G; homeobox protein Hox-B3 [Homo sapiens]

GGGGGGGGGGGSGGSGGGGGGGGGG
chromosome 2 open reading frame 29 [Homo sapiens]

GGSGGGRGGASGPGSGSGGPGGPAG
DKFZP564F0522 protein [Homo sapiens]

GGHHGDRGGGRGGRGGRGGRGGRAG
PREDICTED: similar to Homeobox even-skipped homolog protein 2 (EVX-2)
[Homo sapiens]

TABLE 22-continued

Additional examples of human Glycine Rich Sequences for use in designing human-specific URPs GSRGGGGGGGGGGGGGGGAGAGGG
ras homolog gene family, member U; Ryu GTPase; Wnt-1 responsive Cdc42 homolog;
2310026M05Rik; GTP-binding protein like 1; CDC42-like GTPase [Homo sapiens]

GGRGGRGPGEPGGRGRAGGAEGRG
scratch 2 protein; transcriptional repressor scratch 2; scratch (drosophila
homolog) 2, zinc finger protein [Homo sapiens]

GGGGGDAGGSGDAGGAGGRAGRAG
nucleolar protein family A, member 1; GAR1 protein [Homo sapiens]

GGGRGGRGGGRGGGRGGGRGGG
keratin 1; Keratin-1; cytokeratin 1; hair alpha protein [Homo sapiens]

GGSGGGGGSSGGRGSGGGSSGG
hypothetical protein FLJ31413 [Homo sapiens]

GSGPGTGGGGSGSGGGGGSGGG
one cut domain, family member 2; onecut 2 [Homo sapiens]

GARGGGSGGGGGGGGGGGGGPG
POU domain, class 3, transcription factor 2 [Homo sapiens]

GGGGGGGGGGGGGGGGGGGGDG
PREDICTED: similar to THO complex subunit 4 (Tho4) (RNA and export factor
binding protein 1) (REF1-I) (Ally of AML-1 and LEF-1) (Aly/REF) [Homo sapiens]

GGTRGGTRGGTRGGDRGRGRGAG
PREDICTED: similar to THO complex subunit 4 (Tho4) (RNA and export factor binding
protein 1) (REF1-I) (Ally of AML-1 and LEF-1) (Aly/REF) [Homo sapiens]

GGTRGGTRGGTRGGDRGRGRGAG
POU domain, class 3, transcription factor 3 [Homo sapiens]

GAGGGGGGGGGGGGGAGGGGGG
nucleolar protein family A, member 1; GAR1 protein [Homo sapiens]

GGGRGGRGGGRGGGGRGGGRGGG
fibrillarin; 34-kD nucleolar scleroderma antigen; RNA, U3 small nucleolar
interacting protein 1 [Homo sapiens]

GRGRGGGGGGGGGGGRGGGG
zinc finger protein 579 [Homo sapiens]

GRGRGRGRGRGRGRGRGRGGAG
calpain, small subunit 1; calcium-activated neutral proteinase; calpain,
small polypeptide; calpain 4, small subunit (30 K); calcium-dependent
protease, small subunit [Homo sapiens]

GAGGGGGGGGGGGGGGGGGGG
keratin 9 [Homo sapiens]

GGGSGGGHSGGSGGGHSGGSGG
forkhead box D1; forkhead-related activator 4;
Forkhead, homolog-like 8; forkhead (Drosophila)-like 8 [Homo sapiens]

GAGAGGGGGGGAGGGGSAGSG
PREDICTED: similar to RIKEN cDNA C230094B15 [Homo sapiens]

GGPGTGSGGGGAGTGGGAGGPG

GGGGGGGGGAGGAGGAGSAGGG
cadherin 22 precursor; ortholog of rat PB-cadherin [Homo sapiens]

GGDGGGSAGGGAGGGSGGGAG
AT-binding transcription factor 1; AT motif-binding factor 1 [Homo sapiens]

GGGGGGSGGGGGGGGGGGGG
eomesodermin; t box, brain, 2; eomesodermin (Xenopus laevis) homolog
[Homo sapiens]

GPGAGAGSGAGGSSGGGGGPG
phosphatidylinositol transfer protein, membrane-associated 2; PYK2 N-
terminal domain-interacting receptor 3; retinal degeneration B alpha
2 (Drosophila) [Homo sapiens]

TABLE 22-continued

Additional examples of human Glycine Rich Sequences for use in designing human-specific URPs GGGGGGGGGGGSSGGGGSSGG
sperm associated antigen 8 isoform 2; sperm membrane protein 1 [Homo sapiens]

GSGSGPGPGSGPGSGPGHGSG
PREDICTED: RNA binding motif protein 27 [Homo sapiens]

GPGPGPGPGPGPGPGPGPGPG
AP1 gamma subunit binding protein 1 isoform 1; gamma-synergia; adaptor-related protein complex 1 gamma subunit-binding protein 1 [Homo sapiens]

GAGSGGGGAAGAGAGSAGGGG
AP1 gamma subunit binding protein 1 isoform 2; gamma-synergia; adaptor-related protein complex 1 gamma subunit-binding protein 1 [Homo sapiens]

GAGSGGGGAAGAGAGSAGGGG
ankyrin repeat and sterile alpha motif domain containing 1; ankyrin repeat and SAM domain containing 1 [Homo sapiens]

GGGGGGGSGGGGGGSGGGGGG
methyl-CpG binding domain protein 2 isoform 1 [Homo sapiens]

GRGRGRGRGRGRGRGRGRGRG
triple functional domain (PTPRF interacting) [Homo sapiens]

GGGGGGGSGGSGGGGGSGGGG
forkhead box D3 sapiens

GGEEGGASGGGPGAGSGSAGG
sperm associated antigen 8 isoform 1; sperm membrane protein 1 [Homo sapiens]

GSGSGPGPGSGPGSGPGHGSG
methyl-CpG binding domain protein 2 testis-specific isoform [Homo sapiens]

GRGRGRGRGRGRGRGRGRGRG
cell death regulator aven; programmed cell death 12 [Homo sapiens]

GGGGGGGGDGGGRRGRGRGRG
regulator of nonsense transcripts 1; delta helicase; up-frameshift mutation 1 homolog (S. cerevisiae); nonsense mRNA reducing factor 1; yeast Upf1p homolog [Homo sapiens]

GGPGGPGGGGAGGPGGAGAG
small conductance calcium-activated potassium channel protein 2 isoform a; apamin-sensitive small-conductance Ca2+-activated potassium channel [Homo sapiens]

GTGGGGSTGGGGGGGGSGHG
SRY (sex determining region Y)-box 1; SRY-related HMG-box gene 1 uz,1/43 [Homo sapiens]

GPAGAGGGGGGGGGGGGGGG
transcription factor 20 isoform 2; stromelysin-1 platelet-derived growth factor-responsive element binding protein; stromelysin 1 PDGF-responsive element-binding protein; SPRE-binding protein; nuclear factor SPBP [Homo sapiens]

GGTGGSSGSSGSGSGGGRRG
transcription factor 20 isoform 1; stromelysin-1 platelet-derived growth factor-responsive element binding protein; stromelysin 1 PDGF-responsive element-binding protein; SPRE-binding protein; nuclear factor SPBP [Homo sapiens]

GGTGGSSGSSGSGSGGGRRG
Ras-interacting protein 1 [Homo sapiens]

GS GTGTTGSS GAGGPGTPGG
BMP-2 inducible kinase isoform b [Homo sapiens]

GGSGGGAAGGGAGGAGAGAG
BMP-2 inducible kinase isoform a [Homo sapiens]

GGSGGGAAGGGAGGAGAGAG
forkhead box C1; forkhead-related activator 3; Forkhead, drosophila, homolog-like 7; forkhead (Drosophila)-like 7; iridogoniodysgenesis type 1 [Homo sapiens]

GSSGGGGGGAGAAGGAGGAG
splicing factor p54; arginine-rich 54 kDa nuclear protein [Homo sapiens]

TABLE 22-continued

Additional examples of human Glycine Rich Sequences for use in designing human-specific URPs GPGPSGGPGGGGGGGGGGG
v-maf musculoaponeurotic fibrosarcoma oncogene homolog; Avian musculoaponeurotic fibrosarcoma (MAF) protooncogene; v-maf musculo- aponeurotic fibrosarcoma (avian) oncogene homolog [Homo sapiens]

GGGGGGGGGGGGGGAAGAGG
small nuclear ribonucleoprotein D1 polypeptide 16 kDa; snRNP core protein D1; Sm-D autoantigen; small nuclear ribonucleoprotein D1 polypeptide (16 kD) [Homo sapiens]

GRGRGRGRGRGRGRGRGRGG
hypothetical protein H41 [Homo sapiens]
GSAGGSSGAAGAAGGGAGAG

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10370453B2). An electronic copy of the "Sequence Listing" will also be available from the USPTO upon request and payment of the fee set forth in 37 CFR 1.19(b)(3).

We claim:

1. A method of treating edema in a subject, the method comprising:
    administering an antibody that binds to the active form of human plasma kallikrein to a subject in need thereof, wherein the antibody comprises:
    (i) a heavy chain variable region comprising a complementary determining region (CDR) 1 set forth as HYIMM (SEQ ID NO: 166), a CDR2 set forth as GIYSSGGITVYADSVKG (SEQ ID NO: 167), and a CDR3 set forth as RRIGVPRRDEFDI (SEQ ID NO: 1171) or RRTGVPRWDDFDI (SEQ ID NO: 1177); and
    (ii) a light chain variable region comprising a CDR1 set forth as RASQSISSWLA (SEQ ID NO: 1172), a CDR2 set forth as KASTLES (SEQ ID NO: 1173), and a CDR3 set forth as QQYNTYWT (SEQ ID NO: 1174).

2. The method of claim 1, wherein
    the heavy chain variable region of the antibody comprises the amino acid sequence of EVQLLESGGGLVQPGGSLRLSCAASGFTFSHYIMMWVRQAPGKGLEWVSGIYSSGGITVY ADSVKGRFTISRDNSK-NTLYLQMNSLRAEDTAVYYCAYRRIGVPRRDEFDIWGQGTMVTVSS (SEQ ID NO: 2410) or EVQLLESGGGLVQPGGSLRLSCAASGFTFSHYIMMWVRQAPGKGLEWVSGIYSSGGITVYADSVKGRFTISRDNSKNTLYLQMNSLRAEDTAVYYCAFRRTGVP RWDDFDIWGQGTMVTVSSASTKGPSVFPLAPSSKS (SEQ ID NO: 1801), and
    the light chain variable region of the antibody comprises the amino acid sequence of DIQMTQSPSTLSASVGDRVTITCRASQSISSWLAWYQQKPGKAPKLLIYKASTLESGVPSRF SGSGSGTEFTLTISSLQPDDFATYYCQQYNTYWTFGQGTKVEIK (SEQ ID NO: 2394).

3. The method of claim 1, wherein
    the heavy chain variable region of the antibody comprises the amino acid sequence of EVQLLESGGGLVQPGGSLRLSCAASGFTFSHYIMMWVRQAPGKGLEWVSGIYSSGGITVYADSVKGRFTISRDNSKNTLYLQMNSLRAEDTAVYYCAYRRIGVPRRDEFDIWGQGTMVTV SS (SEQ ID NO: 2410) or EVQLLESGGGLVQPGGSLRLSCAASGFTFSHYIMMWVRQAPGK GLEWVSGIYSSGGITVYADSVKGRFTISRDNSKNTLYLQMNSLRAEDTAVYYCAFRRTGVP RWDDFDIWGQGTMVTVSSASTKGPSVFPLAPSSKS (SEQ ID NO: 1801), and
    the light chain variable region of the antibody comprises the amino acid sequence of DIQMTQSPSTLSASVGDRVTITCRASQSISSWLAWYQQKPGKAPKLLIYKASTLESGVPSRFSGSGSGTEFTLTISSLQPDDFATYYCQQYNTYWTFGQGTKVEI (SEQ ID NO: 2395).

4. The method of claim 1, wherein the antibody is a full-length antibody.

5. The method of claim 4, wherein the antibody is an IgG molecule.

6. The method of claim 1, wherein the antibody is an antigen-binding fragment of a full-length antibody.

7. The method of claim 1, wherein the subject is a human patient having or at risk for edema.

8. The method of claim 1, wherein the edema is hereditary angioedema.

9. The method of claim 7, wherein the edema is hereditary angioedema.

* * * * *